(12) United States Patent
Andersson et al.

(10) Patent No.: US 8,278,043 B2
(45) Date of Patent: Oct. 2, 2012

(54) METHODS AND MATERIALS RELATED TO GREY ALLELES

(75) Inventors: Leif Andersson, Uppsala (SE); Gerli Rosengren Pielberg, Uppsala (SE); Anna Olegovna Golovko, Uppsala (SE); Kjell Robert Johan Lennartsson, Heby (SE); Carl-Henrik Heldin, Uppsala (SE)

(73) Assignee: Melica HB, Uppsala (SE)

( * ) Notice: Subject to any disclaimer, the term of this patent is extended or adjusted under 35 U.S.C. 154(b) by 104 days.

(21) Appl. No.: 12/663,138

(22) PCT Filed: Jun. 5, 2008

(86) PCT No.: PCT/EP2008/057034
§ 371 (c)(1),
(2), (4) Date: Jun. 24, 2010

(87) PCT Pub. No.: WO2008/148862
PCT Pub. Date: Dec. 11, 2008

(65) Prior Publication Data
US 2010/0285462 A1    Nov. 11, 2010

Related U.S. Application Data

(60) Provisional application No. 60/942,080, filed on Jun. 5, 2007.

(51) Int. Cl.
*C07H 21/04* (2006.01)
*C12Q 1/68* (2006.01)
(52) U.S. Cl. ...... 435/6.1; 435/6.11; 435/6.12; 435/91.1; 435/91.2

(58) Field of Classification Search .................. None
See application file for complete search history.

(56) References Cited

U.S. PATENT DOCUMENTS
2003/0175721 A1    9/2003    Box et al.

FOREIGN PATENT DOCUMENTS
WO    WO 99/57318    11/1999
WO    WO 2005/075983    8/2005

OTHER PUBLICATIONS

The Horse Genome Project, EquCab 1, released Jan. 2007. http://genome.ucsc.edu/.*
The Horse Genome Browser Gateway, Jan. 2007, http://genome.ucsc.edu/cgi-bin/hgGateway.*

(Continued)

*Primary Examiner* — Jeanine A Goldberg
(74) *Attorney, Agent, or Firm* — Fish & Richardson P.C.

(57) ABSTRACT

This document relates to methods and materials for determining whether or not a horse contains a Grey allele. For example, diagnostic methods such as nucleic acid-based detection methods and materials such as nucleic acid probes and primer pairs that can be used to determine whether or not a horse contains a duplication in intron 6 of STX17 nucleic acid are provided. This document also relates to methods and materials for treating a mammal having or being likely to develop cancer (e.g., benign, malignant, or metastatic cancer). For example, methods and materials for treating cancer in a mammal by administering an agent having the ability to reduce expression of an STX17 polypeptide and/or an NR4A polypeptide (e.g., an NR4A1, NR4A2, or NR4A3 polypeptide) in the mammal are provided.

22 Claims, 45 Drawing Sheets

OTHER PUBLICATIONS

Bailey et al., "Recent Segmental Duplications in the Human Genome" *Science*, 2002, 297:1003-1007.

Bonetto et al., "Isolation and characterization of antagonist and agonist peptides to the human melanocortin 1 receptor," *Peptides*, 2005, 26:2302-2313.

Bonifacino and Glick, "The mechanisms of vesicle budding and fusion," *Cell*, 2004, 116:153-166.

Comfort, "Coat-Colour and Longevity in Thoroughbred Mares," *Nature*, 1958, 182:1531-1532.

De Snoo et al., "Cutaneous melanoma susceptibility and progression genes," *Cancer Letters*, 2005, 230(2):153-186.

Duffy et al., Interactive effects of MC1R and OCA2 on melanoma risk phenotypes, *Human Molecular Genetics*, 2004, 13(4):447-461.

Fleury et al., "The study of cutaneous melanomas in Camargue-type gray-skinned horses (2): epidemiological survey," Pigment Cell Res., Feb. 2000, 13(1):47-51.

Green et al., "Production of Polyclonal Antisera," Immunochemical Protocols, 1992, 10:1-5.

Henner et al., Genetic mapping of the (G)-locus responsible for the coat color phontype "progressive graying with age," *Mamm. Genome*, 2002, 13:535-537.

Karolchik et al., "The UCSC Genome Browser Database," *Nucl. Acids Res.*, 2003, 31(1):51-54.

Kohler & Milstein, "Continuous cultures of fused cells secreting antibody of predefined specificity," *Nature* 1975, 256:495-497.

Leevers and Marshall, "Activation of extracellular signal-regulated kinase, ERK2, by p21ras oncoprotein," *EMBO J.*, 1992, 11:569-574.

Locke et al., "Linkage of the grey coat colour locus to microsatellites on horse chromosome 25," *Anim. Genet.*, 2002, 33:329-337.

Maxwell and Muscat,"The NR4A subgroup. immediate early response genes with pleiotropic physiological roles," *Nucl. Recept. Signal.*, 2006, 4:e002.

Mayorov et al., "Effects of macrocycle size and rigidity on melanocortin receptor-1 and -5 selectivity in cyclic lactam alpha-melanocyte-stimulating hormone analogs," *Chem. Biol. Drug Des.*, 2006, 67(5):329-335.

Mossner et al., "Variations in the peroxisome proliferator-activated receptor-gamma gene and melanoma risk," *Cancer Letters*, 2006, 246(1-2):218-223.

Nomiyama et al., "The NR4A Orphan Nuclear Receptor NOR1 Is Induced by Platelet-derived Growth Factor and Mediates Vascular Smooth Muscle Cell Proliferation," *J. Biol. Chem.*, 2006, 281:33467-33476.

Pedersen et al., "Identification and classification of conserved RNA secondary structures in the human genome," *PLoS Computat. Biol.*, 2:e33 (2006.

Pei et al., NR4A orphan nuclear receptors are transcriptional regualtors of hepatic glucose metabolism, *Nature Medicine*, 2006, 12(6):1048-1055.

Pielberg et al., "A cis-acting regulatory mutation causes premature hair greying and susceptibility to melanoma in the horse," *Nature Genetics*, 2008, 40(8):1004-1009.

Pielberg et al., "Comparative linkage mapping of the Grey coat colour gene in horses," *Anim. Genet.*, 2005, 36:390-395.

Prince et al., "Robust and Accurate Single Nucleotide Polymorphism Genotyping by Dynamic Allele Specific Hybridization (DASH): Design Criteria and Assay Validation," *Genome Res.*, 2001, 11(1):152-162.

Schafer and Hawkins, "DNA variation and the future of human genetics," *Nat. Biotechnol.*, 1998, 16:33-39.

Seltenhammer et al., "Comparative histopathology of grey-horse-melanoma and human malignant melanoma," *Pigment Cell Res.*, 2004, 17:674-681.

Sponenberg, *Equine Coat Color Genetics*, 2009, Blackwell, Ames, Iowa.

Steegmaier et al., "Three novel proteins of the syntaxin/SNAP-25 family," *J. Biol. Chem.*, 1998, 273:34171-34179.

Stoneking et al., "Population variation of human mtDNA control region sequences detected by enzymatic amplification and sequence-specific oligonucleotide probes," *Am. J. Hum. Genet.*, 1991, 48:370-382.

Sundstrom et al., "Cis-acting regulatory mutation causes premature hair greying and susceptibility to melanoma in the horse," *Pigment Cell & Melanoma Research*, 2008, 21(2):274-275.

Sutton and Coleman, "Melanoma and the Greying Horse," In: RIRDC Research Paper Series No. 97/55 RIRDC Project No. UQ-28 University of Queensland, 1997.

Swanton, "Cell-cycle targeted therapies," *Lancet*, 2004, 6:27-36.

Swinburne et al., "Assignment of the horse grey colt coulur gene to ECA25 using whole genome scanning," *Animal Genetics*, 2002, 33:338-342.

Thirumoorthy et al., "Novel agouti-related-protein-based melanocortin-1 receptor antagonist ," *J. Med. Chem.*, 2001, 44(24):4114-4124.

Underhill et al., "Detection of Numerous Y Chromosome Biallelic Polymorphisms by Denaturing High-Performance Liquid Chromatography," *Genome Res.*, 1997, 7:996-1005.

Vaysberg et al., "Rapamycin Inhibits Proliferation of Epstein-Barr Virus-Positive B-cell Lymphomas Through Modulation of Cell-Cycle Protein Expression," *Transplantation*, 2007, 83(8):1114-1121.

Yin et al., Suberoylanilide Hydroxamic Acid, a Histone Deacetylase Inhibitor: Effects on Gene Expression and Growth of glimoa Cells, *Clin Canc Res.*, 13(3):1045-1052.

Zhang et al., "The Subcellular Localization of Syntaxin 17 Varies Among Different Cell Types and Is Altered in Some Malignant Cells," *J. Histochem. Cytochem.*, 2005, 53:1371-1382.

Authorized Officer Anja Bruma, International Search Report in PCT/EP2008/057034, mailed Nov. 14, 2008, 4 pages.

Authorized Officer Anja Bruma, International Preliminary Report on Patentability in PCT/EP2008/057034, mailed Dec. 17, 2009, 10 pages.

* cited by examiner

FIGURE 11

TGAGTATATAACTGTTTTTGGCTCAGAGACGTTAGATTAATAGGATAAGAGG
CTTTTATAAATCACTAGGCTTTTGATTAGGATTTTAATAGAAGTTACAATTTG
TAAGACTGGTATTGAACCATGGATAGAAGTCTAACTGTCCTCAAATTCCAGA
TCAATTCAATAAACATTTATTAAGCACTTGTTATATAAAAGGCACTGTCTTAG
GTGCTTGGCATTGGGGATCTGACAAGGTTGGATAAAGAAAGAAAGGAAGCA
TGCTGTCTGCCTTCAGGGGTTTACAGTGGGTGGAGATATGCTTGGACCCCCAA
AACTGAAATTTCAAGTGTGATTGTTAAATGCAAAGACAAGGTATGAAGAGAA
GTATTATCCGCTCCAAGGGAAGGAGGCAGGGATTGTGAGGTGGAAGCGTCAA
GGGTAGCTTCACAAGATAGGTAGTATTTGCTTAAGCCTTGAAAACTGAGTAA
AGTTTCCGCAGGTGGGAGAGAGGGAGTGCATTTGAAGAACGCTGAACAAAG
CCTTGGAGTAGTGAAGTGTATGGCCTCCCAGGAATGACAAGTTCTGCAGTGT
AACCAAAGCACAAGGTACCATGGGCAAGCAAAGCAGAGTGGCTGAGGGCCA
GGTTTAGATGGTACTGAAGGCCATACCAAAGAATTTGCACTTTGTAGGCATT
AAGGAGCCAATACAGGTTTTTGAGCAGGTTAGAGTGATGTGATCCTGTCCGT
GTTTCAGGAAGATCACTGTTAGCGGTATGAGTAATGGCCTTAAGAGAGGAGG
AGGTTATAGGCAGGACAGCTAGTTAGGAGTCATTGCAAGAGTTGCACCAAGA
GCAATGGCAATACAAGTGTGAAGGTAAAGGAGAGCTGAGAGGCATTTCTGG
GGTGCACTTATTAGGAATTGGAGGAAGATGAAAGAGTCAAAGATAAGAAAC
ATTAAGGCTTTATTCGGCATAATCGGGTAGACAGTGATACTGTTAACATAGAT
TAGGGAACATAAAGTAGATTTGGTGGGAAAGATAGATTTTCTGTTGTTATTTT
TTTAAATTATTCTTATTTTTCCTTCCCAGGAATTATGGGAAGGTTGGATATGTG
GATGTGTGTGTATATGTATGTACATAACAGGCTCGAGCCTGTTTCTGCTTATG
CTTCTCTTAGGTTTAATTCTTTGTTCTTGATCAGACTGTGATTTGAGGGTTGCG
CATCTTTGAGTTAGGGTTTCCCTGACATCTGGCTTTAAATTATAAGAAGTTCC
CAGATCACACAATCTCAGAATTGGAATTGAACTTAAAAGGACAACTAGTCTA
ATCCTTCTGCTCTTGCCCAACTTCTCAAATAGATGGTTTTTGCCTCTTTTTGAA
CAATTACTGCAAGGATGCTTTCTGCTTCAACCATTCCGTTTTGAGGCTCTAAC
TCCAGAAGTTATTCCTTGTACACAGTAAGCTCTGCCCTGTGATAACTTCCCTC
TGGCACTTTGGCCCTCTGGAGCCGTATACTGAACAAATTTTGTCTTTTTCCCAT
ATAAATGTCTCTACTTTTTGAGACCAACATTTTCCTCCTTCACCCTACCCCACC
TCACTGTATTTTCTTCTCTTAAGAACCCTTGACTGTCTAATGTGTTCCTTCTAG
AATGTGATTTCTAGTCTTTTAGTACTGGCCCTTTACTCTGCTTGTTTTCTAGT
TTGTGGATTTTTCTTGAAATGTAATGCAAAAAATTGAATGCAGTAAATTGTTT
AAAGCGTTTTTCTTTTTTGATGGCTTTAAGTCAGAAAAGCAAAATGTTTGAA
GTTTATGGAGTAGATATCTGTACAATATATTAATATATTTACGTATAAAAGGG
AATGATACAAGAATCCCAAACTATTTTGTTTCTAGAATCAAGATTTATTCAA
TTATTCTAACTCATAATCTCTGATCTAATGTAGTTTTTAAAATCTGTAATGTAT
GATTACACAAATATATACATTTGTCAAAGTCATCAATATGTACACATTACAA
TGTGTGAGTTACAATGTATGTGAATTATACCCAATAAAATTGATTTAAAAAAC
AAACTAAACATGTATAAAGTTCTTCTCATTCAAGACAAGTACGTTTCCCTCCT
AGTGGGATAGACACATGAAAGGAAAGTTAGGGGTTTGTGGCCATGTAACAGT

FIGURE 11 (continued)

```
TACATATCCGATTAGGTTACGTAAGCAGCTCCTAACCCCTAATCTAAGGAGGT
TCGTACAGGAAGACTTTGGCCATAGCCATAGCTCTATACAAATGTCCTTTTTA
TAATAATCTGTAAGGACATGAGACGGAATGCTATTAGGCAAAAGCTCAAAGG
AGAACCTCTGATTACTATCCCCAGGGTGACTGAGTTCTCGTGACCACATGGTC
AAGGATTCACAGAAGCTCCATTTAGGCACCAAATGACTTGGGAACATAACCA
GAGTGACCACACATCCTCTCGTTATCATCACATGGTCATGGTAGTATCTGGGC
CAATTAACCGTGTGTTTCTGGAGCACTTTCTATGCGCATAGTACTGTGCTAAG
CTCCGTGAAAAACAGAGAATCGTATAAAAAGAACCTATAGGATGGTCGCGGT
AGCTGCACAGCATCGTGGATGCGTTTAATGTACTGAACTGTATATTTAAAACT
GTTAAAAGTTCAAGTTTTATGTTGTGCGTATTTTACCACAATCAAAAAGAAC
CTTCAAGGCCCTTGGGAGATCCAGGTGTGGTCCAGTAGATGTGAATAAATTC
CTATCTACTAAGCACCCTGCATCGTCTTTCCTCTGCCATTATTGCTCAAGTGCC
CTCTTCTCTTCCTGTGACTGTGAAGCCAGCCTTATTTCTAGTCAAGGGGATGT
AAAGAACTGTGGGCCAGTCGCTTAATAGCATGGCACCCTTGGTGCTGGTCCA
GTTTTGTCTCTCCTTTTGCCTTATTCCTTATGGCTTTTATAATCTATTTTACTCT
GGATGCATAAAAACTGGGTTGTGATGGATTAGATCAGATTCCTCCATTTATTA
CCTATGTGACCTTCGGGGTATTGTGTTGACAGCAATGAGCTTTGTAAAATTAA
TCAGAAGACTCAATGAGATAGTGCCTATTACTTCCCACCCCTTCTCTTCTAC
TGACCCCAACTGCATTTCTGCTTTTGTCCCTCTCTCATTTGATTCCCTCTGTGG
CTCCTTGCTTAGAATTCTGCTTTTGCCACCATCATTATGTTTAAACATTTTAGT
ACGTAGTTCCTGACTCCCTCTTTTATTGCTGGATCTCTTGCTGTCAACATTTTA
CTTACCTACTCTGTTTACCGCCTACTCTAGGCCAATATAATTCTTACTGTGCCT
GTATGTCATAGTGTTTGTAAGCTTGTTTCTGGGCTTTTCTGTGTATATAAGTGC
ATGTGATTAAGGAGTATAGATTACTTACCTTTGGAGTTCAGAACCAGGATAG
CTCAGTGTTATCTGGGATGGTCAAGCTGTAAGACTAGAGCTGCTATTGAAAG
TAGCCTGGAAGTTAGAGAGTCAGAAATAAAGGAAAATACCTAGAGTTCTGAT
GTTAGCTTCTTCAAAGAAACCTGTAGCTTTCCAAGCACATTAATAAAACTACA
CAGCCACTAGCAAGACTCTCCGTGGGAGAGCATGTATTATGGCTCCAGAAGG
ATTTGGGGGTGGGTTTGTTGAATGCATTATTGTTGCTTGATGCAGAGAATGCT
GGGCCTACAAGTGTCCACCACAAGCTTTCAAGGGAAAAACTTCTTCATTAGTT
TTGACTTCAGATGCCCAAACTGCATTATAATTGAACAAGTATTAACTTAGTAA
GTCAAATTTTCTTCAAAATCTTAGGTGCTCCTATAACTGCTCATTAAGATTCA
CTTATTTTTTCACGCAGGTAAGGGGACCTAATTCAGTGTTTCTTAAAATGAA
ATTCATAGACATATTCTTAGAGTCTTTGAAAATTCTTTTTCTTTAAAAAGGAA
AGTTTTTATAGTACTCTAGTTTGAGAAACACTACGGTGTCCCTCATAAATGGT
TTAGTTCATTGTTAAAGGGATGCTGAGAACATATATGAGGTGCCAAAGTATA
AAATGTCAGGAAGGGAGTTTGAAGGTTGTCAAATGTTGGAGGCCCAGGGAG
GTGAAAGCAAACATAAGCACATCGGAAGCAAAAAGGGGAGGTTGGTGGATA
GAGGTGAGAAGGCTGCTGAGCCACCATTGCTGTCAGCTTGGTTTCCTATACTG
GGGTAAGTTTGTGTATGTGTGGTTTGGCCCAGCATAAAGAGCCAAAGACATA
GCGGACAAGTGGTGACCAGATTCAGCTCTGAATGGATTCTAGTTTGGCAATC
TCTGGGGAGTGATTAACAACTTTGACACCAGTTTGCTGCCTAACAGTAATTGC
```

FIGURE 11 (continued)

TGTGTCATTGAGTCCTTCTTACTCAAGAAGCAGAATTTGAAGATATGGGCAA
AGTTTGGGATTCAAACCAAGCAAAATAGGGAAGGAGCAGGCAGATCTGTAC
AATGAGGGACGACTTTTGATCCCAGGGTAGAGGCTGGTCTTCCCTCTGCCTTG
TCTCCAGGCCCGTGTTTAAGCAAGCGCCCTGATGTCAGTGAATGAATCCTTAC
AGGTGTGGGCTACTCCCCATGGTGAGACAGGCCTCATCAGGTTCTGGGATTG
CGGTGATGGGGAGCATTGCAGTTCAAATAACCACTGAGCTCAGGCTTCATTT
GGCCCTGTGATCCTTTCTCCAATTATTCTAAAGGATCTTTATGAAAAAATAAT
AAAGTAAAATTTTAAATTTCACTTAAAAAAACTCATAGAGCTGCAATATGC
AACCTTTTTAGGAAGGAGCATTAAAAAATATTTCCCTGAGGCCTCGAGATTA
CACTTGGGGTACAGAAATGGCAATAATTATGGCAGATTCCACCATCTTGACG
GAACAATTTTGGGGCTGAGAGAAAGACAGTTGGCTATTTTCCCTCTACGCCTC
AACTTGTCAAGATACGGAGGTTGATGATCGAGTTTTACATCTGTGATTTATCT
GGTAGCATAGACTTGATGCAAGAACAGAAAGTGTTGGGGATGTCCCAAATAG
AAACAAGGATAGGGTATCAGAAATCCTGACAAGTGGCACTTATGCTTCTGTG
GGTTGGGAAAGGAGAGCTAACATTAAAGAAGTTTTATTGTCTGAGGAAAATA
AAAACTGAGTACATGAATGCTAGGAGAGATCTAATGTTTTAGTGCCCTAGAA
TTTTCAAGCATTATAGGAAAAGTTTAATATTTTTTGATAGCAAAGAATGAT
GAGAGTTAAGCTTTCTTTGGAAGATCAGCATGACTTTTTCTATTTTTCCCCTCA
TATTCTACAGACACTATCTCATTTTATCCTCACTTCAACTCTGTGAGGTATGA
GTATCATTATCCTCACTTGGCAGACGAGAGTACTGACATATAGGGAGCTTGA
GTAGTTTATCCAAGGGCACACAGTGCTCGTGCTGGGATCTGAACACAGGACA
TCCAACCAAAGGTTGTGCCCTTAATCCTATCATATATATACTTGTGGTTTG
TTTTTTTCTTTGCTTAGGAAGATTCGCCCTGAGCTAACTTCTGTTGCCAACCTT
CCTCTTTTTGCTTGAGGAAGATTCGCCCTGAGCTAACATCTGTGCCAGTCTTC
CTTTGTTTTGTATGTGGGTCACCACCACAGTATGGCTGCCAAAGAGTGGTGTA
GGTCTGCACCCAGGAACCAAACCAGGGCCGCCAAAGCGGAGCATGCCGAAC
AACCATGAGGCCATGAGGCTGGCCCTGCTAGTGGCTTTTAAAGTTTGAGAAT
CATGGACTTGTAGTATCAGCACCACCTGGGAACTCATTAGAAATGCAA↓AAT
CTCAGAATTGGAATTGAACTTAAAAGGACAACTAGTCTAATCCTTCTGCTCTT
GCCCAACTTCTCAAATAGATGGTTTTTGCCTCTTTTTGAACAATTACTGCAAG
GATGCTTTCTGCTTCAACCATTCCGTTTTGAGGCTCTAACTCCAGAAGTTATTC
CTTGTACACAGTAAGCTCTGCCCTGTGATAACTTCCCTCTGGCACTTTGGCCC
TCTGGAGCCGTATACTGAACAAATTTTGTCTTTTCCCATATAAATGTCTCTAC
TTTTTGAGACCAACATTTTCCTCCTTCACCCTACCCCACCTCACTGTATTTTCT
TCTCTTAAGAACCCTTGACTGTCTAATGTGTTCCTTCTAGAATGTGATTTCTAG
TCTTTTTAGTACTGGCCCTTTACTCTGCTTGTTTTCTAGTTTGTGGATTTTCTT
GAAATGTAATGCAAAAAATTGAATGCAGTAAATTGTTTAAAGCGTTTTTCTTT
TTTGATGGCTTTAAGTCAGAAAAAGCAAAATGTTTGAAGTTTATGGAGTAGA
TATCTGTACAATATATTAATATATTTACGTATAAAAGGGAATGATACAAGAA
TCCCAAACTATTTTTGTTTCTAGAATCAAGATTTATTCAATTATTCTAACTCAT
AATCTCTGATCTAATGTAGTTTTTAAAATCTGTAATGTATGATTACACAAATA
TATACATTTGTCAAAAGTCATCAATATGTACACATTACAATGTGTGAGTTACA
ATGTATGTGAATTATACCCAATAAAATTGATTTAAAAAACAAACTAAACATG

FIGURE 11 (continued)

```
TATAAAGTTCTTCTCATTCAAGACAAGTACGTTTCCCTCCTAGTGGGATAGAC
ACATGAAAGGAAAGTTAGGGGTTTGTGGCCATGTAACAGTTACATATCCGAT
TAGGTTACGTAAGCAGCTCCTAACCCCTAATCTAAGGAGGTTCGTACAGGAA
GACTTTGGCCATAGCCATAGCTCTATACAAATGTCCTTTTTATAATAATCTGT
AAGGACATGAGACGGAATGCTATTAGGCAAAAGCTCAAAGGAGAACCTCTG
ATTACTATCCCCAGGGTGACTGAGTTCTCGTGACCACATGGTCAAGGATTCAC
AGAAGCTCCATTTAGGCACCAAATGACTTGGGAACATAACCAGAGTGACCAC
ACATCCTCTCGTTATCATCACATGGTCATGGTAGTATCTGGGCCAATTAACCG
TGTGTTTCTGGAGCACTTTCTATGCGCATAGTACTGTGCTAAGCTCCGTGAAA
AACAGAGAATCGTATAAAAAGAACCTATAGGATGGTCGCGGTAGCTGCACA
GCATCGTGGATGCGTTTAATGTACTGAACTGTATATTTAAAACTGTTAAAAGT
TCAAGTTTTATGTTGTGCGTATTTTACCACAATCAAAAAGAACCTTCAAGGC
CCTTGGGAGATCCAGGTGTGGTCCAGTAGATGTGAATAAATTCCTATCTACTA
AGCACCCTGCATCGTCTTTCCTCTGCCATTATTGCTCAAGTGCCCTCTTCTCTT
CCTGTGACTGTGAAGCCAGCCTTATTTCTAGTCAAGGGGATGTAAAGAACTG
TGGGCCAGTCGCTTAATAGCATGGCACCCTTGGTGCTGGTCCAGTTTTGTCTC
TCCTTTTGCCTTATTCCTTATGGCTTTTATAATCTATTTTACTCTGGATGCATA
AAAACTGGGTTGTGATGGATTAGATCAGATTCCTCCATTTATTACCTATGTGA
CCTTCGGGGTATTGTGTTGACAGCAATGAGCTTTGTAAAATTAATCAGAAGA
CTCAATGAGATAGTGCCTATTACTTCCCACCCCTTCTCTTCTACTGACCCCA
ACTGCATTTCTGCTTTTGTCCCTCTCTCATTTGATTCCCTCTGTGGCTCCTTGCT
TAGAATTCTGCTTTTGCCACCATCATTATGTTTAAACATTTTAGTACGTAGTTC
CTGACTCCCTCTTTTATTGCTGGATCTCTTGCTGTCAACATTTTACTTACCTAC
TCTGTTTACCGCCTACTCTAGGCCAATATAATTCTTACTGTGCCTGTATGTCAT
AGTGTTTGTAAGCTTGTTTCTGGGCTTTTCTGTGTATATAAGTGCATGTGATTA
AGGAGTATAGATTACTTACCTTTGGAGTTCAGAACCAGGATAGCTCAGTGTT
ATCTGGGATGGTCAAGCTGTAAGACTAGAGCTGCTATTGAAAGTAGCCTGGA
AGTTAGAGAGTCAGAAATAAAGGAAAATACCTAGAGTTCTGATGTTAGCTTC
TTCAAAGAAACCTGTAGCTTTCCAAGCACATTAATAAAACTACACAGCCACT
AGCAAGACTCTCCGTGGGAGAGCATGTATTATGGCTCCAGAAGGATTTGGGG
GTGGGTTTGTTGAATGCATTATTGTTGCTTGATGCAGAGAATGCTGGGCCTAC
AAGTGTCCACCACAAGCTTTCAAGGGAAAAACTTCTTCATTAGTTTTGACTTC
AGATGCCCAAACTGCATTATAATTGAACAAGTATTAACTTAGTAAGTCAAAT
TTTCTTCAAAATCTTAGGTGCTCCTATAACTGCTCATTAAGATTCACTTATTTT
TTTCACGCAGGTAAGGGGACCTAATTCAGTGTTTCTTAAAATGAAATTCATAG
ACATATTCTTAGAGTCTTTGAAAATTCTTTTTCTTTAAAAAGGAAAGTTTTTAT
AGTACTCTAGTTTGAGAAACACTACGGTGTCCCTCATAAATGGTTTAGTTCAT
TGTTAAAGGGATGCTGAGAACATATATGAGGTGCCAAAGTATAAAATGTCAG
GAAGGGAGTTTGAAGGTTGTCAAATGTTGGAGGCCCAGGGAGGTGAAAGCA
AACATAAGCACATCGGAAGCAAAAAGGGGAGGTTGGTGGATAGAGGTGAGA
AGGCTGCTGAGCCACCATTGCTGTCAGCTTGGTTTCCTATACTGGGGTAAGTT
TGTGTATGTGTGGTTTGGCCCAGCATAAAGAGCCAAAGACATAGCGGACAAG
TGGTGACCAGATTCAGCTCTGAATGGATTCTAGTTTGGCAATCTCTGGGGAGT
```

FIGURE 11 (continued)

GATTAACAACTTTGACACCAGTTTGCTGCCTAACAGTAATTGCTGTGTCATTG
AGTCCTTCTTACTCAAGAAGCAGAATTTGAAGATATGGGCAAAGTTTGGGAT
TCAAACCAAGCAAAATAGGGAAGGAGCAGGCAGATCTGTACAATGAGGGAC
GACTTTTGATCCCAGGGTAGAGGCTGGTCTTCCCTCTGCCTTGTCTCCAGGCC
CGTGTTTAAGCAAGCGCCCTGATGTCAGTGAATGAATCCTTACAGGTGTGGG
CTACTCCCCATGGTGAGACAGGCCTCATCAGGTTCTGGGATTGCGGTGATGG
GGAGCATTGCAGTTCAAATAACCACTGAGCTCAGGCTTCATTTGGCCCTGTGA
TCCTTTCTCCAATTATTCTAAAGGATCTTTATGAAAAAATAATAAAGTAAAAT
TTTTAAATTTCACTTAAAAAAACTCATAGAGCTGCAATATGCAACCTTTTAG
GAAGGAGCATTAAAAAATATTTCCCTGAGGCCTCGAGATTACACTTGGGGTA
CAGAAATGGCAATAATTATGGCAGATTCCACCATCTTGACGGAACAATTTTG
GGGCTGAGAGAAAGACAGTTGGCTATTTTCCCTCTACGCCTCAACTTGTCAAG
ATACGGAGGTTGATGATCGAGTTTTACATCTGTGATTTATCTGGTAGCATAGA
CTTGATGCAAGAACAGAAAGTGTTGGGGATGTCCCAAATAGAAACAAGGAT
AGGGTATCAGAAATCCTGACAAGTGGCACTTATGCTTCTGTGGGTTGGGAAA
GGAGAGCTAACATTAAAGAAGTTTTATTGTCTGAGGAAAATAAAAACTGAGT
ACATGAATGCTAGGAGAGATCTAATGTTTAGTGCCCTAGAATTTTCAAGCAT
TATAGGAAAAGTTTAATATTTTTTGATAGCAAAGAATGATGAGAGTTAAG
CTTTCTTTGGAAGATCAGCATGACTTTTTCTATTTTTCCCCTCATATTCTACAG
ACACTATCTCATTTTATCCTCACTTCAACTCTGTGAGGTATGAGTATCATTATC
CTCACTTGGCAGACGAGAGTACTGACATATAGGGAGCTTGAGTAGTTTATCC
AAGGGCACACAGTGCTCGTGCTGGGATCTGAACACAGGACATCCAACCAAA
GGTTGTGCCCTTAATCCTATCATATATATATACTTGTGGTTTGTTTTTTTCTTT
GCTTAGGAAGATTCGCCCTGAGCTAACTTCTGTTGCCAACCTTCCTCTTTTTGC
TTGAGGAAGATTCGCCCTGAGCTAACATCTGTGCCAGTCTTCCTTTGTTTTGT
ATGTGGGTCACCACCACAGTATGGCTGCCAAAGAGTGGTGTAGGTCTGCACC
CAGGAACCAAACCAGGGCCGCCAAAGCGGAGCATGCCGAACAACCATGAGG
CCATGAGGCTGGCCCTGCTAGTGGCTTTTAAAGTTTGAGAATCATGGACTTGT
AGTATCAGCACCACCTGGGAACTCATTAGAAATGCAAATTCTCAGGCCTCAT
CCCAAGCCCCCTGAATCAGAAACTCTGGATGAAGTTCTCCAGGTGATTCTGGT
GCACACTCCAGTGTGGAAACCACTGTTGTATTGGTCTCTGACGACGTTAGAA
GAAGACTTATAGAGGACTTTTTTAGGGATTGTGTTAGAGATGTCAAGATGGT
GGAGAATATAGCAATGAAGGGATACCATGAAAGGTCTAACGGTGAAGAGGT
ACATACCTGGCGTCTGAGAAGGGAAGGAATGTCAATAATGTGATAGGAAGC
AACTGTGAGGAAACAATTAGCTGTGTTGTTTGGGTGTCCTGTTCTCGGATGAA
ATGATGATTGGAATTAGAAGAGTGTTGGTCACATACGCTTCACTATAAGTGA
CTAGGTCAGTTATATAAGGACAATCAAATACTTCAGGGTTCAAATTGAATTAT
TTCACAGTCATCGAAGAAGTTGGCATTTAGCTAGGATCAAAGAGGGATTCTC
TTCTTTTTTCTGTGAATTAAAAAGACTAGTCTGTATATTGATGTGATGGTGGT
TACGTGGGTTTATGCATTTATCAGAAATCATCATACTATACCCTTAAAATGGG
TGCATATTATTATATGTAAATTCTGTCTAAATAAAGTTGATTTAAAAATGGGA
ATGTGGGGGCTGGCCCTGTGTGCCCGAGCGGTTAAGTTCGCGCCCTCCGCTG
CAGGCGGCCCAGTGTTTCGTTGGTTCGAATCCTGGGCACGGACATGACACTG

FIGURE 11 (continued)

CTCATCAAACCACGCTGAGGCAGCATCCCACATGCCACAACTAGAAGGACCC
ACAACAAAGAATATACAACTATGTACCGGGGTGCTTTGGGGAGAAAAAGGA
AAAAATAAAATCTTAAAAAAAAAAAAAAAATAGGGTATAGTGTACTCGTGGC
CAGTTAATGAGTTTCTGTCACTGAGGTGTTTGAGCAGAGGTTCAGTAAGCGCT
TGTCAGATATGTCGTAGTGGGGCTTCCCACATCTGAGGGAGAAATCGCACTC
AGCAACCTAAACATTCCTTCTACCCAGAGGTTCCATGAGTCACAATTTCTGTT
GTGTCAGCCGCAGGTGTTGCCATTTTGTGTAGAATGCTTGGTTAATATATTTG
ATCTGAAACATTTTAACTTGTCATGATTTTAAAATGTATTAAAGTGTCCACGT
GTGAAACACAGGACAGTGAATTCATTCACCACTCCCTACTGCATATCACAAG
TAGAAAGATTTCATGGCAGATCAAACCATATTGTATTCTTATTCCTAAAACAG
TAATTTGTATTTATCGTGGCATCAAGGGTGTTTTACTCCTAAGGCAAATTTGC
CTGTTTTAAACTGAATCTTCAAAGAAGATAAGTTAGGGAGGATTTTTGCTTTG
ATCCTGTTTTTGTTTTTTTCCATCAAACCCAACATGACATGTAAATACTTATTT
GGACTTTTTTTCTTTCTCGAAAGCAGATTTATTTGGAGAACAATATGCTTGTA
TGTTTGAATGAAGTTTAGAGTAAGATGCTTTTTCCTATAAAGGTGCCACTCTT
TTATTACTGAATAATTAAGTCACCTTTTTTTATACAAGTGAATTTGTGCTTTCG
ACGTGGTTTGTCAGATGCTGTTAAATGAACTGCTGTTAGACTCCAAGGCTGCG
GCACACAGGCCCTGATTACAGGAGTTAAAATAGTGTGCATTGGCTGACTGCT
GCTCCGCAGCAGGAGCGCTCACTCATAATTCCTTTGCATCTAG

FIGURE 12

TGAGTATATAACTGTTTTTGGCTCAGAGACTGTTAGATTAATAGGATAAGAG
GCTTTTATAAATCACTAGGCTTTTGATTAGGATTTTAATAGAAGTTACAATTT
GTAAGACTGGTATTGAACCATGGATAGAAGTCTAACTGTCCTCAAATTCCAG
ATCAATTCAATAAACATTTATTAAGCACTTGTTATATAAAAGGCACTGTCTTA
GGTGCTTGGCATTGGGGATCTGACAAGGTTGGATAAAGAAAGAAAGGAAGC
ATGCTGTCTGCCTTCAGGGGTTTACAGTGGGTGGAGATATGCTTGGACCCCA
AAACTGAAATTTCAAGTGTGATTGTTAAATGCAAAGACAAGGTATGAAGAGA
AGTATTATCCGCTCCAAGGGAAGGAGGCAGGGATTGTGAGGTGGAAGCGTC
TAAGGGTCAGCTTCACAAGCATAGGTAGTATTTGCTTAAGCCTTGAAAACT
TGAGTAAAGTTGTCCGCAGGTGGGAGAGAGGGAGTGCATTTGAAGAACGCT
GAACAAAGCCTTGGAGTAGTGAAGTGTATGGCCTCCCAGGAATGACAAGTTC
TGCAGTGTAACCAAAGCACAAGGTACCATCGGGCAAGCAAAGCAGAGTCG
GCTGAGGGCCAGGTTTAGATGGTACTGAAGGCCATACCAAAGAATTTGCACT
TTGTAGGCATTAAGGAGCCAATACAGGTTTTTGAGCAGGTTAGAGTGATGTG
ATCCTGTCCGTGTTTCAGGAAGATCACTGTTAGCGGTAGTGAGAGTAATGG
CCTTAAGAGAGGAGGAGGTTATAGGCAGGACAGCTAGTTAGGAGTCATTGCA
AGAGTTGCACCAAGAGCAATGGCAATACAAGTGTGAAGGTAAAGGAGAGCT
GAGAGGCATTTCTGGGGTGCACTTATTAGGAATTGGAGGAAGATGAAAGAGT
CAAAGATAAGAAACATTAAGGCTTTATTCGGCATAATCGGGTAGACAGTGAT
ACTGTTAACATAGATTAGGGAACATAAAGTAGATTTGGTGGGAAAGATAGAT
TTTCTGTTGTTATTTTTTAAATTATTCTTATTTTTCCTTCCCAGGAATTATGGG
AAGGTTGGATATGTGGATGTGTGTATATGTATGTACATAACAGGCTCGAG
CCTGTTTCTGCTTATGCTTCTCTTAGGTTTAATTCTTTGTTCTTGATCAGACTGT
GATTTGAGGGTTGCGCATCTTTGAGTTAGGGTTTCCCTGACATCTGGCTTTAA
ATTATAAGAAGTTCCCAGATCACAC<u>AATCTCAGAATTGGAATTGAACTTAAA
AGGACAACTAGTCTAATCCTTCTGCTCTTGCCCAACTTCTCAAATAGATGGTT
TTTGCCTCTTTTTGAACAATTACTGCAAGGATGCTTTCTGCTTCAACCATTCCG
TTTTGAGGCTCTAACTCCAGAAGTTATTCCTTGTACACAGTAAGCTCTGCCCT
GTGATAACTTCCCTCTGGCACTTTGGCCCTCTGGAGCCGTATACTGAACAAAT
TTTGTCTTTTTCCCATATAAATGTCTCTACTTTTTGAGACCAACATTTTCCTCC
TTCACCCTACCCCACCTCACTGTATTTTCTTCTCTTAAGAACCCTTGACTGTCT
AATGTGTTCCTTCTAGAATGTGATTTCTAGTCTTTTTAGTACTGGCCCTTTACT
CTGCTTGTTTCTAGTTTGTGGATTTTTCTTGAAATGTAATGCAAAAAATTGA
ATGCAGTAAATTGTTTAAAGCGTTTTCTTTTTTGATGGCTTTAAGTCAGAAA
AAGCAAAATGTTTGAAGTTTATGGAGTAGATATCTCGTACAATATATTAATA
TATTTACGTATAAAAGGGAATGATACAAGAATCCCAAACTATTTTGTTTCTA
GAGATCAAGATTTATTCAATTATTCTAACTCATAATCTCTGATCTAATGTAGT</u>
TTTTAAAATCTGTAATGTATGATTACACAAATATATACATTTGTCAAAAGTCA
TCAATATGTACACATTACAATGTGTGAGTTACAATGTATGTGAATTATACCCA

FIGURE 12 (continued)

ATAAAATTGATTTAAAAAACAAACTAAACATGTATAAAGTTCTTCTCATTCAA
GACAAGTACGTTTCCCTCCTAGTGGGATAGACACATGAAAGGAAAGTTAGGG
GTTTGTGGCCATGTAACAGTTACATATCCGATTAGGTTACGTAAGCAGCTCCT
AACCCCTAATCTAAGGAGGTTCGTACAGGAAGACTTTGGCCATAGCCATAGC
TCTATACAAATGTCCTTTTTATAATAATCTGTAAGGACATGAGACGGAATGCT
ATTAGGCAAAAGCTCAAAGGAGAACCTCTGATTACTATCCCCAGGGTGACTG
AGTTCTCGTGACCACATGGTCAAGGATTCACAGAAGCTCCATTTAGGCACCA
AATGACTTGGGAACATAACCAGAGTGACCACACATCCTCTCGTTATCATCAC
ATGGTCATGGTAGTATCTGGGCCAATTAACCGTGTGTTTCTGGAGCACTTTCT
ATGCGCATAGTACTGTGCTAAGCTCCGTGAAAGAACAGAGAATCGATATAA
AAAGAACCTATAGGATGGTCGCGGTAGCTGCACAGCATCGTGGATGCGTTTA
ATGTACTGAACTGTATATTTAAAACTGTTAAAAGTTCAAGTTTTATGTTGTGC
GTATTTTTACCACAATCAAAAAGAACCTTCAAGGCCCTTGGGAGATCCAGGT
GTGGTCCAGTAGATGTGAATAAATTCCTATCTACTAAGCACCCTGCAGTCGT
CTTTCCTCTGCCAGTTATTGCTCAAGTGCCCTCTTCTCTTCCTGTGACTGTGAA
GCCAGCCTTATTTCTAGTCAAGGGGATGTAAAGAACTGTGGGCCAGTCGCTT
AATAGCATGGCACCCTTGGTGCTGGTCCAGTTTTGTCTCTCCTTTTGCCTTATT
CCTCTATGGCTTTTATAATCTATTTTACTCTGGATGCATAAAAACTGGGTTGT
GATGGATTAGATCAGATTCCTCCATTTATTACCTATGTGACCTTCGGGGTATT
GTGTTGACAGCAATGAGCTTTGTAAAATTAATCAGAAGACTCAATGAGATAG
TGCTCTATTACTTCCCACCCCCTTCTCTTCTACTGACCCCAACTGCATTTCTGC
TTTTGTCCCTCCTCTCATTTGATTCCCTCTGTGGCTCCTTGCTTAGAATTCTGC
TTTTGCCACCATCATTATGTTTAAACATTTTAGTACGTAGTTCCTGACTCCCTC
TTTTATTGCTGGATCTCTTGCTGTCAACATTTTACTTACCTACTCTGTTTACCG
CCTACTCTAGGCCAATATAATCTCTTACTGTGCCTGTATGTCATAGTGTTTGT
AAGCTTGTTTCTGGGCTTTTCTGTGTATATAAGTGCATGTGATTAAGGAGTAT
GAGATTACTTACCTTTGGAGTTCAGAACCAGGATAGCTCAGTGTTATCTGGG
ATGGTCAAGCTGTAAGACTAGAGCTGCTATTGAAAGTAGCCTGGAAGTTAGA
GAGTCAGAAATAAAGGAAAATACCTAGAGTTCTGATGTTAGCTTCTTCAAAG
AAACCTGTAGCTTTCCAAGCACATTAATAAAACTACACAGCCACTAGCAAGA
CTCTCCGTGGGAGAGCATGTATTATGGCTCCAGAAGGATTTGGGGGTGGGTT
TGTTGAATGCATTATTGTTGCTTGATGCAGAGAATGCTGGGCCTACAAGTGTC
CACCACAAGCTTTCAAGGGAAAAACTTCTTCATTAGTTTTGACTTCAGATGCC
CAAACTGCATTATAATTGAACAAGTATTAACTTAGTAAGTCAAATTTTCTTCA
AAATCTTAGGTGCTCCTATAACTGCTCATTAAGATTCACTTATTTTTTCACGC
AGGTAAGGGGACCTAATTCAGTGTTTCTTAAAATGAAATTCATAGACATATTC
TTAGAGTCTTTGAAAATTCTTTTTCTTTAAAAAGGAAAGTTTTTATAGTACTCT
AGTTTGAGAAACACTACGGTGTCCCTCATAAATGGTTTAGTCTCATTGTTAA
AGGGATGCTGAGAACATATATGAGGTGCCAAAGTATAAAATGTCAGGAAGG
GAGTTTGAAGGTTGTCAAATGTTGGAGGCCCAGGGAGGTGAAAGCAAACATA
AGCACATCGGAAGCAAAAAGGGGAGGTTGGTGGATAGAGGTGAGAAGGCTG

FIGURE 12 (continued)

CTGAGCCACCATTGCTGTCAGCTTGGTTTCCTATACTGGGGTAAGTTTGTGTA
TGTGTGGTTTGGCCCAGCATAAAGAGCCAAAGACATAGCGGACAAGTGGTGA
CCAGATTCAGCTCTGAATGGATTCTAGTTTGGCAATCTCTGGGGAGTGATTAA
CAACTTTGACACCAGTTTGCTGCCTAACAGTAATTGCTGTGTCATTGAGTCCT
TCTTACTCAAGAAGCAGAATTTGAAGATATGGGCAAAGTTTGGGATTCAAAC
CAAGCAAAATAGGGAAGGAGCAGGCAGATCTGTACAATGAGGGACGACTTT
TGATCCCTAGGGTAGAGGCTGGTCTTCCCTCTGCCTTGTCTCCAGGCCCGTGT
TTAAGCAAGCGCCCTGATGTCAGTGAATGAATCCTTACAGGTGTGGGCTACT
CCCCATGGTGAGACAGGCCTCATCAGGTTCTGGGATTGCGGTGATGGGGAGC
ATTGCAGTTCAAATAACCACTGAGCTCAGGCTTCATTTGGCCCTGTGATCCTT
TCTCCAATTATTCTAAAGGATCTTTATGAAAAAATAATAAAGTAAAATTTTA
AATTTCACTGTAAAAAAACTCATAGAGCTGCAATATGCAACCTTTTTAGGAA
GGAGCATTAAAAAATATTTCCCTGAGGCCTCGAGATTACACTTGGGGTACAG
AAATGGCAATAATTATGGCAGATTCCACCATCTTGACGGAACAATTTTGGGG
CTGAGAGAAAGACAGTTGGCTATTTTCCCTCTACGCCTGCAACTTCGTCAAG
ATACGGAGGTTGATGATCGAGTTTTACATCTGTGATTTATCTGGTAGCATAGA
CTTGATGCAAGAACAGGAAAGTGTTGGGGATGTCCCAAATAGAAACAAGGA
TAGGGTATCAGAAATCCTGACAAGTGGCACTTATGCTTCTGTGGGTTGGGAA
AGGAGAGCTAACATTAAAGAAGTTTTATTGTCTGAGGAAAATAAAAACTG
AGTAGCATGAATGCTAGGAGAGATCTAATGTTTTAGTGCCCTAGAATTTTCA
AGCATTTATAGGAAAAAGTTTAATATTTTTTGATAGCAAAGAATGATGAGA
GTTAAGCTTTCTTTGGAAGATCAGCACTGACTTTTCTATTTTCCCCTCATAT
TCTACAGACACTATCTCATTTTATCCTCACTTCAACTCTGTGAGGTATGAGTA
TCATTATCCTCACTTGGCAGACGAGAGTACTGACATATAGGAGAGCTTGAGT
AGTTTATCCAAGGGCACACAGTGCTCGTGCTGGGATCTGAACACAGGACATC
CAACCAAAGGTTGTGCCCTTAATCCTATCATATATATACTTCGTGGTTTGT
TTTTTCTTTGCTTAGGAAGATTCAGCCCTGAGCTAACTTCTGTTGCCAACCT
TCCTCTTTTTGCTTGAGGAAGATTCGCCCTGAGCTAACATCTGTGCCAGTCTT
CCTTCTGTTTTGTATGTGGGTCACCACCACAGTATGGCTGCCAAAGAGTGGT
CGTAGGTCTGCACCCAGGAACCAAACCAGGGCCGCCAAAGCGAGAGCATGC
CGAACAACCATG/AAGGCCATGAGGCTGGCCCTGCTAGTGGCTTTTAAAGTT
GTGAGAATCATGGACTTGTAGTATCAGCACCACCTGGGAACTCATTAGAAAT
GCAAATTCTCAGGCCTCATCCCCAAGCCCCCTGAATCAGAAACTCTGGATGA
AGTTCTCCAGGTGATTCTGGTGCACACTCCAGTGTGGAAACCACTGTTGTATT
GGTCTCTGACGACGTTAGAAGAAGACTTATAGAGGACTTTTTAGGGATTGT
GTTAGAGATGTCAAGATGGTGGAGAATATAGCAATGAAGGGATACCATGAA
AGGTCTAACGGTGAAGAGGTACATACCTGGCGTCTGAGAAGGGAAGGAATG
TCAATAATGTGATAGGAAGCAACTGTGAGGAAACAATTAGCTGTGTTGTTTG
GGTGTCCTGTTCTCGGATGAAATGATGATTGGAATTAGAAGAGTGTTGGTCA
CATACGCTTCACTATAAGTGACTAGGTCAGTTATATAAGGACAATCAAATAC
TTCAGGGTTCAAATTGAATTATTTCACAGTCATCGAAGAAGTTGGCATTTAGC
TAGGATCAAAGAGGGATTCTCTTCTTTTTTCTGTGAATTAAAAGACTAGTC
TGTATATTGATGTGATGGTGGTTACGTGGGTTTATGCATTTATCAGAAATCAT

FIGURE 12 (continued)

CATACTATACCCTTAAAATGGGTGCATATTATTATATGTAAATTCTGTCTAAA
TAAAGTTGATTTAAAAATGGGAATGTGGGGGCTGGCCCTCGTGTGCCCGAGC
GGTTAAGTTCGCGCCGCTCCGCTGCAGGCGGCCCAGTGTTTCGTTGGTTCGA
AATCCTGGGCACGGACATGACACTGCTCATCAAACCACGCTGAGGCAGCATC
CCACATGCCACAACTAGAAGGACCCACAACAAAGAATATACACACTATGTA
CCGGGGTGCTTTGGGGAGAAAAAGGAAAAAATAAAATCTTAAAAAAAAAAA
AAAATAGGGTATAGTGTACTCGTGGCCAGTTAATGAGTTTCTGTCACTGAGGT
GTTTGAGCAGAGGTTCAGTAAGCGCTTGTCAGATATGTCGTAGTGGGGCTTCC
CACATCTGAGGGAGAAATCGCACTCAGCAACCTAAACATTCCTTCTACCCAG
AGGTTCCATGAGTCACAATTTCTGTTGTGTCAGCCGCAGGTGTTGCCATTTTG
TGTAGAATGCTTGGTTAATATATTTGATCTGAAACATTTTAACTTGTCATGAT
TTTAAAATGTATTAAAGTGTCCACGTGTGAAACACAGGACAGTCGAATTCAT
TCACCAGCTCCCTACTGCATATCACAAGTAGAAAGATTTCATGGCAGATCAA
ACCATATTGTATTCTTATTCCTAAAACAGTAATTTGTATTTATCGTGGCATCA
AGGGTGTTTTACTCCTAAGGCAAATTTGCCTGTTTTAAACTGAATCTTCAAAG
AAGATAAGTTAGGGAGGATTTTTGCTTTGATCCTGTTTTTGTTTTTTTCCATCA
AACCCAACATGACATGTAAATACTTATTTGGACTTTTTTTCTTTCTCGAAAGC
AGATTTATTTGGAGAACAATATGCTTGTATGTTTGAATGAAGTTTAGAGTAAG
ATGCTTTTTCCTATAAAGGTGCCACTCTTTTATTACTGAATAATTAAGTCACCT
TTTTTTATACAAGTGAATTTGTGCTTTCGACGTGGTTTGTCAGATGCTGTTAAA
TGAACTGCTGTTAGACTCCAAGGCTGCGGCACACAGGCCCTGATTAGCAGGA
GTTAAAATAGTGTGCATTGGCTGACTGCTGCTCCGCAGCAGGAGCGCTCACT
CATAATTCCTTTGCATCTAG

FIGURE 13

GAAATCACCGAAACCGGCCTCCAGCGCCCCGGCCGGAGGTTTTTCTGTATGA
GTGGAGAAGACAGTTGTTACAAGTAGAAGTGACACAACATTTTTTAGG<u>ATG</u>
TCTGAAGATGAAGAAAAGTGAAATTACGCCGTCTTGAGCCAGCTATCCAGA
AATTCATTAAGATAGTAATCCCAACAGACCTGGAGAGGTTAAGAAAGCACCA
GATAAATATTGAGAAGTATCAAAGGTGCAGAATCTGGGATAAGTTACATGAA
GAACATATCAATGCAGGACGTACAGTTCAGCAACTCCGCTCCAATATTCGAG
AAATGGAGAAACTTTGTTTGAAAGTCCGAAAGGATGATGTAGGACTTCTAAA
GAGAATGATAGATCCTGTTAAAGAAGAAGCATCAGTAGCAACAGCAGAATTT
CTCCAGCTCCATCTGGAATCTGTAGAAGAACTTAAGAAACAGTTTAATGATG
AAGAAACTTTGTTACAGCCTTCTCTGACCAGATCCATGACTGTTGGTGGAGCT
TTTCACACTGCTGAAGCTGAAACCGATCCTCAGAGTGTGACTCAGATATACG
CATTGCCTGAAATCCCTCGAGATCAAAATGCTGCCGAATCCTGGGAAACCTT
AGAAGCGGACTTAATCGAACTTAGCCAACTGGTCACTGATTTCTCTCTCCTAG
TAAATTCCCAGCAGGAGAAGATTGACAGCATTGAAGACCATGTCAACACTGC
TGCTGTGAATGTTGAAGTGGGAACCAAAAACTTGGGGAAGGCTGCAAAATAC
AAGCTGGCAGCTCTGCCTGTGGCAGGTGCACTCATCGGAGGAGCGGTAGGGG
GTCCGATTGGCCTCCTTGCAGGCTTCAAAGTGGCAGGAATTGCAGCTGCACTT
GGTGGTGGGGTGTTGGGCTTCACAGGTGGAAAATTGATACAAAGAAAAAAA
CAGAAAATGATGGAGAAGCTCGCTTCCAGCTGTCCAGATCTTCCCAGCCAAA
GTGACAAAAAATGCAGT<u>TAA</u>AAACCAAACTTTAGTATTATTGGTGCCAACAT
GTCTATCCTAATGAGGACCTTTTCTGCTGTTGGACACTCAGTCAGCTTTTGGA
ACATGATTATATCAAAATAGTGGCTGTAGATGCTCCAGTGGGACTGAACTGT
GATGAGCGGGTATATTTCGTTGTTTACTGGGTTTTTAATGGAGATGTTAGAGA
TCAAGGAGCCTGGGCTGAGGGTGTATAATGGTTGTCAGGTAAAGTTTAAAGA
GTGCCAGGGAGCAGATTTTCTACCTGGAAATATGAAAACTGAACCCATAACT
TTGATAAGGTCTTGAGATGTGTGGACATGTTGGGTTACAGAAGAATAGTTTCT
TCCATAACCTTGACTTGGAAACCCTAGGGCTAAGCATATTGCAAATATGCTTA
TTTGTCTCCTAAATATGGGAGATTATTAGGCCTGTTAGCAAGGAAAGAATG
GGAGTTCAGGAGCCTATCTTGTCAAATAGGGAGATCAGGATCCAGCGAGATC
CTGGTGAGCTACATAACACAGTCCATTTGGTGAACCCTATTACAGTTTGGTCC
AACTGTACTTCTGGTGAAGGAAACTAATAATGTAAGAAAATGGAAAGAGAG
GCCCAGCTTCTCTTTCAGATATCTTAATTTGTGATACTGGCTTCTTCTCTGAAC
TCTTCCTTCTGCCTCTCTTTAAATAAAGAACACTGAATCTCAAATGGTAGGAG
ACTTATTAGCCCAGTCACTAAGCTTGCTCTGTCAGCCTGTATCTTAAGACCTC
AAAGATCCAGTGCCCTGTGTCTTTCCTCCCTTGTAATTTTGAAAAGGTCTTAG
ACTTGTAGGGTGAATTTTACCCATGTGTAATGAGGACTTTTCTCATAATCTCC
TTTTTTGTACTGTCTCCCATCTCTGTTCACCCTTTCCTGTAGCCCCTAGGTGGA
AAAAAAAAAAAAAAAAAAA

FIGURE 14

CATGACACTGCTCATCAAACCACGCTGAGGCAGCATCCCACATGCCACAACT
AGAAGGACCCACAACAAAGAATATACAACTATGTACCGGGGTGCTTTGGGGA
GAAAAAGGAAAAAATAAAATCTTAAAAAAAAAAAAAAAATAGGGTATAGTGT
ACCTGTGGCCAGTAATGAGTTTCTGTCACTGAGGTGTTTGAGCAGAGGTTCAG
TAAGCGCTTGTCAGAATGTCGTAGTGGGGCTTCCCACATCTGAGGGAGAAAT
CGCACTCAGCAACCTAAACATTCCTTCTACCCAGAGGTTCCATGAGTCACAAT
TTCTGTTGTGTCAGCCGCAGGTGTTGCCATTTTGTGTAGAATGCTTGGTTAAT
ATATTTGATCTGAAACATTTTAACTTGTCATGATTTTAAAATGTATAAAGTGT
CCACGTGTGAAACACAGGACAGTGAATTCATTCACCACTCCCTACTGCATAT
CACAAGTAGAAAGATTTCATGGCAGATCAAACCATATTGTATTCTTATTCCTA
AAACAGTAATTTGTATTTATCGTGGCATCAAGGGTGTTTTACTCCTAAGGCAA
ATTTGCCTGTTTTAAACTGAATCTTCAAAGAAGATAAGTTAGGGAGGATTTTT
GCTTTGATCCTGTTTTTGTTTTTTCCATCAAACCCAACATGACATGTAAATAC
TTATTTGGACTTTTTTTCTTTCTCGAAAGCAGATTTATTTGGAGAACAATATGC
TTGTATGTTTGAATGAAGTTTAGAGTAAGATGCTTTTTCCTATAAAGGTGCCA
CTCTTTTATTACTGAATAATTAAGTCACCTTTTTTTATACAAGTGAATTTGTGC
TTTCGACGTGGTTTGTCAGATGCTGTTAATGAACTGCTGTTAGACTCCAAGGC
TGCGGCACACAGGCCCTGATTNCAGGAGTTAAAATAGTGTGCATTGGCTGAC
TGCTGCTCCGCAGCAGGAGCGCTCACTCATAATTCCTTTGCATCTAGTCCCAG
CAGGAGAAGATTGACAGCATTGAAGACCATGTCAACACTGCTGCTGTGAATG
TTGAAGTGGGAACCAAAAACTTGGGGAAGGCTGCAAAATACAAGC<u>TGG</u>CAG
CTCTGCCTGTGGCAGGTGCACTCATCGGAGGAGCGGTAGGGGGTCCGATTGG
CCTCCTTGCAGGCTTCAAAGTGGCAGGAATTGCAGCTGCACTTGGTGGTGGG
GTGTTGGGCTTCACAGGTGGAAAATTGATACAAAGAAAAAAACAGAAAATG
ATGGAGAAGCTCGCTTCCAGCTGTCCAGATCTTCCCAGCCAAAGTGACAAAA
AATGCAGT<u>TAA</u>AAACCAAACTTTAGTATTATTGGTGCCAACATGTCTATCCTA
ATGAGGACCTTTTCTGCTGTTGGACACTCAGTCAGCTTTTGGAACATGATTAT
ATCAAAATAGTGGCTGTAGATGCTCCAGTGGGACTGAACTGTGATGAGCGGG
TATATTTCGTTGTTTACTGGGTTTTTAATGGAGATGTTAGAGATCAAGGAGCC
TGGGCTGAGGGTGTATAATGGTTGTCAGGTAAAGTTTAAAGAGTGCCAGGGA
GCAGATTTTCTACCTGGAAATATGAAAACTGAACCCATAACTTTGATAAGGT
CTTGAGATGTGTGGACATGTTGGGTTACAGAAGAATAGTTTCTTCCATAACCT
TGACTTGGAAACCCTAGGGCTAAGCATATTGCAAATATGCTTATTTGTCTCCT
AAATATGGGAGATTATTTAGGCCTGTTAGCAAGGAAAGAATGGGAGTTCAGG
AGCCTATCTTGTCAAATAGGGAGATCAGGATCCAGCGAGATCCTGGTGAGCT
ACATAACACAGTCCATTTGGTGAACCCTATTACAGTTTGGTCCAACTGTACTT
CTGGTGAAGGAAACTAATAATGTAAGAAAATGGAAAGAGAGGCCCAGCTTC
TCTTTCAGATATCTTAATTTGTGATACTGGCTTCTTCTCTGAACTCTTCCTTCT
GCCTCTCTTTAAATAAAGAACACTGAATCTCAAATGGTAGGAGACTTATTAG

FIGURE 14 (continued)

CCCAGTCACTAAGCTTGCTCTGTCAGCCTGTATCTTAAGACCTCAAAGATCCA
GTGCCCTGTGTCTTTCCTCCCTTGTAATTTTGAAAAGGTCTTAGACTTGTAGG
GTGAATTTTACCCATGTGTAATGAGGACTTTTCTCATAATCTCCTTTTTTGTAC
TGTCTCCCATCTCTGTTCACCCTTTCCTGTAGCCCCTAGGTGGAAAAAAAAAA
AAAAAAAAA

FIGURE 15

MSEDEEKVKLRRLEPAIQKFIKIVIPTDLERLRKHQINIEKYQRCRIWDKLHEEHIN
AGRTVQQLRSNIREMEKLCLKVRKDDVGLLKRMIDPVKEEASVATAEFLQLHLE
SVEELKKQFNDEETLLQPSLTRSMTVGGAFHTAEAETDPQSVTQIYALPEIPRDQ
NAAESWETLEADLIELSQLVTDFSLLVNSQQEKIDSIEDHVNTAAVNVEVGTKNL
GKAAKYKLAALPVAGALIGGAVGGPIGLLAGFKVAGIAAALGGGVLGFTGGKLI
QRKKQKMMEKLASSCPDLPSQSDKKCS

FIGURE 16

ATATGCCCTGCGTGCAAGCCCAGTATAGCCCTTCGCCTCCAGGTTCCAGTTAT
GCAGCGCAGACCTACGGCTCAGCGGAATACACCACCGAGATCATGAACCCCG
ACTACACCAAGCTGACCATGGACCTCGGCAGCACCGAGATCACGGCCACGGC
CACCACGTCCCTGCCCAGCTTCAGTACCTTCATGGAGGGCTACTCGAGCAACT
ACGAACTCAAGCCCTCCTGCCTGTACCAAATGCCGCCATCGGGGCCGCGGCC
CTTGATCAAGATGGAGGAGGGCCGCGCGCACGGCTACCACCATCACCACCAT
CACCACCACCACCACCACCATCACCAGCAGCAGCAGCAGCAGCCATCCATTC
CGCCCCCCTCCGGCCCGGAGGACGAGGTGCTGCCCAGCACCTCCATGTACTT
CAAGCAGTCCCCGCCGTCCACCCCGACCACGCCGGGCTTCCCCCCGCAGGCG
GGGGCGCTGTGGGACGACGCGCTGCCCTCCGCGCAGGGCTGCCTCGCGCCCG
GCCCGCTGCTCGACCCGCCGATGAAGGCGGTGCCCACGGTGGCCGGCGCGCG
CTTCCCGCTCTTCCACTTCAAGACCTCGCCGCCGCACCCGCCTGCGCCCAGCC
CGGCCGGCGGCCACCACCTGGCCTACGACCCGACGGCCGCCGCCGCGCTCAG
CCTGCCGCTTGGAGCCGCCGCCGCCGCGGGCAGCCAGGCCGCCGCGCTCGAG
GGCCACTCGTACGGGCTGCCGCTGCCCAAGAGGGCGGCCGCGCTGGCCTTCT
CGCCGCTCGGCCTCACCGCCTCCCCACCGCGTCCAGCCTGCTGGCCGAGAG
CCCCAGCCTGCCGTCGCCGCCCAACAGGAGTTTGTCGTCGGGCGAGGGAACG
TGCGCCGTGTGCGGGGACAACGCCGCCTGCCAGCACTACGGCGTGCGAACCT
GCGAGGGCTGCAAGGGCTTTTTCAAGAGAACGGTGCAGAAAAATGCAAAAT
ATGTTTGCCTGGCAAATAAAAACTGCCCTGTAGACAAGAGACGTCGAAACCG
ATGTCAGTACTGTCGATTTCAGAAGTGTCTCAGTGTCGGAATGGTTAAAGAA
GTTGTCCGTACAGATAGTCTGAAAGGGAGGAGAGGTCGGCTGCCTTCCAAAC
CAAAGAGCCCGTTACAGCAGGAACCTTCTCAGCCCTCTCCACCGTCTCCTCCG
ATCTGCATGATGAATGCCCTTGTCCGAGCTTTAACAGACTCAACGCCCAGAG
ATCTCGATTATTCCAGATACTGCCCCACTGACCAGGCCGCTGCCGGCACAGA
TGCTGAGCATGTGCAACAGTTCTACAACCTTCTGACAGCCTCCATTGATGTAT
CCAGAAGCTGGGCAGAAAAGATTCCCGGATTTACTGATCTCCCCAAAGAAGA
TCAGACATTACTTATAGAATCAGCCTTTTTGGAGCTGTTTGTTCTCAGACTTTC
CATCAGGTCGAACACTGCTGAAGATAAGTTTGTGTTCTGCAATGGACTTGTCC
TGCATCGACTTCAGTGCCTTCGTGGATTTGGGGAGTGGCTCGACTCCATTAAA
GACTTTTCCTTAAGTTTGCAGAGCCTGAACCTGGATATCCAAGCCTTAGCATG
CCTGTCAGCACTGAGCATGATCACAGAACGACATGGGTTAAAAGAACCAAAG
AGAGTGGAGGAGCTATGCAACAAGATCACAAGCAGCTTAAAAGACCACCAG
AGCAAGGGGCAGGCTTTGGAGCCCACGGAGCCCAAGGTCCTGCGCGCCCTGG
TAGAACTGCGGAAGATATGCACCCTGGGCCTCCAGCGCATCTTCTACCTGAA
GCTGGAAGACTTGGTGTCTCCACCTTCCATCATCGACAAGCTCTTCCTGGACA
CCCTGCCTTTCTGAGCAGGAGCAGCCTCATCTGCTAGCACCTGCTTGCTAAGC
AGCAGAGGGATGGGTCTGGACACCTACCATTTTCTGTCCTTCCTTAAGAGAA

FIGURE 16 (continued)

```
AAAGCAGCTCCTGTAGAAAAGAAAGACTTTTTTTTTTTTCTGGCACTTTTCCT
TACAAGCTAAAGCCAGAAAACTTGCAGAGTATTGTGTTGGGGTTGTGTTTTAT
ATTTAGGCTTTGGGGTTGGGGTGGGAGGTGGGTATAGTTCATGAGGGTTTTCT
AAGAAATTGCTAACAGAGCACTTTTGGACGATGCTATCCCAGCAGGAAAAAA
AAAAAAAAA
```

FIGURE 17

MPCVQAQYSPSPPGSSYAAQTYGSAEYTTEIMNPDYTKLTMDLGSTEITATATTS
LPSFSTFMEGYSSNYELKPSCLYQMPPSGPRPLIKMEEGRAHGYHHHHHHHHH
HHHQQQQQQPSIPPPSGPEDEVLPSTSMYFKQSPPSTPTTPGFPPQAGALWDDALP
SAQGCLAPGPLLDPPMKAVPTVAGARFPLFHFKTSPPHPPAPSPAGGHHLAYDPT
AAAALSLPLGAAAAAGSQAAALEGHSYGLPLPKRAAALAFSPLGLTASPTASSLL
AESPSLPSPPNRSLSSGEGTCAVCGDNAACQHYGVRTCEGCKGFFKRTVQKNAK
YVCLANKNCPVDKRRRNRCQYCRFQKCLSVGMVKEVVRTDSLKGRRGRLPSKP
KSPLQQEPSQPSPPSPPICMMNALVRALTDSTPRDLDYSRYCPTDQAAAGTDAEH
VQQFYNLLTASIDVSRSWAEKIPGFTDLPKEDQTLLIESAFLELFVLRLSIRSNTAE
DKFVFCNGLVLHRLQCLRGFGEWLDSIKDFSLSLQSLNLDIQALACLSALSMITE
RHGLKEPKRVEELCNKITSSLKDHQSKGQALEPTEPKVLRALVELRKICTLGLQRI
FYLKLEDLVSPPSIIDKLFLDTLPF

FIGURE 18

GGCCTCGAGCGCCCCGGCGGGAGGTTTTTCTATATGAGTGGAGAAGACAGCT
GTTACCAGGGAGGTCATACAACATTTTTTAGG<u>ATG</u>TCTGAAGATGAAGAAA
AAGTGAAATTACGCCGTCTTGAACCAGCTATCCAGAAATTCATTAAGATAGT
AATCCCAACAAACCTGGAAAGGTTAAGAAAGCACCAGATAAATATTGAGAA
GTATCAAAGGTGCAGAATCTGGGACAAGTTGCATGAAGAGCATATCAATGCA
GGACGTACAGTTCAGCAACTCCGATCCAATATCCGAGAAATTGAGAAACTTT
GTTTGAAAGTCCGAAAGGATGACCTAGTACTTCTGAAGAGAATGATAGATCC
TGTTAAAGAAGAAGCATCAGCAGCAACAGCAGAATTTCTCCAACTCCATTTG
GAATCTGTAGAAGAACTTAAGAAGCAATTTAATGATGAAGAAACTTTGCTAC
AGCCTCCTTTGACCAGATCCATGACTGTTGGTGGAGCATTTCATACTACTGAA
GCTGAAGCTAGTTCTCAGAGTTTGACTCAGATATATGCCTTACCTGAAATTCC
TCAAGATCAAAATGCTGCAGAATCGCGGGAAACCTTAGAAGCGGACTTAATT
GAACTTAGCCAACTGGTCACTGACTTCTCTCTCCTAGTGAACTCTCAGCAGGA
GAAGATTGACAGCATTGCAGACCATGTCAACAGTGCTGCTGTGAATGTTGAA
GAGGGAACCAAAAACTTAGGGAAGGCTGCAAAATACAAGCTGGCAGCTCTG
CCTGTGGCAGGTGCACTCATCGGGGGAATGGTAGGGGGTCCTATTGGCCTCC
TTGCATGCTTCAAAGTGGCAGGAATTGCAGCTGCACTTGGTGGTGGGGTGTT
GGGCTTCACAGGTGGAAAATTGATACAAAGAAAGAAACAGAAAATGATGGA
GAAGCTCACTTCCAGCTGTCCAGATCTTCCCAGCCAAACTGACAAGAAATGC
AGTT<u>AAA</u>AACCAAATTTCAGTATTATTGGTGCCAACATGTCTATCCTGAGGAC
CTTTGCTGCTGTTGGACACTCCGTCACCTTTTGGAACACAAGTATATCAAGAT
AGTGGCTACTGATGTTCAAGTGGGATTGAAGTGTGATAAATGGATATATTTTG
TTGTTTGCTGGGGTGTTCATGGAGATGTTAAGAGATTGAGGCCCTGGGCTGA
GGGTATATAATGTATGTCAGGTAAAGTTTGAAGACTGCCAAGGAGCAGATTT
TCTCCCTGGAAATGTGAAAACTGAACCTATAACTCTGATAAGGACTTGAGAT
GTGTAGAAACGTTGGGTTATGGAAGACTAGTTTCTTCCATAACCCTGAATTGG
AGACCTTAATGCTAAGTGTAGATTATTGAGGTTTGTTAGTGAGGAAAAGAAT
AAGAGTTCAGAAGCCTTTGTTATCAGATAGCGAAATCAGGGCCTAGTGAGGA
GCACAGGTCGACTACATAATGGAGTCCATTGGCGAACCCTATTGCAATTTGG
TCCAACTATATCTTCTGGTGAAGGAAATTAATGATGTAAGAAAATGCAAGAG
GCTCAACTTCTCTTCCAAAAATCTTCTGGCTTCTGAACTCTTCCTCTGCCTCTC
TTTAAATAAATAACACAGAATTTCAAGTGGTAGGAGACTTATTAAGCCAGTC
ACCAAGCTTGGTCTGTCAGCCTGTCTTCTAACACCTCAAAGATCTTGTGCCCT
GTGCTGTCCCTCCCTTGTAATTATGAAAGTTCTTTGGTTTCTGGGGTGAACT
CTACCCATGTATAATGAGGAATTCTCTCATAACCTTTTTGTCTTGTCTGTCAT
CTCTGTTCATCCCCTCCTATAACCTCTAGGTAAAAGAAAAGAAAAAAAGAA
ATTTCGAGATATTTTCAACATTGTTAGAGTTTGGGCTAAAATGAGCAAGGAG
AAAAAAACCACCAAGAACATTTCCTGGGGCATGTTCCAGTTTTGAGGGGTGA
TATATCTGCCAGATAGGGGGTATCTGACCCAGTCTTCTTTTCAGCTGGTCTCT
GGGGGGAGCTGAGAACTCGCTTGCTACCTCACATCCTTTTCCCCAGACTTTTT
ATCTCCTATGCATCCCTTTGCTTTCTATAGCTGGTGTTTCTTCCCCAAAATGGC
GTTCCCATGCTTACCTTTCTCACATTCTAGACAATGATGGACAAAGACGCATG

FIGURE 18 (continued)

CAAGACTCAGACCCGGGGAATGGTGTGGTGCTAATCTCAACACCTGACATTC
ACAGCAAGCATGGCCCAGCCCAACCGCATGTCTATCTCAAACCGCAGAAAGG
CTTTAATACTGGAAAAAAAGAATTCAAGACTACAGGCAGCTCCCCTCTGTAC
CCCAACTCATTTAAAATAGGAGGAATCACTTTTTGCCTTACTTAACGCTTTTT
CTGAGCACAGGGATGGGCACCTGCACCCCAGAAGGTGTGAGCTGTCTCTCTG
CCAGGAGCTAAGGTTCATTAGGGGATTGGATGGTTTATCACTTCTTTCTTTCT
GAGTTTACTTTTAGTAACTTTTATTGATGGCTACCTTTCATGTCCCTGTCTAAA
GAGACTTTCTCTTTCATACGTCTTAAATCTCATCAATGAAATCCAGTGAAACA
GCACCATTTCTTAGTATCATTAAATAACTAGAAAGTATCAAAAAAAAAAAAA
AAAAA

FIGURE 19

TCATACTATACCATTAAAAGCAGTACTTGTTATATGTAAATTCTATCTAAATA
AAGTTGAATTAAAAATGGGAATGTGTTCCTACAGCAAGTAATGAGTTCGTGT
CACTGGAGGTATCTGAGCAGAGGTTCAGTAACCACTTGTCAGGAATGTTACA
GTAGGGCTTCGCACATCAGAGAGGAGATTGACCTGATGACCTCAACATTCCT
TCTACCCAGAGATTCCATGAGTCACAGTTGCTGTTGTGCCAGCACAGGTGTTG
CCATTTTATGTAGAATGCTTTATTAATATATTTGATCTGAAACATTTTAAACTG
TCATGATTTTAAAATGTATTAAGATACACAGGTGTAAAGCACAGAACAGTGA
TTTCATTCACTGTTCCCTACTGCATATTACAAATGGAAAGATCTCATAATAGA
TCAAACCGTATTGTAGTCTTGTTCCTGAAACATAACAATTTGTATTTATTGGA
CCAAGGGCATTTTACTCCTAAGGTAAATGTGCCTGATTTAAACTGAATCCTCA
AAGAAGGTAAGTTAGGGAGGTATTTTGGGGTTTGATTTTGTTGGGTTTTTTTT
TTCCATCAAACCCAACATGACATGTAAATGCTTATTTGGATTTTTTTTTCTGG
AAAGTAGATTCATTTGGAGAATAATATGTTTGTATGTTTGAGTGAATTTTAGC
GTGAGATGCTTTTTGCTGTAAAGTTGCCACCCTTTTATTACCTAATAATTAAG
ACCCCCCCCTTTTTTTTATGAAAGTTAATTTGTCCTTTCGACATGGCTTATCAG
ATGCTATTAATGAACCACTATTAAGATGGCAAGGCTGCAGTACCCAGGGCCC
TGATTACAGGAATTAAAATAGTGTGTGTTGGCTCCCTGCTGCTCCCCAGCAGG
ACCGCTCACTCATAATTCCTTTGCATCTAGTCTCAGCAGGAGAAGATTGACAG
CATTGCAGACCATGTCAACAGTGCTGCTGTGAATGTTGAAGAGGGAACCAAA
AACTTAGGGAAGGCTGCAAAATACAAG<u>CT</u>GGCAGCTCTGCCTGTGGCAGGTG
CACTCATCGGGGGAATGGTAGGGGGTCCTATTGGCCTCCTTGCAGGCTTCAA
AGTGGCAGGAATTGCAGCTGCACTTGGTGGTGGGGTGTTGGGCTTCACAGGT
GGAAAATTGATACAAAGAAAGAAACAGAAAATGATGGAGAAGCTCACTTCC
AGCTGTCCAGATCTTCCCAGCCAAACTGACAAGAAATGCAGT<u>TAAAAACCAA</u>
ATTTCAGTATTATTGGTGCCAACATGTCTATCCTGAGGACCTTTGCTGCTGTT
GGACACTCCGTCACCTTTTGGAACACAAGTATATCAAGATAGTGGCTACTGA
TGTTCAAGTGGGATTGAAGTGTGATAAATGGATATATTTTGTTGTTTGCTGGG
GTGTTCATGGAGATGTTAAGAGATTGAGGCCCTGGGCTGAGGGTATATAATG
TATGTCAGGTAAAGTTTGAAGACTGCCAAGGAGCAGATTTTCTCCCTGGAAA
TGTGAAAACTGAACCTATAACTCTGATAAGGACTTGAGATGTGTAGAAACGT
TGGGTTATGGAAGACTAGTTTCTTCCATAACCCTGAATTGGAGACCTTAATGC
TAAGTGTAGATTATTGAGGTTTGTTAGTGAGGAAAAGAATAAGAGTTCAGAA
GCCTTTGTTATCAGATAGCGAAATCAGGGCCTAGTGAGGAGCACAGGTCGAC
TACATAATGGAGTCCATTGGCGAACCCTATTGCAATTTGGTCCAACTATATCT
TCTGGTGAAGGAAATTAATGATGTAAGAAAATGCAAGAGGCTCAACTTCTCT
TCCAAAAATCTTCTGGCTTCTGAACTCTTCCTCTGCCTCTCTTTAAATAAATAA
CACAGAATTTCAAGTGGTAGGAGACTTATTAAGCCAGTCACCAAGCTTGGTC
TGTCAGCCTGTCTTCTAACACCTCAAAGATCTTGTGCCCTGTGCTGTCCCTCC
CTTGTAATTATGAAAGTTCTTGGTTTCTGGGGTGAACTCTACCCATGTATA
ATGAGGAATTCTCTCATAACCTTTTTGTCTTGTCTGTCATCTCTGTTCATCCC
CTCCTATAACCTCTAGGTAAAAGAAAAGAAAAAAGAAATTTCGAGATATT

FIGURE 19 (continued)

TTCAACATTGTTAGAGTTTGGGCTAAAATGAGCAAGGAGAAAAAAACCACCA
AGAACATTTCCTGGGGCATGTTCCAGTTTTGAGGGGTGATATATCTGCCAGAT
AGGGGGTATCTGACCCAGTCTTCTTTTCAGCTGGTCTCTGGGGGGAGCTGAGA
ACTCGCTTGCTACCTCACATCCTTTTCCCCAGACTTTTTATCTCCTATGCATCC
CTTTGCTTTCTATAGCTGGTGTTTCTTCCCCAAAATGGCGTTCCCATGCTTACC
TTTCTCACATTCTAGACAATGATGGACAAAGACGCATGCAAGACTCAGACCC
GGGGAATGGTGTGGTGCTAATCTCAACACCTGACATTCACAGCAAGCATGGC
CCAGCCCAACCGCATGTCTATCTCAAACCGCAGAAAGGCTTTAATACTGGAA
AAAAAGAATTCAAGACTACAGGCAGCTCCCCTCTGTACCCCAACTCATTTAA
AATAGGAGGAATCACTTTTTGCCTTACTTAACGCTTTTTTCTGAGCACAGGGA
TGGGCACCTGCACCCCAGAAGGTGTGAGCTGTCTCTCTGCCAGGAGCTAAGG
TTCATTAGGGGATTGGATGGTTTATCACTTCTTTCTTTCTGAGTTTACTTTTAG
TAACTTTTATTGATGGCTACCTTTCATGTCCCTGTCTAAAGAGACTTTCTCTTT
CATACGTCTTAAATCTCATCAATGAAATCCAGTGAAACAGCACCATTTCTTAG
TATCATTAAATAACTAGAAAGTATCAAAAAAAAAAAAAAAAAA

FIGURE 20

MSEDEEKVKLRRLEPAIQKFIKIVIPTNLERLRKHQINIEKYQRCRIWDKLHEEHIN
AGRTVQQLRSNIREIEKLCLKVRKDDLVLLKRMIDPVKEEASAATAEFLQLHLES
VEELKKQFNDEETLLQPPLTRSMTVGGAFHTTEAEASSQSLTQIYALPEIPQDQNA
AESRETLEADLIELSQLVTDFSLLVNSQQEKIDSIADHVNSAAVNVEEGTKNLGK
AAKYKLAALPVAGALIGGMVGGPIGLLACFKVAGIAAALGGGVLGFTGGKLIQR
KKQKMMEKLTSSCPDLPSQTDKKCS

FIGURE 21

ATAAATGACGTGCCGAGAGAGCGAGCGAACGCGCAGCCGGGAGAGCGGAGT
CTCCTGCCTCCCGCCCCCACCCCTCCAGCTCCTGCTCCTCCTCCGCTCCCCAT
ACACAGACGCGCTCACACCCGCTCCCTCACTCGCACACACAGACACAAGCGC
GCACACAGGCTCCGCACACACTTCGCTCTCCCGCGCGCTCACACCCCTCTT
GCCCTGAGCCCTTGCCGGTGCAGCGCGGCGCCGCAGCTGGACGCCCTCCCG
GGCTCACTTTGCAACGCTGACGGTGCCGGCAGTGGCCGTGGAGGTGGGAACA
GCGGCGGCATCCTCCCCCCTGGTCACAGCCCAAGCCAGGACGCCCGCGGAAC
CTCTCGGCTGTGCTCTCCCATGAGTCGGGATCGCAGCATCCCCCACCAGCCGC
TCACCGCCTCCGGGAGCCGCTGGGCTTGTACACCGCAGCCCTTCCGGGACAG
CAGCTGTGACTCCCCCCCAGTGCAGATTTCGGGACAGCTCTCTAGAAACTCG
CTCTAAAGACGGAACCGCCACAGCACTCAAAGCCCACTGCGGAAGAGGGCA
GCCCGGCAAGCCCGGGCCCTGAGCCTGGACCCTTAGCGGTGCCGGGCAGCAC
TGCCGGCGCTTCGCCTCGCCGGACGTCCGCTCCTCCTACACTCTCAGCCTCCG
CTGGAGAGACCCCCAGCCCCACCATTCAGCGCGCAAGATAGTGTGTATATAT
ATATATATGGGTGGGTGTTTTGTTGCAGCTGCTGATCTTTTTCTTTGCAGATGG
TACAAACTCTCCCGAGTCAATTTCCTGGGCCTATGTCCCCACCTAGCTGACTG
AAGTTATCAACAGGGGTCCAGTTTGTGCAGGCTGCTAGCCCTATTGGAAGAG
TGGGGATGAGGTGGGAGAAAGCAACCACAACGTGTGTGGGCAACCTCAATT
GGCACTCATAAAATGTTAGAATGTCAACTCTCTCCCTTGGCCACTAAATCTCT
CACAGGGTAGTTTTTCTTGCCTAACTCAGGTTTACAAATCAATGTGTATGCCT
TGGGGGACCAATGGCCTCTTTCCTCCCAAATAAACCACTGGCTTTCTCTTTGT
CCCCCTAGGTTATAGCTGAGGAGCCCACTCCAATTAGTTTATAGGATTCAAAG
CCTCTTTTTAAAAACATCTCTGAGCTTATGAGGAAAGACTTCAAGTTTCCCAA
ATCTAGTGGAGGACAGGGCAAGGGAGGAAAGATAGGTACAGGAGTCCACAG
GAGGCCAGGTTTTGGCACCCCTTTGTCAGGAATTCAGCTTCCTTACTAGGGAT
GAAGAAAATAAGTGTGGGCTTTGTGTCTATGCTACCAGAAGGAGGAGAGG
ATGACACTTCCTCTCTGTTTCCCAGATTAGAGAACAGTGAACCCAATGCTGCC
TGTTGGCTAGAAAACAAGTGTTAACTTGCTTCTGAGAGACCCTTTTCTCTGTC
CCTGCAGAT<u>ATG</u>CCCTGCGTCCAAGCCCAATATAGCCCTTCCCCTCCAGGTTC
CAGTTATGCGGCGCAGACATACAGCTCGGAATACACCACGGAGATCATGAAC
CCCGACTACACCAAGCTGACCATGGACCTTGGCAGCACTGAGATCACGGCTA
CAGCCACCACGTCCCTGCCCAGCATCAGTACCTTCGTGGAGGGCTACTCGAG
CAACTACGAACTCAAGCCTTCCTGCGTGTACCAAATGCAGCGGCCCTTGATC
AAAGTGGAGGAGGGGCGGGCGCCCAGCTACCATCACCATCACCACCACCAC
CACCACCACCACCACCATCACCAGCAGCAGCATCAGCAGCCATCCATTCCTC
CAGCCTCCAGCCCGGAGGACGAGGTGCTGCCCAGCACCTCCATGTACTTCAA
GCAGTCCCCACCGTCCACCCCCACCACGCCGGCCTTCCCCCCGCAGGCGGGG
GCGTTATGGGACGAGGCACTGCCCTCGGCGCCGGCTGCATCGCACCCGGCC
CGCTGCTGGACCCGCCGATGAAGGCGGTCCCCACGGTGGCCGGCGCGCGCTT
CCCGCTCTTCCACTTCAAGCCCTCGCCGCCGCATCCCCCGCGCCCAGCCCGG
CCGGCGGCCACCACCTCGGCTACGACCCGACGGCCGCTGCCGCGCTCAGCCT
GCCGCTGGGAGCCGCAGCCGCCGCGGGCAGCCAGGCCGCCGCGCTTGAGAG

FIGURE 21 (continued)

CCACCCGTACGGGCTGCCGCTGGCCAAGAGGGCGGCCCCGCTGGCCTTCCCG
CCTCTCGGCCTCACGCCCTCCCCTACCGCGTCCAGCCTGCTGGGCGAGAGTCC
CAGCCTGCCGTCGCCGCCCAGCAGGAGCTCGTCGTCTGGCGAGGGCACGTGT
GCCGTGTGCGGGGACAACGCCGCCTGCCAGCACTACGGCGTGCGAACCTGCG
AGGGCTGCAAGGGCTTTTTCAAGAGAACAGTGCAGAAAAATGCAAAATATGT
TTGCCTGGCAAATAAAAACTGCCCAGTAGACAAGAGACGTCGAAACCGATGT
CAGTACTGTCGATTTCAGAAGTGTCTCAGTGTTGGAATGGTAAAAGAAGTTG
TCCGTACAGATAGTCTGAAAGGGAGGAGAGGTCGTCTGCCTTCCAAACCAAA
GAGCCCATTACAACAGGAACCTTCTCAGCCCTCTCCACCTTCTCCTCCAATCT
GCATGATGAATGCCCTTGTCCGAGCTTTAACAGACTCAACACCCAGAGATCTT
GATTATTCCAGATACTGTCCCACTGACCAGGCTGCTGCAGGCACAGATGCTG
AGCATGTGCAACAATTCTACAACCTCCTGACAGCCTCCATTGATGTATCCAGA
AGCTGGGCAGAAAAGATTCCGGGATTTACTGATCTCCCCAAAGAAGATCAGA
CATTACTTATTGAATCAGCCTTTTGGAGCTGTTTGTCCTCAGACTTTCCATCA
GGTCAAACACTGCTGAAGATAAGTTTGTGTTCTGCAATGGACTTGTCCTGCAT
CGACTTCAGTGCCTTCGTGGATTTGGGGAGTGGCTCGACTCTATTAAAGACTT
TTCCTTAAATTTGCAGAGCCTGAACCTTGATATCCAAGCCTTAGCCTGCCTGT
CAGCACTGAGCATGATCACAGAAAGACATGGGTTAAAAGAACCAAAGAGAG
TCGAAGAGCTATGCAACAAGATCACAAGCAGTTTAAAAGACCACCAGAGTA
AGGGACAGGCTCTGGAGCCCACCGAGTCCAAGGTCCTGGGTGCCCTGGTAGA
ACTGAGGAAGATCTGCACCCTGGGCCTCCAGCGCATCTTCTACCTGAAGCTG
GAAGACTTGGTGTCTCCACCTTCCATCATTGACAAGCTCTTCCTGGACACCCT
ACCTTTC<u>TAA</u>TCAGGAGCAGTGGAGCAGTGAGCTGCCTCCTCTCCTAGCACCT
GCTTGCTACGCAGCAAAGGGATAGGTTTGGAAACCTATCATTTCCTGTCCTTC
CTTAAGAGGAAAAGCAGCTCCTGTAGAAAGCAAAGACTTTCTTTTTTTTCTGG
CTCTTTTCCTTACAACCTAAAGCCAGAAAACTTGCAGAGTATTGTGTTGGGGT
TGTGTTTTATATTTAGGCATTGGGGGATGGGGTGGGAGGGGGTTATAGTTCAT
GAGGGTTTTCTAAGAAATTGCTAACAAAGCACTTTGGACAATGCTATCCCA
GCAGGAAAAAAAGGATAATATAACTGTTTTAAAACTCTTTCTGGGGAATCC
AATTATAGTTGCTTTGTATTTAAAAACAAGAACAGCCAAGGGTTGTTCGCCA
GGGTAGGATGTGTCTTAAAGATTGGTCCCTTGAAAATATGCTTCCTGTATCAA
AGGTACGTATGTGGTGCAAACAAGGCAGAAACTTCCTTTTAATTTCCTTCTTC
CTTTATTTTAACAAATGGTGAAAGATGGAGGATTACCTACAAATCAGACATG
GCAAAACAATAATGGCTGTTTGCTTCCATAAACAAGTGCAATTTTTTAAAGTG
CTGTCTTACTAAGTCTTGTTTATTAACTCTCCTTTATTCTATATGGAAATAAAA
AGGAGGCAGTCATGTTAGCAAATGACACGTTAATATCCCTAGCAGAGGCTGT
GTTCACCTTCCCTGTCGATCCCTTCTGAGGTATGGCCCATCCAAGACTTTTAG
GCCATTCTTGATGGAACCAGATCCCTGCCCTGACTGTCCAGCTATCCTGAAAG
TGGATCAGATTATAAACTGGATTACATGTAACTGTTTTGGTTGTGTTCTATCA
ACCCCACCAGAGTTCCCTAAACTTGCTTCAGTTATAGTAACTGACTGGTATAT

FIGURE 21 (continued)

TCATTCAGAAGCGCCATAAGTCAGTTGAGTATTTGATCCCTAGATAAGAACA
TGCAAATCAGCAGGAACTGGTCATACAGGGTAAGCACCAGGGACAATAAGG
ATTTTTATAGATATAATTTAATTTTTGTTATTGGTTAAGGAGACAATTTTGGA
GAGCAAGCAAATCTTTTTAAAAAATAGTATGAATGTGAATACTAGAAAAGAT
TTAAAAAATAGTATGAGTGTGAGTACTAGGAAGGATTAGTGGGCTGCGTTTC
AACATTCCGTGTTCGTACTCCCTTTTGTATGTTTCTACTGTTAATGCCATATTA
CTATGAGATAATTTGTTGCATAGTGTCCTTATTTGTATAAACATTTGTATGCA
CGTTATATTGTAATAGCTTTGCCTGTATTTATTGCAAGACCACCAGCTCCTGG
AAGCTGAGTTACAGAGTAATTAAATGGGGTGTTCACAGTGACTTGGATACAC
CAATTAGAAATTAAATAAGCAAATATATATATATATAAATATAGCAGGTT
ACATATATATATTTATAATGTGTCTTTTTATTAACCATTTGTACAATAAATGTC
ACTTCCCATGCCGTTATTTATGGTTCATTTGCAGTGACTTTTAAGGCAGTACT
GTTAGCACTTTGATATTAAAATTTTGCTTATGTTTTGCTAAATTCGAATAATG
TTTGAAGATTTTTAGGTCTAAAAGTCTTTATATTATATACTCTGTATCAAGTCA
AAATATCTTTGGCCATTTTGCTAAGAAACAAACTTTGAATGTCAAACTGATGT
CACAGTAGTTTTTGTTAGCTTTAAATCATTTTTGCTTTAGTCTTTTTAAAGGAA
AATAACAAAACTATGCTGTTTATATTGTCATTAAATTATACAATCAAACAAAT
GCCAAATGAATTGCCTAATTGCTGCAAAGTATAACCCAGATAGGAAATCATA
TGTTTTTTTCCAAGAGTCATTCTAATATTTGATTATGTTATGTGTGCTTTTATG
AAAGATTGTTATTTTATATATCAAGATGATAGAACCTGGAATGTTAGGATTT
TGAAATGTTAGACTTGGAAGGGGCCTGGTCTGTCAACTAGTCCAACCCCTTA
AAATTCATAGAGGAGCAAACTGGGGCCCATTGAAGGGTGAAGAGTTACTCAA
GGTCAAACAGCTGGTAACAGAATCAAGACTAAGACCTAATTTACCTTTCCAT
ACTCTTTTTTTTTCTCAACTTCATCTATATAAAATCAGGCTTTTAAACATAACC
ACTAATATTTACCTGAAGATAACCATGAGTAAAGTATACTTTTGCATTAATTT
TTTGAGCTTATATGCAAACATAATAAATATTATTAAATATCAGGAAAGCTAA
CATTTCATACAAGATAGCTTCAGACCAAATTCAAATTGAATTTGAATAAATTA
GAAATACTGTGCATACATAACCTTCTTGTGCACCATGAGTATTTGGAAAGTTA
ATCCTTGTTTTTGTCGTGTCTATAAAGGAAGAACAAAACAAAATAAAAACAG
AGCCCTAGAGAAATGCTGTTACTTTTTATTTTTACACCCATCAGATTTAAGGA
AAAGACTTTTTAGCCATTATAATCTAGTGGTTGGAAGGAATGAAGAAGCTTTT
TTAGTAATAGGTCCAGATATGAGTGCTAAAAATAAAGATGATAGCATGTTCT
TCTGTCTTCCATAGTTATTACAACTATGAGAGCCTCCCAAGTCATCTTATCAA
CTCAACTCCCTTTTTTTGTCTTAATGTTGCACATAAGTTTATACAGAGTGGAT
GACCACACTAGCACAGAAGAGAACAACATGTATTAAAGCAGGTGATTCCTCC
CCTTGGCGGGAGAGCTCTCTCAGTGTGAACATGCCTTCTGTGGGCGGAAATC
AGGAAGCCACCAGCTGTTAATGGAGAGTGCCTTGCTTTTATTTCAGACAGCA
GAGTTTTCCAAAGTTTCTCTGCTCCTCAACAGCATTGCTCTTTAGTGTGTGTT
AACCTGTGGTTTGAAAGAAATGCTCTTGTACATTAACAATGTAAATTTAAATG
ATTAAATTACATTTTATCAATGGCA

FIGURE 22

MPCVQAQYSPSPPGSSYAAQTYSSEYTTEIMNPDYTKLTMDLGSTEITATATTSL
PSISTFVEGYSSNYELKPSCVYQMQRPLIKVEEGRAPSYHHHHHHHHHHHHHHQ
QQHQQPSIPPASSPEDEVLPSTSMYFKQSPPSTPTTPAFPPQAGALWDEALPSAPG
CIAPGPLLDPPMKAVPTVAGARFPLFHFKPSPPHPPAPSPAGGHHLGYDPTAAAA
LSLPLGAAAAAGSQAAALESHPYGLPLAKRAAPLAFPPLGLTPSPTASSLLGESPS
LPSPPSRSSSSGEGTCAVCGDNAACQHYGVRTCEGCKGFFKRTVQKNAKYVCLA
NKNCPVDKRRRNRCQYCRFQKCLSVGMVKEVVRTDSLKGRRGRLPSKPKSPLQ
QEPSQPSPPSPPICMMNALVRALTDSTPRDLDYSRYCPTDQAAAGTDAEHVQQF
YNLLTASIDVSRSWAEKIPGFTDLPKEDQTLLIESAFLELFVLRLSIRSNTAEDKFV
FCNGLVLHRLQCLRGFGEWLDSIKDFSLNLQSLNLDIQALACLSALSMITERHGL
KEPKRVEELCNKITSSLKDHQSKGQALEPTESKVLGALVELRKICTLGLQRIFYLK
LEDLVSPPSIIDKLFLDTLPF

FIGURE 23

```
human    MSEDEEKVKLRRLEPAIQKFIKIVIPTNLERLRKHQINIEKYQRCRIWDKLHEEHINAGR
horse    MSEDEEKVKLRRLEPAIQKFIKIVIPTDLERLRKHQINIEKYQRCRIWDKLHEEHINAGR
         *************************:***************************** human    TVQQLRSNIREIEKLCLKVRKDDLVLLKRMIDPVKEEASAATAEFLQLHLESVEELKKQF
horse    TVQQLRSNIREMEKLCLKVRKDDVGLLKRMIDPVKEEASVATAEFLQLHLESVEELKKQF
         *********:*******: **********.****************** human    NDEETLLQPPLTRSMTVGGAFHTTEAEASSQSLTQIYALPEIPQDQNAAESRETLEADLI
horse    NDEETLLQPSLTRSMTVGGAFHTAEAETDPQSVTQIYALPEIPRDQNAAESWETLEADLI
         *******.*********:*:..:*******:*** ****** human    ELSQLVTDFSLLVNSQQEKIDSIADHVNSAAVNVEEGTKNLGKAAKYKLAALPVAGALIG
horse    ELSQLVTDFSLLVNSQQEKIDSIEDHVNTAAVNVEVGTKNLGKAAKYKLAALPVAGALIG
         ********************* :** ********************** human    GMVGGPIGLLACFKVAGIAAALGGGVLGFTGGKLIQRKKQKMMEKLTSSCPDLPSQTDKK
horse    GAVGGPIGLLAGFKVAGIAAALGGGVLGFTGGKLIQRKKQKMMEKLASSCPDLPSQSDKK
         * ******* *****************************:*****:* human    CS
horse    CS
         **
```

FIGURE 24

```
human   MPCVQAQYSPSPPGSSYAAQTY-SSEYTTEIMNPDYTKLTMDLGSTEITATATTSLPSIS
horse   MPCVQAQYSPSPPGSSYAAQTYGSAEYTTEIMNPDYTKLTMDLGSTEITATATTSLPSFS
        ********************* *:************************************:* human   TFVEGYSSNYELKPSCVYQMQR----PLIKVEEGRAPSYHHHHHHHHHHHHHQQQHQQP
horse   TFMEGYSSNYELKPSCLYQMPPSGPRPLIKMEEGRAHGYHHHHHHHHHHHHHQQQQQQ-P
        :*********:*    **:* .*********:*:* * human   SIPPASSPEDEVLPSTSMYFKQSPPSTPTTPAFPPQAGALWDEALPSAPGCIAPGPLLDP
horse   SIPPPSGPEDEVLPSTSMYFKQSPPSTPTTPGFPPQAGALWDDALPSAQGCLAPGPLLDP
        ****.*.**********************.******:* :******** human   PMKAVPTVAGARFPLFHFKPSPPHPPAPSPAGGHHLGYDPTAAAALSLPLGAAAAAGSQA
horse   PMKAVPTVAGARFPLFHFKTSPPHPPAPSPAGGHHLAYDPTAAAALSLPLGAAAAAGSQA
        *****************.************.********************* human   AALESHPYGLPLAKRAAPLAFPPLGLTPSPTASSLLGESPSLPSPPSRSSSSGEGTCAVC
horse   AALEGHSYGLPLPKRAAALAFSPLGLTASPTASSLLAESPSLPSPPNRSLSSGEGTCAVC
        ****.*.***..*.***:****.*****..********* human   GDNAACQHYGVRTCEGCKGFFKRTVQKNAKYVCLANKNCPVDKRRRNRCQYCRFQKCLSV
horse   GDNAACQHYGVRTCEGCKGFFKRTVQKNAKYVCLANKNCPVDKRRRNRCQYCRFQKCLSV
        ************************************************************ human   GMVKEVVRTDSLKGRRGRLPSKPKSPLQQEPSQPSPPSPPICMMNALVRALTDSTPRDLD
horse   GMVKEVVRTDSLKGRRGRLPSKPKSPLQQEPSQPSPPSPPICMMNALVRALTDSTPRDLD
        ************************************************************ human   YSRYCPTDQAAAGTDAEHVQQFYNLLTASIDVSRSWAEKIPGFTDLPKEDQTLLIESAFL
horse   YSRYCPTDQAAAGTDAEHVQQFYNLLTASIDVSRSWAEKIPGFTDLPKEDQTLLIESAFL
        ************************************************************ human   ELFVLRLSIRSNTAEDKFVFCNGLVLHRLQCLRGFGEWLDSIKDFSLNLQSLNLDIQALA
horse   ELFVLRLSIRSNTAEDKFVFCNGLVLHRLQCLRGFGEWLDSIKDFSLSLQSLNLDIQALA
        *********************************************.********** human   CLSALSMITERHGLKEPKRVEELCNKITSSLKDHQSKGQALEPTESKVLGALVELRKICT
horse   CLSALSMITERHGLKEPKRVEELCNKITSSLKDHQSKGQALEPTEPKVLRALVELRKICT
        *******************************************.* ********** human   LGLQRIFYLKLEDLVSPPSIIDKLFLDTLPF
horse   LGLQRIFYLKLEDLVSPPSIIDKLFLDTLPF
        *******************************
```

FIGURE 25

MPCIQAQYGTPAPSPGPRDHLASDPLTPEFIKPTMDLASPEAAPAAPTALPSFSTF
MDGYTGEFDTFLYQLPGTVQPCSSASSSASSTSSSSATSPASASFKFEDFQVYGCY
PGPLSGPVDEALSSSGSDYYGSPCSAPSPSTPSFQPPQLSPWDGSFGHFSPSQTYEG
LRAWTEQLPKASGPPQPPAFFSFSPPTGPSPSLAQSPLKLFPSQATHQLGEGESYS
MPTAFPGLAPTSPHLEGSGILDTPVTSTKARSGAPGGSEGRCAVCGDNASCQHYG
VRTCEGCKGFFKRTVQKNAKYICLANKDCPVDKRRRNRCQFCRFQKCLAVGMV
KEVVRTDSLKGRRGRLPSKPKQPPDASPANLLTSLVRAHLDSGPSTAKLDYSKFQ
ELVLPHFGKEDAGDVQQFYDLLSGSLEVIRKWAEKIPGFAELSPADQDLLLESAF
LELFILRLAYRSKPGEGKLIFCSGLVLHRLQCARGFGDWIDSILAFSRSLHSLLVD
VPAFACLSALVLITDRHGLQEPRRVEELQNRIASCLKEHVAAVAGEPQPASCLSR
LLGKLPELRTLCTQGLQRIFYLKLEDLVPPPPIIDKIFMDTLPF

FIGURE 26

MPCVQAQYGSSPQGASPASQSYSYHSSGEYSSDFLTPEFVKFSMDLTNTEITATTS
LPSFSTFMDNYSTGYDVKPPCLYQMPLSGQQSSIKVEDIQMHNYQQHSHLPPQSE
EMMPHSGSVYYKPSSPPTPTTPGFQVQHSPMWDDPGSLHNFHQNYVATTHMIEQ
RKTPVSRLSLFSFKQSPPGTPVSSCQMRFDGPLHVPMNPEPAGSHHVVDGQTFAV
PNPIRKPASMGFPGLQIGHASQLLDTQVPSPPSRGSPSNEGLCAVCGDNAACQHY
GVRTCEGCKGFFKRTVQKNAKYVCLANKNCPVDKRRRNRCQYCRFQKCLAVG
MVKEVVRTDSLKGRRGRLPSKPKSPQEPSPPSPPVSLISALVRAHVDSNPAMTSL
DYSRFQANPDYQMSGDDTQHIQQFYDLLTGSMEIIRGWAEKIPGFADLPKADQD
LLFESAFLELFVLRLAYRSNPVEGKLIFCNGVVLHRLQCVRGFGEWIDSIVEFSSN
LQNMNIDISAFSCIAALAMVTERHGLKEPKRVEELQNKIVNCLKDHVTFNNGGL
NRPNYLSKLLGKLPELRTLCTQGLQRIFYLKLEDLVPPPAIIDKLFLDTLPF

FIGURE 27

```
NR4A2    MPCVQAQYGSSPQGASPASQSYSYHSSGEYSSDFLTPEFVKFSMDLTNTEITATTS--LP
NR4A3    MPCVQAQYSPSPPGSSYAAQTYS----SEYTTEIMNPDYTKLTMDLGSTEITATATTSLP
NR4A1    MPCIQAQYGTPAPSPGPRDHLAS--------DPLTPEFIKPTMDLASPEAAPAAPTALP
         ***:****.... ..   : *         : :.*:: * :***  .* :.::.  **

NR4A2    SFSTFMDNYS---TGYDVKPPCLYQMP------LSGQQSSIKVEDIQMHNYQQHSHLPPQ
NR4A3    SISTFVEGYS---SNYELKPSCVYQMQRPLIKVEEGRAPSYHHHHHHHHHHHHHQQQHQ
NR4A1    SFSTFMDGYTGEFDTFLYQLPGTVQPCSSASSSASSTSSSSATSPASASFKFEDFQVYGC
         *:***::.*:       : :.  *        ..  .*            .. :

NR4A2    SEEMMPHSG---------SVYYKPSSPPTPTTPGFQVQHSPMWDDPGSLHN--FHQNYVA
NR4A3    QPSIPPASSPEDEVLPSTSMYFKQSPPSTPTTPAFFPPQAGALWDEALPSAPGCIAPGPLL
NR4A1    YPGPLSGPVDEALSSSGSDYYGSPCSAPSPSTPSFQPPQLSPWDGSFGHFSP-SQTYEGL
                  . .       . * .  ....:*:**.*    . **  .

NR4A2    TTHMIEQRKTPVSRLSLFSFKQSPPGTPVSSCQMRFDG--------PLHVPMNPEPAGSH
NR4A3    DPPMKAVPTVAGARFPLFHFKPSPPHPPAPSPAGGHHLGYDPTAAAALSLPLGAAAAAGS
NR4A1    RAWTEQLPKASGPPQPPAFFSFSPPTGPSPSLAQSPLKLFP--------------SQATH
            . ... . *.  *** * .*

NR4A2    HVVDGQTFAVPNPIR---KPAS------MGFPGLQIGHASQLLDTQVPSPPSRGSPSNEG
NR4A3    QAAALESHPYGLPLA---KRAAPLAFPPLGLTPSPTASSLLGESPSLPSPPSRSSSSGEG
NR4A1    QLGEGESYSMPTAFPGLAP-----------TSPHLEGSGILDTPVTSTKARSGAPGGSEG
         :   ::..   .:           .            ... *  .. ..**

NR4A2    LCAVCGDNAACQHYGVRTCEGCKGFFKRTVQKNAKYVCLANKNCPVDKRRRNRCQYCRFQ
NR4A3    TCAVCGDNAACQHYGVRTCEGCKGFFKRTVQKNAKYVCLANKNCPVDKRRRNRCQYCRFQ
NR4A1    RCAVCGDNASCQHYGVRTCEGCKGFFKRTVQKNAKYICLANKDCPVDKRRRNRCQFCRFQ
          ********:**********************:*****:*************:****

NR4A2    KCLAVGMVKEVVRTDSLKGRRGRLPSKPKS-----PQEPSPPSPPVSLISALVRAHVDSN
NR4A3    KCLSVGMVKEVVRTDSLKGRRGRLPSKPKSPLQQEPSQPSPPSPPICMMNALVRALTDS-
NR4A1    KCLAVGMVKEVVRTDSLKGRRGRLPSKPKQ---------PPDASPANLLTSLVRAHLDSG
         ***:*********************** .        .* ..*   ::.:**** **

NR4A2    PAMTSLDYSRFQANPDYQMSGDDTQHIQQFYDLLTGSMEIIRGWAEKIPGFADLPKADQD
NR4A3    -TPRDLDYSRYCP-TDQAAAGTDAEHVQQFYNLLTASIDVSRSWAEKIPGFTDLPKEDQT
NR4A1    PSTAKLDYSKFQELVLPHFGKEDAGDVQQFYDLLSGSLEVIRKWAEKIPGFAELSPADQD
          :  .****::     . *:  .:****:**:.*:::  * ********:*.  **

NR4A2    LLFESAFLELFVLRLAYRSNPVEGKLIFCNGVVLHRLQCVRGFGEWIDSIVEFSSNLQNM
NR4A3    LLIESAFLELFVLRLSIRSNTAEDKFVFCNGLVLHRLQCLRGFGEWLDSIKDFSLNLQSL
NR4A1    LLLESAFLELFILRLAYRSKPGEGKLIFCSGLVLHRLQCARGFGDWIDSILAFSRSLHSL
         **:********:***: **:.  .*.*::**.*:******:****:*:***   ** .*:..

NR4A2    NIDISAFSCIAALAMVTERHGLKEPKRVEELQNKIVNCLKDHVTFNNGGLNRPNYLSKLL
NR4A3    NLDIQALACLSALSMITERHGLKEPKRVEELCNKITSSLKDHQSK---GQALEPTESKVL
NR4A1    LVDVPAFACLSALVLITDRHGLQEPRRVEELQNRIASCLKEHVAAVAGEPQPASCLSRLL
          :*: *::*::** ::*:****:**:***** *:: . **:*            *::*

NR4A2    GKLPELRTLCTQGLQRIFYLKLEDLVPPPAIIDKLFLDTLPF
NR4A3    GALVELRKICTLGLQRIFYLKLEDLVSPPSIIDKLFLDTLPF
NR4A1    GKLPELRTLCTQGLQRIFYLKLEDLVPPPPIIDKIFMDTLPF
         * * ***.:** ***************.**.****:*:*****
```

FIGURE 28

MEHQLLCCEVETIRRAYPDANLLNDRVLRAMLKAEETCAPSVSYFKCVQKEVLP
SMRKIVATWMLEVCEEQKCEEEVFPLAMNYLDRFLSLEPVKKSRLQLLGATCMF
VASKMKETIPLTAEKLCIYTDNSIRPEELLQMELLLVNKLKWNLAAMTPHDFIEH
FLSKMPEAEENKQIIRKHAQTFVALCATDVKFISNPPSMVAAGSVVAAVQGLNL
RSPNNFLSYYRLTRFLSRVIKCDPDCLRACQEQIEALLESSLRQAQQNMDPKAAE
EEEEEEEEVDLACTPTDVRDVDI

FIGURE 29

MELLCHEVDPVRRAVRDRNLLRDDRVLQNLLTIEERYLPQCSYFKCVQKDIQPY
MRRMVATWMLEVCEEQKCEEEVFPLAMNYLDRFLAGVPTPKSHLQLLGAVCM
FLASKLKETSPLTAEKLCIYTDNSIKPQELLEWELVVLGKLKWNLAAVTPHDFIE
HILRKLPQQREKLSLIRKHAQTFIALCATDFKFAMYPPSMIATGSVGAAICGLQQD
EEVSSLTCDALTELLAKITNTDVDCLKACQEQIEAVLLNSLQQYRQDQRDGSKSE
DELDQASTPTDVRDIDL

FIGURE 30

```
cyclinD1    MEHQLLCCEVETIRRAYPDANLLN-DRVLRAMLKAEETCAPSVSYFKCVQKEVLPSMRKI
cyclinD2    --MELLCHEVDPVRRAVRDRNLLRDDRVLQNLLTIEERYLPQCSYFKCVQKDIQPYMRRM
              :*** **:..:***   * ***. ****: :*. **    *. ********:: * **::

cyclinD1    VATWMLEVCEEQKCEEEVFPLAMNYLDRFLSLEPVKKSRLQLLGATCMFVASKMKETIPL
cyclinD2    VATWMLEVCEEQKCEEEVFPLAMNYLDRFLAGVPTPKSHLQLLGAVCMFLASKLKETSPL
            ******************************:   *. :** .*:*:* ** cyclinD1    TAEKLCIYTDNSIRPEELLQMELLLVNKLKWNLAAMTPHDFIEHFLSKMPEAEENKQIIR
cyclinD2    TAEKLCIYTDNSIKPQELLEWELVVLGKLKWNLAAVTPHDFIEHILRKLPQQREKLSLIR
            *************:*:***: **:::.********:********.* *:*: .*: ..:**

cyclinD1    KHAQTFVALCATDVKFISNPPSMVAAGSVVAAVQGLNLRSPNNFLSYYRLTRFLSRVIKC
cyclinD2    KHAQTFIALCATDFKFAMYPPSMIATGSVGAAICGLQQDEEVSSLTCDALTELLAKITNT
            ******:******.**    ****:*:*** **: **:   . . *:   **.:*::: :

cyclinD1    DPDCLRACQEQIEALLESSLRQAQQNMDPKAAEEEEEEEEEVDLACTPTDVRDVDI
cyclinD2    DVDCLKACQEQIEAVLLNSLQQYRQ-----DQRDGSKSEDELDQASTPTDVRDIDL
            * ***:********:* .**:* :*      .: ..:*:*:* *.********:*:
```

FIGURE 31

MPLQGPQRRLLGSLNSTLPATPYLGLTTNQTEPPCLEVSIPDGLFLSLGLVSLVEN
VLVVTAIAKNRNLHSPMYYFICCLAVSDLLVSMSNVLEMAILLLLEAGVLATQA
SVLQQLDNIIDVLICGSMVSSLCFLGSIAVDRYISIFYALRYHSIMMLPRVWRAIV
AIWVVSVLSSTLFIAYYNHTAVLLCLVTFFVAMLVLMAVLYVHMLARACQHAR
GIARLHKRQHPIHQGFGLKGAATLTILLGVFFLCWGPFFLHLSLLILCPQHPTCGC
VFKNFKLFLTLILCSAIVDPLIYAFRSQELRKTLQEVLLCSW

FIGURE 32

TCTGGGCAGGTCCAGAGGAGGCCACACCTGGAGCAGAGGCCCAGCTGGGAG
TGCTGGTTGGCTGAGTACAGGGAGGCTGGGAGTGCAAAGGGGAGATGTCCTG
CTGTGTCTAGGAGTCTGGGGGCCCGGGGAGCCCAGACGGTCGTGGGTGCCAT
TTGCGCCACTTGGCGGCGGCGGCAGGAGGGTGTGTGGGCGCTCTGATGGTGC
CTTCCCGGGCACCCACCCATCATGTGACTGCCCTCAGGAGGAGGGGCTCCAT
GGAAGCCTTTAAAGATGCTGAGAAAGGCTCCATTCTTCCCAGTTTCCCCAACC
CACCCCTGCTCTGGGGAGGCAGGAGGCCTGGCAGGCCAGGAGGCAGCAAGA
GCTAGAGATGTGCGGACCTGAGCAACAGCACCTCCAGGGAGAGGCCGGGAG
GTGGGCTGAGAACCCAATGAGACTCCAGAGCCCAGAGGGTTGGTGCCACAG
AGCTTGGGTCTTGGCTGGGAAGTGACCAGACTCTGGTGGAGAGGCCAGGTTC
TCTGGCTGGGCCACGGTTGGGCCAACATTTTTCCAGCCAGGGAGAGCGTGAG
TGTGAGGGCAGCCCTGCGGGTGGCACCATGAGCTGAGTGGGACGCCTGGAGA
GTGAGGACCCCTTCCTGCTTCCTAGAGGGACT<u>ATG</u>CCTCTGCAGGGGCCCCA
GAGGAGGCTGCTGGGCTCCCTCAACTCCACCCTCCCAGCCACCCCCTACCTCG
GGCTGACCACCAACCAGACGGAGCCCCCGTGCCTGGAAGTGTCCATTCCTGA
TGGGCTCTTCCTCAGCCTGGGGCTGGTGAGCCTAGTGGAAAATGTACTGGTG
GTGACTGCCATCGCCAAGAACCGCAACCTGCACTCACCCATGTACTACTTCAT
CTGCTGCCTGGCCGTGTCCGACCTGCTGGTGAGCATGAGCAACGTGCTGGAG
ATGGCAATCTTGCTGCTGCTGGAGGCCGGAGTCCTGGCCACCCAGGCCTCGG
TGTTGCAGCAGCTGGACAACATCATTGATGTGCTCATCTGCGGCTCCATGGTG
TCCAGCCTCTGCTTCCTGGGCAGCATTGCCGTAGACCGCTACATCTCCATCTT
CTATGCGCTGCGGTACCACAGCATCATGATGCTGCCCCGTGTGTGGCGTGCCA
TCGTGGCCATCTGGGTGGTTAGTGTCCTCTCTAGCACCCTCTTCATCGCTTACT
ACAACCACACGGCTGTCCTGCTCTGTCTCGTCACCTTCTTTGTGGCCATGCTG
GTGCTCATGGCAGTGCTGTACGTGCACATGCTCGCCAGGGCGTGCCAGCACG
CCCGGGGCATCGCCCGGCTCCACAAGAGGCAGCACCCCATCCACCAGGGCTT
TGGCCTCAAGGGTGCCGCCACCCTCACCATCCTGCTGGGCGTTTTCTTCCTCT
GCTGGGGCCCCTTTTTCCTGCACCTCTCACTCCTTATCCTCTGCCCTCAACACC
CCACCTGCGGCTGTGTCTTCAAGAACTTCAAGCTCTTCCTCACCCTCATCCTG
TGCAGCGCCATCGTCGACCCCCTCATCTATGCCTTCCGCAGCCAGGAACTTCG
AAAGACGCTCCAGGAGGTGCTGCTGTGCTCCTGG<u>TGA</u>GGGGAGGGGAGCCTG
CGGGCCAAGGCAGAGGGCTGTGCACAGGGAGGTGGTGACATCAGGGGGCTC
GGTTCCTGTGTGACCGGGGCAGTCACTTGCCAAAGAGGGTGGCCTATA

US 8,278,043 B2

METHODS AND MATERIALS RELATED TO GREY ALLELES

CROSS-REFERENCE TO RELATED APPLICATIONS

This application is a National Stage application under 35 U.S.C. §371 and claims benefit under 35 U.S.C. §119(a) of International Application No. PCT/EP2008/057034, having an International Filing Date of Jun. 5, 2008, which claims the benefit of U.S. Provisional Application Ser. No. 60/942,080, filed Jun. 5, 2007. The disclosure of the prior applications are considered part of (and are incorporated by reference in) the disclosure of this application.

BACKGROUND

1. Technical Field

This document relates to methods and materials involved in detecting genetic mutations involved in loss of hair pigmentation and increased cancer susceptibility (e.g., increase susceptibility to form melanomas). This document also relates to methods and materials involved in treating cancer (e.g., melanoma).

2. Background Information

Grey horses are born colored but gradually loose hair pigmentation and eventually, by the age of 6-8 years, become shining white. The dominant Grey allele, manifested as a splendid white horse, has had a high impact on human culture and has left numerous marks in art and literature (e.g., Pegasus and the Unicorn) from Asia and Europe. It has most certainly been selected by humans due to the prestige of riding a white horse with its mystic charisma. Numerous kings, emperors, and other prominent people have been portrayed on a white horse. The mutation appears to have arisen more than 2,000 years ago since white horses are mentioned in ancient Greek literature as well as in the Bible; the Grey locus is by far the most common cause of white coat color in horses (Sponenberg, "Equine Coat Color Genetics," (Blackwell, Ames, Iowa, 2003)).

Grey causes a gradual loss of hair pigmentation whereas dark skin pigmentation is maintained. Furthermore, Grey horses can exhibit vitiligo and a very high incidence of dermal melanomas. It has been estimated that 70-80% of Grey horses older than 15 years of age possess melanomas (Sutton and Coleman, 1-34, RIRDC, Barton, Australia (1997) and Fleury et al., *Pigment Cell Res.*, 13:47-51 (2000)) and that the Grey mutation reduces longevity (Comfort, *Nature*, 182:1531-1532 (1958)).

The melanomas occur primarily as jet black firm nodules in the dermis of glabrous skin (e.g., under the tail root, in the anal, perianal, and genital regions, perineum, lips, and eyelids; Seltenhammer et al., *Pigment Cell Res.*, 17:674-681 (2004)). Initially, these primary multiple melanomas are benign but some develop metastases in several internal organs.

SUMMARY

This document relates to methods and materials for determining whether or not a horse contains a Grey allele. For example, this document provides diagnostic methods such as nucleic acid-based detection methods and materials such as nucleic acid probes and primer pairs that can be used to determine whether or not a horse contains a duplication in intron 6 of STX17 nucleic acid. The presence of a duplication in intron 6 of STX17 nucleic acid can indicate that the horse contains a Grey allele and can gradually loose hair pigmentation and eventually, by the age of 6-8 years, become shining white. The presence of a duplication in intron 6 of STX17 nucleic acid also can indicate that the horse is susceptible to developing cancer (e.g., melanoma). Identifying horses that are heterozygous or homozygous for a Grey allele can provide horse breeders and horse owners important information about individual horses and their offspring. For example, a newborn horse that is born pigmented can be assessed as described herein to determine whether or not that horse will loose its pigment and become a shining white horse.

This document also relates to methods and materials for treating a mammal having or being likely to develop cancer (e.g., benign, malignant, or metastatic cancer). For example, this document provides methods and materials for treating cancer in a mammal by administering an agent having the ability to reduce expression of an STX17 polypeptide and/or an NR4A polypeptide (e.g., an NR4A3 polypeptide) in the mammal. Having the ability to treat cancer can help clinicians reduce the considerable morbidity and mortality associated with cancer.

The methods and materials provided herein are based, in part, on the discovery that a duplication in intron 6 of STX17 nucleic acid is responsible for the phenotype observed in horses that are homozygous or heterozygous for a Grey allele. The horse STX17 gene is located at chromosome 25 between positions 28,971,292 and 29,022,566 by on the horse genome assembly as presented on the UCSC server at "genome.ucsc.edu" (Build January 2007 (equCab1) assembly), and nucleic acid sequences for an intron 6 of an STX17 nucleic acid from a Grey allele and a non-Grey allele are provided in FIGS. 11 and 12, respectively. The methods and materials provided herein also are based, in part, on the discovery that a duplication in intron 6 of STX17 nucleic acid can be a cis-acting mutation that allows for over-expression of both STX17 nucleic acid and neighboring NR4A3 nucleic acid in melanomas from Grey horses. NR4A3 polypeptides are members of the NR4A orphan nuclear receptor family. Over-expression of an STX17 nucleic acid (e.g., over-expression of an STX17 polypeptide or STX17 RNA sequence) or an NR4A3 nucleic acid (e.g., over-expression of an NR4A3 polypeptide or NR4A3 RNA sequence) can be a cause for the Grey phenotypes. Without being limited to any particular mechanism of action, the Grey allele can cause premature hair graying, due to a hyperproliferation of melanocytes in hair follicles depleting the pool of melanocyte stem cells, and melanomas, due to the proliferation of certain dermal melanocytes present in glabrous skin.

In general, one aspect of this document features a method for identifying a horse having a Grey allele. The method comprises, or consists essentially of, obtaining sequence information from the region of nucleic acid located between single nucleotide polymorphisms NR4A3.2 and INVS.3 (see, e.g., Table 4) to determine whether or not the horse comprises a duplication in intron 6 of STX17 nucleic acid, wherein the presence of the duplication indicates that the horse contains the Grey allele. The horse can be a foal. The horse can comprise black, brown, or chestnut hair. The obtaining sequence information step can comprise sequencing a portion of the intron 6 to determine whether or not the horse comprises the duplication. The obtaining sequence information step can comprise determining whether or not the horse comprises a polymorphism linked to the duplication. The obtaining sequence information step can comprise using a nucleic acid probe capable of detecting a breakpoint of the duplication to determine whether or not the horse comprises the duplication. The nucleic acid probe can comprise the nucleic acid sequence set forth in SEQ ID NO:32. The obtaining sequence information step can comprise using a nucleic acid primer pair capable of amplifying nucleic acid comprising a breakpoint of the duplication to determine whether or not the horse comprises the duplication. The method can comprise determining whether or not the horse is homozygous for the duplication. The method can comprise determining whether or not the horse is heterozygous for the duplication.

In another aspect, this document features a method for genotyping a horse. The method comprises, or consists essentially of, (a) determining whether or not the horse comprises a duplication in intron 6 of STX17 nucleic acid, and (b) classifying the horse as containing a Grey allele if the horse comprises the duplication, and classifying the horse as lacking a Grey allele if the horse does not comprise the duplication. The horse can be a foal. The horse can comprise black, brown, or chestnut hair. The determining step can comprise sequencing a portion of the intron 6. The determining step can comprise determining whether or not the horse comprises a polymorphism linked to the duplication. The determining step can comprise using a nucleic acid probe capable of detecting a breakpoint of the duplication. The nucleic acid probe can comprise the nucleic acid sequence set forth in SEQ ID NO:32. The determining step can comprise using a nucleic acid primer pair capable of amplifying nucleic acid comprising a breakpoint of the duplication. The method can comprise determining whether or not the horse is homozygous for the duplication. The method can comprise classifying the horse as being homozygous for the Grey allele if the horse is homozygous for the duplication. The method can comprise determining whether or not the horse is heterozygous for the duplication. The method can comprise classifying the horse as being heterozygous for the Grey allele if the horse is heterozygous for the duplication.

In another aspect, this document features an isolated nucleic acid molecule comprising, or consisting essentially of, a nucleic acid sequence, wherein the nucleic acid sequence comprises a sequence present in a duplication of intron 6 of STX17 nucleic acid of a Grey allele from a horse, and wherein the nucleic acid molecule is capable of detecting a breakpoint of the duplication. The isolated nucleic acid molecule can comprise a label. The isolated nucleic acid molecule can be between 15 and 100 nucleotides in length.

In another aspect, this document features an isolated nucleic acid primer pair comprising a first primer and a second primer, wherein each of the first and second primers comprises a sequence present in a duplication of intron 6 of STX17 nucleic acid of a Grey allele from a horse, and wherein the primer pair is capable of amplifying nucleic acid containing a breakpoint of the duplication.

In another aspect, this document features a method for treating a mammal having cancer. The method comprises, or consists essentially of, administering, to the mammal, a composition comprising an agent having the ability to reduce an NR4A3 polypeptide activity or an STX17 polypeptide activity in the mammal. The mammal can be a horse or a human. The cancer can be melanoma. The agent can comprise a nucleic acid molecule capable of inducing RNA interference against expression of a NR4A3 polypeptide. The agent can comprise a nucleic acid molecule capable of inducing RNA interference against expression of a STX17 polypeptide. The composition can comprise a nucleic acid molecule capable of inducing RNA interference against expression of a NR4A3 polypeptide and a nucleic acid molecule capable of inducing RNA interference against expression of a STX17 polypeptide. The composition can comprise a nucleic acid molecule having a nucleic acid sequence capable of inducing RNA interference against expression of a NR4A3 polypeptide and a nucleic acid sequence capable of inducing RNA interference against expression of a STX17 polypeptide. The agent can comprise an anti-NR4A3 antibody. The agent can comprise an anti-STX17 antibody. The composition can comprise an anti-NR4A3 antibody and an anti-STX17 antibody. The composition can comprise a cyclin D2 inhibitor. The cyclin D2 inhibitor can be selected from the group consisting of flavopiridols, nucleic acid molecules capable of inducing RNA interference against expression of a cyclin D2 polypeptide, anti-cyclin D2 antibodies, suberoylanilide hydroxamic acid, rapamycin, Rugosin E, and THRX-165724. The composition can comprise a MC1R inhibitor. The MC1R inhibitor can be selected from the group consisting of nucleic acid molecules capable of inducing RNA interference against expression of a MC1R polypeptide, anti-MC1R antibodies, and polypeptide antagonists of MC1R polypeptide activity.

In another aspect, this document features a method for treating a horse suspected to develop a melanoma. The method comprises, or consists essentially of, administering, to the horse, a composition comprising an agent having the ability to reduce an NR4A3 polypeptide activity or an STX17 polypeptide activity in the horse. The horse can comprise a homozygous Grey allele genotype. The horse can comprise a heterozygous Grey allele genotype. The agent can comprise a nucleic acid molecule capable of inducing RNA interference against expression of a NR4A3 polypeptide. The agent can comprise a nucleic acid molecule capable of inducing RNA interference against expression of a STX17 polypeptide. The composition can comprise a nucleic acid molecule capable of inducing RNA interference against expression of a NR4A3 polypeptide and a nucleic acid molecule capable of inducing RNA interference against expression of a STX17 polypeptide. The composition can comprise a nucleic acid molecule having a nucleic acid sequence capable of inducing RNA interference against expression of a NR4A3 polypeptide and a nucleic acid sequence capable of inducing RNA interference against expression of a STX17 polypeptide. The agent can comprise an anti-NR4A3 antibody. The agent can comprise an anti-STX17 antibody. The composition can comprise an anti-NR4A3 antibody and an anti-STX17 antibody. The composition can comprise a cyclin D2 inhibitor. The cyclin D2 inhibitor can be selected from the group consisting of flavopiridols, nucleic acid molecules capable of inducing RNA interference against expression of a cyclin D2 polypeptide, anti-cyclin D2 antibodies, suberoylanilide hydroxamic acid, rapamycin, Rugosin E, and THRX-165724. The composition can comprise a MC1R inhibitor. The MC1R inhibitor can be selected from the group consisting of nucleic acid molecules capable of inducing RNA interference against expression of a MC1R polypeptide, anti-MC1R antibodies, and polypeptide antagonists of MC1R polypeptide activity.

In another aspect, this document features a method for identifying an agent for treating cancer. The method comprises, or consists essentially of, (a) identifying a test agent as having the ability to reduce an NR4A3 polypeptide activity or an STX17 polypeptide activity in a mammal, (b) administering the test agent to a horse comprising a Grey allele and a melanoma, and (c) determining whether or not the melanoma is reduced in the horse, wherein a reduction in the melanoma indicates that the test agent is the agent for treating cancer.

In another aspect, this document features a method for identifying an agent for reducing the probability of developing cancer. The method comprises, or consists essentially of, (a) administering a test agent to a population of horses having a heterozygous or homozygous Grey allele genotype, wherein the population of horses comprises horses without observable melanomas, and (b) determining whether or not the population of horses develops melanomas at a lower degree of incidence than a control population of horses not administered the test agent, wherein a presence of the lower degree of incidence indicates that the test agent is the agent for reducing the probability of developing cancer.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 11 is a sequence listing of a nucleotide sequence for an intron 6 of an STX17 nucleic acid from a Grey allele (SEQ ID NO:1). Polymorphic positions that are different for Grey alleles plus ancestral, non-grey alleles versus non-ancestral, non-Grey alleles are shaded. The first copy of the duplication is singly underlined (SEQ ID NO:2), and the second copy of the duplication is doubly underlined (SEQ ID NO:2). The breakpoint between the two copies is indicated by an arrow.

FIG. 12 is a sequence listing of a nucleotide sequence for an intron 6 of an STX17 nucleic acid from a non-Grey allele (SEQ ID NO:3). Polymorphic positions that are different for Grey alleles plus ancestral non-Grey alleles versus non-ancestral, non-Grey alleles are shaded. The sequence duplicated in the nucleic acid sequence of a Grey allele is underlined (SEQ ID NO:4).

FIG. 13 is a sequence listing of a nucleotide sequence of a cDNA of a horse STX17 nucleic acid (SEQ ID NO:5). The start and stop codons are underlined.

FIG. 14 is a sequence listing of a nucleotide sequence of a cDNA of a horse short STX17 nucleic acid (SEQ ID NO:6). The start and stop codons are underlined.

FIG. 15 is a sequence listing of an amino acid sequence of a horse STX17 polypeptide (SEQ ID NO:7).

FIG. 16 is a sequence listing of a nucleotide sequence of a cDNA of a horse NR4A3 nucleic acid (SEQ ID NO:8). The start and stop codons are underlined.

FIG. 17 is a sequence listing of an amino acid sequence of a horse NR4A3 polypeptide (SEQ ID NO:9).

FIG. 18 is a sequence listing of a nucleotide sequence of a cDNA of a human STX17 nucleic acid (SEQ ID NO:10). The start and stop codons are underlined.

FIG. 19 is a sequence listing of a nucleotide sequence of a cDNA of a human short STX17 nucleic acid (SEQ ID NO:11). The start and stop codons are underlined.

FIG. 20 is a sequence listing of an amino acid sequence of a human STX17 polypeptide (SEQ ID NO:12).

FIG. 21 is a sequence listing of a nucleotide sequence of a cDNA of a human NR4A3 nucleic acid (SEQ ID NO:13). The start and stop codons are underlined.

FIG. 22 is a sequence listing of an amino acid sequence of a human NR4A3 polypeptide (SEQ ID NO:14).

FIG. 23 is a sequence alignment of amino acid sequences of a human STX17 polypeptide (SEQ ID NO:12) and a horse STX17 polypeptide (SEQ ID NO:7). The "*" indicates positions that have a single, fully conserved residue. The ":" indicates that the amino acid difference between the horse and human sequences is a highly conservative difference within one of the following groups of amino acid residues: STA; NEQK; NHQK; NDEQ; QHRK; MILV; MILF; HY; and FYW. The "." indicates that the amino acid difference between the horse and human sequences is a moderately conservative difference within one of the following groups of amino acid residues: CSA; ATV; SAG; STNK; STPA; SGND; SNDEQK; NDEQHK; NEQHRK; FVLIM; and HFY.

FIG. 24 is a sequence alignment of amino acid sequences of a human NR4A3 polypeptide (SEQ ID NO:14) and a horse NR4A3 polypeptide (SEQ ID NO:9). The "*" indicates positions that have a single, fully conserved residue. The ":" indicates that the amino acid difference between the horse and human sequences is a highly conservative difference within one of the following groups of amino acid residues: STA; NEQK; NHQK; NDEQ; QHRK; MILV; MILF; HY; and FYW. The "." indicates that the amino acid difference between the horse and human sequences is a moderately conservative difference within one of the following groups of amino acid residues: CSA; ATV; SAG; STNK; STPA; SGND; SNDEQK; NDEQHK; NEQHRK; FVLIM; and HFY.

FIG. 25 is a sequence listing of an amino acid sequence of a human NR4A1 polypeptide (SEQ ID NO:15).

FIG. 26 is a sequence listing of an amino acid sequence of a human NR4A2 polypeptide (SEQ ID NO:16).

FIG. 27 is a sequence alignment of amino acid sequences of a human NR4A1 polypeptide (SEQ ID NO:15), a human NR4A2 polypeptide (SEQ ID NO:16), and a human NR4A3 polypeptide (SEQ ID NO:14). The "*" indicates positions that have a single, fully conserved residue. The ":" indicates that the amino acid difference is a highly conservative difference within one of the following groups of amino acid residues: STA; NEQK; NHQK; NDEQ; QHRK; MILV; MILF; HY; and FYW. The "." indicates that the amino acid difference is a moderately conservative difference within one of the following groups of amino acid residues: CSA; ATV; SAG; STNK; STPA; SGND; SNDEQK; NDEQHK; NEQHRK; FVLIM; and HFY.

FIG. 28 is a sequence listing of an amino acid sequence of a human cyclin D1 polypeptide (SEQ ID NO:17).

FIG. 29 is a sequence listing of an amino acid sequence of a human cyclin D2 polypeptide (SEQ ID NO:18).

FIG. 30 is a sequence alignment of amino acid sequences of a human cyclin D1 polypeptide (SEQ ID NO:17) and a human cyclin D2 polypeptide (SEQ ID NO:18). The "*" indicates positions that have a single, fully conserved residue. The ":" indicates that the amino acid difference is a highly conservative difference within one of the following groups of amino acid residues: STA; NEQK; NHQK; NDEQ; QHRK; MILV; MILF; HY; and FYW. The "." indicates that the amino acid difference is a moderately conservative difference within one of the following groups of amino acid residues: CSA; ATV; SAG; STNK; STPA; SGND; SNDEQK; NDEQHK; NEQHRK; FVLIM; and HFY.

FIG. 31 is a sequence listing of an amino acid sequence of a horse MC1R polypeptide (SEQ ID NO:19).

FIG. 32 is a sequence listing of a nucleotide sequence of a cDNA of a horse MC1R nucleic acid (SEQ ID NO:20). The start and stop codons are underlined.

DETAILED DESCRIPTION

Figure 1:
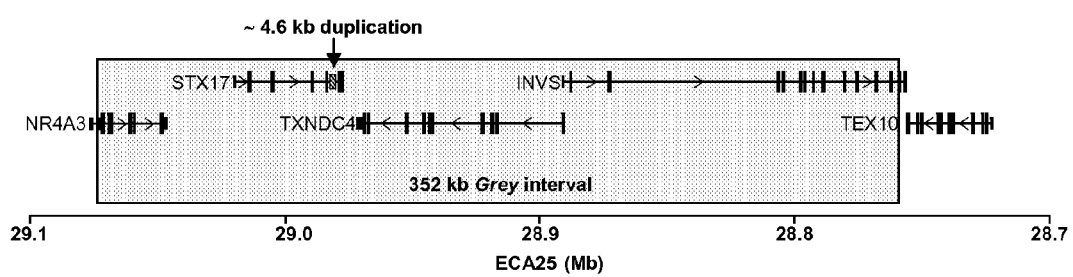
FIG. 1 is a schematic diagram of the gene content of the Grey interval based on the human genome assembly as presented on the UCSC server at "genome.ucsc.edu"; Build March 2006 (hg18) assembly/NCBI Build 36.1; Karolchik et al., *Nucl. Acids Res.*, 31(1):51-54 (2003)). The 472 kb region exhibiting complete association with Grey is indicated by a box, and the location of the 4.6 kb duplication in STX17 intron 6 is marked with an arrow.

This document relates to methods and materials for determining whether or not a horse contains a Grey allele (e.g., contains a heterozygous Grey allele genotype or a homozygous Grey allele genotype). For example, this document provides diagnostic methods and materials such as nucleic acid probes and primer pairs that can be used to determine whether or not a horse contains a duplication in intron 6 of STX17 nucleic acid. The presence of a duplication in intron 6 of STX17 nucleic acid can indicate that the horse contains a Grey allele and can gradually loose hair pigmentation and eventually, by the age of 6-8 years, become shining white.

The methods and materials provided herein can be used to determine whether or not any type of horse contains a Grey allele. For example, the horse can be an American quarter horse, an American standard bred horse, an Arabian horse, an Hanoverian horse, a Morgan horse, a Palomino horse, a Thoroughbred horse, a Miniature horse, a Mustang horse, a Lippizaner horse, a Connemara horse, or an Icelandic horse. In some cases, the horse can be a horse fetus, a newborn horse, a foal, a colt, a filly, a stallion, a mare, or an adult horse. The horse can be any color including, without limitation, white, grey, black, brown, or chestnut. In some cases, a newborn horse that is black, brown, or chestnut can be assessed using the methods and materials provided herein to determine whether or not it has a heterozygous or homozygous Grey allele genotype. In some cases, an adult horse that gradually changed from a dark colored horse (e.g., brown colored horse) to a light colored horse (e.g., a white colored horse) can be assessed using the methods and materials provided herein to confirm the presence of a Grey allele or to distinguish between a heterozygous Grey allele genotype and a homozygous Grey allele genotype.

The term "intron 6 of STX17 nucleic acid" as used herein refers to a non-STX17 polypeptide-encoding nucleic acid sequence located between exons 6 and 7 of STX17 polypeptide-encoding nucleic acid. Examples of horse nucleic acid sequences for an intron 6 of an STX17 nucleic acid from a Grey allele and a non-Grey allele are provided in FIGS. 11 and 12, respectively. The nucleic acid sequence set forth in FIG. 11 contains a 4,577 nucleotide duplication. As described herein, a duplication present in intron 6 of STX17 nucleic acid such as the 4,577 nucleotide duplication set forth in FIG. 11 can be the genetic mutation responsible for the Grey allele in horses and the phenotypic characteristics associated with the Grey allele.

Any appropriate method can be used to detect a duplication in intron 6 of STX17 nucleic acid and the presence of a Grey allele. For example, a duplication can be detected by nucleic acid sequencing, denaturing high performance liquid chromatography (DHPLC; Underhill et al., *Genome Res.*, 7:996-1005 (1997)), allele-specific hybridization (Stoneking et al., *Am. J. Hum. Genet.*, 48:370-382 (1991); and Prince et al., *Genome Res.*, 11(1):152-162 (2001)), allele-specific restriction digests, polymorphism specific polymerase chain reactions, single-stranded conformational polymorphism detection (Schafer et al., *Nat. Biotechnol.*, 15:33-39 (1998)), infrared matrix-assisted laser desorption/ionization mass spectrometry (WO 99/57318), and combinations of such methods.

Genomic DNA can be used to detect a duplication in intron 6 of STX17 nucleic acid. Genomic DNA can be extracted from a biological sample such as peripheral blood samples, hair roots, or tissues (e.g., mucosal scrapings of the lining of the mouth or from renal or hepatic tissue). Any appropriate method can be used to extract genomic DNA from a blood or tissue sample, including, for example, phenol extraction. In some cases, genomic DNA can be extracted with kits such as the QIAamp® Tissue Kit (Qiagen, Chatsworth, Calif.), the Wizard® Genomic DNA purification kit (Promega, Madison, Wis.), the Puregene DNA Isolation System (Gentra Systems, Minneapolis, Minn.), or the A.S.A.P.3 Genomic DNA isolation kit (Boehringer Mannheim, Indianapolis, Ind.).

Amplification methods such as PCR techniques can be used to determine whether or not a horse contains a duplication in intron 6 of STX17 nucleic acid. For example, a primer pair designed to amplify PCR products containing a duplication breakpoint can be used to detect the presence of a duplication in intron 6 of STX17 nucleic acid. Such a primer pair can contain a first primer that anneals upstream of the duplication breakpoint such that extension from that primer proceeds toward the duplication breakpoint and a second primer that anneals downstream of the duplication breakpoint such that extension from that primer also proceeds toward the duplication breakpoint. When a sample contains nucleic acid with the duplication, an appropriately sized PCR product containing the duplication breakpoint can be generated and detected, thereby identifying the sample as containing a duplication in intron 6 of STX17 nucleic acid. When a sample contains nucleic acid lacking the duplication, an appropriately sized PCR product containing the duplication breakpoint will not be generated and detected, thereby the sample can be identified as lacking a duplication in intron 6 of STX17 nucleic acid.

Examples of primer pairs that can be used to detect the presence of a duplication in intron 6 of STX17 nucleic acid can include, without limitation, those set forth in Table 1.

acid probe can contain the 5'-CAA↓AAT-3' duplication breakpoint set forth in FIG. 11 or its complement. Examples of nucleic acid probes that can be used to detect the presence of a duplication in intron 6 of STX17 nucleic acid can include, without limitation, 5'-ACCTGGGAA-CTCATTAGAAATGCAA↓AATCTCAGAATTGGAATT-GAACTTA-3' (SEQ ID NO:27); 5'-GGAACT-CATTAGAAATGCAA↓AATCTCAGAATTGGAATTGA-3' (SEQ ID NO:28); 5'-AACTCATTAGAAAT-GCAA↓AATCTCAGAATTGGAATT-3' (SEQ ID NO:29); 5'-TCATTAGAAATGCAA↓AATCTCAGAATTGGA-3' (SEQ ID NO:30); 5'-CATTAGAAATGCAA↓AATCTCAGAATTGG-3' (SEQ ID NO:31); 5'-AGAAATGCAA↓AATCTCAGAA-3' (SEQ ID NO:32); 5'-AAATGCAA↓AATCTCAG-3' (SEQ ID NO:33); 5'-TGCAA↓AATCT-3' (SEQ ID NO:34); 5'-GAAATGCAA↓AATCTCAG-3' (SEQ ID NO:35), and complements thereof. The nucleic acid sequences set forth in FIGS. 11 and 12 can be used to confirm that a particular nucleic acid probe can distinguish between nucleic acid of a Grey allele and nucleic acid of a non-Grey allele.

An amplification process can be performed before proceeding with a detection method. For example, nucleic acid such as nucleic acid from intron 6 of STX17 nucleic acid can be amplified and then directly sequenced. Dye primer

TABLE 1

Primer pairs

| Primer pair | Sequence | SEQ ID NO: | Tm | Product size (bp) |
|---|---|---|---|---|
| #1 | Forward 5'-TTGTAGTATCAGCACCACCTGGGAACTC-3' | 21 | 68 | 902 |
|    | Reverse 5'-TCATGTGTCTATCCCACTAGGAGGGA-3' | 22 | | |
| #2 | Forward 5'-GTAGGTCTGCACCCAGGAAC-3' | 23 | 60 | 221 |
|    | Reverse 5'-AGAAGTTGGGCAAGAGCAGA-3' | 24 | | |
| #3 | Forward 5'-CACAGTATGGCTGCCAAAGA-3' | 25 | 59 | 391 |
|    | Reverse 5'-CAAAGTGCCAGAGGGAAGTT-3' | 26 | | |

The nucleic acid sequences set forth in FIGS. 11 and 12 can be used to confirm that a particular primer pair can produce amplification product that can be used to distinguish between nucleic acid of a Grey allele and nucleic acid of a non-Grey allele.

Any appropriate method can be used to detect the presence or absence of amplification products. For example, a gel electrophoresis or real-time PCR techniques that include the use of dyes such as Sybergreen can be used.

The term "duplication breakpoint" as used herein refers to a nucleotide junction site of duplicated nucleic acid that is (1) present in the nucleic acid containing the duplication and (2) is not present in nucleic acid lacking the duplication. The duplication breakpoint for the nucleic acid set forth in FIG. 11 is the labeled CAA↓AAT duplication breakpoint. The arrow represents the junction between the two copies of the duplicated nucleic acid.

In some cases, a nucleic acid probe having the ability to hybridize to nucleic acid containing a duplication in intron 6 of STX17 nucleic acid can be used to detect the presence of a duplication in intron 6 of STX17 nucleic acid. For example, a nucleic acid probe having the ability to hybridize to the duplication breakpoint of a Grey allele and not to nucleic acid from a non-Grey allele can be used to detect the presence of a duplication in intron 6 of STX17 nucleic acid. Such a nucleic sequencing can be used to increase the accuracy of detecting heterozygous samples. In some cases, an amplification process can be performed to amplify a duplication breakpoint, if present, and a nucleic acid probe having the ability to hybridize to the duplication breakpoint of a Grey allele and not to nucleic acid from a non-Grey allele can be used to detect the presence or absence of a duplication in intron 6 of STX17 nucleic acid.

In some cases, a polymorphism that co-segregates with a duplication in intron 6 of STX17 nucleic acid can be used as a marker to detect the presence or absence of the duplication in intron 6 of STX17 nucleic acid. Such a polymorphism can be present in the region of nucleic acid located between NR4A3.2 and INVS.3. Any appropriate method can be used to identify nucleic acid containing a polymorphism versus nucleic acid not containing the polymorphism. For example, a polymorphism in the region of nucleic acid located between NR4A3.2 and INVS.3 can be detected by, for example, DHPLC analysis. Genomic DNA can be isolated from a horse and sequences from a region of nucleic acid located between NR4A3.2 and INVS.3 can be amplified (e.g., by PCR) using primer pairs. After amplification, PCR products can be denatured and reannealed, such that an allele containing a polymorphism can reanneal with a wild-type allele to form a heteroduplex (i.e., a double-stranded nucleic acid with a mismatch at one or more positions). The reannealed products then can be subjected to DHPLC, which detects heteroduplexes based on their altered melting temperatures, as compared to homoduplexes that do not contain mismatches. Samples containing heteroduplexes can be sequenced by standard methods to identify mutant nucleotides.

Allele specific hybridization also can be used to detect a polymorphism in the region of nucleic acid located between NR4A3.2 and INVS.3. For example, samples of DNA or RNA from a horse can be amplified using a primer pair, and the resulting amplification products can be immobilized on a substrate (e.g., in discrete regions). Hybridization conditions can be selected such that a nucleic acid probe specifically binds to the sequence of interest, e.g., a region of nucleic acid located between NR4A3.2 and INVS.3 containing a particular polymorphism. Such hybridizations typically are performed under high stringency, as nucleotide polymorphisms can include only a single nucleotide difference versus a wild-type sequence. High stringency conditions can include the use of low ionic strength solutions and high temperatures for washing. For example, nucleic acid molecules can be hybridized at 42° C. in 2×SSC (0.3 M NaCl/0.03 M sodium citrate/0.1% sodium dodecyl sulfate (SDS)) and washed in 0.1×SSC (0.015 M NaCl/0.0015 M sodium citrate) with 0.1% SDS at 65° C. Hybridization conditions can be adjusted to account for unique features of the nucleic acid molecule, including length and sequence composition. Probes can be labeled (e.g., fluorescently) to facilitate detection. In some cases, one of the primers used in the amplification reaction can be biotinylated (e.g., 5' end of reverse primer), and the resulting biotinylated amplification product can be immobilized on an avidin or streptavidin coated substrate.

Allele-specific restriction digests can be performed in the following manner. For polymorphisms that introduce a restriction site into nucleic acid, a restriction digest with the particular restriction enzyme can differentiate alleles.

Other methods also can be used to detect a polymorphism in the region of nucleic acid located between NR4A3.2 and INVS.3. For example, conventional and field-inversion electrophoresis can be used to visualize base pair changes. In some cases, quantitative PCR analysis of the genomic copy number for the 4,577 nucleotide duplication set forth in FIG. 11 can be used to detect the presence or absence of a duplication in intron 6 of STX17 nucleic acid.

In some cases, polypeptide or mRNA levels can be determined to detect the presence or absence of a duplication in intron 6 of STX17 nucleic acid and the presence or absence of a Grey allele. For example, STX17 polypeptide levels, STX17 mRNA levels, NR4A3 polypeptide levels, NR4A3 mRNA levels, or a combination thereof can be used to detect the presence or absence of a duplication in intron 6 of STX17 nucleic acid. In such cases, an elevated level of STX17 or NR4A3 expression in a horse can indicate that that horse contains a duplication in intron 6 of STX17 nucleic acid.

The term "elevated level" as used herein with respect to a level of STX17 or NR4A3 expression is any level of STX17 or NR4A3 expression that is greater than a median level of STX17 or NR4A3 polypeptide or STX17 or NR4A3 RNA expression in a random population of horses (e.g., a random population of 5, 10, 20, 30, 40, 50, 100, or more horses) that lack Grey alleles (e.g., horses homozygous for non-Grey alleles). In some cases, an elevated level of STX17 or NR4A3 expression can be a level of STX17 or NR4A3 expression that is at least one (e.g., at least 1.0, 1.2, 1.4, 1.6, 1.8, 2.0, or 2.2) standard deviation greater than a mean level of STX17 or NR4A3 expression in a random population of horses that do not contain a Grey allele.

It will be appreciated that STX17 or NR4A3 expression levels from comparable samples (e.g., blood samples) are used when determining whether or not a particular STX17 or NR4A3 expression level is an elevated level. For example, an mRNA level of STX17 expression in a skin biopsy from a horse is compared to the median mRNA level of STX17 expression in skin biopsies from a random population of horses that do not contain a Grey allele. STX17 or NR4A3 expression levels can be compared to a median STX17 or NR4A3 expression level measured using the same or a comparable method.

Any appropriate method can be used to assess STX17 or NR4A3 mRNA levels including, without limitation, PCR-based methods (e.g., RT-PCR and quantitative PCR), Northern blotting, and in-situ hybridization techniques. The level of STX17 or NR4A3 mRNA expression in a sample (e.g., blood sample, plasma sample, or tissue biopsy sample such as a skin biopsy) from a horse can be determined by measuring the level of an STX17 or NR4A3 mRNA, or any fragment of an STX17 or NR4A3 mRNA. A horse STX17 mRNA can have an RNA sequence corresponding to the nucleic acid sequence set forth in FIG. 13 or 14. A horse NR4A3 mRNA can have an RNA sequence corresponding to the nucleic acid sequence set forth in FIG. 16.

Any appropriate method can be used to assess STX17 or NR4A3 polypeptide levels including, without limitation, immunological methods, chromatographic methods, and spectroscopic methods. The level of STX17 or NR4A3 polypeptide expression in a sample (e.g., blood sample, plasma sample, or tissue biopsy sample such as a skin biopsy) from a horse can be determined by measuring the level of an STX17 or NR4A3 polypeptide, or any fragment of an STX17 or NR4A3 polypeptide. A horse STX17 polypeptide can have the amino acid sequence set forth in FIG. 15. A horse NR4A3 polypeptide can have the amino acid sequence set forth in FIG. 17.

In some cases, mass spectrometry can be used to determine a level of an STX17 or NR4A3 polypeptide. In some cases, a level of an STX17 or NR4A3 polypeptide can be detected using a method that relies on an anti-STX17 polypeptide antibody or an anti-NR4A3 polypeptide antibody. Such methods include, without limitation, FACS, Western blotting, ELISA, immunohistochemistry, and immunoprecipitation. Antibody based assays (e.g., sandwich enzyme-linked immunosorbent assays) can include using combinations of antibodies that bind to one or more sites of the amino-terminal, central, and carboxy-terminal portions of a STX17 or NR4A3 polypeptide or a fragment thereof. An anti-STX17 polypeptide antibody or an anti-NR4A3 polypeptide antibody can be labeled for detection. For example, an anti-STX17 polypeptide antibody can be labeled with a radioactive molecule, a fluorescent molecule, or a bioluminescent molecule. STX17 or NR4A3 polypeptides can also be detected indirectly using a labeled antibody that binds to an anti-STX17 polypeptide antibody or an anti-NR4A3 polypeptide antibody that binds to a STX17 or NR4A3 polypeptide, respectively.

An antibody can be, without limitation, a polyclonal, monoclonal, human, humanized, chimeric, or single-chain antibody, or an antibody fragment having binding activity, such as a Fab fragment, F(ab') fragment, Fd fragment, fragment produced by a Fab expression library, fragment comprising a VL or VH domain, or epitope binding fragment of any of the above. An antibody can be of any type (e.g., IgG, IgM, IgD, IgA or IgY), class (e.g., IgG1, IgG4, or IgA2), or subclass. In addition, an antibody can be from any animal including birds and mammals. For example, an antibody can be a human, rabbit, sheep, or goat antibody. An antibody can be naturally occurring, recombinant, or synthetic. Antibodies can be generated and purified using any suitable methods known in the art. For example, monoclonal antibodies can be prepared using hybridoma, recombinant, or phage display technology, or a combination of such techniques. In some cases, antibody fragments can be produced synthetically or recombinantly from a gene encoding the partial antibody sequence. An anti-STX17 polypeptide antibody can bind to a STX17 polypeptide at an affinity of at least $10^4$ mol$^{-1}$ (e.g., at least $10^5$, $10^6$, $10^7$, $10^8$, $10^9$, $10^{10}$, $10^{11}$, or $10^{12}$ mol$^{-1}$). An anti-NR4A3 polypeptide antibody can bind to a NR4A3 polypeptide at an affinity of at least $10^4$ mol$^{-1}$ (e.g., at least $10^5$, $10^6$, $10^7$, $10^8$, $10^9$, $10^{10}$, $10^{11}$, or $10^{12}$ mol$^{-1}$).

An anti-STX17 polypeptide antibody or an anti-NR4A3 polypeptide antibody provided herein can be prepared using any appropriate method. For example, any substantially pure STX17 or NR4A3 polypeptide (e.g., horse STX17 or NR4A3 polypeptide), or fragment thereof (e.g., a truncated STX17 or NR4A3 polypeptide), can be used as an immunogen to elicit an immune response in an animal such that specific antibodies are produced. Thus, a horse STX17 or NR4A3 polypeptide or a fragment thereof can be used as an immunizing antigen. In addition, the immunogen used to immunize an animal can be chemically synthesized or derived from translated cDNA. Further, the immunogen can be conjugated to a carrier polypeptide, if desired. Commonly used carriers that are chemically coupled to an immunizing polypeptide include, without limitation, keyhole limpet hemocyanin (KLH), thyroglobulin, bovine serum albumin (BSA), and tetanus toxoid.

The preparation of polyclonal antibodies is well-known to those skilled in the art. See, e.g., Green et al., Production of Polyclonal Antisera, in IMMUNOCHEMICAL PROTOCOLS (Manson, ed.), pages 1-5 (Humana Press 1992) and Coligan et al., Production of Polyclonal Antisera in Rabbits, Rats, Mice and Hamsters, in CURRENT PROTOCOLS IN IMMUNOLOGY, section 2.4.1 (1992). In addition, those of skill in the art will know of various techniques common in the immunology arts for purification and concentration of polyclonal antibodies, as well as monoclonal antibodies (Coligan, et al., Unit 9, CURRENT PROTOCOLS IN IMMUNOLOGY, Wiley Interscience, 1994).

The preparation of monoclonal antibodies also is well-known to those skilled in the art. See, e.g., Kohler & Milstein, *Nature* 256:495 (1975); Coligan et al., sections 2.5.1 2.6.7; and Harlow et al., ANTIBODIES: A LABORATORY MANUAL, page 726 (Cold Spring Harbor Pub. 1988). Briefly, monoclonal antibodies can be obtained by injecting mice with a composition comprising an antigen, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well established techniques. Such isolation techniques include affinity chromatography with Protein A Sepharose, size exclusion chromatography, and ion exchange chromatography. See, e.g., Coligan et al., sections 2.7.1 2.7.12 and sections 2.9.1 2.9.3; Barnes et al., Purification of Immunoglobulin G (IgG), in METHODS IN MOLECULAR BIOLOGY, Vol. 10, pages 79-104 (Humana Press 1992).

Once hybridoma clones that produce antibodies to an antigen of interest (e.g., a horse STX17 or NR4A3 polypeptide) have been selected, further selection can be performed for clones that produce antibodies having a particular specificity. For example, clones can be selected that produce antibodies that bind to a horse STX17 or NR4A3 polypeptide and lack detectable binding to a human STX17 or NR4A3 polypeptide.

The antibodies provided herein can be substantially pure. The term "substantially pure" as used herein with reference to an antibody means the antibody is substantially free of other polypeptides, lipids, carbohydrates, and nucleic acid with which it is naturally associated in nature. Thus, a substantially pure antibody is any antibody that is removed from its natural environment and is at least 60 percent pure. A substantially pure antibody can be at least about 65, 70, 75, 80, 85, 90, 95, or 99 percent pure.

Once a horse is determined to contain a duplication in intron 6 of STX17 nucleic acid, the horse can be classified as having an elevated risk of developing cancer (e.g., melanomas). Horses classified as having an elevated risk of developing cancer can be inspected frequently (e.g., daily, weekly, or monthly) for signs of cancer. For example, a horse determined to contain a duplication in intron 6 of STX17 nucleic acid can be inspected by a veterinarian for signs of melanomas every other month. In some cases, a horse determined to contain a duplication in intron 6 of STX17 nucleic acid can be treated using the methods and materials provided herein to reduce the chance of developing cancer, to reduce the progression of cancer, or to reduce the severity of cancer.

This document also provides isolated nucleic acids having a nucleotide sequence of at least about contiguous 20 nucleotides (e.g., at least about 20, 25, 30, 40, 50, 75, 100, 150, 300, 500, or more nucleotides) from an intron 6 of an STX17 nucleic acid (e.g., an intron 6 of an STX17 nucleic acid having the nucleic acid sequence set forth in FIG. 11). In some cases, an isolated nucleic acid can contain the CAA↓AAT duplication breakpoint for the nucleic acid set forth in FIG. 11. For example, an isolated nucleic acid provided herein can contain the following sequence: 5'-AGAAATGCAA↓AAT-CTCA-GAA-3' (SEQ ID NO:32). Such a nucleic acid can be between 10 and 500 nucleotides in length (e.g., between 15 and 500 nucleotides in length, between 20 and 500 nucleotides in length, between 25 and 500 nucleotides in length, between 50 and 500 nucleotides in length, between 25 and 450 nucleotides in length, between 25 and 400 nucleotides in length, or between 25 and 300 nucleotides in length).

The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

Isolated nucleic acids can be produced by standard techniques, including, without limitation, common molecular cloning and chemical nucleic acid synthesis techniques. For example, polymerase chain reaction techniques can be used to obtain an isolated nucleic acid containing the CAA↓AAT duplication breakpoint for the nucleic acid set forth in FIG. 11.

Isolated nucleic acids provided herein can be used for diagnostic purposes. For example, an isolated nucleic acid comprising a portion of a intron 6 of STX17 nucleic acid (e.g., a PCR amplicon) can be used in DHPLC or allele specific hybridization analyses. In some cases, an isolated nucleic acid containing a portion of a intron 6 of STX17 nucleic acid containing a duplication breakpoint can be labeled (e.g., with a fluorescent label) and used to determine whether or not a horse contain the duplication.

This document also provides kits that can be used to determine whether or not a horse contains a duplication in intron 6 of STX17 nucleic acid. Such kits can include nucleic acid molecules (e.g., primer pairs or probes), antibodies (e.g., anti-STX17 polypeptide antibodies or anti-NR4A3 polypeptide antibodies), secondary antibodies, control nucleic acid molecules (e.g., nucleic acid representing a Grey homozygote, nucleic acid representing a Grey heterozygote, or nucleic acid representing a non-Grey homozygote), control polypeptides (e.g., horse STX17 or NR4A3 polypeptides), DNA aptamers, microarrays, ELISA plates, or data analysis software optionally together with any other appropriate reagents, tools, or instructions for performing the methods described herein. Appropriate informational material can be descriptive, instructional, marketing, or other materials that relate to the methods described herein or the use of the reagents for the methods described herein. For example, the informational material can relate to performing a genetic analysis on a horse and subsequently classifying the horse as being at risk (or not) for developing melanomas. In addition, or in an alternative, the informational material of a kit can be contact information, for example, a physical address, email address, website, or telephone number, where a user of the kit can obtain substantive information about performing a genetic analysis and interpreting the results.

The informational material of the kits can be in any form. In some cases, the informational material, for example, instructions, can be provided in printed matter (e.g., a printed text, drawing, photograph, or label). Informational material can be provided in other formats, such as Braille, computer readable materials, video recordings, or audio recordings. Informational material also can be provided in any combination of formats.

The kit can include one or more containers for the reagents for performing a genetic analysis, such as reagents for performing PCR, FISH, CGH, or any appropriate method described herein. The kit can contain separate containers, dividers, or compartments for the reagents and informational material. A container can be labeled for use for the genotyping of horses.

This document also provides methods and materials to assist horse owners or horse breeders in determining whether or not breed two particular horses. A horse owner or horse breeder can be assisted by (1) determining each horse's genotype (e.g., determining whether or not each horse to be mated contains a duplication in intron 6 of STX17 nucleic acid, is homozygous for a duplication in intron 6 of STX17 nucleic acid, or is heterozygous for a duplication in intron 6 of STX17 nucleic acid), and (2) communicating information about each horse's genotype to that professional.

Any appropriate method can be used to communicate information to another person (e.g., a horse owner or horse breeder). For example, information can be given directly or indirectly to a horse owner or horse breeder. In addition, any type of communication can be used to communicate the information. For example, mail, e-mail, telephone, and face-to-face interactions can be used. The information also can be communicated to a horse owner or horse breeder by making that information electronically available to the horse owner or horse breeder. For example, the information can be communicated to a horse owner or horse breeder by placing the information on a computer database such that the horse owner or horse breeder can access the information. In addition, the information can be communicated to a clinic or research facility serving as an agent for a horse owner or horse breeder.

This document provides methods and materials for treating cancer in mammals and for reducing the likelihood that a mammal will develop cancer. For example, this document provides methods and materials related to the use of agents that reduce STX17 polypeptide activity, STX17 polypeptide expression, STX17 RNA expression, NR4A polypeptide activity (e.g., NR4A1, NR4A2, or NR4A3 polypeptide activity), NR4A polypeptide expression (e.g., NR4A1, NR4A2, or NR4A3 polypeptide expression), NR4A RNA expression (e.g., NR4A1, NR4A2, or NR4A3 RNA expression), or combinations thereof to treat cancer in a mammal. In some cases, a human having melanoma can be treated by administering an agent that reduces human STX17 polypeptide activity, human STX17 polypeptide expression, human STX17 RNA expression, human NR4A polypeptide activity (e.g., a human NR4A1, NR4A2, or NR4A3 polypeptide activity), human NR4A polypeptide expression (e.g., a human NR4A1, NR4A2, or NR4A3 polypeptide expression), human NR4A RNA expression (e.g., a human NR4A1, NR4A2, or NR4A3 RNA expression), or a combination thereof.

A human STX17 mRNA can have an RNA sequence corresponding to the nucleic acid sequence set forth in FIG. 18 or 19. A human STX17 polypeptide can have the amino acid sequence set forth in FIG. 20. A human NR4A3 mRNA can have an RNA sequence corresponding to the nucleic acid sequence set forth in FIG. 21. A human NR4A3 polypeptide can have the amino acid sequence set forth in FIG. 22. A human NR4A1 polypeptide and a human NR4A2 polypeptide can have the amino acid sequence set forth in FIG. 25 and FIG. 26, respectively. An alignment of amino acid sequences of a human STX17 polypeptide and a horse STX17 polypeptide is provided (FIG. 23). An alignment of amino acid sequences of a human NR4A3 polypeptide and a horse NR4A3 polypeptide is provided (FIG. 24). An alignment of amino acid sequences of a human NR4A1 polypeptide, a human NR4A2 polypeptide, and a human NR4A3 polypeptide is provided (FIG. 27).

The methods and materials provided herein can be used to treat cancer (e.g., skin cancer) in any type of mammal including, without limitation, dogs, cats, horses, cows, pigs, monkeys, and humans. Any type of cancer, such as melanoma, brain tumors, colon cancer, and leukemia, can be treated. For example, stage I, stage II, stage III, or stage IV melanoma can be treated. In some cases, a lymph node positive, a lymph node negative, or a metastatic melanoma can be treated.

In general, cancer (e.g., melanoma) can be treated by administering an agent that reduces the activity or expression of an STX17 polypeptide or RNA or an NR4A polypeptide or RNA. Such agents can include, without limitation, antibodies (e.g., anti-STX17 polypeptide antibodies or anti-NR4A3 polypeptide antibodies), antisense oligonucleotides (e.g., antisense oligonucleotides targeting STX17 or NR4A expression), siRNA molecules (siRNA molecules targeted against STX17 or NR4A expression), or nucleic acid constructs having the ability to induce RNA interference against STX17 or NR4A expression.

In some cases, cancer (e.g., melanoma) can be treated by administering a cyclin inhibitor (e.g., a cyclin D1 inhibitor or a cyclin D2 inhibitor) to a mammal having cancer. A human cyclin D1 polypeptide and a human cyclin D2 polypeptide can have the amino acid sequence set forth in FIG. 28 and FIG. 29, respectively. An alignment of amino acid sequences of a human cyclin D1 polypeptide and a human cyclin D2 polypeptide is provided (FIG. 30). Examples of cyclin D1 inhibitors includes, without limitation, nucleic acid molecules capable of inducing RNA interference against expression of a cyclin D1 polypeptide, anti-cyclin D1 antibodies, all-trans-retinoic acid, dihydro-β-carboline, and Leptomycin B. Examples of cyclin D2 inhibitors includes, without limitation, flavopiridols, nucleic acid molecules capable of inducing RNA interference against expression of a cyclin D2 polypeptide, anti-cyclin D2 antibodies, suberoylanilide hydroxamic acid, rapamycin, Rugosin E, and THRX-165724 (Theravance, Inc., CA).

In some cases, cancer (e.g., melanoma) can be treated by administering a MC1R inhibitor to a mammal having cancer. A horse MC1R polypeptide can have the amino acid sequence set forth in FIG. 31. A human MC1R mRNA can have an RNA sequence corresponding to the nucleic acid sequence set forth in FIG. 32. Examples of MC1R inhibitors includes, without limitation, nucleic acid molecules capable of inducing RNA interference against expression of a MC1R polypeptide, anti-MC1R antibodies, and polypeptide antagonists of MC1R polypeptide activity. A polypeptide antagonist of MC1R polypeptide activity can contain the following amino acid sequence: SPRRSERLGW (SEQ ID NO:36; Bonetto et al., *Peptides,* 26:2302-2313 (2005)). Additional examples of a polypeptide antagonist of MC1R polypeptide activity can be designed and obtained as described elsewhere (e.g., Mayorov et al., *Chem. Biol. Drug Des.,* 67(5):329-35 (2006) and Thirumoorthy et al., *J. Med. Chem.,* 44(24):4114-24 (2001)).

An agent having the ability to reduce the activity or expression of an STX17 polypeptide or RNA or an NR4A polypeptide or RNA can be administered individually or in combination with one or more other agents having the ability to reduce the activity or expression of an STX17 polypeptide or RNA or an NR4A polypeptide or RNA. For example, an anti-STX17 polypeptide antibody can be administered together with an anti-NR4A3 polypeptide antibody. In some cases, an agent having the ability to reduce the activity or expression of an STX17 polypeptide or RNA or an NR4A polypeptide or RNA can be administered together with a cyclin inhibitor (e.g., a cyclin D2 inhibitor) and/or a MC1R inhibitor.

Any appropriate method can be used to administer an agent having the ability to reduce the activity or expression of an STX17 polypeptide or RNA or an NR4A polypeptide or RNA, a cyclin inhibitor (e.g., a cyclin D2 inhibitor), or a MC1R inhibitor. For example, an NR4A3 siRNA molecule and a cyclin D2 inhibitor can be administered orally or via injection (e.g., subcutaneous injection, intramuscular injection, intravenous injection, or intrathecal injection). In some cases, an agent having the ability to reduce the activity or expression of an STX17 polypeptide or RNA or an NR4A polypeptide or RNA, a cyclin inhibitor (e.g., a cyclin D2 inhibitor), and a MC1R inhibitor can be administered by different routes. For example, a cyclin D2 inhibitor can be administered orally, and an anti-NR4A3 polypeptide antibody can be administered via injection.

Before administering an agent or inhibitor described herein to a mammal, the mammal can be assessed to determine whether or not the mammal has cancer or is likely to develop cancer. Any appropriate method can be used to determine whether or not a mammal has cancer (e.g., skin cancer such as melanoma). For example, a mammal (e.g., human) can be identified as having cancer using standard diagnostic techniques. In some cases, a tissue biopsy can be collected and analyzed to determine whether or not a mammal has skin cancer such as melanoma.

After identifying a mammal as having cancer, the mammal can be administered an agent or inhibitor described herein or any combination thereof. For example, agents having the ability to reduce STX17 and NR4A3 polypeptide expression can be administered prior to or in lieu of surgical resection of a tumor. In some cases, agents having the ability to reduce STX17 and NR4A3 polypeptide expression can be administered following resection of a tumor. An agent or inhibitor described herein can be administered to a mammal in any amount, at any frequency, and for any duration effective to achieve a desired outcome (e.g., to increase progression-free survival or to increase the time to progression). In some cases, an agent or inhibitor described herein can be administered to a mammal having cancer to reduce the progression rate of melanoma by 5, 10, 25, 50, 75, 100, or more percent. For example, the progression rate can be reduced such that no additional cancer progression is detected. Any method can be used to determine whether or not the progression rate of cancer is reduced. For example, the progression rate of skin cancer can be assessed by imaging tissue at different time points and determining the amount of cancer cells present. The amounts of cancer cells determined within tissue at different times can be compared to determine the progression rate. After treatment as described herein, the progression rate can be determined again over another time interval. In some cases, the stage of skin cancer after treatment can be determined and compared to the stage before treatment to determine whether or not the progression rate was reduced.

In some cases, an agent or inhibitor described herein can be administered to a mammal having cancer (e.g., skin cancer) under conditions where progression-free survival or time to progression is increased (e.g., by 5, 10, 25, 50, 75, 100, or more percent) as compared to the median progression-free survival or time to progression, respectively, of corresponding mammals having untreated cancer (e.g., skin cancer). Progression-free survival and time to progression can be increased by any amount (e.g., 5%, 7.5%, 10%, 25%, 50%, 75%, 100%, or more). Progression-free survival can be measured over any length of time (e.g., one month, two months, three months, four months, five months, six months or longer).

An effective amount of an agent or inhibitor described herein can be any amount that treats cancer (e.g., reduces the progression rate of cancer, increases the progression-free survival rate, or increases the median time to progression) without producing significant toxicity to the mammal. Typically, an effective amount of an agent or inhibitor described herein can be from about 1 ng/kg to about 500 mg/kg (e.g., between about 10 ng/kg and 500 mg/kg, between about 100 ng/kg and 500 mg/kg, between about 1 µg/kg and 500 mg/kg, between about 10 µg/kg and 500 mg/kg, between about 100 µg/kg and 500 mg/kg, between about 1 ng/kg and 250 mg/kg, between about 1 ng/kg and 10 mg/kg, between about 1 ng/kg and 1 mg/kg, between about 1 ng/kg and 100 µg/kg, between about 10 ng/kg and 100 µg/kg, between about 100 ng/kg and 100 µg/kg, or between about 1 µg/kg and 100 µg/kg). If a particular mammal fails to respond to a particular amount, then the amount can be increased by, for example, two fold. After receiving this higher concentration, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the cancer may require an increase or decrease in the actual effective amount administered.

The frequency of administration can be any frequency that treats cancer without producing significant toxicity to the mammal. For example, the frequency of administration can be from about once a month to about three times a month, or from about twice a month to about six times a month, or from about once every two months to about three times every two months. The frequency of administration can remain constant or can be variable during the duration of treatment. In some case, multiple agents and/or inhibitors can be administered with the frequency of administration of each being the same or different. For example, a cyclin D2 inhibitor can be administered daily, while an anti-NR4A3 polypeptide antibody can be administered two times a week. As with the effective amount, various factors can influence the actual frequency of administration used for a particular application. For example, the effective amount, duration of treatment, use of multiple treatment agents, route of administration, and severity of the cancer may require an increase or decrease in administration frequency.

An effective duration for administering an agent or inhibitor described herein can be any duration that treats cancer without producing significant toxicity to the mammal. Thus, the effective duration can vary from several days to several weeks, months, or years. In general, the effective duration for the treatment of cancer (e.g., skin cancer) can range in duration from several weeks to several months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the cancer.

A composition containing an agent or inhibitor described herein can be in any appropriate form. For example, a composition containing an agent or inhibitor described herein can be in the form of a solution or powder with or without a diluent to make an injectable suspension. A composition containing an agent or inhibitor described herein also can contain additional ingredients including, without limitation, pharmaceutically acceptable vehicles. A pharmaceutically acceptable vehicle can be, for example, saline, water, lactic acid, and mannitol.

After administering a composition containing an agent or inhibitor described herein provided herein to a mammal, the mammal can be monitored to determine whether or not the cancer was treated. For example, a mammal can be assessed after treatment to determine whether or not the progression rate of cancer (e.g., melanoma) was reduced (e.g., stopped). As described herein, any method can be used to assess progression and survival rates.

In some cases, the treatment methods and materials provided herein can be used to reduce a mammal's risk of developing cancer. For example, a combination of agents and inhibitors described herein can be administered to a mammal at risk for cancer under conditions that reduce that mammal's risk for developing cancer.

The invention will be further described in the following examples, which do not limit the scope of the invention described in the claims.

EXAMPLES

Example 1

Cis-Acting Regulatory Mutation Causes Premature Hair Greying and Susceptibility to Melanoma in the Horse Genotyping Long range PCR using Expand Long Template PCR system Mix 1 (Roche Diagnostics GmbH, Mannheim, Germany) was performed to genotype the 4.6 kb duplication. One forward primer (Fwd 5'-GGAACATAAAGTAGATTTGGTG-GGAAAG-3'; SEQ ID NO:37) and two different reverse primers (N-Rev: 5'-TTCT-GATAAATGCATAAACCCACG-TAAC-3 (SEQ ID NO:38) for the normal copy and D-Rev: 5'-TTCCAATTCTGAGATTTTGCATTTCTAA-3' (SEQ ID NO:39) for the duplicated copy) were used in the same reaction. The PCR was performed using 125 ng of genomic DNA and the primer content was 3.75 pmoles of Fwd primer, 2.5 pmoles of N-Rev primer, and 5 pmoles of D-Rev primer.

Western Blotting

Rabbit polyclonal antibodies against amino acids 1-229 of horse STX17 were generated by immunization (AgriSera, Sweden) with purified soluble bacterially expressed amino-terminal cytoplasmic domain of horse STX17 (amino acids 1-229) produced as a GST-STX17 fusion polypeptide. For affinity purification, the antiserum was incubated with the 6×His-tagged amino-terminal portion of horse STX17 (amino acids 1-229) coupled to CNBr-activated Sepharose beads (Amersham, Sweden; 2 mg protein/mL beads). The beads were then washed extensively, and bound antibodies were eluted in 0.1 M glycine pH 2.7 and quickly neutralized.

The following primary antibodies were used for Western blot analysis: murine monoclonal ANTI-FLAG (M2; Sigma, Saint Louis, Mo.); rabbit polyclonal anti-phospho-p44/42 Map Kinases (Thr202/Tyr204; Cell Signalling Technology, Inc.), and rabbit anti-ERK2 (EET) (Leevers and Marshall, *EMBO J.*, 11:569-574 (1992).

Equal amounts of lysates were boiled with SDS sample buffer containing dithiothreitol and separated by SDS-PAGE. Samples were electro-transferred to Immobilon-P membranes (Millipore) and blocked in 5% bovine serum albumin in tris-buffered saline solution containing 0.1% Tween 20. Primary antibodies were used at concentrations and buffers recommended by the suppliers and incubated overnight at 4° C. After washing, the membranes were incubated with horseradish peroxidase-conjugated anti-mouse or anti-rabbit IgG antibodies (both from Amersham Biosciences), and polypeptides were visualized using ECL Western blotting detection system from Roche Applied Science on a cooled charge-coupled device (CCD) camera (Fuji). For detection of total amount of polypeptides after analysis of phosphorylation status, membranes were stripped with 0.4 M NaOH for 10 minutes at room temperature, blocked, and incubated with the corresponding antibody.

Northern Blot Hybridizations

Total RNA from horse tissues was extracted according to the TRIzol® (Life Technologies, Inc.) protocol. mRNA was prepared using Oligotex® mRNA kit (QIAGEN GmbH, Germany) following the manufacturer's protocol. Poly A+RNA was electrophoretically separated on a denaturing formaldehyde agarose gel, transferred to a nylon membrane (Nybond N+; Amersham Biosciences, Inc.), and immobilized by UV irradiation. A random-primed $^{32}$P probe was generated using full-length coding region for each of NR4A3, STX17, TXNDC4, INVS, CCND1, CCND2, and β-actin. Hybridizations and washings were performed using ExpressHyb™ (CLONTECH Laboratories, Inc.).

Real-Time PCR

Relative expression of STX17, NR4A3, and 18S-RNA were analyzed by comparative $C_T$ method using the primers and probes given in Table 2. The PCR was performed in 25 μL reaction volumes using the TaqMan Buffer A (Applied Biosystems), 0.7 μM of both forward and reverse primer, 0.25 μM of TaqMan probe, 3.5 mM $MgCl_2$, 0.2 mM dNTPs, and 0.625 units of AmpliTaq Gold DNA polymerase (Applied Biosystems). The PCR reactions were performed using the ABI7700 instrument (Applied Biosystems), and cycling conditions were 50° hold for 5 seconds and 95° hold for 10 minutes, followed by 40 cycles of 95° for 15 seconds and 60° for 1 minute. All samples were analyzed in triplicates.

TABLE 2

Primers and probes for real-time PCR analysis of NR4A3 and STX17 in Grey and non-grey horses.

| Primer/Probe | Sequence |
| --- | --- |
| STXForward | 5'-CCTGCCACAGGCAGAGCT-3' (SEQ ID NO: 40) |
| STXLongReverse | 5'-TGGTCACTGATTTCTCTCTCCTAGTAAA-3' (SEQ ID NO: 41) |
| STXShortReverse | 5'-GCTCACTCATAATTCCTTTGCATCT-3' (SEQ ID NO: 42) |
| STXTaqMan probe | 5'-FAM-CTTGTATTTTGCAGCCTTCCCCAAGTTTTT-TAMRA-3' (SEQ ID NO: 43) |
| NR4Forward | 5'-GAATCAGCCTTTTTGGAGCTGT-3' (SEQ ID NO: 44) |
| NR4Reverse: | 5'-CATTGCAGAACACAAACTTATCTTCA-3' (SEQ ID NO: 45) |
| NR4TaqMan probe: | 5'-FAM-TGTTCTCAGACTTTCCATCAGGTCGAACACT-TAMRA-3' (SEQ ID NO: 46) |
| 18SForward | 5'-AGTCCCTGCCCTTTGTACACA-3' (SEQ ID NO: 47) |
| 18SReverse | 5'-GATCCGAGGGCCTCACTAAAC-3' (SEQ ID NO: 48) |
| 18STaqMan probe | 5'-FAM-CGCCCGTCGCTACTACCGATTGG-TAMRA-3' (SEQ ID NO: 49) |

Primers and Template Sequences

Primers were designed and used for pyrosequencing (Table 3). Template sequences for the pyrosequencing are as follows with polymorphisms identified:

SNP.1&2:

(SEQ ID NO: 50)
GAGACTTCAGTCAGATGACCATGCTTAGGAAATATCCTTATCCCTTCCTCATA

TGAATGTGCAGTCTAAACTTTTCCGTCTGAACATGTTTAAAGTGTATATATGT

ATAAGTTTTATACATCTTTATGGTTTTCTTCTTTCAGCGACCTTTTTCAATAAA

TTGGTCAACCTAACACGT/CTATAAAAGAGGGCTCCTGCTGTATTTAAAAACA

CAGATAGTGCATTCCAGATAGGGGT/CGAGTGGAAGGGGAATACACCATGGA

TATAGGTCAAGTTGACGTGGAGAAGGACCTCCAATGTCACAGTGAGGAATTT

GGACATTGCAATAAGCAATAAGGGAACAGTAAGAGGTTGTCGTTTTGTCATT

TGATAGTACAGATTTTTGAGCATATCAAAGGACATGCCCTTTATGAAATTAGT

TTGGCAGCTAGTAGGCTTGCTGCTCCGGTCCCCGTAGTCCACGTCATTCCTCC

CCATAGCAAAGGCTGCTGGAGTCTTGCTCCTTAGGCTCCAGACCTGCGCTGTC

CAATAGGTAGCGGTAGCCACATGTGGCTATTGAGCACTTAAACGTGGCTAGC

CGGAACTGAGATGTGCTGTAAGTGTAAAATAAACCCAGATTTCAGAGACTTA

-continued

```
GTATGAGAAAAGGAATGTAAAATATCTTATTAACGATGTTTTATTGCTTACAT

GTTGAAACGATGATAGCATATACTGGGTTAAATAAAATATACTATTAAAATT

CATTTCCACTTATTTCTTTTTACTTTTTTAAAATGTGACTACTTGAAAATTTAG

AACTTTAACATGTAGCTCGGCATCTGGAGGCTCACATTATATTTATCTTTCTG

GACAGAAATGGCTCTAGTTCTAGATCAATCCTGACACGAGATAGGAGAGTTG

AGCCATCCTGCCCCCTAGCCCAATGCTTTGGGACTCATTTCTCCTACTGGGTG

TCTGATTTCAAATAAAGAATCTTTGTCACACTCCTCTTTCTCCACTTTGGGATG

TGGTCTGGTTTCCTTGATTTCTGCTTTGTAATGTTTAAGGCTCAGGTTGCTGGC

TCCTTAGAGATTTGTCTTCTCTCATTTTCCGTCATGCACAAATCCATGTTTC

CTCCTTATGATGACTCCTTCCTCTGGAGAAGCAGACACTTCCAGAAAGATGG

AGATCAACAATAGGGCATTGGATTTGGTGATCAGGGAATCACTACCTTTAAG

AGAACGACCATATCAACTATTTGAGCGGACGGCTGAGCAGTTGTCAGGATTG

CCACACCAACGATCTCATAGGCTTAAAGACCAGAAGAAAAACCAAATCACA

CCTTAGCCAATGGTAGAACAATGACAAGCACACTGGCACATCCCTCACCCAG

TCTTTGTCTACCGGTGGAACTGAGACTTCCAGAATGAAGGGCCTCCTCCCTGT

CATTTATTATTTTGAAGTAGTGTTACCAAGTGCTCACTTTGAAGAAGCATTCA

GCTAGACAGTTAGGGATCACAATCAAGTTAAAAAGAAAAGGAAATAAGTTT

GCAGCACTGGGGCTGCATTCAGAAATGGGAGAGACATCCCCACAAGTCACGT

CACCCTCATGCAAGCAAAGCTGAATACACCTGATTTATTTGCCTATCCAGGGA

CCTGGCCAGATTTTTTCTAAACTCTGGAGGCAGTCTTGGTT
SNP.3:
                                                       (SEQ ID NO: 51)
TGACTTGTTAGAGGCGGTTCTAATTCTCTTGGGCTGCTGGGGAATCTCAACAG

AAAATGGTTTAGTACGTATGAGCACGTGCATATCTGAGTGTACGTACATATG

CCTCCATCTTATGTGTGTACGTGTGTTTATGCATCAGGGCACAGTAGCTGATA

CAATGCAATAGATACCTAAAAACACGGCACCAACAAAATCAAATGGACTAT

TCACTAGAAAATAACACCAACGAGGTTGGCTAGGTATATGTGTTTTATTTTGT

CTTCATTTTTTTAAGTCCCCACATTGAACTGCATAACCTCTTACATTTCATCTT

AAAGAATTTCATAACATCTTGTAAAAAGCTA/GCTTCCTTCTGTTCTTCAGTCT

TGCAAAGTGCTCACTGACGTTGCTGTTGCAGTCTGGAAGAATTGAAAGCTTTA

GCATTCGGTTCTCAAGGAGCTCTCCCTCCTGACCACATTGAAGGCAGCATGG

CGTGGTACAAAGGGTCCTAAACAGTGAGCCACAGGACATGGGTTTAAGCCAG

AATCCTACCCATTGTGAAGTTAGGCTAGACCCTCACAGCCCTGAGTCTATTTC

CTCATTTGTAAAAAAGGGCTAATAACCCTTGACCTGTCCTTAAAAAGAGTCTC

TGGGAATGGGCTTCGTAAACTCTGCAGCACTGAGGCAAGCCATGGAAAGGGA

TTAGTACCGCCACAATTGTGGAAGTAAGTCTCACGCCTAAGAAGCAGTCCCA

GCGAGGAGGTTTTCGGTACAGGGAGACAGGAAGGAAAGCA/GCAGGATTCCA

ACACACACCTGTGACTTCATTCATGAAATTCAGGGGAGAAATTTAAAATATTT

CCCTAGACTTCCCTCAGAACTACATTGGCTTCAAAGGAGGCAAAAGTCAAGA

TGTAACAGGAATTTTTATTCTGATTTGTTCTGAAATATGGGTTTTCAATCATCA

TGATTCCTTAAATTAGAATGGATCTGCAAAAATAGATACATGCAAACATTTTT

TCCTAAATTTTTTTCATGTAAGAGTATGCAGCCTGCTGTGTAATGTCACACAC
```

-continued

TAAAATAACATTGGCATAGAATGGGAGTAAAATCCTTTCTCTGGAAATAAGC

ATATGTTATTAAAATTATATATCATTTGTAT/GCCAACTACTAGAAAAGAATC

CACACTGCAGTGTTTAAGTTTAGGATTGACTTGGCGTACTGTGACATTGTGCA

ATCAAGGATAGGACCAGGAGGCAAGGGCTTGAGTTCTACTTCCAGCTATTCC

GCTAAC/TTAACCTGGTGACTTGAATAAAGCATTGGCCTCCATGAGCTTTATTT

CTTCCATGGGGAAAATGAATTACCACATGTGCCTACTCACCTGCTTCATAGGG

TTCTTATGGGGATCAAATGAAAGTGTCTATGAAAATGGCTCTCTATAACTATG

AAATGGTTGGGT

SNP.4:
(SEQ ID NO: 52)
AGAAGTTGTGGGAGCTCTAATGTGGCAGTGGAGGTGAAGGTGGGGCCCACTT

GCTACGAACAGTCTGCTCTCACAAAAAATTTAAAGCAAGGCAATATTTTTGC

ACACTTTTCTGTAATTGAATATCATTAAGGTACTAAATAGATAATGCACCTTG

CCTTTCTTTTTTTCAAAAACTATTTATTGAATGCCTACTATATACCAGGC/AA

TTGTGCAAGAGATAAAGGGATAAAATGGTGATCAAAGAAAAAGAGCAAAGA

AAGCTAAAAGACAGTCGAGTGGAAAGAGTAGGAATGGAAAAGAAAAAGCG

GATTGCTGGTGGGCTCCTTTATTGCCAAAGTCTTTGTATGTTTTGGGGTCCTTG

AGTCAGGAAAAAAGTAGTTATGCTGGATCCCTCTGACAT/CGTATGGCAAGG

AGTGTGTGTGTGTGCATGCATGCACGTGTGTGGTGTGTTTTGGAGAAGA

TGAGAGAGCATAAGGAGAATACCTCAATTTCTGC/TCCAATAGAAGTGGGAG

GATGGAATCACTGATGTTCCAGAAGCTAAGAAAGGAAAAATGTAAATTATTT

TCTTTACGCATGTGGTTTGCACAACATCCTCCAACATAAGACTCCCACTTGGG

TCCTAAAGTTGGAAAAATCTAGGGAGTACGGAGAAAGAGAACAGAGCAACA

AGACGACACAGTATACCAGGTGTCAGCGCTAGCACATCAACTCCGAAAGGG

AGACCTTTGCAAGACATTCTCCAGGTTCACTAGCCATGTGCATTACGAATCTG

GAATTAATGCTATTTACCTAAATTATAAAGACGTATTTCTCACATAAGTCCCT

TATGTGCAAGCAGGGTAGCAAAGGAAGAGTTCTTTATATGGGGGTAACTTGA

AGAGCCCCTAAGAATTTCCTACCCCAAATAGTTCACTGAAATTCTTCATTTTG

TTTCGCTCTTTGGAACCTGTCTTTAATTATCTCCCTATGACCACAGAAGCAGTT

ATAACACAGTACAGTAATTAAAGATTCTGAAATCAGATTGCTTTGTTCACCCT

GGGCT

SNP.5:
(SEQ ID NO: 53)
GAATCATCGCACTGTGGTGGATTCATGTTCCAGAAGCTAAGAAGGAAAAATG

TAAATTATTTTCTTTACGCATGTGGTTTGCACAACATCCTCCAACATAAGACT

CCCACTTGGGTCCTAAAGTTGGAAAAATCTAGGGAGTACGGAGAAAGAGAA

CAGAGCAACAAGACGACACAGTATACCAGGTGTCAGCGCTAGCACATCAACT

CCGAAAGGGAGACCTTTGCAAGACATTCTCCAGGTTCACTAGCCATGTGCAT

TACGAATCTGGAATTAATGCTATTTACCTAAATTATAAAGACGTATTTCTCAC

ATAAGTCCCTAATGTGCAAGCAGGGTAGCAAAGGAAGAGTTCTTTATATGGG

GGTAACTTGAAGAGCCCCTAAGAATTTCCTACCCCAAATAGTTCACTGAAATT

CTTCATTTTGTTTCGCTCTTTGGAACCTGTCTTTAATTATCTCCCTATGACCAC

```
AGAAGCAGTTATAACACAGTACAGTAATTAAAGATTCTGAAATCAGATTGCT

TTGTTCACCCTGGGCTTCACCACTAGTCACTCCTGTGATTATTGGGTATGCTTC

TTACTAACAGCTAAGAATTACATTTATTGAGCATGTAATCACTTAGCAACTAT

AGGCACAAGCATTTTACATGTATTGGCAGGTATCATTAATCCTCACAATACCC

CCATGAGGTATGACGTAGGTA/GTCATGATCATGATGTCATCTTACGGATGAG

GAAACTGAGGCACATATGGAACTTTCAGGTCCAAAAGTAATAAGAGTGAGCT

GAAATTCAAACCTAAACAGACTTAACTATATACTACAGGCCCCTCACTTAAA

CGCTCTAAGCCACCATACCTACT

NR4A3.2:
                                          (SEQ ID NO: 54)
CGCGTTTTTTAGCCTCGATTCGGGTGCCACAAAACGGCGGTGAACGCACTGG

GTGCTGGGCAACCCATACTCGGCTCCCCCAAGGCGGTGTAATGCTTCTTGCCC

AGGGACTCCGTTCACCTTAAGCACTGCTTTCTTACCCTTATAATTCTTTGTAAT

TAACGTAGCATTCCTCGAGGCCCCCACCAACACCCCAACGCGCCCGGCCCAG

GCCGCGGTGACCCCGCCTGGTCCCGCTGTGACCTCTGTCCTCTCTCCCGGTGC

CCGCAGAGCCCACTGCGGAAGAGCGCAGCCCGGCAAGCCCCAGGCCTGAGA

CTGGACCCTCGGCAGAGCCGGGCAGCACCGCAGCCGCTTCGCCTCGCCA/GG

ACGTCCCCGCTTCTACACTCTCAGCCTCCGCTGGAGAGACCCCCAGCCCCAC

CATTCAGCGCGCAAGATATCCTCCAGGTAGGTCTGAAGGCACGACCCCTTAT

TCCTCGCAGGCTGGAAGAAGTGGGGGAGGGGATGGGCCCTGGGTCCCTGGCA

GGGGCGGGCTGGTCGACTTGCCTAGCGCCAGGACAGTGACTGCTGGCCGAGC

ATTTCACAGCACAGGTGGCTTCTTTGCACGAAGCTCCTCTGGATACCACACCC

TGTTGCTACCGAGTGGAGGAGCCAGATTAAATTAAGCGTTGCATTTTTCAAA

AATATTTTTCCTAAGAAAAATGCAAATACACCGATAGATTAGGATCTTTTAAT

ACACTGTAATGTCATGTTTGCTGTCCTTTTATATCCGGTTTACGCATTTAAGAG

TATTGGG

NR4A3.1:
                                          (SEQ ID NO: 55)
TTAAAATACAGGAAAGGCAAAGTTAAGGTATGGACCACATAGAGTTCAGATT

AGTCACGCCTGATACTCATCAAGCTCCTCTTGTGTACCAGGCACTGGGCA/GT

GGGCTTTCAAATCTTTTAC/GTTTACAGTCATGCATCACTTAACAACAGAGGT

ATGCTCTGAGAAACGCATCATTAGGTGATTTTATCATTATGCGAACATCGTAG

AGTGGACTAACACAAATCTGGACGGCATAGCCTG/ACTACACACCTAGGCTCT

G/ATGGTACTAATCTTATGGGAGCACGGTCGCATATGTGGTCCGTCGTTGACT

GAATGTTGTTATGCAGCACATGACTCTATTTAATTCCCACAACGATCGTAGGA

GGTAGCAATTAGAAGTCCTGTTTTATACATAAGGAAAAGGAAGCCCAGAGAG

ATTAGAAGTGCCCAGGGCCCCTTAGCTAGGTGGTGATGTTTCACCAGAAGTTT

CAGGGTGTCTTTCATGAGAGAGAGAAGAGTGGGATGATTATGGACATAATAT

AAACTATCACGGCAGATTTAGAAACAGCCCTCCGCAGCCCCCCTGTTAAAAG

CAGAGAGGGTAATACAAAATAAGCTCTCTTTTCACTTTAAGGCGCTTGTCAGT

TTCTGATTGACTTCTGGCGGTCGCAGTGACTCGGTGGTTTTAGAGTCTGCACA

ATGGAATTGTAGTGTCTAGCGTCAGGCCTTATCAGTTTCTGACATTCAAGGAA

ATGAGGGGGAAGTCCTGGTGAGGGAGCGCTAAAGAGAACAGTCTCAGGTTC
```

```
ATGGCAGAGGCCACGCACTGGGCTTCACTTCCACAGTCTGTGAGCGCCTGCT

CCTCTGTGTCCCGTCCCAGGGGGAGCCAGTAATTGACTCTAGTAATAAGAAA

TCAGGTGCCCCACCGCCAGCTTCCCCGGGGGCTGATGCTCAGCAAGAAAGTT

AGCACAGACGCCTGGTGGTGGCTGTGCATCCCTGGAGTACCCTCTTCTTCCTC

GAGGGCACCCGGGCAGATTTCACAACACCACACTACTTCTGAACGCTGCCCC

ATGGCTGTGCGGGTATCTCTGTGGTGTGATGGTGTCCTGTCCGACAGACCGAA

CAGACCTGTCTAACGTATCTCCATCCTCCGCCCCCCACGACTTTGTCTTGTAG

GTCGAACACTGCTGAAGATAAGTTTGTGTTCTGCAATGGACTTGTCCTGCATC

GACTTCAGTGCCTTCGTGGATTTGGGGAGT
```
TXNDC4:
(SEQ ID NO: 56)
```
TATAGTTTTAACCGTAATTTGAATACACGTCTAGTATAATCTATAGTTTTATA

CATGTTAGTGTTCACAGTCATAGAATTTTAGTATCGAAGGGAACCTCAAAGC

ATCATCTTGTGCTAATGCAAACCTTTCAAAGTAACGATGGGGACTT/CAGAGG

CCTGAAGGCGCAGAGGCGTTTAGTGACAGAGCTGGGACTAGAGAGCCCTGGT

CCCCGGGCCTTATCGGCCTGTTTTGTGTTCAGCCTGGGACCCAAATTCAAAAA

ACTGCTCCCATGATCTGTGATCATAACTCATACCTGAATCAGAATAGCCATCT

CCCAGGCCTTCTGGGGTATAAATTAACCTGCTACTTGCCAGATAATAAGGAG

TGCTAGGGTTTTTTTTGCTTTTAGGAAGATTAGCCCTGAGCTAACTGCTGCC

AGTCCTCTTTTTGCTGGGGAAGACTGGCAGTGAGCTAACATCCATGCCCATCC

TCCTCTACTTTATATGTGGGACGCCTACCACAGCATGGCTTGCCAAGCGGTGC

CATGTCCACACCCGGGATCTGAACTGGCGAACCCTGGGCCGCCAAGAAGCGG

ACCGAGCGAACTTAACTGCTGCACCACTGGGCCGGCCTCTGGGAGTGCTAGG

TTTTTAACCCTTAGCTGAGAAGTTAAGTATGTCTGAACCTAGAAGGAGCTCCT

TAGGCCCAAGACAATGGTGGCCACAACTAAGAGGCAAAAA
```
INVS.1:
(SEQ ID NO: 57)
```
TTACTGAACTGGCAAGACTACGAGGGACGAACACCTCTTCATTTTGCAGTCG

CCGATGGGAATGTGACGGTGGTTGATGTCTTGACCTCGTACGAGAGCTGCAA

CATAACA/GTCTTATGATAACTTATTTCGAACCCCACTTCACTGGGCAGCTC
```
INVS.2&3&4:
(SEQ ID NO: 58)
```
CGGAGATATGGACAGATGGAACCAAGAGTGCATGGTATTGCTCCTCCAGGTC

TGGAGGAAGGAACTGCAAGTAAAACCCCAAAGATTATCCCAGTAAGCAGG

ACCACCAAGAGTCCATCCAAGGGCATCTCGGGCACAAAGTCCACCAGGCACT

CAGTGCTCAAGCAAATCTATGGTAACTATCCTTCTGGGCACTTTGTAGTTTAC

AA/GTTAGCACCCCAGAGAGTGTCACGTCATAATCTGGAATGGGATTTAATT

ACATTGGGCAAACATCCATTCAGGTAGGAACTTTATTATACCTCCAGGCACC

AAGAGAATCCTCAGCACCACATTTAGTGCCTCCCTCCCAGCCATTCTGGGTCA

GAATTGGTTTCATAAGACATTCTGGCATCACAACAAAGAGCTTCTCTGCTGGG

CTCCATGACTGAAAGCCTCACCG/ATCTCTCCAGGCCATTGCTTGGGTCTTCCC

CTTACATTGTCCTCTTGGAGGAACCCAGGCACAGACCAACCTTGCCTGCCTCA

CTTGGACC/GTTTCCTATGCTACGAT/CAGTGCAGGGTTGTCCATCTGTGGGAC
```

TGCCCCAGACCGAGCACCGCAGTAAACACGCGTTTAGCAGATGAACTGCTCC

ACCTCTGGAAGAGCCCACCCAGAGAAAGGCAGCAGGCAACAAGTCTGGCTG

GCTCCCG/AA/GCAGAAGAAAGTTGAGCTGAGGCACCGTTAGAAACAATCTGT

GAACAGGCAGGAAACTCTCAGGAGTTGACCTGGGTCTACATGGTATTTCCAT

ACCATGCCTAATTTATCTTGGCAGACACCTGAAGCCTCAAGCCTTCACCTCAA

CAAAGAATTCAGAACCTGGTCAGGCCACAGCTCTCAG/TGGTCAGAGATACAT

GATTATTGTTGGTTGATTGCAGGTTGTTCTCAAGAAGGGAAAGTACATCATCC

CACAAGATCTTCAAAAGCTCATTCTGTGCTGCGTCTCAACTCAGGTAAGGCA

AACCACTGCACTGGCAAAAAAAACGTTAGAACAGAGATGGCCAGGGGTTCC

CAAAGGTCATTTTGATTTCCACTAGGCATGGGTTTCATCCCCGTTTCATGGAG

TTGTTACTGCAGTCAACATCTGTCTCTATAAGGGGCAAGTTATTTTCCAAATA

AAAGCTAACATTACCTCCAGTAGAAACTTGTTCACATAAAGGAAGGGGGAAA

TGAAAATGCTATCGTTCTTCAAAGTAATACCTTGGGAATTCTTGTTTCATTTTG

GTTTCACATTAGG/TATCCTCCAGTTCCTTCCCAAAGATGACAAAAAGTCCTTT

ACCACAAATTCTGGCTTTTGCCTTTTAGGACCTACTCCATAAAGATGTGTAAT

ATTTAATAGCATGTTCAGCTCAGGCTCAGCTGTGCACATTTTCACTCATCCAA

GAGCAGCTCAGGGAACTTTCTTTTCAGCCACAAGACAGGAGTGC/TTTACTCA

GAG

INVS.UTR:
(SEQ ID NO: 59)
CTTACAACCTGCAATCAGCTATTCAATCAAAAAACAAAACAAAAGCTTCGAC

CGCCTGC/TGGAGGAAGACTGTGTCCAGGGGCGCTGGAATAGCTAGTGCAGA

GTGCTAATTCTCCGCTCATTATCTCCGACATCTTGGGAAAACGTTAATACCCA

TGCCTGCAGCCTTACTGGCCTGAAAACGTGTTAACAACTGAAAGAGAATGTC

AGAATG/ATTTTCTTTCTGCTCTCACACAGCACTGTTTTGTAAATTCTCTTAGC

CTGAGCTCAAGGACCAGGGGAAACTATGCCTGTGCAAAACTGCCCAGCTGTC

TGCCTTCACCTCAGTCACGACGGCTGGAAAGAAGAATTTATAATTAACGGTA

AAGTCTAAGTAACACTAAGAACATAGGTGCTAAAGAGGCTGCTGGGTTGGGA

TTTCGGCCAGCCAGCTGCTGCTGGCCTGGTGTTTTGGTTCCAGTGAAGAACTG

GAATCAGATGAGGAGGAGCCTGTCCTACAGTAGCTGCCTTGTTTCACTACTTT

TCTGGAATCTAATGCAACAAACTTCCTTAGAGATACCGCATCCTGTTATTCCA

ACATTATTAGTTTTAAATTTTAGACCAGAATCATAATCCAGCCTTTGCTTTTA

GAAACTGCAAGACCATAAGAGGTATACTGTTGATTCCTTACATTTACAGTTCC

CATGTTGGCCTCTGAAGGCCACAGGTTGCTGCCTCGTCCTCTCAGAATGGTGT

TCTCGTCGCTGAGCACCAGCAGCAGTATTGGGCACTAAGGAATCAGTCGGGC

AGGTTTACAGACCAGACCATTCAT

TEX10.3:
(SEQ ID NO: 60)
CGTCTGCAGAGAAAACAACAGCAATGTGACACTGCACCCGAACC/TGCTGTCT

CCTCACCGTATTCTTCACACCCAAACGAACAGTATCCTCATCTGTAAGTCACC

ACAGGAAATCTTACTGGAAAAGGGGACCTATTAACTGGGCATTACCACAGGC

AGCGAAAATTCCTAGTTACGACCTCAAGTACAAGTACTACC/TGGTTTCTCGT

TTGGTCTGTGCCCTCCCATACATGCTAGAGACTAATGAAATTTCACCATCAAC

-continued

AATCCTACACTCCAGACTCCCCCCA/CCCTTGGCATTCTAGTCTCTCGCTCTCT

GCACTCAAATCAACTGAGAACACTTCCACAGAGCCGCCTGCCAAGTCCTGTC

ATTCTCTTCCTTATGGAGGTGAGCTGATTCTCTAACCTCAGAATAATCCAAAT

TCTTGACTTTTCTTCCCTTCTACTATTTCTGAATTATTATTATATATACCAATTA

ATAAACCCCCCCAATCC/AAATACCTATACAAAAAACCCTCTAACTCTCCCAA

ACCAAAAACACCAAAAGGAATCCTAGATTACAGAGCTGCCTCCACAACACA

GAGAACCAAGCTCCAGACAAAGCTGAAGCTGTGACTTCCTTCTTCCAACTTCT

TCTTACTCTCCGGTGAACTAAGTGACTAGAGATTGGCCTAAAATTTATTACTG

CCAAATAATTTCCCTAATGACAGCTAGCATTTGGTGAGCACTTAATAAATGTT

AGCTATACTAAAAACATTATTTGGATTATCTCATTTAACGGTCACCAA

TEX10.1:

(SEQ ID NO: 61)
TTTTCTGTTACACAAAAAAAGAGATTCATTGGTAAAGATTGGGTTTGCCATAG

CCAGGAGTGAGTGAGTCTT/CCAGAAGTCTAAGCTTAATACATTCCATGGCCT

TTCACAGCATGATGCTGTGGCAAGAACTGAGAAATCTTGGTGTTTTTCCTGGC

TGCTAACTAATTAATTCTGTGCCCTTGGGAAAATCTCTTTTCCCAGGACCTTA

CTTTCTACATCTGTGCAATGAAGGACCTTGAAATTCTACCTCAGATCCTTCTG

TCTTGTAATGCTTTAATTAACATGTGTCTGGTGTCAGTGTATTGTGAATCCAG

CATCCAGACTGGGGTCTAATTTTCACCTAGAGCTTTGGGGTCTAAAGCTGGGA

TGTCACCTGGCAGGCTCAAGGCCTAG/ATCACTGGAAGCAGGGAGCTCAGCC

ATGAGCCTGACTTGTCTTCTGGCCAGTCTCTTGTTCCCTCGGTATTAAATTCAC

ACTAGGTATGCCTGGGTTTTTGCTTTTAACTTCTTCCAGTGTTTCCACTTTGAC

CTCTGGCTTTTATTATAATAATTTATTAAGTGCAAGGAAGGGATCACAAACTT

TATCTTCCAGAGGACTTTCACCTGTTTGGATATTTTTCAGGCGTATCTATTCCC

TCTTTTCTTTAAATATTATTTTCCTTAAGTTGGAAGAGTACTGCTTTGAATTCC

CCGTGCTCTTTTCTCCCTGCTCTCAAACTTCCAATCCTTAGCCCGTGTGTCTCC

AAAGATCCCCACTTTTTTTTAACCTG

TEX10.2:

(SEQ ID NO: 62)
GAGCAACTTAAAGAAGATGGGACACTTCCAACAAACAATAGAAAGCTTAAC

ATAAAGGTAAGTCA/TTAAGTGTTGTTTTGATAAAATAAGATTTTCTTTCAAAT

CATCTA/GGAATGTTGTGTTTTTGTGAAAAGTTGTTTTAACTCTTAGGGTTTAT

TAATGGCTGAAGTTTGGAGTTCATCTGTTATTCATATGTGATGTTGCCATGGC

AGCTTTCCCACCTCGTCCAGAAAGACTTGCTCAGCTAAACCCACAGTGGTTTC

TCCCTGTCTACTTATTTGATGATTTAATATATCATCTCAAAGT/GAA/GTTCTTG

TGTTTAACTTTTTGATGTGTCAAGGTGTTTTTTTTGTTTGTTTGTTTTGGTGAG

GAAGATTGGCCCTACACTAACATCTGTTGCCAGTCCTCCTCTTTTTAGTTGAA

GAAGATTGTTACTGAGCTAATACTGTGCTAGTCTTCCTCTATTTTGTGTGTGCC

ACACACTGCCACAC/GTGTGGCTTAACGAGTGGTGCTAGGTCTGCGCCATGGA

TCCGAACCTGCAAACCTT/CGGGCTCCCAAAGCAGAGGACAT

TABLE 3

Primers for pyrosequencing.

| Gene | Primers | Tm | SEQ ID NO: |
|---|---|---|---|
| TGFBR1 | F: AGCATGGTTTAGCTGTTTTTTAAA | | 63 |
| | Rbio: CTGTGTGGTAGTAATGGAATG | | 64 |
| | Seq: CCCAAAGGACATAAAGGACA | | 65 |
| | T: AAGA/TGAAACATCATTCC | 56/54 | 66 |
| SNP.1 | F: CAATAAATTGGTCAACCTAACACG | | 67 |
| | Rbio: CATGGTGTATTCCCCTTCCA | | 68 |
| | Seq: CAATAAATTGGTCAACCTAACACG | | 67 |
| | T: T/CTATAAAAAGAGGGCT | 58/55 | 69 |
| SNP.2 | F: CAATAAATTGGTCAACCTAACACG | | 70 |
| | Rbio: CATGGTGTATTCCCCTTCCA | | 71 |
| | Seq: CACAGATAGTGCATTCCAGATAGG | | 72 |
| | T: GGT/CGAGATGGAGGGGAATA | 58/55 | 73 |
| SNP.3 | F: CTGCAGTGTTTAAGTTTAGGATTGA | | 74 |
| | Rbio: TAAAGCTCATGGAGGCCAAT | | 75 |
| | Seq: TTCTACTTCCAGCTATTCCGCT | | 76 |
| | T: AAC/TTAACCTGGTGAC | 58/55 | 77 |
| SNP.4 | Fbio: TGCACCTTGCCTTTCTTTTT | | 78 |
| | R: CAGCAATCCGCTTTTTCTTT | | 79 |
| | Seq: TCCCTTTATCTCTTGCACAAT | | 80 |
| | T: T/GCCTGGTATATAGT | 60/58 | 81 |
| SNP.5 | F: GCATTTTACATGTATTGGCAGGT | | 82 |
| | Rbio: CCTCAGTTTCCTCATCCGTAA | | 83 |
| | Seq: CCCATGAGGTATGACGTAGG | | 84 |
| | T: TA/GTCATGATCATGATGTC | 60/58 | 85 |
| NR4A3.2 | Fbio: TGTGACCTCTGTCCTCTCTCC | | 86 |
| | R: ATATCTTGCGCGCTGAATG | | 87 |
| | Seq: GTGTAGAAGCGGGGGACGTC | | 88 |
| | T: T/CGGCGAGGCGAAGCGGCTG | 60/58 | 89 |
| NR4A3.1 | F: CATGCATCACTTAACAACAGAGG | | 90 |
| | Rbio: GTCAACGACGGACCACATA | | 91 |
| | Seq: CTACACACCTAGGCTCT | | 92 |
| | T: A/GTGGTACTAATCTT | 58/56 | 93 |
| TXNDC4 | F: AACCTCAAAGCATCATCTTGTG | | 94 |
| | Rbio: TCTCTAGTCCCAGCTCTG | | 95 |
| | Seq: TCAAAGTAACGATGGGGACT | | 96 |
| | T: C/TAGAGGCCTGAAGGCGC | 57/55 | 97 |
| INVS.1 | Fbio: GTACGAGAGCTGCAACATAAC | | 98 |
| | R: GAGCTGCCCAGTGAAGTG | | 99 |
| | Seq: GGTTCGAAATAAGTTATCATAAGA | | 100 |
| | T: T/CGTTATGTTGCA | 59/58 | 101 |
| INVS.2 | F: TCAGTGCTCAAGCAAATCTATG | | 102 |
| | Rbio: AATCCCATTCCAGATTATGACG | | 103 |
| | Seq: CTGGGCACTTTGTAGTTTACA | | 104 |
| | T: A/GTTAGCACCCCCAGA | 57/55 | 105 |
| INVS.3 | Fbio: AGAACCTGGTCAGGCCACA | | 106 |
| | R: TCTTGTGGGATGATGTACTTTCC | | 107 |
| | Seq: ATAATCATGTATCTCTGACC | | 108 |
| | T: C/ATGAGAGCTGT | 59/57 | 109 |
| INVS.4 | F: CAAGAGCAGCTCAGGGAACT | | 110 |
| | Rbio: CTGGCATTAGCTGCTGACAG | | 111 |
| | Seq: TCAGCCACAAGACAGGAGTG | | 112 |
| | T: C/TTTACTCAGAG | 60/58 | 113 |
| INVS.UTR | Fbio: CATGCCTGCAGCCTTACTG | | 114 |
| | R: GGTCCTTGAGCTCAGGCTAA | | 115 |
| | Seq: CTGTGTGAGAGCAGAAAGAAA | | 116 |
| | T: T/CATTCTGACATTCAC | 59/57 | 117 |
| TEX10.3 | F: CGTCTGCAGAGAAAACAA | | 118 |
| | Rbio: GAGGATACTGTTCGTTTG | | 119 |
| | Seq: TGTGACACTGCACCCGAAC | | 120 |
| | T: C/TGCTGTCTCCTCACC | 52/50 | 121 |

TABLE 3-continued

Primers for pyrosequencing.

| Gene | Primers | Tm | SEQ ID NO: |
|---|---|---|---|
| TEX10.1 | F: GGGGTCTAAAGCTGGGATGT | | 122 |
| | Rbio: CAGTCTCTTGTTCCCTCGG | | 123 |
| | Seq: TGGCAGGCTCAAGGCCTA | | 124 |
| | T: G/ATCACTGGAAGCAGGG | 59/58 | 125 |
| TEX10.2 | Fbio: TGGGACACTTCCAACAAACA | | 126 |
| | R: CCAAACTTCAGCCATTAATAAACC | | 127 |
| | Seq: TTATCAAAACAACACTTA | | 128 |
| | T: T/AGACTTACCTTTATGTTAA | 60/58 | 129 |
| TMEFF1 | F: CCTATGTCGACAATCTTTGTAC | | 130 |
| | Rbio: ATTAGTAGCAGAACGAAGAAATTC | | 131 |
| | Seq: TGAGAAATATTTGATGCTTT | | 132 |
| | T: A/GTTGGCTTTTTA | 58/57 | 133 |

F refers to forward primer;
Fbio refers to biotinylated forward primer;
R refers to reverse primer;
Rbio refers to biotinylated reverse primer;
Seq refers to sequencing primer; and
T refers to target sequence to be analyzed.

Identical-By-Descent (IBD) Mapping Assigns Grey to a ~350 kb Region

Grey was first assigned to horse chromosome 25 (Swinburne et al., *Animal Genetics*, 33:338-342 (2002); Henner et al., *Mamm. Genome*, 13:535-537 (2002); and Locke et al., *Anim. Genet.*, 33:329-337 (2002)) and subsequently fine-mapped to a region corresponding to 6.9 Mbp on human chromosome 9q (Pielberg et al., *Anim. Genet.*, 36:390-395 (2005)). The region did not harbour any identifiable candidate genes for a pigmentation phenotype. It was hypothesized that Grey represents a single mutation event, because of its unique phenotypic characteristics and the presumed strong selection, and consequently that all Grey horses have inherited the mutation from a common ancestor.

Coding sequences from the 6.9 Mbp region in human were aligned with homologous sequences in other mammals and PCR primers were designed for sequencing and detection of Single Nucleotide Polymorphisms (SNPs). SNPs were screened on a panel of Grey (G/G or G/g) and non-grey (g/g) horses. SNPs in the interval from position 29,095,813 to 28,743,518 on horse chromosome 25 and approximately corresponding to position 101.6 to 102.1 Mbp (~470 kb) on human chromosome 9q31 defined the Grey critical interval since markers within this interval exhibited complete linkage disequilibrium (LD) with Grey (Table 4). The Grey interval is surprisingly large given the fact that the material includes as divergent populations as Icelandic and Arabian horses that have been separated for at least 1,000 years. The results implicate a very low rate of recombination in the region as also indicated in a linkage study (Pielberg et al., *Anim. Genet.*, 36:390-395 (2005)). Based on these results, it was concluded that the causative mutation is located in this ~350 kb interval and that all Grey horses tested (>700 from eight breeds) have inherited Grey from a common ancestor. Interestingly, one non-grey haplotype was identical to the Grey haplotype for all tested SNPs, suggesting that it may represent the ancestral haplotype for Grey.

TABLE 4

Single Nucleotide Polymorphisms tested for association with the Grey allele on horse chromosome 25. NR4A3.2 and INVS.3 (in bold italics) represent the flanking markers for the Grey interval.

| Marker | Position[a] | Allele[b] | | Grey horses | | | Non-grey horses | | |
|---|---|---|---|---|---|---|---|---|---|
| | | A | B | AA | AB | BB | AA | AB | BB |
| TGFBR1 | 29,687,971 | A | T | 9 | 18 | 11 | 4 | 8 | 20 |
| SNPgrey1 | 29,243,371 | T | C | 32 | 6 | 0 | 27 | 4 | 1 |
| SNPgrey2 | 29,243,313 | T | C | 7 | 24 | 7 | 2 | 8 | 22 |
| SNPgrey3 | 29,240,577 | C | T | 12 | 20 | 6 | 6 | 9 | 17 |
| SNPgrey4 | 29,121,942 | T | G | 28 | 12 | 0 | 14 | 12 | 5 |
| SNPgrey5 | 29,120,937 | A | G | 33 | 7 | 0 | 13 | 16 | 4 |
| *NR4A3.2* | *29,095,813* | *C* | *T* | *26* | *6* | *2* | *26* | *3* | *1* |
| NR4A3.1 | 29,076,114 | G | A | 33 | 8 | 0 | 15 | 17 | 6 |
| TXNDC4 | 28,940,160 | T | C | 30 | 13 | 0 | 12 | 18 | 8 |
| INVS.1 | 28,800,463 | T | C | 29 | 13 | 0 | 7 | 16 | 9 |
| INVS.2 | 28,744,174 | A | G | 33 | 11 | 0 | 15 | 17 | 6 |
| *INVS.3* | *28,743,518* | *C* | *A* | *24* | *17* | *2* | *17* | *14* | *7* |
| INVS.4 | 28,742,934 | T | C | 6 | 33 | 4 | 0 | 4 | 34 |
| INVS.UTR | 28,740,562 | C | T | 10 | 30 | 4 | 1 | 10 | 27 |
| TEX10.3 | 28,738,799 | T | C | 13 | 25 | 1 | 2 | 17 | 13 |
| TEX10.1 | 28,730,901 | A | G | 27 | 14 | 0 | 9 | 16 | 6 |
| TEX10.2 | 28,686,743 | T | A | 6 | 29 | 5 | 0 | 3 | 28 |
| TMEFF1 | 28,524,848 | A | G | 3 | 19 | 15 | 2 | 8 | 20 |

[a]Position in the horse genome (see internet site: "genome.ucsc.edu"; Build January 2007 (equCab1) assembly).
[b]Definition of the SNP alleles for each marker.

TABLE 5

Complete association between the 4.6 kb duplication in intron 6 of STX17 and the Grey allele across breeds.

| Breed | n | Genotype | | |
|---|---|---|---|---|
| | | D/D | D/— | —/— |
| Grey horses | | | | |
| Arabian | 22 | 4 | 18 | 0 |
| Connemara | 3 | 0 | 3 | 0 |
| Icelandic | 1 | 0 | 1 | 0 |
| Lipizzaner | 10 | 5 | 5 | 0 |
| New forest pony | 1 | 0 | 1 | 0 |
| Shetland pony | 1 | 0 | 1 | 0 |
| Thoroughbred | 3 | 0 | 3 | 0 |
| Welsh | 2 | 1 | 1 | 0 |
| Total: | 43 | 10 | 33 | 0 |
| Non-grey horses | | | | |
| Arabian | 18 | 0 | 0 | 18 |
| Connemara | 4 | 0 | 0 | 4 |
| Fjord horse | 10 | 0 | 0 | 10 |
| Friesian | 5 | 0 | 0 | 5 |
| Haflinger | 10 | 0 | 0 | 10 |
| Icelandic | 11 | 0 | 0 | 11 |
| Morgan horse | 10 | 0 | 0 | 10 |
| New forest pony | 10 | 0 | 0 | 10 |
| North Swedish Horse | 10 | 0 | 0 | 10 |
| Shetland pony | 10 | 0 | 0 | 10 |
| Swedish warmblood | 4 | 0 | 0 | 4 |
| Thoroughbred | 7 | 0 | 0 | 7 |
| Welsh | 4 | 0 | 0 | 4 |
| Total: | 113 | 0 | 0 | 113 |

D = presence of STX17 duplication

The Grey Critical Region Contains Four Genes

Figure 2:
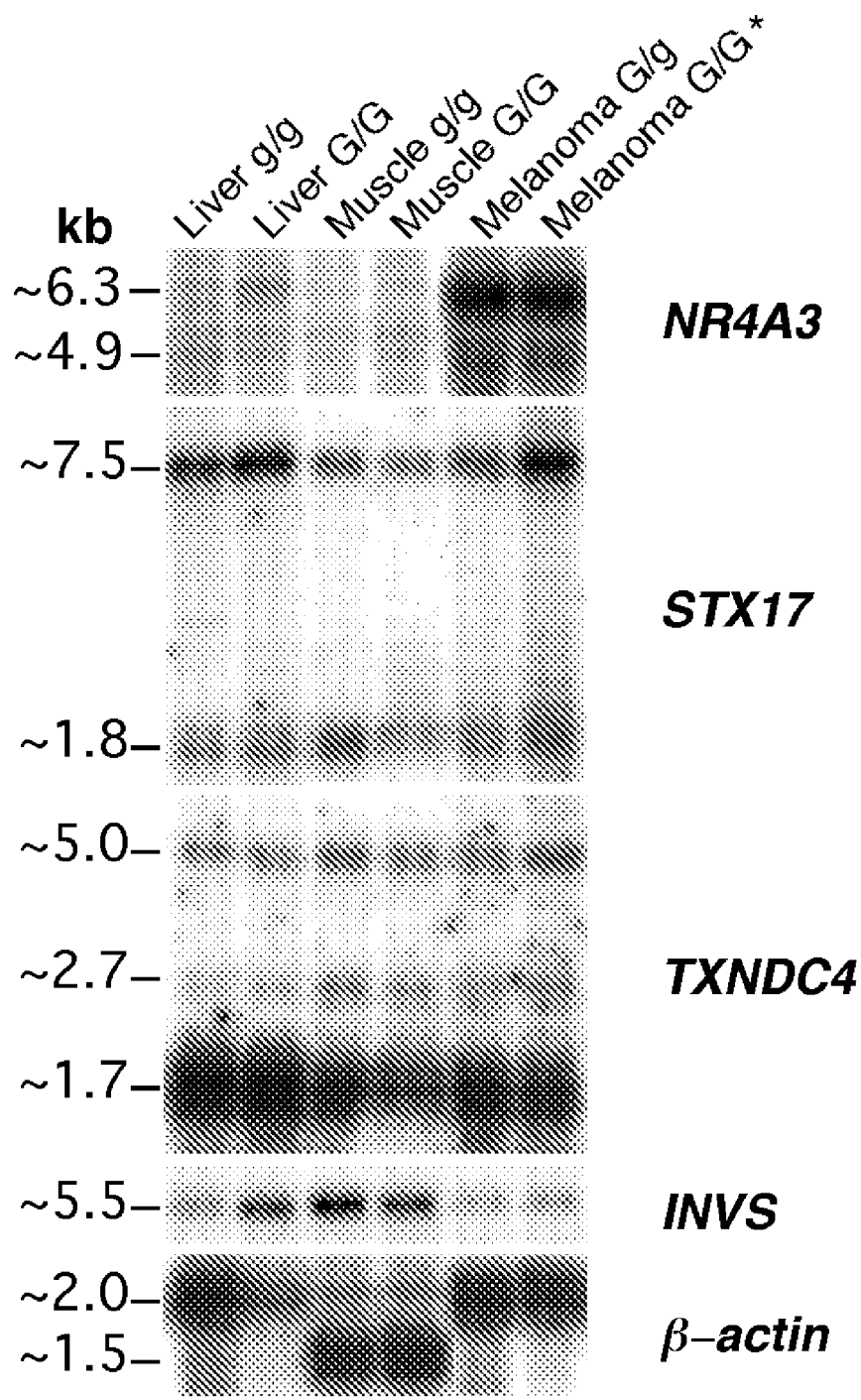
FIG. 2 is a photograph of a multiple-tissue Northern blot analysis of the genes in the Grey critical region and from horses of the indicated genotype. β-actin was used as internal control. The estimated transcript sizes are indicated.

The corresponding region in humans, mice, and dogs contains four known genes: NR4A3 (nuclear receptor subfamily 4, group A, member 3), STX17 (syntaxin 17), TXNDC4 (thioredoxin domain containing 4), and INVS (inversin) (FIG. 1). SNPs were developed for these genes and genetic analysis confirmed that they are all located in the Grey critical interval (Table 4). None of the genes has previously been associated with pigmentation defects or development of melanoma. Northern blot and reverse transcriptase (RT)-PCR analysis revealed that all four genes are expressed in Grey melanoma tissue and no variant transcript was detected in Grey horses (FIG. 2). However, the high expression of NR4A3 in melanomas from Grey horses was striking.

Figure 3:
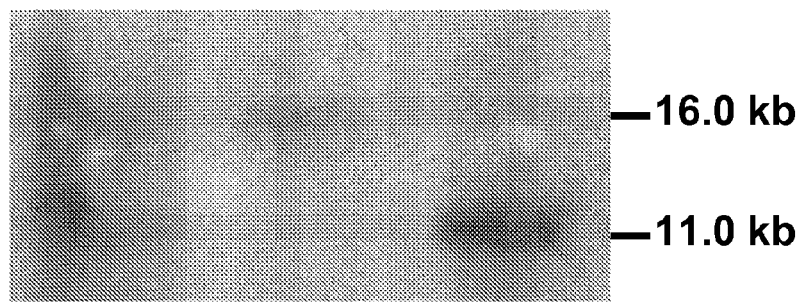
FIG. 3 is a photograph of a Southern blot analysis of genomic DNA restricted with BamHI and probed with a horse STX17 cDNA fragment (exon 2-8). Three horses representing the three different genotypes at the Grey locus are shown. The fragment sizes of the two fragments in kilobases are indicated.

A 4.6 kb Duplication in STX17 Intron 6 Exhibits a Complete Association with Grey Sequence analysis of all exons from the four genes (as defined in the human assembly) revealed no unique sequence polymorphism associated with Grey. Southern blot analysis of genomic DNA revealed no polymorphism for NR4A3, TXNDC4, or INV but a ~4.6 kb duplication was present within STX17 (FIG. 3). Fine mapping of the duplication revealed that it is located in intron 6. The entire intron was sequenced from several horses to determine the exact position of the duplication. The sequenced Grey alleles exhibited 39 SNPs in comparison with non-grey haplotypes. The "ancestral" non-grey haplotype exhibited an identical sequence as Grey but did not include the duplication.

A diagnostic PCR-based test for the STX17 duplication was used to screen more than 43 Grey horses and more than 100 non-grey horses representing eight breeds. The duplication was detected in the homozygous or heterozygous condition in all Grey horses but in none of the non-grey horses (Table 5) and thus qualifies as a candidate causal mutation.

Characterization of STX17

Figure 4:
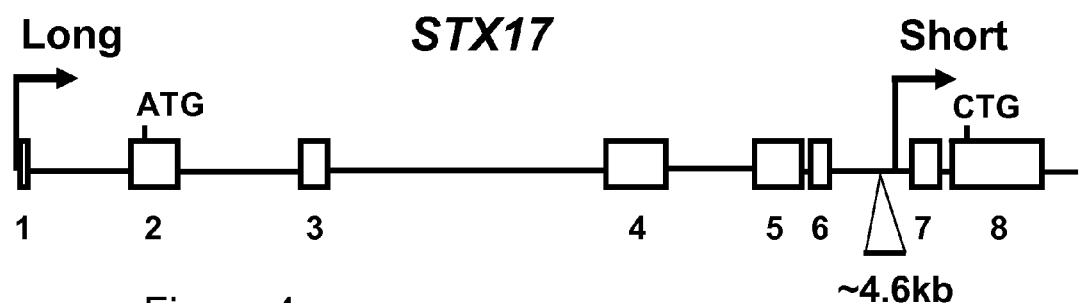
FIG. 4 is a schematic diagram of an STX17 exon/intron organization including the start of transcription for long and short isoforms. The location of the 4.6 kb duplication in intron 6 associated with Grey is indicated.

ESTs from several mammals, including humans, revealed that an alternative STX17 transcript can be initiated just downstream of the Grey duplication breakpoint (FIG. 4). The expression of this transcript was confirmed both in normal tissues from all horses and in melanoma tissue from Grey horses. This truncated transcript was spliced exactly as the long transcript and includes a part of intron 6 and exons 7 and 8. The only ATG codons in frame with the coding sequence could only generate short polypeptides (20 or 21 residues). There was a putative alternative CTG start codon in exon 8 that may generate a polypeptide with 74 residues. This CTG was confirmed to be used as a start codon by transfection experiments using two different vectors in which FLAG was fused to the N-terminal end directly followed by the CTG codon in frame, or by keeping the entire 5'UTR from the alternative transcript and fusing FLAG in frame at the 3' end. These two constructs generated recombinant polypeptides of identical molecular weights as determined by Western blot analysis. These results indicate that the alternative transcript is translated into a short polypeptide of 74 amino acids. Interestingly, the part of the 5'UTR of the short transcript encoded by intron 6 is evolutionary well conserved down to fishes. The EvoFold program (Pedersen et al., *PLoS Computat. Biol.*, 2:e33 (2006)) predicted an evolutionary conserved RNA structure for this 5'UTR sequence.

Figure 5:
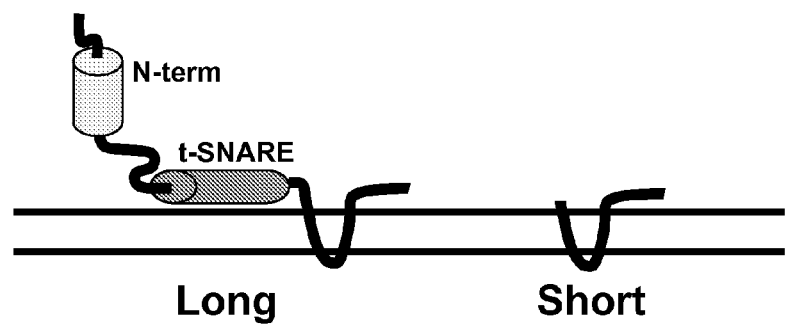
FIG. 5 is a schematic diagram of the predicted polypeptide corresponding to the two different STX17 transcripts.

The full-length transcript encodes a polypeptide of 302 amino acids with an N-terminal region of unknown function, a well conserved syntaxin domain followed by two transmembrane regions and a carboxyterminal tail (FIG. 5). The short transcript only includes the transmembrane regions and the carboxyterminal tail. The presence of two transmembrane regions implies that the N-terminal domains and the carboxyterminal tails are located on the same side of the membrane (FIG. 5). STX17 is the only syntaxin with such a carboxyterminal tail (Steegmaier et al., *J. Biol. Chem.*, 273:34171-34179 (1998)), suggesting that it has a distinct function.

Expression of both STX17 and NR4A3 from Grey Chromosomes are Upregulated in Melanomas.

STX17 and NR4A3 were further investigated for their involvement in the Grey phenotype due to the presence of a duplication in the former (FIG. 3) and the high expression in Grey melanoma of the latter (FIG. 2). Syntaxins contain SNARE domains and are involved in intracellular membrane trafficking (Bonifacino and Glick, Cell, 116:153-166 (2004)). Syntaxin 17 was first isolated in a two-hybrid screen using STX3 as bait (Steegmaier et al., *J. Biol. Chem.*, 273:34171-34179 (1998)). It is a divergent member of the syntaxin family with a broad tissue distribution. STX17 was reported to be partially associated with the endoplasmic reticulum and exhibited a nuclear localization in some malignant cells (Zhang et al., *J. Histochem. Cytochem.*, 53:1371-1382 (2005)). NR4A3, also denoted NOR-1, belongs to the NR4A subgroup of the nuclear hormone receptor superfamily (Maxwell and Muscat, *Nucl. Recept. Signal.*, 4:e002 (2006)).

Figure 6:
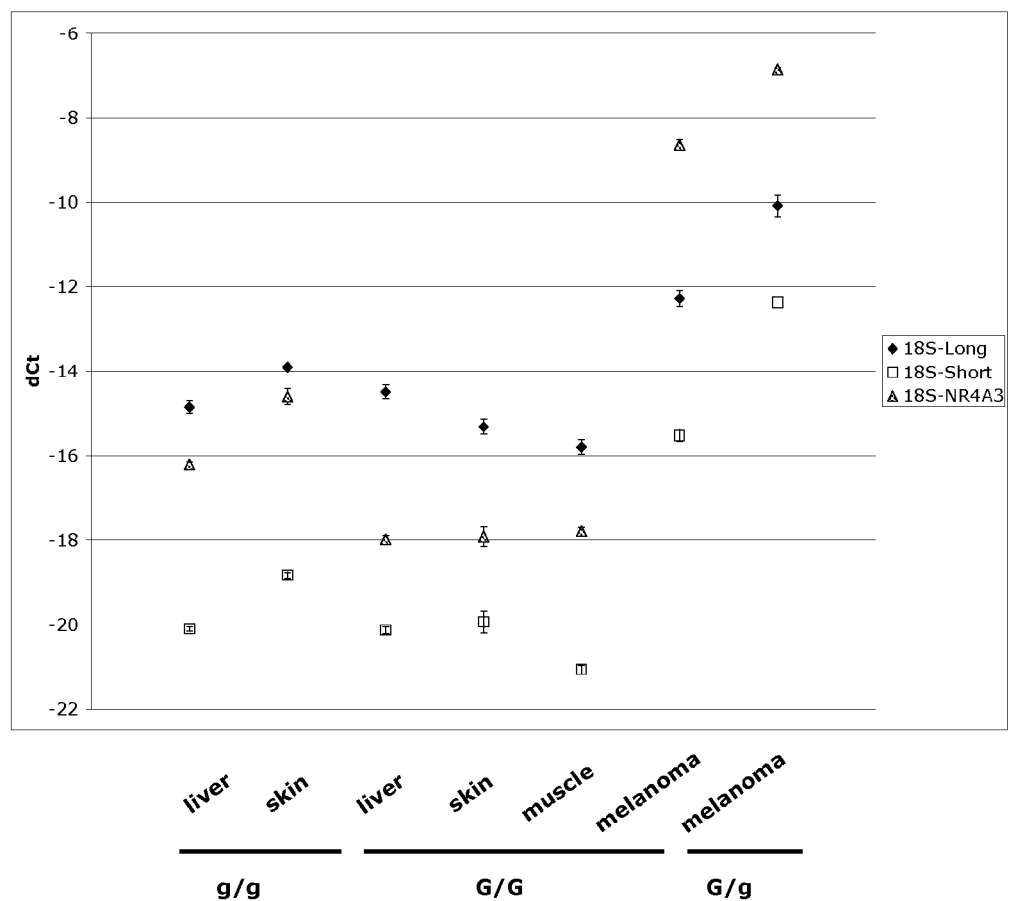
FIG. 6 is a graph plotting real-time PCR analysis of STX17 (short and long transcripts) and NR4A3 expression in relation to the expression of 18S-rRNA in different tissues from Grey and non-grey horses.
Figure 7:
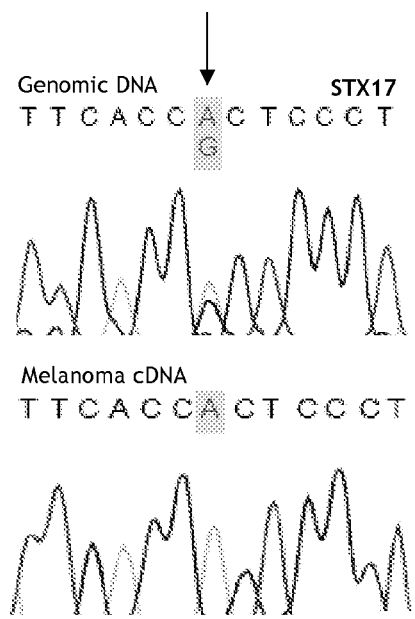
FIG. 7 contains results from a differential expression analysis for STX17 using melanoma tissue from a G/g heterozygous horse. The upper case letter "G" is an abbreviation for the dominant allele causing Grey coat color. The lower case letter "g" is an abbreviation for the recessive wild-type allele at this locus. Genomic DNA was used as reference.

The STX17 duplication in Grey horses is located in intron 6 just upstream of the initiation of a short alternative transcript. A bioinformatic analysis of the duplicated region did not reveal any obvious protein- or microRNA-coding sequences. However, the region contains several elements that are well conserved among mammals indicating that the duplication may include regulatory elements. The relative expression of the long and short isoform of STX17 in different tissues from Grey and non-grey horses was assessed by real-time PCR analysis using 18S as an internal control (FIG. 6). The long isoform was clearly the predominant form in all tissues tested, and there was a strong correlation between the expressions levels of the two forms. Both the long and short isoforms of STX17 were markedly upregulated in melanoma tissue from Grey horses compared with skin, liver, and muscle from both Grey and non-grey horses (FIG. 6). In order to more directly study differential expression between alleles, the relative expression of alleles in Grey heterozygotes was quantified using SNPs located in the part of intron 6 encoding the 5'UTR of the short transcript. This analysis was not possible for the long form due to the lack of suitable polymorphisms. Sequence analysis of genomic DNA from three G/g heterozygotes confirmed that they were heterozygous for two SNPs in this region. However, sequence analysis of cDNA from melanoma tissue revealed only expression of one allele, demonstrating differential expression of the short isoform in these three Grey heterozygotes (FIG. 7). The strong correlation between the two isoforms (FIG. 7) implies that this differential expression can occur for the long form as well.

Figure 8:
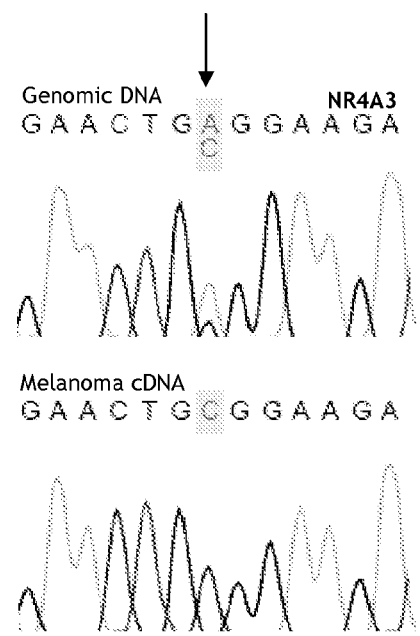
FIG. 8 contains results from a differential expression analysis for NR4A3 using melanoma tissue from a G/g heterozygous horse. Genomic DNA was used as reference.
Figure 9:
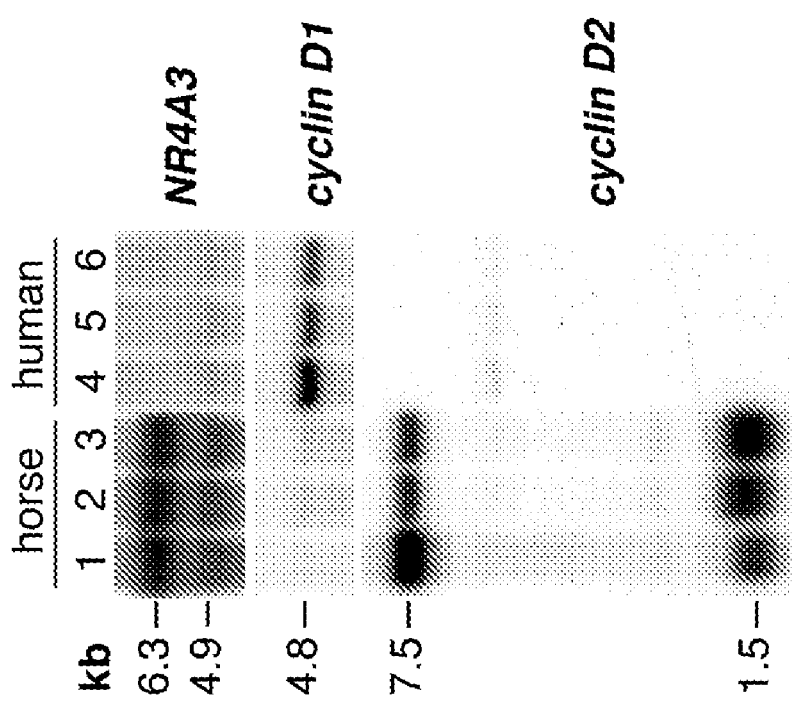
FIG. 9 contains photographs of a Northern blot analysis demonstrating that enhanced expression of NR4A3 nucleic acid is associated with high expression of a cyclin D2 transcript but not a cyclin D1 transcript in Grey horse melanoma. Lanes 1, 2, and 3: horse melanoma; Lanes 4, 5, and 6: human melanoma.
Figure 10:
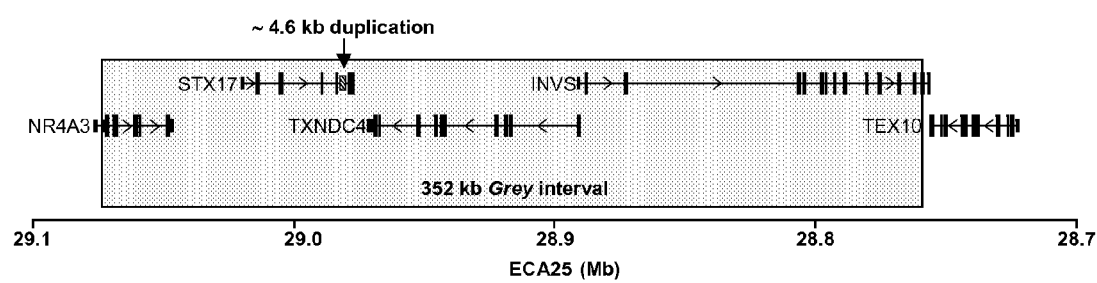
FIG. 10 is a schematic diagram of the gene content of the Grey interval based on the horse genome assembly as presented on the UCSC server at "genome.ucsc.edu"; Build January 2007 (equCab1) assembly); Karolchik et al., *Nucl. Acids Res.*, 31(1):51-54 (2003)). The 352 kb region exhibiting complete association with Grey is indicated by a box, and the location of the 4.6 kb duplication in STX17 intron 6 is marked with an arrow.

Northern blot analysis revealed a high expression of NR4A3 in horse melanomas (FIG. 2) whereas no expression of another NR4A member (NR4A1) was detected. This result was confirmed by real-time PCR analysis (FIG. 6). Sequence analysis of cDNA from Grey heterozygotes revealed only NR4A3 expression from the Grey allele demonstrating that a cis-acting regulatory mutation is underlying the upregulation of expression (FIG. 8). The expression levels of cyclin D1 and D2 in Grey melanoma cells were investigated, and both Northern blot analysis revealed high expression of cyclin D2 but not D1 (FIG. 9).

The results provided herein demonstrate that Greying with age in horses is caused by a cis-acting regulatory mutation since the two neighbouring genes STX17 and NR4A3 both exhibit differential expression in horse melanomas. The 4.6 kb duplication in intron 6 of STX17 constitutes this regulatory mutation because (i) a complete association to Grey was found for >100 horses, (ii) the duplication is the only observed difference between the Grey and non-grey "ancestral" haplotypes, and (iii) tandem duplications are notoriously unstable (Bailey et al., *Science*, 297:1003-1007 (2002)); it appears extremely unlikely that such a complete association between the duplication and the phenotype could have been maintained over thousands of years unless it is the causative mutation. In fact, the observed "ancestral" haplotype may not be an ancestral haplotype but a Grey haplotype that has lost the duplication and thereby the association with the Grey phenotype. There appears to be no documented cases of revertants (e.g., a homozygous Grey stallion that produces a non-grey progeny) although such events are difficult to verify in an outbred species like the horse. However, somatic revertants are expected to cause pigmented spots and, interestingly, speckling is a characteristic feature of the Grey phenotype.

The results provided herein also demonstrate that overexpression of STX17 or NR4A3 can be a cause for the phenotypes associated with greying with age. The results that cyclin D2, which has been shown to be a target gene for NR4A3 (Nomiyama et al., *J. Biol. Chem.*, 281:33467-33476 (2006)), is upregulated in melanomas from Grey horses suggests a plausible mechanism for how the Grey mutation predisposes horses to the development of melanoma. For example, the overexpression of NR4A3 can result in over expression of cyclin D2, which can to promote cell proliferation and thereby lead to melanoma development.

Example 2

Silencing of STX17 and NR4A3 in a Grey Melanoma Cell Line Inhibits Proliferation siRNA Treatment Synthetic double-stranded small interfering RNAs (Ambion Silencer® Select Pre-designed siRNA, cat. 4392420) were designed to silence the expression of NR4A3 (siNR4A3__1 and __2) and the short form of STX17 (siSTX-short1, 2, 3). Scrambled siRNA (Ambion Silencer® Select Negative Control siRNA, cat. 4390843) and siRNA for GAPDH (Ambion Silencer® Select Pre-designed siRNA, cat. 4392420) were used as negative controls.

TABLE 6

List of siRNA oligonucleotides used for silencing STX17 and NR4A3

| siRNAs ID | Target | senseSeq | antisenseSeq |
|---|---|---|---|
| s219844 | STXshort3 | CUGCUGCUGUGAAUGUUGAtt (SEQ ID NO: 134) | UCAACAUUCACAGCAGCAGtg (SEQ ID NO: 135) |
| s219846 | STXshort1 | GUUUUAAACUGAAUCUUCAtt (SEQ ID NO: 136) | UGAAGAUUCAGUUUAAAACag (SEQ ID NO: 137) |

TABLE 6-continued

List of siRNA oligonucleotides used for silencing STX17 and NR4A3

| siRNAs ID | Target | senseSeq | antisenseSeq |
|---|---|---|---|
| s219848 | STXshort2 | GAUCAAACCAUAUUGUAUUtt (SEQ ID NO: 138) | AAUACAAUAUGGUUUGAUCtg (SEQ ID NO: 139) |
| s219856 | NR4A3_1 | CACUGAGCAUGAUCACAGAtt (SEQ ID NO: 140) | UCUGUGAUCAUGCUCAGUGct (SEQ ID NO: 141) |
| s219857 | NR4A3_2 | CAUUAAAGACUUUUCCUUAtt (SEQ ID NO: 142) | UAAGGAAAAGUCUUUAAUGga (SEQ ID NO: 143) |
| s219852 | GAPDH | CCACGAGAAAUAUGACAAUtt (SEQ ID NO: 144) | AUUGUCAUAUUUCUCGUGGtt (SEQ ID NO: 145) |

Melanoma cells from a Grey horse (provided by Monika H. Seltenhammer, University of Veterinary Medicine, Vienna, Austria) were split to 75-cm² tissue culture plates (NUNC) three days before transfection. Cell suspension (5×10⁵ cells per 1 mL growth medium without antibiotics) was harvested by trypsinizing with 0.05% Trypsin-EDTA solution (Invitrogen), suspended, centrifuged at 1500 rpm for 5 minutes, and re-suspended in growth medium. The cell suspension was added to an equal volume of the transfection solution that consisted of 5-20 pmol siRNA and 5 µL lipofectamine2000 CD (Invitrogen) per 0.5 mL OptiMEM (Invitrogen) in 12-well plates. After 24 hours, the solution was replaced with fresh growth medium, and the transfected cells were incubated for an additional 2-3 days. PBS was used to wash and collect cells for silencing validation by qPCR and Western blotting. For each treatment with every single siRNA oligonucleotides, biological triplicates were prepared for statistical analysis.

Proliferation Assay

Every 24 hours after transfection, growth medium with 10% AlamarBlue (Invitrogen) was added 4 hours before absorbance reading at wavelengths 570 and 600 nm using Sunrise microplate reader (Tecan). Proliferation curves after silencing were generated according to the manufacturer's protocol.

Results

Figure 33:
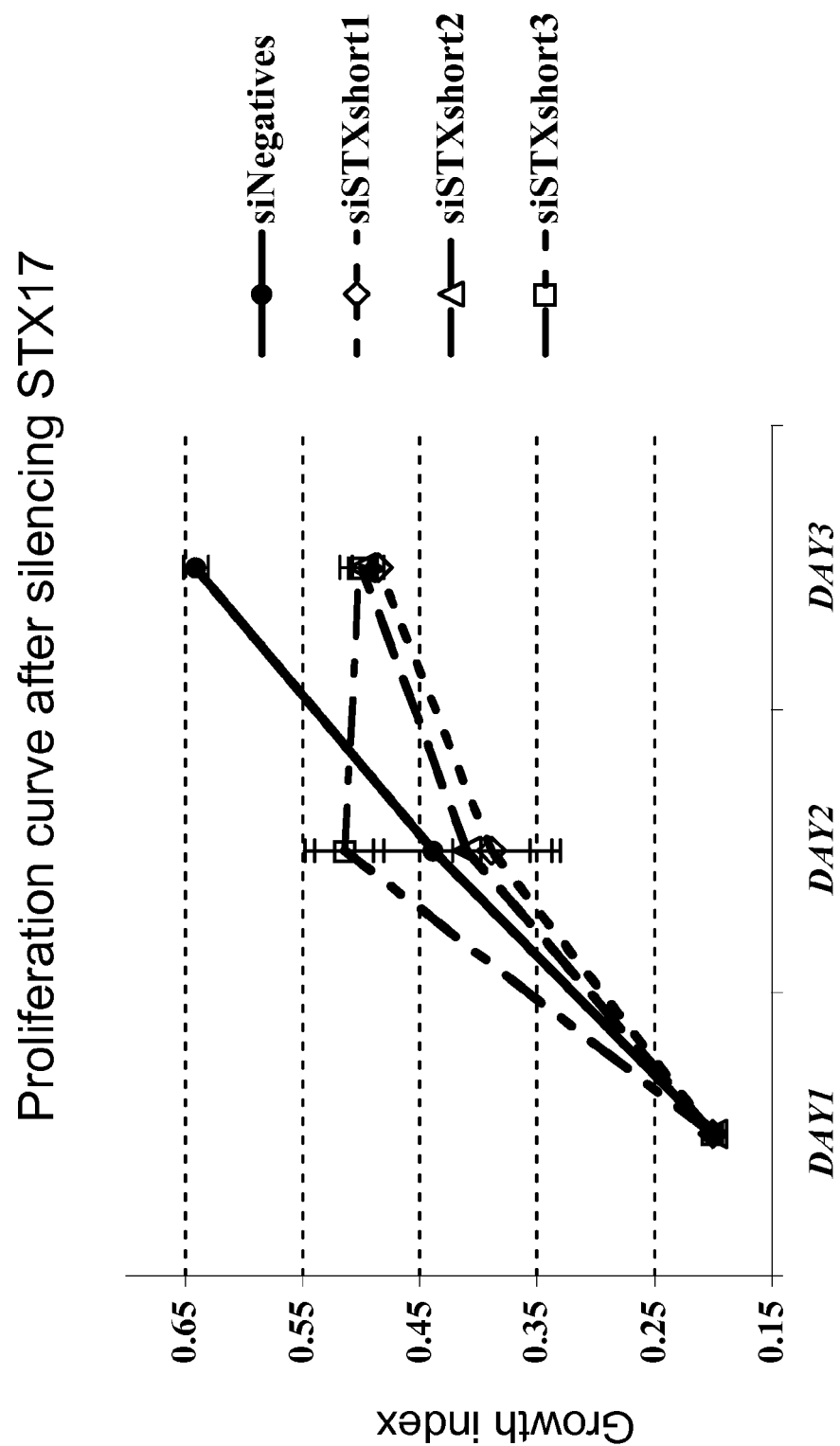
FIG. 33 is a graph showing the results of silencing the STX17 short transcript. The solid line represents the negative control, and the broken lines represent the results obtained using three different siRNA oligonucleotides. The differences at day 3 are statistically significant (P<0.05).
Figure 34:
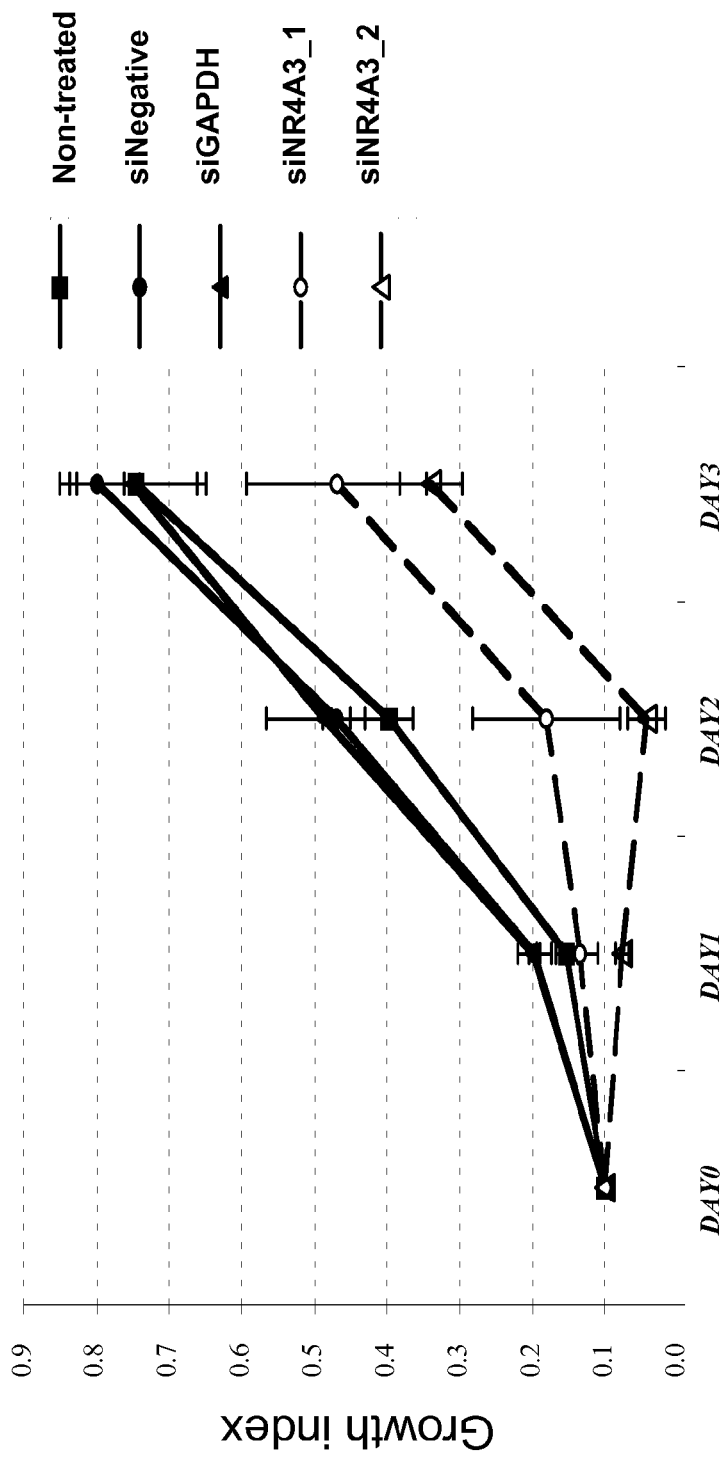
FIG. 34 is a graph showing the results of silencing the NR4A3 transcript using two different siRNA oligonuclueotides. The solid lines represent negative controls, and the broken lines represent the results obtained using two different siRNA oligonucleotides. The differences at day 3 are statistically significant (P<0.05).

Silencing of the short form of STX17 using three different oligonucleotides led in all cases to significant inhibition of proliferation of the grey melanoma cell line (FIG. 33). Similarly, silencing of NR4A3 also inhibited the proliferation of the Grey melanoma cell line significantly (FIG. 34). These results indicate that RNA interference against STX17 and/or NR4A3 can be used to treat Grey melanomas.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for assisting a horse breeder or horse owner in assessing a horse for the presence of a Grey allele, wherein said method comprises:
   (a) sequencing a portion of intron 6 of STX17 nucleic acid of said horse to determine whether or not said horse comprises a duplication in said intron 6,
   (b) classifying said horse as containing a Grey allele if said horse comprises said duplication, and
   (c) classifying said horse as lacking a Grey allele if said horse does not comprise said duplication.

2. The method of claim 1, wherein said horse is a foal.

3. The method of claim 1, wherein said horse comprises black, brown, or chestnut hair.

4. The method of claim 1, wherein said method comprises determining whether or not said horse is homozygous for said duplication.

5. The method of claim 4, wherein said method comprises classifying said horse as being homozygous for said Grey allele if said horse is homozygous for said duplication.

6. The method of claim 1, wherein said method comprises determining whether or not said horse is heterozygous for said duplication.

7. The method of claim 6, wherein said method comprises classifying said horse as being heterozygous for said Grey allele if said horse is heterozygous for said duplication.

8. A method for assisting a horse breeder or horse owner in assessing a horse for the presence of a Grey allele, wherein said method comprises:
   (a) using a nucleic acid probe capable of detecting a breakpoint of a duplication in intron 6 of STX17 nucleic acid to determine whether or not said horse comprises said duplication,
   (b) classifying said horse as containing a Grey allele if said horse comprises said duplication, and
   (c) classifying said horse as lacking a Grey allele if said horse does not comprise said duplication.

9. The method of claim 8, wherein said nucleic acid probe comprises the nucleic acid sequence set forth in SEQ ID NO:32.

10. The method of claim 8, wherein said horse is a foal.

11. The method of claim 8, wherein said horse comprises black, brown, or chestnut hair.

12. The method of claim 8, wherein said method comprises determining whether or not said horse is homozygous for said duplication.

13. The method of claim 12, wherein said method comprises classifying said horse as being homozygous for said Grey allele if said horse is homozygous for said duplication.

14. The method of claim 8, wherein said method comprises determining whether or not said horse is heterozygous for said duplication.

15. The method of claim 14, wherein said method comprises classifying said horse as being heterozygous for said Grey allele if said horse is heterozygous for said duplication.

16. A method for assisting a horse breeder or horse owner in assessing a horse for the presence of a Grey allele, wherein said method comprises:
   (a) using a nucleic acid primer pair capable of amplifying nucleic acid comprising a breakpoint of a duplication in intron 6 of STX17 nucleic acid to determine whether or not said horse comprises said duplication,
   (b) classifying said horse as containing a Grey allele if said horse comprises said duplication, and
   (c) classifying said horse as lacking a Grey allele if said horse does not comprise said duplication.

17. The method of claim 16, wherein said horse is a foal.

18. The method of claim 16, wherein said horse comprises black, brown, or chestnut hair.

19. The method of claim 16, wherein said method comprises determining whether or not said horse is homozygous for said duplication.

20. The method of claim 19, wherein said method comprises classifying said horse as being homozygous for said Grey allele if said horse is homozygous for said duplication.

21. The method of claim 16, wherein said method comprises determining whether or not said horse is heterozygous for said duplication.

22. The method of claim 21, wherein said method comprises classifying said horse as being heterozygous for said Grey allele if said horse is heterozygous for said duplication.

* * * * *

SEQUENCE LISTING

```
<160> NUMBER OF SEQ ID NOS: 145

<210> SEQ ID NO 1
<211> LENGTH: 12157
<212> TYPE: DNA
<213> ORGANISM: Equus caballus Grey allele

<400> SEQUENCE: 1
tgagtatata actgttttg gctcagagac gttagattaa taggataaga ggcttttata      60
aatcactagg cttttgatta ggattttaat agaagttaca atttgtaaga ctggtattga     120
accatggata gaagtctaac tgtcctcaaa ttccagatca attcaataaa catttattaa     180
gcacttgtta tataaaaggc actgtcttag gtgcttggca ttggggatct gacaaggttg     240
gataaagaaa gaaaggaagc atgctgtctg ccttcagggg tttacagtgg gtggagatat     300
gcttggaccc ccaaaactga aatttcaagt gtgattgtta aatgcaaaga caaggtatga     360
agagaagtat tatccgctcc aagggaagga ggcagggatt gtgaggtgga agcgtcaagg     420
gtagcttcac aagataggta gtatttgctt aagccttgaa aactgagtaa agtttccgca     480
ggtgggagag agggagtgca tttgaagaac gctgaacaaa gccttggagt agtgaagtgt     540
```

```
atggcctccc aggaatgaca agttctgcag tgtaaccaaa gcacaaggta ccatgggcaa    600
gcaaagcaga gtggctgagg gccaggttta gatggtactg aaggccatac caaagaattt    660
gcactttgta ggcattaagg agccaataca ggttttttgag caggttagag tgatgtgatc    720
ctgtccgtgt ttcaggaaga tcactgttag cggtatgagt aatggcctta agagaggagg    780
aggttatagg caggacagct agttaggagt cattgcaaga gttgcaccaa gagcaatggc    840
aatacaagtg tgaaggtaaa ggagagctga gaggcatttc tggggtgcac ttattaggaa    900
ttggaggaag atgaaagagt caaagataag aaacattaag gctttattcg gcataatcgg    960
gtagacagtg atactgttaa catagattag ggaacataaa gtagatttgg tgggaaagat   1020
agattttctg ttgttatttt tttaaattat tcttattttt ccttcccagg aattatggga   1080
aggttggata tgtggatgtg tgtgtatatg tatgtacata acaggctcga gcctgtttct   1140
gcttatgctt ctcttaggtt taattctttg ttcttgatca gactgtgatt tgagggttgc   1200
gcatctttga gttagggttt ccctgacatc tggctttaaa ttataagaag ttcccagatc   1260
acacaatctc agaattggaa ttgaacttaa aaggacaact agtctaatcc ttctgctctt   1320
gcccaacttc tcaaatagat ggttttttgcc tcttttttgaa caattactgc aaggatgctt   1380
tctgcttcaa ccattccgtt ttgaggctct aactccagaa gttattcctt gtacacagta   1440
agctctgccc tgtgataact tccctctggc actttggccc tctggagccg tatactgaac   1500 aaatttttgtc ttttttcccat ataaatgtct ctacttttttg agaccaacat tttcctcctt   1560
caccctaccc cacctcactg tattttcttc tcttaagaac ccttgactgt ctaatgtgtt   1620
ccttctagaa tgtgatttct agtctttttta gtactggccc tttactctgc ttgttttcta   1680
gtttgtggat ttttcttgaa atgtaatgca aaaaattgaa tgcagtaaat tgtttaaagc   1740 gttttttcttt tttgatggct ttaagtcaga aaaagcaaaa tgtttgaagt ttatggagta   1800
gatatctgta caatatatta atatatttac gtataaaagg gaatgataca agaatcccaa   1860
actatttttg tttctagaat caagatttat tcaattattc taactcataa tctctgatct   1920
aatgtagttt ttaaaatctg taatgtatga ttacacaaat atatacattt gtcaaaagtc   1980
atcaatatgt acacattaca atgtgtgagt tacaatgtat gtgaattata cccaataaaa   2040
ttgatttaaa aaacaaacta acatgtgtata aagttcttct cattcaagac aagtacgttt   2100
ccctcctagt gggatagaca catgaaagga aagttagggg tttgtggcca tgtaacagtt   2160
acatatccga ttaggttacg taagcagctc ctaacccta atctaaggag gttcgtacag   2220
gaagactttg gccatagcca tagctctata caaatgtcct ttttataata atctgtaagg   2280
acatgagacg gaatgctatt aggcaaaagc tcaaggaga acctctgatt actatcccca   2340
gggtgactga gttctcgtga ccacatggtc aaggattcac agaagctcca tttaggcacc   2400
aaatgacttg ggaacataac cagagtgacc acacatcctc tcgttatcat cacatggtca   2460
tggtagtatc tgggccaatt aaccgtgtgt ttctggagca ctttctatgc gcatagtact   2520
gtgctaagct ccgtgaaaaa cagagaatcg tataaaaaga acctatagga tggtcgcggt   2580
agctgcacag catcgtggat gcgtttaatg tactgaactg tatatttaaa actgttaaaa   2640
gttcaagttt tatgttgtgc gtattttttac cacaatcaaa aagaaccttc aaggcccttg   2700
ggagatccag gtgtggtcca gtagatgtga ataaattcct atctactaag caccctgcat   2760 cgtcttttcct ctgccattat tgctcaagtg ccctcttctc ttcctgtgac tgtgaagcca   2820
gccttatttc tagtcaaggg gatgtaaaga actgtgggcc agtcgcttaa tagcatggca   2880
cccttggtgc tggtccagtt ttgtctctcc ttttgcctta ttccttatgg ctttttataat   2940
```

```
ctattttact ctggatgcat aaaaactggg ttgtgatgga ttagatcaga ttcctccatt  3000
tattacctat gtgaccttcg gggtattgtg ttgacagcaa tgagctttgt aaaattaatc  3060
agaagactca atgagatagt gcctattact tcccaccccc ttctcttcta ctgaccccaa  3120
ctgcatttct gcttttgtcc ctctctcatt tgattccctc tgtggctcct tgcttagaat  3180
tctgcttttg ccaccatcat tatgtttaaa cattttagta cgtagttcct gactccctct  3240
tttattgctg gatctcttgc tgtcaacatt ttacttacct actctgttta ccgcctactc  3300
taggccaata taattcttac tgtgcctgta tgtcatagtg tttgtaagct tgtttctggg  3360
cttttctgtg tatataagtg catgtgatta aggagtatag attacttacc tttggagttc  3420
agaaccagga tagctcagtg ttatctggga tggtcaagct gtaagactag agctgctatt  3480
gaaagtagcc tggaagttag agagtcagaa ataaaggaaa ataccagag ttctgatgtt  3540 agcttcttca agaaacctg tagctttcca agcacattaa taaaactaca cagccactag  3600
caagactctc cgtgggagag catgtattat ggctccagaa ggatttgggg gtgggtttgt  3660
tgaatgcatt attgttgctt gatgcagaga atgctgggcc tacaagtgtc caccacaagc  3720
tttcaaggga aaaacttctt cattagtttt gacttcagat gcccaaactg cattataatt  3780
gaacaagtat taacttagta agtcaaattt tcttcaaaat cttaggtgct cctataactg  3840
ctcattaaga ttcacttatt tttttcacgc aggtaagggg acctaattca gtgtttctta  3900
aaatgaaatt catagacata ttcttagagt ctttgaaaat tcttttctt taaaaggaa  3960 agttttata gtactctagt ttgagaaaca ctacggtgtc cctcataaat ggtttagttc  4020
attgttaaag ggatgctgag aacatatatg aggtgccaaa gtataaaatg tcaggaaggg  4080
agtttgaagg ttgtcaaatg ttggaggccc agggaggtga agcaaacat aagcacatcg  4140 gaagcaaaaa ggggaggttg gtggatagag gtgagaaggc tgctgagcca ccattgctgt  4200
cagcttggtt tcctatactg gggtaagttt gtgtatgtgt ggtttggccc agcataaaga  4260
gccaaagaca tagcggacaa gtggtgacca gattcagctc tgaatggatt ctagtttggc  4320
aatctctggg gagtgattaa caactttgac accagtttgc tgcctaacag taattgctgt  4380
gtcattgagt ccttcttact caagaagcag aatttgaaga tatgggcaaa gtttgggatt  4440
caaaccaagc aaaatagga aggagcaggc agatctgtac aatgagggac gactttgat  4500 cccagggtag aggctggtct tccctctgcc ttgtctccag gcccgtgttt aagcaagcgc  4560
cctgatgtca gtgaatgaat ccttacaggt gtgggctact ccccatggtg agacaggcct  4620
catcaggttc tgggattgcg gtgatgggga gcattgcagt tcaaataacc actgagctca  4680
ggcttcattt ggccctgtga tccttttctcc aattattcta aaggatcttt atgaaaaaat  4740
aataaagtaa aattttttaaa tttcacttaa aaaaactcat agagctgcaa tatgcaacct  4800
ttttaggaag gagcattaaa aaatatttcc ctgaggcctc gagattacac ttggggtaca  4860
gaaatggcaa taattatggc agattccacc atcttgacgg aacaattttg gggctgagag  4920
aaagacagtt ggctattttc cctctacgcc tcaacttgtc aagatacgga ggttgatgat  4980
cgagttttac atctgtgatt tatctggtag catagacttg atgcaagaac agaaagtgtt  5040
ggggatgtcc caaatagaaa caaggatagg gtatcagaaa tcctgacaag tggcacttat  5100
gcttctgtgg gttgggaaag gagagctaac attaaagaag ttttattgtc tgaggaaaat  5160
aaaaactgag tacatgaatg ctaggagaga tctaatgttt tagtgcccta gaattttcaa  5220
gcattatagg aaaagtttta atattttttt gatagcaaag aatgatgaga gttaagcttt  5280
ctttggaaga tcagcatgac ttttttctatt tttcccctca tattctacag acactatctc  5340
```

```
attttatcct cacttcaact ctgtgaggta tgagtatcat tatcctcact tggcagacga   5400
gagtactgac atatagggag cttgagtagt ttatccaagg gcacacagtg ctcgtgctgg   5460
gatctgaaca caggacatcc aaccaaaggt tgtgcccttta atcctatcat atatatatac   5520
ttgtggtttg ttttttttctt tgcttaggaa gattcgccct gagctaactt ctgttgccaa   5580
ccttcctctt tttgcttgag gaagattcgc cctgagctaa catctgtgcc agtcttcctt   5640
tgttttgtat gtgggtcacc accacagtat ggctgccaaa gagtggtgta ggtctgcacc   5700
caggaaccaa accagggccg ccaaagcgga gcatgccgaa caaccatgag gccatgaggc   5760
tggccctgct agtggctttt aaagtttgag aatcatggac ttgtagtatc agcaccacct   5820
gggaactcat tagaaatgca aaatctcaga attggaattg aacttaaaag gacaactagt   5880
ctaatccttc tgctcttgcc caacttctca aatagatggt ttttgcctct ttttgaacaa   5940
ttactgcaag gatgctttct gcttcaacca ttccgttttg aggctctaac tccagaagtt   6000
attccttgta cacagtaagc tctgcccctgt gataacttcc ctctggcact ttggccctct   6060
ggagccgtat actgaacaaa ttttgtcttt ttcccatata aatgtctcta cttttttgaga   6120 ccaacatttt cctccttcac cctaccccac ctcactgtat tttcttctct taagaacccct   6180 tgactgtcta atgtgttcct tctagaatgt gatttctagt cttttttagta ctggcccttt   6240 actctgcttg ttttctagtt tgtggatttt tcttgaaatg taatgcaaaa aattgaatgc   6300
agtaaattgt ttaaagcgtt tttctttttt gatggcttta agtcagaaaa agcaaaatgt   6360
ttgaagttta tggagtagat atctgtacaa tatattaata tatttacgta taaaagggaa   6420
tgatacaaga atcccaaact attttgttt ctagaatcaa gatttattca attattctaa   6480
ctcataatct ctgatctaat gtagtttttta aaatctgtaa tgtatgatta cacaaatata   6540
tacatttgtc aaaagtcatc aatatgtaca cattacaatg tgtgagttac aatgtatgtg   6600 aattatatccc aataaaattg atttaaaaaaa caaactaaac atgtataaag ttcttctcat   6660
tcaagacaag tacgtttccc tcctagtggg atagacacat gaaaggaaag ttaggggttt   6720
gtggccatgt aacagttaca tatccgatta ggttacgtaa gcagctccta acccctaatc   6780
taaggaggtt cgtacaggaa gactttggcc atagccatag ctctatacaa atgtcctttt   6840
tataataatc tgtaaggaca tgagacggaa tgctattagg caaaagctca aaggagaacc   6900
tctgattact atccccaggg tgactgagtt ctcgtgacca catggtcaag gattcacaga   6960
agctccattt aggcaccaaa tgacttggga acataaccag agtgaccaca catcctctcg   7020
ttatcatcac atggtcatgg tagtatctgg gccaattaac cgtgtgtttc tggagcactt   7080
tctatgcgca tagtactgtg ctaagctccg tgaaaaacag agaatcgtat aaaaagaacc   7140
tataggatgt tcgcggtagc tgcacagcat cgtggatgcg tttaatgtac tgaactgtat   7200
atttaaaact gttaaaagtt caagttttat gttgtgcgta ttttaccac aatcaaaaag   7260 aaccttcaag gcccttggga gatccaggtg tggtccagta gatgtgaata aattcctatc   7320
tactaagcac cctgcatcgt ctttcctctg ccattattgc tcaagtgccc tcttctcttc   7380
ctgtgactgt gaagccagcc ttatttctag tcaaggggat gtaaagaact gtgggccagt   7440
cgcttaatag catggcaccc ttggtgctgg tccagttttg tctctccttt tgccttattc   7500 cttatgcett ttataatcta ttttactctg gatgcataaa aactgggttg tgatggatta   7560
gatcagattc ctccatttat tacctatgtg accttcgggg tattgtgttg acagcaatga   7620
gctttgtaaa attaatcaga agactcaatg agatagtgcc tattacttcc cacccccttc   7680
tcttctactg accccaactg catttctgct tttgtccctc tctcatttga ttccctctgt   7740
```

```
ggctccttgc ttagaattct gcttttgcca ccatcattat gtttaaacat tttagtacgt   7800
agttcctgac tccctctttt attgctggat ctcttgctgt caacatttta cttacctact   7860
ctgtttaccg cctactctag gccaatataa ttcttactgt gcctgtatgt catagtgttt   7920
gtaagcttgt ttctgggctt ttctgtgtat ataagtgcat gtgattaagg agtatagatt   7980
acttaccttt ggagttcaga accaggatag ctcagtgtta tctgggatgg tcaagctgta   8040
agactagagc tgctattgaa agtagcctgg aagttagaga gtcagaaata aaggaaaata   8100
cctagagttc tgatgttagc ttcttcaaag aaacctgtag cttccaagc acattaataa    8160
aactacacag ccactagcaa gactctccgt gggagagcat gtattatggc tccagaagga   8220
tttgggggtg ggtttgttga atgcattatt gttgcttgat gcagagaatg ctgggcctac   8280
aagtgtccac cacaagcttt caagggaaaa acttcttcat tagttttgac ttcagatgcc   8340
caaactgcat tataattgaa caagtattaa cttagtaagt caaattttct tcaaaatctt   8400
aggtgctcct ataactgctc attaagattc acttatttt ttcacgcagg taaggggacc     8460
taattcagtg tttcttaaaa tgaaattcat agacatattc ttagagtctt tgaaaattct   8520
ttttctttaa aaaggaaagt ttttatagta ctctagtttg agaaacacta cggtgtccct   8580
cataaatggt ttagttcatt gttaaaggga tgctgagaac atatatgagg tgccaaagta   8640
taaaatgtca ggaagggagt ttgaaggttg tcaaatgttg gaggcccagg gaggtgaaag   8700
caaacataag cacatcggaa gcaaaaggg gaggttggtg gatagaggtg agaaggctgc     8760
tgagccacca ttgctgtcag cttggttttcc tatactgggg taagtttgtg tatgtgtggt   8820
ttggcccagc ataaagagcc aaagacatag cggacaagtg gtgaccagat tcagctctga   8880
atggattcta gtttggcaat ctctggggag tgattaacaa cttgacacc agtttgctgc     8940
ctaacagtaa ttgctgtgtc attgagtcct tcttactcaa gaagcagaat ttgaagatat   9000
gggcaaagtt tgggattcaa accaagcaaa atagggaagg agcaggcaga tctgtacaat   9060
gagggacgac ttttgatccc agggtagagg ctggtcttcc ctctgccttg tctccaggcc   9120
cgtgtttaag caagcgccct gatgtcagtg aatgaatcct tacaggtgtg ggctactccc   9180
catggtgaga caggcctcat caggttctgg gattgcggtg atggggagca ttgcagttca   9240
ataaccact gagctcaggc ttcatttggc cctgtgatcc tttctccaat tattctaaag     9300
gatctttatg aaaaaataat aaagtaaaat ttttaaattt cacttaaaaa aactcataga   9360
gctgcaatat gcaacctttt taggaaggag cattaaaaaa tatttccctg aggcctcgag   9420
attcacttg gggtacagaa atggcaataa ttatggcaga ttccaccatc ttgacggaac    9480
aattttgggg ctgagagaaa gacagttggc tattttccct ctacgcctca acttgtcaag   9540
atacggaggt tgatgatcga gttttacatc tgtgatttat ctggtagcat agacttgatg   9600
caagaacaga aagtgttggg gatgtcccaa atagaaacaa ggatagggta tcagaaatcc   9660
tgacaagtgg cacttatgct tctgtgggtt gggaaaggag agctaacatt aaagaagttt   9720
tattgtctga ggaaaataaa aactgagtac atgaatgcta ggagagatct aatgttttag   9780
tgccctagaa ttttcaagca ttataggaaa agtttaata ttttttttgat agcaaagaat    9840
gatgagagtt aagctttctt tggaagatca gcatgacttt ttctattttt cccctcatat   9900
tctacagaca ctatctcatt ttatcctcac ttcaactctg tgaggtatga gtatcattat   9960
cctcacttgg cagacgagag tactgacata tagggagctt gagtagttta tccaagggca  10020
cacagtgctc gtgctgggat ctgaacacag gacatccaac caaaggttgt gcccttaatc  10080
ctatcatata tatatacttg tggtttgttt ttttctttgc ttaggaagat tcgccctgag  10140
```

```
ctaacttctg ttgccaacct tcctctttt gcttgaggaa gattcgccct gagctaacat    10200
ctgtgccagt cttcctttgt tttgtatgtg ggtcaccacc acagtatggc tgccaaagag    10260
tggtgtaggt ctgcacccag gaaccaaacc agggccgcca agcggagca tgccgaacaa    10320
ccatgaggcc atgaggctgg ccctgctagt ggcttttaaa gtttgagaat catggacttg    10380
tagtatcagc accacctggg aactcattag aaatgcaaat tctcaggcct catcccaagc    10440
cccctgaatc agaaactctg gatgaagttc tccaggtgat tctggtgcac actccagtgt    10500
ggaaaccact gttgtattgg tctctgacga cgttagaaga agacttatag aggactttt    10560
tagggattgt gttagagatg tcaagatggt ggagaatata gcaatgaagg gataccatga    10620
aaggtctaac ggtgaagagg tacatacctg gcgtctgaga agggaaggaa tgtcaataat    10680
gtgataggaa gcaactgtga ggaaacaatt agctgtgttg tttgggtgtc ctgttctcgg    10740
atgaaatgat gattggaatt agaagagtgt tggtcacata cgcttcacta taagtgacta    10800
ggtcagttat ataaggacaa tcaaatactt cagggttcaa attgaattat ttcacagtca    10860
tcgaagaagt tggcatttag ctaggatcaa agagggattc tcttctttt ttctgtgaat    10920
taaaaagact agtctgtata ttgatgtgat ggtggttacg tgggtttatg catttatcag    10980
aaatcatcat actataccct taaaatgggt gcatattatt atatgtaaat tctgtctaaa    11040
taagttgat ttaaaaatgg gaatgtgggg ctggccctg tgtgcccgag cggttaagtt    11100
cgcgccctcc gctgcaggcg gcccagtgtt tcgttggttc gaatcctggg cacggacatg    11160
acactgctca tcaaaccacg ctgaggcagc atcccacatg ccacaactag aaggacccac    11220
aacaaagaat atacaactat gtaccggggt gctttgggga gaaaaaggaa aaaataaaat    11280
cttaaaaaaa aaaaaaaata gggtatagtg tactcgtggc cagttaatga gtttctgtca    11340
ctgaggtgtt tgagcagagg ttcagtaagc gcttgtcaga tatgtcgtag tggggcttcc    11400
cacatctgag ggagaaatcg cactcagcaa cctaaacatt ccttctaccc agaggttcca    11460
tgagtcacaa tttctgttgt gtcagccgca ggtgttgcca ttttgtgtag aatgcttggt    11520
taatatattt gatctgaaac atttaactt gtcatgattt taaaatgtat taaagtgtcc    11580
acgtgtgaaa cacaggacag tgaattcatt caccactccc tactgcatat cacaagtaga    11640
aagatttcat ggcagatcaa accatattgt attcttattc ctaaaacagt aatttgtatt    11700
tatcgtggca tcaagggtgt tttactccta aggcaaattt gcctgtttta aactgaatct    11760
tcaaagaaga taagttaggg aggattttg ctttgatcct gttttgttt ttttccatca    11820
aacccaacat gacatgtaaa tacttatttg gactttttt cttctcgaa agcagattta    11880
tttggagaac aatatgcttg tatgtttgaa tgaagtttag agtaagatgc ttttcctat    11940
aaaggtgcca ctcttttatt actgaataat taagtcacct ttttttatac aagtgaattt    12000
gtgctttcga cgtggtttgt cagatgctgt taaatgaact gctgttagac tccaaggctg    12060
cggcacacag gccctgatta caggagttaa aatagtgtgc attggctgac tgctgctccg    12120
cagcaggagc gctcactcat aattcctttg catctag                             12157
```

```
<210> SEQ ID NO 2
<211> LENGTH: 9154
<212> TYPE: DNA
<213> ORGANISM: Equus caballus

<400> SEQUENCE: 2
aatctcagaa ttggaattga acttaaaagg acaactagtc taatccttct gctcttgccc      60
aacttctcaa atagatggtt tttgcctctt tttgaacaat tactgcaagg atgctttctg     120
```

-continued

```
cttcaaccat tccgttttga ggctctaact ccagaagtta ttccttgtac acagtaagct    180 ctgcccgtg ataacttccc tctggcactt tggccctctg agccgtata ctgaacaaat     240 tttgtctttt tcccatataa atgtctctac tttttgagac caacatttc ctccttcacc    300 ctaccccacc tcactgtatt ttcttctctt aagaaccctt gactgtctaa tgtgttcctt    360
ctagaatgtg atttctagtc tttttagtac tggccctta ctctgcttgt tttctagttt    420 gtggatttt cttgaaatgt aatgcaaaaa attgaatgca gtaaattgtt taaagcgttt    480
ttcttttttg atggctttaa gtcagaaaaa gcaaatgtt tgaagtttat ggagtagata    540
tctgtacaat atattaatat atttacgtat aaaagggaat gatacaagaa tcccaaacta    600
tttttgtttc tagaatcaag atttattcaa ttattctaac tcataatctc tgatctaatg    660
tagtttttaa aatctgtaat gtatgattac acaaatatat acatttgtca aaagtcatca    720
atatgtacac attacaatgt gtgagttaca atgtatgtga attataccca ataaaattga    780
tttaaaaaac aaactaaaca tgtataaagt tcttctcatt caagacaagt acgtttccct    840
cctagtggga tagacacatg aaaggaaagt taggggtttg tggccatgta acagttacat    900
atccgattag gttacgtaag cagctcctaa cccctaatct aaggaggttc gtacaggaag    960
actttggcca tagccatagc tctatacaaa tgtcctttt ataataatct gtaaggacat   1020
gagacggaat gctattaggc aaaagctcaa aggagaacct ctgattacta tccccagggt   1080
gactgagttc tcgtgaccac atggtcaagg attcacagaa gctccattta ggcaccaaat   1140
gacttgggaa cataaccaga gtgaccacac atcctctcgt tatcatcaca tggtcatggt   1200
agtatctggg ccaattaacc gtgtgtttct ggagcacttt ctatgcgcat agtactgtgc   1260
taagctccgt gaaaaacaga gaatcgtata aaagaacct ataggatggt cgcggtagct    1320
gcacagcatc gtggatgcgt ttaatgtact gaactgtata tttaaaactg ttaaaagttc   1380
aagttttatg ttgtgcgtat ttttaccaca atcaaaaaga accttcaagg cccttgggag   1440
atccaggtgt ggtccagtag atgtgaataa attcctatct actaagcacc ctgcatcgtc   1500
tttcctctgc cattattgct caagtgccct cttctcttcc tgtgactgtg aagccagcct   1560
tatttctagt caagggatg taaagaactg tgggccagtc gcttaatagc atggcaccct    1620
tggtgctggt ccagttttgt ctctcctttt gccttattcc ttatggcttt tataatctat   1680
tttactctgg atgcataaaa actgggttgt gatggattag atcagattcc tccatttatt   1740
acctatgtga ccttcgggt attgtgttga cagcaatgag ctttgtaaaa ttaatcagaa    1800
gactcaatga gatagtgcct attacttccc acccccttct cttctactga ccccaactgc   1860
atttctgctt ttgtccctct ctcatttgat tccctctgtg gctccttgct tagaattctg   1920
cttttgccac catcattatg tttaaacatt ttagtacgta gttcctgact ccctcttta    1980 ttgctggatc tcttgctgtc aacattttac ttacctactc tgtttaccgc ctactctagg   2040
ccaatataat tcttactgtg cctgtatgtc atagtgtttg taagcttgtt tctgggcttt   2100
tctgtgtata taagtgcatg tgattaagga gtatagatta cttacctttg gagttcagaa   2160
ccaggatagc tcagtgttat ctgggatggt caagctgtaa gactagagct gctattgaaa   2220
gtagcctgga agttagagag tcagaaataa aggaaaatac ctagagttct gatgttagct   2280
tcttcaaaga aacctgtagc tttccaagca cattaataaa actacacagc cactagcaag   2340
actctccgtg ggagagcatg tattatggct ccagaaggat ttgggggtgg gtttgttgaa   2400
tgcattattg ttgcttgatg cagagaatgc tgggcctaca agtgtccacc acaagctttc   2460
aagggaaaaa cttcttcatt agttttgact tcagatgccc aaactgcatt ataattgaac   2520
```

```
aagtattaac ttagtaagtc aaattttctt caaaatctta ggtgctccta taactgctca    2580
ttaagattca cttattttt tcacgcaggt aaggggacct aattcagtgt ttcttaaaat     2640
gaaattcata gacatattct tagagtcttt gaaaattctt tttctttaaa aaggaaagtt    2700
tttatagtac tctagtttga gaaacactac ggtgtccctc ataaatggtt tagttcattg    2760
ttaaagggat gctgagaaca tatatgaggt gccaaagtat aaaatgtcag gaagggagtt    2820
tgaaggttgt caaatgttgg aggcccaggg aggtgaaagc aaacataagc acatcggaag    2880 caaaagggg aggttggtgg atagaggtga aaggctgct gagccaccat tgctgtcagc      2940
ttggtttcct atactggggt aagtttgtgt atgtgtggtt tggcccagca taaagagcca    3000
aagacatagc ggacaagtgg tgaccagatt cagctctgaa tggattctag tttggcaatc    3060
tctggggagt gattaacaac tttgacacca gtttgctgcc taacagtaat tgctgtgtca    3120
ttgagtcctt cttactcaag aagcagaatt tgaagatatg ggcaaagttt gggattcaaa    3180
ccaagcaaaa tagggaagga gcaggcagat ctgtacaatg agggacgact tttgatccca    3240
gggtagaggc tggtcttccc tctgccttgt ctccaggccc gtgtttaagc aagcgccctg    3300
atgtcagtga atgaatcctt acaggtgtgg gctactcccc atggtgagac aggcctcatc    3360
aggttctggg attgcggtga tggggagcat tgcagttcaa ataaccactg agctcaggct    3420
tcatttggcc ctgtgatcct ttctccaatt attctaaagg atctttatga aaaataata    3480 aagtaaaatt tttaaatttc acttaaaaaa actcatagag ctgcaatatg caaccttttt    3540
aggaaggagc attaaaaaat atttccctga ggcctcgaga ttacacttgg ggtacagaaa    3600
tggcaataat tatggcagat tccaccatct tgacggaaca attttggggc tgagagaaag    3660
acagttggct atttttcctc tacgcctcaa cttgtcaaga tacggaggtt gatgatcgag    3720
ttttacatct gtgattatc tggtagcata gacttgatgc aagaacagaa agtgttgggg    3780
atgtcccaaa tagaaacaag gatagggtat cagaaatcct gacaagtggc acttatgctt    3840
ctgtggggtg ggaaaggaga gctaacatta aagaagtttt attgtctgag gaaaataaaa    3900
actgagtaca tgaatgctag gagagatcta atgttttagt gccctagaat tttcaagcat    3960
tataggaaaa agtttaatat ttttttgata gcaaagaatg atgagagtta agcttctctt    4020
ggaagatcag catgactttt tctatttttc ccctcatatt ctacagacac tatctcattt    4080
tatcctcact tcaactctgt gaggtatgag tatcattatc ctcacttggc agacgagagt    4140
actgacatat agggagcttg agtagtttat ccaagggcac acagtgctcg tgctgggatc    4200
tgaacacagg acatccaacc aaaggttgtg cccttaatcc tatcatatat atatacttgt    4260
ggtttgtttt tttctttgct taggaagatt cgccctgagc taacttctgt tgccaacctt    4320 cctcttttg cttgaggaag attcgccctg agctaacatc tgtgccagtc ttcctttgtt    4380
ttgtatgtgg gtcaccacca cagtatggct gccaaagagt ggtgtaggtc tgcacccagg    4440
aaccaaacca gggccgccaa agcggagcat gccgaacaac catgaggcca tgaggctggc    4500
cctgctagtg gcttttaaag tttgagaatc atggacttgt agtatcagca ccacctggga    4560
actcattaga aatgcaaaat ctcagaattg gaattgaact taaaaggaca actagtctaa    4620
tccttctgct cttgcccaac ttctcaaata gatggttttt gcctcttttt gaacaattac    4680
tgcaaggatg ctttctgctt caaccattcc gttttgaggc tctaactcca gaagttattc    4740
cttgtacaca gtaagctctg ccctgtgata acttccctct ggcactttgg ccctctggag    4800
ccgtatactg aacaaatttt gtctttttcc catataaatg tctctacttt ttgagaccaa    4860
cattttcctc cttcacccta ccccacctca ctgtatttc ttctcttaag aacccttgac     4920
```

```
tgtctaatgt gttccttcta gaatgtgatt tctagtcttt ttagtactgg ccctttactc    4980
tgcttgtttt ctagtttgtg gattttctt gaaatgtaat gcaaaaaatt gaatgcagta    5040
aattgtttaa agcgttttc ttttttgatg gctttaagtc agaaaaagca aaatgtttga    5100
agtttatgga gtagatatct gtacaatata ttaatatatt tacgtataaa agggaatgat    5160
acaagaatcc caaactattt ttgtttctag aatcaagatt tattcaatta ttctaactca    5220
taatctctga tctaatgtag ttttttaaaat ctgtaatgta tgattacaca aatatataca    5280
tttgtcaaaa gtcatcaata tgtacacatt acaatgtgtg agttacaatg tatgtgaatt    5340
atacccaata aaattgattt aaaaaacaaa ctaaacatgt ataaagttct tctcattcaa    5400
gacaagtacg tttccctcct agtgggatag acacatgaaa ggaaagttag gggtttgtgg    5460
ccatgtaaca gttacatatc cgattaggtt acgtaagcag ctcctaaccc ctaatctaag    5520
gaggttcgta caggaagact ttggccatag ccatagctct atacaaatgt ccttttata    5580 ataatctgta aggacatgag acggaatgct attaggcaaa agctcaaagg agaacctctg    5640
attactatcc ccagggtgac tgagttctcg tgaccacatg gtcaaggatt cacagaagct    5700
ccatttaggc accaaatgac ttgggaacat aaccagagtg accacacatc ctctcgttat    5760
catcacatgg tcatggtagt atctgggcca attaaccgtg tgtttctgga gcactttcta    5820
tgcgcatagt actgtgctaa gctccgtgaa aaacagagaa tcgtataaaa agaacctata    5880
ggatggtcgc ggtagctgca cagcatcgtg gatgcgttta atgtactgaa ctgtatattt    5940
aaaactgtta aaagttcaag ttttatgttg tgcgtatttt taccacaatc aaaaagaacc    6000
ttcaaggccc ttgggagatc caggtgtggt ccagtagatg tgaataaatt cctatctact    6060
aagcaccctg catcgtcttt cctctgccat tattgctcaa gtgccctctt ctcttcctgt    6120
gactgtgaag ccagccttat ttctagtcaa ggggatgtaa agaactgtgg gccagtcgct    6180
taatagcatg gcacccttgg tgctggtcca gttttgtctc tccttttgcc ttattcctta    6240 tggctttat aatctatttt actctggatg cataaaaact gggttgtgat ggattagatc    6300
agattcctcc atttattacc tatgtgacct tcggggtatt tgtgttgacag caatgagctt    6360 tgtaaaatta atcagaagac tcaatgagat agtgcctatt acttcccacc cccttctctt    6420
ctactgaccc caactgcatt tctgcttttg tccctctctc atttgattcc ctctgtggct    6480
ccttgcttag aattctgctt ttgccaccat cattatgttt aaacatttta gtacgtagtt    6540
cctgactccc tcttttattg ctggatctct tgctgtcaac attttactta cctactctgt    6600
ttaccgccta ctctaggcca atataattct tactgtgcct gtatgtcata gtgtttgtaa    6660
gcttgtttct gggcttttct gtgtatataa gtgcatgtga ttaaggagta tagattactt    6720
acctttggag ttcagaacca ggatagctca gtgttatctg ggatggtcaa gctgtaagac    6780
tagagctgct attgaaagta gcctggaagt tagagagtca gaaataaagg aaaatccta    6840 gagttctgat gttagcttct tcaaagaaac ctgtagcttt ccaagcacat taataaaact    6900
acacagccac tagcaagact ctccgtggga gagcatgtat tatggctcca gaaggatttg    6960
ggggtgggtt tgttgaatgc attattgttg cttgatgcag agaatgctgg gcctacaagt    7020
gtccaccaca agctttcaag ggaaaaactt cttcattagt tttgacttca gatgcccaaa    7080
ctgcattata attgaacaag tattaactta gtaagtcaaa ttttcttcaa atcttaggt    7140 gctcctataa ctgctcatta agattcactt atttttttca cgcaggtaag gggacctaat    7200
tcagtgtttc ttaaaatgaa attcatagac atattcttag agtctttgaa aattcttttt    7260
ctttaaaaag gaaagttttt atagtactct agtttgagaa acactacggt gtccctcata    7320
```

| | |
|---|---|
| aatggtttag ttcattgtta aagggatgct gagaacatat atgaggtgcc aaagtataaa | 7380 |
| atgtcaggaa gggagtttga aggttgtcaa atgttggagg cccagggagg tgaaagcaaa | 7440 |
| cataagcaca tcggaagcaa aaggggagg ttggtggata gaggtgagaa ggctgctgag | 7500 |
| ccaccattgc tgtcagcttg gtttcctata ctggggtaag tttgtgtatg tgtggtttgg | 7560 |
| cccagcataa agagccaaag acatagcgga caagtggtga ccagattcag ctctgaatgg | 7620 |
| attctagttt ggcaatctct ggggagtgat taacaacttt gacaccagtt tgctgcctaa | 7680 |
| cagtaattgc tgtgtcattg agtccttctt actcaagaag cagaatttga agatatgggc | 7740 |
| aaagtttggg attcaaacca agcaaaatag gaaggagca ggcagatctg tacaatgagg | 7800 |
| gacgactttt gatcccaggg tagaggctgg tcttccctct gccttgtctc caggcccgtg | 7860 |
| tttaagcaag cgccctgatg tcagtgaatg aatccttaca ggtgtgggct actccccatg | 7920 |
| gtgagacagg cctcatcagg ttctgggatt gcggtgatgg ggagcattgc agttcaaata | 7980 |
| accactgagc tcaggcttca tttggccctg tgatcctttc tccaattatt ctaaaggatc | 8040 |
| tttatgaaaa aataataaag taaaatttt aaatttcact taaaaaaact catagagctg | 8100 |
| caatatgcaa ccttttagg aaggagcatt aaaaaatatt tccctgaggc ctcgagatta | 8160 |
| cacttggggt acagaaatgg caataattat ggcagattcc accatcttga cggaacaatt | 8220 |
| ttggggctga gagaaagaca gttggctatt ttccctctac gcctcaactt gtcaagatac | 8280 |
| ggaggttgat gatcgagttt tacatctgtg atttatctgg tagcatagac ttgatgcaag | 8340 |
| aacagaaagt gttggggatg tcccaaatag aaacaaggat agggtatcag aaatcctgac | 8400 |
| aagtggcact tatgcttctg tgggttggga aaggagagct aacattaaag aagttttatt | 8460 |
| gtctgaggaa aataaaaact gagtacatga atgctaggag agatctaatg ttttagtgcc | 8520 |
| ctagaatttt caagcattat aggaaaaagt ttaatatttt tttgatagca aagaatgatg | 8580 |
| agagttaagc tttctttgga agatcagcat gactttttct attttccccc tcatattcta | 8640 |
| cagacactat ctcattttat cctcacttca actctgtgag gtatgagtat cattatcctc | 8700 |
| acttggcaga cgagagtact gacatatagg gagcttgagt agtttatcca agggcacaca | 8760 |
| gtgctcgtgc tgggatctga acacaggaca tccaaccaaa ggttgtgccc ttaatcctat | 8820 |
| catatatata tacttgtggt ttgttttttt ctttgcttag gaagattcgc cctgagctaa | 8880 |
| cttctgttgc caaccttcct ctttttgctt gaggaagatt cgccctgagc taacatctgt | 8940 |
| gccagtcttc ctttgttttg tatgtgggtc accaccacag tatggctgcc aaagagtggt | 9000 |
| gtaggtctgc acccaggaac caaaccaggg ccgccaaagc ggagcatgcc gaacaaccat | 9060 |
| gaggccatga ggctggccct gctagtggct tttaaagttt gagaatcatg gacttgtagt | 9120 |
| atcagcacca cctgggaact cattagaaat gcaa | 9154 |

<210> SEQ ID NO 3
<211> LENGTH: 7582
<212> TYPE: DNA
<213> ORGANISM: Equus caballus

<400> SEQUENCE: 3

| | |
|---|---|
| tgagtatata actgttttg gctcagagay gttagattaa taggataaga ggcttttata | 60 |
| aatcactagg cttttgatta ggattttaat agaagttaca attgtaaga ctggtattga | 120 |
| accatggata gaagtctaac tgtcctcaaa ttccagatca attcaataaa catttattaa | 180 |
| gcacttgtta tataaaaggc actgtcttag gtgcttggca ttggggatct gacaaggttg | 240 |
| gataaagaaa gaaaggaagc atgctgtctg ccttcagggg tttacagtgg gtggagatat | 300 |

```
gcttggaccc ccaaaactga aatttcaagt gtgattgtta aatgcaaaga caaggtatga    360
agagaagtat tatccgctcc aagggaagga ggcagggatt gtgaggtgga agcgtyaagg    420
gyagcttcac aasataggta gtatttgctt aagccttgaa aaytgagtaa agtktccgca    480
ggtgggagag agggagtgca tttgaagaac gctgaacaaa gccttggagt agtgaagtgt    540
atggcctccc aggaatgaca agttctgcag tgtaaccaaa gcacaaggta ccayggcaa     600 gcaaagcaga gyggctgagg gccaggttta gatggtactg aaggccatac caaagaattt    660
gcactttgta ggcattaagg agccaataca ggttttttgag caggttagag tgatgtgatc   720
ctgtccgtgt ttcaggaaga tcactgttag cggtrtgrrt aatggcctta agagaggagg    780
aggttatagg caggacagct agttaggagt cattgcaaga gttgcaccaa gagcaatggc    840
aatacaagtg tgaaggtaaa ggagagctga gaggcatttc tggggtgcac ttattaggaa    900
ttggaggaag atgaaagagt caaagataag aaacattaag gctttattcg gcataatcgg    960
gtagacagtg atactgttaa catagattag ggaacataaa gtagatttgg tgggaaagat   1020
agattttctg ttgttatttt tttaaattat tcttattttt ccttcccagg aattatggga   1080
aggttggata tgtggatgtg tgtgtatatg tatgtacata acaggctcga gcctgtttct   1140
gcttatgctt ctcttaggtt taattctttg ttcttgatca gactgtgatt tgagggttgc   1200
gcatctttga gttagggttt ccctgacatc tggctttaaa ttataagaag ttcccagatc   1260
acacaatctc agaattggaa ttgaacttaa aaggacaact agtctaatcc ttctgctctt   1320
gcccaacttc tcaaatagat ggttttttgcc tcttttttgaa caattactgc aaggatgctt   1380
tctgcttcaa ccattccgtt ttgaggctct aactccagaa gttattcctt gtacacagta   1440
agctctgccc tgtgataact tccctctggc actttggccc tctggagccg tatactgaac   1500
aaattttgtc ttttttcccat ataaatgtct ctactttttg agaccaacat tttcctcctt   1560
caccctaccc cacctcactg tattttcttc tcttaagaac ccttgactgt ctaatgtgtt   1620
ccttctagaa tgtgatttct agtctttttta gtactggccc tttactctgc ttgttttcta   1680
gtttgtggat ttttcttgaa atgtaatgca aaaaattgaa tgcagtaaat tgtttaaagc   1740 gttttttctttt tttgatggct ttaagtcaga aaaagcaaaa tgtttgaagt ttatggagta   1800
gatatcygta caatatatta atatatttac gtataaaagg gaatgataca agaatcccaa   1860
actatttttg tttctagrat caagatttat tcaattattc taactcataa tctctgatct   1920
aatgtagttt ttaaaatctg taatgtatga ttacacaaat atatacattt gtcaaaagtc   1980
atcaatatgt acacattaca atgtgtgagt tacaatgtat gtgaattata cccaataaaa   2040
ttgatttaaa aaacaaacta acatgtata aagttcttct cattcaagac aagtacgttt    2100
ccctcctagt gggatagaca catgaaagga aagttagggg tttgtggcca tgtaacagtt   2160
acatatccga ttaggttacg taagcagctc ctaaccccta atctaaggag gttcgtacag   2220
gaagactttg gccatagcca tagctctata caaatgtcct ttttataata atctgtaagg   2280
acatgagacg gaatgctatt aggcaaaagc tcaaggaga acctctgatt actatcccca    2340
gggtgactga gttctcgtga ccacatggtc aaggattcac agaagctcca tttaggcacc   2400
aaatgacttg ggaacataac cagagtgacc acacatcctc tcgttatcat cacatggtca   2460
tggtagtatc tgggccaatt aaccgtgtgt ttctggagca ctttctatgc gcatagtact   2520
gtgctaagct ccgtgaaraa cagagaatcr tataaaaga acctatagga tggtcgcggt    2580
agctgcacag catcgtggat gcgtttaatg tactgaactg tatatttaaa actgttaaaa   2640
gttcaagttt tatgttgtgc gtattttttac cacaatcaaa aagaaccttc aaggcccttg   2700
```

```
ggagatccag gtgtggtcca gtagatgtga ataaattcct atctactaag caccctgcrt    2760
cgtctttcct ctgccrttat tgctcaagtg ccctcttctc ttcctgtgac tgtgaagcca    2820
gccttatttc tagtcaaggg gatgtaaaga actgtgggcc agtcgcttaa tagcatggca    2880
cccttggtgc tggtccagtt ttgtctctcc ttttgcctta ttccytatgg cttttataat    2940
ctattttact ctggatgcat aaaaactggg ttgtgatgga ttagatcaga ttcctccatt    3000
tattacctat gtgaccttcg gggtattgtg ttgacagcaa tgagctttgt aaaattaatc    3060
agaagactca atgagatagt gyctattact tcccacccccc ttctcttcta ctgacccaa     3120 ctgcatttct gcttttgtcc ctcyctcatt tgattccctc tgtggctcct tgcttagaat    3180
tctgcttttg ccaccatcat tatgtttaaa cattttagta cgtagttcct gactccctct    3240
tttattgctg atctcttgc tgtcaacatt ttacttacct actctgttta ccgcctactc      3300
taggccaata taatycttac tgtgcctgta tgtcatagtg tttgtaagct tgtttctggg    3360
cttttctgtg tatataagtg catgtgatta aggagtatrg attacttacc tttggagttc    3420
agaaccagga tagctcagtg ttatctggga tggtcaagct gtaagactag agctgctatt    3480
gaaagtagcc tggaagttag agagtcagaa ataaaggaaa atacctagag ttctgatgtt    3540
agcttcttca aagaaacctg tagctttcca agcacattaa taaaactaca cagccactag    3600
caagactctc cgtgggagag catgtattat ggctccagaa ggatttgggg gtgggtttgt    3660
tgaatgcatt attgttgctt gatgcagaga atgctgggcc tacaagtgtc caccacaagc    3720
tttcaaggga aaaacttctt cattagtttt gacttcagat gcccaaactg cattataatt    3780
gaacaagtat taacttagta agtcaaattt tcttcaaaat cttaggtgct cctataactg    3840
ctcattaaga ttcacttatt tttttcacgc aggtaagggg acctaattca gtgtttctta    3900
aaatgaaatt catagacata ttcttagagt ctttgaaaat tctttttctt taaaaaggaa    3960 agttttata gtactctagt ttgagaaaca ctacggtgtc cctcataaat ggtttagytc    4020
attgttaaag ggatgctgag aacatatatg aggtgccaaa gtataaaatg tcaggaaggg    4080
agtttgaagg ttgtcaaatg ttggaggccc agggaggtga aagcaaacat aagcacatcg    4140
gaagcaaaaa ggggaggttg gtggatagag gtgagaaggc tgctgagcca ccattgctgt    4200
cagcttggtt tcctatactg gggtaagttt gtgtatgtgt ggtttggccc agcataaaga    4260
gccaaagaca tagcggacaa gtggtgacca gattcagctc tgaatggatt ctagtttggc    4320
aatctctggg gagtgattaa caactttgac accagtttgc tgcctaacag taattgctgt    4380
gtcattgagt ccttcttact caagaagcag aatttgaaga tatgggcaaa gtttgggatt    4440
caaaccaagc aaaatagggga aggagcaggc agatctgtac aatgagggac gacttttgat    4500
cckagggtag aggctggtct tccctctgcc ttgtctccag gcccgtgttt aagcaagcgc    4560
cctgatgtca gtgaatgaat ccttacaggt gtgggctact ccccatggtg agacaggcct    4620
catcaggttc tgggattgcg gtgatgggga gcattgcagt tcaaataacc actgagctca    4680
ggcttcattt ggccctgtga tcctttctcc aattattcta aaggatcttt atgaaaaaat    4740
aataaagtaa aattttttaaa tttcactkaa aaaaactcat agagctgcaa tatgcaacct    4800
ttttaggaag gagcattaaa aaatatttcc ctgaggcctc gagattacac ttggggtaca    4860 gaaatgcaa taattatggc agattccacc atccttgacgg aacaattttg gggctgagag    4920
aaagacagtt ggctattttc cctctacgcc tsaactygtc aagatacgga ggttgatgat    4980
cgagttttac atctgtgatt tatctggtag catagacttg atgcaagaac rgaaagtgtt    5040
ggggatgtcc caaatagaaa caaggatagg gtatcagaaa tcctgacaag tggcacttat    5100
```

-continued

```
gcttctgtgg gttgggaaag gagagctaac attaaagaak ttttattgtc tgaggaaaat    5160
aaaaactgag trcatgaatg ctaggagaga tctaatgttt tagtgcccta gaattttcaa    5220
gcwmttatag gaaaaagttt aatatttttt tgatagcaaa gaatgatgag agttaagctt    5280
tctttggaag atcagcmtga cttttttctat ttttccctc atattctaca gacactatct    5340
cattttatcc tcacttcaac tctgtgaggt atgagtatca ttatcctcac ttggcagacg    5400
agagtactga catatagrga gcttgagtag tttatccaag ggcacacagt gctcgtgctg    5460
ggatctgaac acaggacatc caaccaaagg ttgtgccctt aatcctatca tatatatata    5520
ctygtggttt gttttttttct ttgcttagga agattcrccc tgagctaact tctgttgcca    5580
accttcctct ttttgcttga ggaagattcg ccctgagcta acatctgtgc cagtcttcct    5640
ytgttttgta tgtgggtcac caccacagta tggctgccaa agagtggygt aggtctgcac    5700
ccaggaacca aaccagggcc gccaaagcrg agcatgccga caaccatga aggccatgag    5760 gctggccctg ctagtggctt ttaaagtktg agaatcatgg acttgtagta tcagcaccac    5820
ctgggaactc attagaaatg caaattctca ggcctcaycc caagcccct gaatcagaaa    5880 ctctggatga agttctccag gtgattctgg tgcacactcc agtgtggaaa ccactgttgt    5940
attggtctct gacgacgtta aagaagact tatagaggac ttttttaggg attgtgttag    6000
agatgtcaag atggtggaga atatagcaat gaagggatac catgaaaggt ctaacggtga    6060
agaggtacat acctggcgtc tgagaaggga aggaatgtca ataatgtgat aggaagcaac    6120
tgtgaggaaa caattagctg tgttgtttgg gtgtcctgtt ctcggatgaa atgatgattg    6180
gaattagaag agtgttggtc acatacgctt cactataagt gactaggtca gttatataag    6240
gacaatcaaa tacttcaggg ttcaaattga attatttcac agtcatcgaa gaagttggca    6300
tttagctagg atcaaagagg gattctcttc tttttttctg tgaattaaaa agactagtct    6360
gtatattgat gtgatggtgg ttacgtgggt ttatgcattt atcagaaatc atcatactat    6420
acccttaaaa tgggtgcata ttattatatg taaattctgt ctaaataaag ttgatttaaa    6480
aatgggaatg tggggctgg cccygtgtgc ccgagcggtt aagttcgcgc sctccgctgc    6540
aggcggccca gtgtttcgtt ggttcraatc ctgggcacgg acatgacact gctcatcaaa    6600
ccacgctgag gcagcatccc acatgccaca actagaagga cccacaacaa agaatatacm    6660
actatgtacc ggggtgcttt ggggagaaaa aggaaaaaat aaaatcttaa aaaaaaaaaa    6720 aaataggggta tagtgtactc gtggccagtt aatgagtttc tgtcactgag gtgtttgagc    6780
agaggttcag taagcgcttg tcagatatgt cgtagtgggg cttcccacat ctgagggaga    6840
aatcgcactc agcaacctaa acattccttc tacccagagg ttccatgagt cacaatttct    6900
gttgtgtcag ccgcaggtgt tgccattttg tgtagaatgc ttggttaata tatttgatct    6960
gaaacatttt aacttgtcat gattttaaaa tgtattaaag tgtccacgtg tgaaacacag    7020
gacagygaat tcattcaccr ctccctactg catatcacaa gtagaaagat ttcatggcag    7080
atcaaaccat attgtattct tattcctaaa acagtaattt gtatttatcg tggcatcaag    7140
ggtgttttac tcctaaggca aatttgcctg ttttaaactg aatcttcaaa gaagataagt    7200
tagggaggat ttttgctttg atcctgtttt tgtttttttc catcaaaccc aacatgacat    7260
gtaaatactt atttggactt ttttttcttc tcgaaagcag atttatttgg agaacaatat    7320
gcttgtatgt ttgaatgaag tttagagtaa gatgcttttt cctataaagg tgccactctt    7380
ttattactga ataattaagt cacctttttt tatacaagtg aatttgtgct ttcgacgtgg    7440
tttgtcagat gctgttaaat gaactgctgt tagactccaa ggctgcggca cacaggccct    7500
```

```
<210> SEQ ID NO 4
<211> LENGTH: 4578
<212> TYPE: DNA
<213> ORGANISM: Equus caballus

<400> SEQUENCE: 4
```

| | | | | | |
|---|---|---|---|---|---|
| gattrcagga | gttaaaatag | tgtgcattgg | ctgactgctg | ctccgcagca | ggagcgctca | 7560 |
| ctcataattc | ctttgcatct | ag | | | | 7582 |

| | | | | | |
|---|---|---|---|---|---|
| aatctcagaa | ttggaattga | acttaaaagg | acaactagtc | taatccttct | gctcttgccc | 60 |
| aacttctcaa | atagatggtt | tttgcctctt | tttgaacaat | tactgcaagg | atgctttctg | 120 |
| cttcaaccat | tccgttttga | ggctctaact | ccagaagtta | ttccttgtac | acagtaagct | 180 |
| ctgccctgtg | ataacttccc | tctggcactt | tggccctctg | gagccgtata | ctgaacaaat | 240 |
| tttgtctttt | tcccatataa | atgtctctac | tttttgagac | caacattttc | ctccttcacc | 300 |
| ctaccccacc | tcactgtatt | ttcttctctt | aagaacccct | gactgtctaa | tgtgttcctt | 360 |
| ctagaatgtg | atttctagtc | tttttagtac | tggcccttta | ctctgcttgt | tttctagttt | 420 |
| gtggattttt | cttgaaatgt | aatgcaaaaa | attgaatgca | gtaaattgtt | taaagcgttt | 480 |
| ttctttttg | atggctttaa | gtcagaaaaa | gcaaaatgtt | tgaagtttat | ggagtagata | 540 |
| tcygtacaat | atattaatat | atttacgtat | aaaagggaat | gatacaagaa | tcccaaacta | 600 |
| tttttgtttc | tagratcaag | atttattcaa | ttattctaac | tcataatctc | tgatctaatg | 660 |
| tagtttttaa | aatctgtaat | gtatgattac | acaaatatat | acatttgtca | aaagtcatca | 720 |
| atatgtacac | attacaatgt | gtgagttaca | atgtatgtga | attatcccca | ataaaattga | 780 |
| tttaaaaaac | aaactaaaca | tgtataaagt | tcttctcatt | caagacaagt | acgtttccct | 840 |
| cctagtggga | tagacacatg | aaaggaaagt | taggggtttg | tggccatgta | acagttacat | 900 |
| atccgattag | gttacgtaag | cagctcctaa | cccctaatct | aaggaggttc | gtacaggaag | 960 |
| actttggcca | tagccatagc | tctatacaaa | tgtccttttt | ataataatct | gtaaggacat | 1020 |
| gagacggaat | gctattaggc | aaaagctcaa | aggagaacct | ctgattacta | tccccagggt | 1080 |
| gactgagttc | tcgtgaccac | atggtcaagg | attcacagaa | gctccattta | ggcaccaaat | 1140 |
| gacttgggaa | cataaccaga | gtgaccacac | atcctctcgt | tatcatcaca | tggtcatggt | 1200 |
| agtatctggg | ccaattaacc | gtgtgtttct | ggagcacttt | ctatgcgcat | agtactgtgc | 1260 |
| taagctccgt | gaaraacaga | gaatcrtata | aaaagaacct | ataggatggt | cgcggtagct | 1320 |
| gcacagcatc | gtgatgcgt | ttaatgtact | gaactgtata | tttaaaactg | ttaaaagttc | 1380 |
| aagttttatg | ttgtgcgtat | ttttaccaca | atcaaaaaga | accttcaagg | cccttgggag | 1440 |
| atccaggtgt | ggtccagtag | atgtgaataa | attcctatct | actaagcacc | ctgcrtcgtc | 1500 |
| ttcctctgc | crttattgct | caagtgccct | cttctcttcc | tgtgactgtg | aagccagcct | 1560 |
| tatttctagt | caaggggatg | taaagaactg | tgggccagtc | gcttaatagc | atggcaccct | 1620 |
| tggtgctggt | ccagttttgt | ctctcctttt | gccttattcc | ytatggcttt | tataatctat | 1680 |
| tttactctgg | atgcataaaa | actgggttgt | gatggattag | atcagattcc | tccatttatt | 1740 |
| acctatgtga | ccttcggggt | attgtgttga | cagcaatgag | ctttgtaaaa | ttaatcagaa | 1800 |
| gactcaatga | gatagtgyct | attacttccc | accccccttct | cttctactga | ccccaactgc | 1860 |
| atttctgctt | ttgtccctcy | ctcatttgat | tccctctgtg | gctccttgct | tagaattctg | 1920 |
| cttttgccac | catcattatg | tttaaacatt | ttagtacgta | gttcctgact | ccctctttta | 1980 |
| ttgctggatc | tcttgctgtc | aacatttttac | ttacctactc | tgtttaccgc | ctactctagg | 2040 |

```
ccaatataat ycttactgtg cctgtatgtc atagtgtttg taagcttgtt tctgggcttt    2100
tctgtgtata taagtgcatg tgattaagga gtatrgatta cttacctttg gagttcagaa    2160
ccaggatagc tcagtgttat ctgggatggt caagctgtaa gactagagct gctattgaaa    2220
gtagcctgga agttagagag tcagaaataa aggaaaatac ctagagttct gatgttagct    2280
tcttcaaaga aacctgtagc tttccaagca cattaataaa actacacagc cactagcaag    2340
actctccgtg ggagagcatg tattatggct ccagaaggat ttgggggtgg gtttgttgaa    2400
tgcattattg ttgcttgatg cagagaatgc tgggcctaca agtgtccacc acaagctttc    2460
aagggaaaaa cttcttcatt agttttgact tcagatgccc aaactgcatt ataattgaac    2520
aagtattaac ttagtaagtc aaattttctt caaaatctta ggtgctccta taactgctca    2580
ttaagattca cttattttt tcacgcaggt aaggggacct aattcagtgt tcttaaaat     2640
gaaattcata gacatattct tagagtcttt gaaaattctt tttctttaaa aaggaaagtt    2700
tttatagtac tctagtttga gaaacactac ggtgtccctc ataaatggtt tagytcattg    2760
ttaaagggat gctgagaaca tatatgaggt gccaaagtat aaaatgtcag gaagggagtt    2820
tgaaggttgt caaatgttgg aggcccaggg aggtgaaagc aaacataagc acatcggaag    2880
caaaaggggg aggttggtgg atagaggtga gaaggctgct gagccaccat tgctgtcagc    2940
ttggtttcct atactggggt aagtttgtgt atgtgtggtt tggcccagca taaagagcca    3000
aagacatagc ggacaagtgg tgaccagatt cagctctgaa tggattctag tttggcaatc    3060
tctggggagt gattaacaac tttgacacca gtttgctgcc taacagtaat tgctgtgtca    3120
ttgagtcctt cttactcaag aagcagaatt tgaagatatg gcaaagtttt gggattcaaa    3180
ccaagcaaaa tagggaagga gcaggcagat ctgtacaatg agggacgact tttgatccka    3240
gggtagaggc tggtcttccc tctgccttgt ctccaggccc gtgtttaagc aagcgccctg    3300
atgtcagtga atgaatcctt acaggtgtgg gctactcccc atggtgagac aggcctcatc    3360
aggttctggg attgcggtga tggggagcat tgcagttcaa ataaccactg agctcaggct    3420
tcatttggcc ctgtgatcct ttctccaatt attctaaagg atctttatga aaaaataata    3480
aagtaaaatt tttaaatttc actkaaaaaa actcatagag ctgcaatatg caaccttttt    3540
aggaaggagc attaaaaaat atttccctga ggcctcgaga ttacacttgg ggtacagaaa    3600
tggcaataat tatggcagat tccaccatct tgacggaaca attttggggc tgagagaaag    3660
acagttggct attttcccctc tacgcctsaa ctygtcaaga tacggaggtt gatgatcgag    3720
ttttacatct gtgatttatc tggtagcata gacttgatgc aagaacrgaa agtgttgggg    3780
atgtcccaaa tagaaacaag gatagggtat cagaaatcct gacaagtggc acttatgctt    3840
ctgtgggttg ggaaaggaga gctaacatta aagaaktttt attgtctgag gaaaataaaa    3900
actgagtrca tgaatgctag gagagatcta atgttttagt gccctagaat tttcaagcwm    3960
ttataggaaa aagtttaata tttttttgat agcaaagaat gatgagagtt aagctttctt    4020
tggaagatca gcmtgacttt ttctattttt cccctcatat tctacagaca ctatctcatt    4080
ttatcctcac ttcaactctg tgaggtatga gtatcattat cctcacttgg cagacgagag    4140
tactgacata tagrgagctt gagtagttta tccaagggca cacagtgctc gtgctgggat    4200
ctgaacacag gacatccaac caaaggttgt gcccttaatc ctatcatata tatatactyg    4260
tggtttgttt ttttctttgc ttaggaagat tcrccctgag ctaacttctg ttgccaacct    4320
tcctcttttt gcttgaggaa gattcgccct gagctaacat ctgtgccagt cttcctytgt    4380
tttgtatgtg ggtcaccacc acagtatggc tgccaaagag tggygtaggt ctgcacccag    4440
```

```
gaaccaaacc agggccgcca aagcrgagca tgccgaacaa ccatgaaggc catgaggctg    4500
gccctgctag tggcttttaa agtktgagaa tcatggactt gtagtatcag caccacctgg    4560
gaactcatta gaaatgca                                                  4578
```

<210> SEQ ID NO 5
<211> LENGTH: 1957
<212> TYPE: DNA
<213> ORGANISM: Equus caballus

<400> SEQUENCE: 5

```
gaaatcaccg aaaccggcct ccagcgcccc ggccggaggt ttttctgtat gagtggagaa      60
gacagttgtt acaagtagaa gtgacacaac attttttttag gatgtctgaa gatgaagaaa    120
aagtgaaatt acgccgtctt gagccagcta tccagaaatt cattaagata gtaatcccaa    180
cagacctgga gaggttaaga agcaccaga taaatattga gaagtatcaa aggtgcagaa     240
tctgggataa gttacatgaa gaacatatca atgcaggacg tacagttcag caactccgct    300
ccaatattcg agaaatggag aaactttgtt tgaaagtccg aaaggatgat gtaggacttc    360
taaagagaat gatagatcct gttaaagaag aagcatcagt agcaacagca gaatttctcc    420
agctccatct ggaatctgta aagaactta agaaacagtt taatgatgaa gaaactttgt     480
tacagccttc tctgaccaga tccatgactg ttggtggagc ttttcacact gctgaagctg    540
aaaccgatcc tcagagtgtg actcagatat acgcattgcc tgaaatccct cgagatcaaa    600
atgctgccga atcctgggaa accttagaag cggacttaat cgaacttagc caactggtca    660
ctgatttctc tctcctagta aattcccagc aggagaagat tgacagcatt gaagaccatg    720
tcaacactgc tgctgtgaat gttgaagtgg gaaccaaaaa cttggggaag gctgcaaaat    780
acaagctggc agctctgcct gtggcaggtg cactcatcgg aggagcggta gggggtccga    840
ttggcctcct tgcaggcttc aaagtggcag gaattgcagc tgcacttggt ggtggggtgt    900
tgggcttcac aggtggaaaa ttgatacaaa gaaaaaaaca gaaaatgatg gagaagctcg    960
cttccagctg tccagatctt cccagccaaa gtgacaaaaa atgcagttaa aaaccaaact   1020
ttagtattat tggtgccaac atgtctatcc taatgaggac cttttctgct gttggacact   1080
cagtcagctt ttggaacatg attatatcaa aatagtggct gtagatgctc cagtgggact   1140
gaactgtgat gagcgggtat atttcgttgt ttactgggtt tttaatggag atgttagaga   1200
tcaaggagcc tgggctgagg gtgtataatg gttgtcaggt aaagtttaaa gagtgccagg   1260
gagcagattt tctacctgga aatatgaaaa ctgaacccat aactttgata aggtcttgag   1320
atgtgtggac atgttgggtt acagaagaat agtttcttcc ataaccttga cttggaaacc   1380
ctagggctaa gcatattgca aatatgctta tttgtctcct aaatatggga gattatttag   1440
gcctgttagc aaggaaagaa tgggagttca ggagcctatc ttgtcaaata gggagatcag   1500
gatccagcga gatcctggtg agctacataa cacagtccat tggtgaacc ctattacagt    1560
ttggtccaac tgtacttctg gtgaaggaaa ctaataatgt aagaaaatgg aaagagaggc   1620
ccagcttctc tttcagatat cttaatttgt gatactggct tcttctctga actcttcctt   1680
ctgcctctct ttaaataaag aacactgaat ctcaaatggt aggagactta ttagcccagt   1740
cactaagctt gctctgtcag cctgtatctt aagacctcaa agatccagtg ccctgtgtct   1800
ttcctcccctt gtaattttga aaaggtctta gacttgtagg gtgaattta cccatgtgta    1860
atgaggactt ttctcataat ctccttttt gtactgtctc ccatctctgt tcacccttc    1920
ctgtagcccc taggtggaaa aaaaaaaaaa aaaaaaa                            1957
```

<210> SEQ ID NO 6
<211> LENGTH: 2271
<212> TYPE: DNA
<213> ORGANISM: Equus caballus
<220> FEATURE:
<221> NAME/KEY: misc_feature
<222> LOCATION: 920
<223> OTHER INFORMATION: n = A,T,C or G

<400> SEQUENCE: 6

```
catgacactg ctcatcaaac cacgctgagg cagcatccca catgccacaa ctagaaggac      60
ccacaacaaa gaatatacaa ctatgtaccg gggtgctttg gggagaaaaa ggaaaaaata     120
aaatcttaaa aaaaaaaaaa aatagggtat agtgtacctg tggccagtaa tgagtttctg     180
tcactgaggt gtttgagcag aggttcagta agcgcttgtc agaatgtcgt agtgggcttt     240
cccacatctg agggagaaat cgcactcagc aacctaaaca ttccttctac ccagaggttc     300
catgagtcac aatttctgtt gtgtcagccg caggtgttgc cattttgtgt agaatgcttg     360
gttaatatat ttgatctgaa acattttaac ttgtcatgat tttaaaatgt ataaagtgtc     420
cacgtgtgaa acacaggaca gtgaattcat tcaccactcc ctactgcata tcacaagtag     480
aaagatttca tggcagatca aaccatattg tattcttatt cctaaaacag taatttgtat     540
ttatcgtggc atcaagggtg ttttactcct aaggcaaatt tgcctgtttt aaactgaatc     600
ttcaaagaag ataagttagg gaggattttt gctttgatcc tgttttttgtt ttttccatc     660
aaacccaaca tgcatgtaa atacttattt ggacttttt tctttctcga agcagatttt     720
atttggagaa caatatgctt gtatgtttga atgaagttta gagtaagatg cttttttccta     780
taaaggtgcc actcttttat tactgaataa ttaagtcacc ttttttttata caagtgaatt     840
tgtgctttcg acgtggtttg tcagatgctg ttaatgaact gctgttagac tccaaggctg     900
cggcacacag gccctgattn caggagttaa aatagtgtgc attggctgac tgctgctccg     960
cagcaggagc gctcactcat aattcctttg catctagtcc cagcaggaga agattgacag    1020
cattgaagac catgtcaaca ctgctgctgt gaatgttgaa gtgggaacca aaaacttggg    1080
gaaggctgca aaatacaagc tggcagctct gcctgtggca ggtgcactca tcggaggagc    1140
ggtaggggggt ccgattggcc tccttgcagg cttcaaagtg gcaggaattg cagctgcact    1200
tggtggtggg gtgttgggct tcacaggtgg aaaattgata caaagaaaaa aacagaaaat    1260
gatggagaag ctcgcttcca gctgtccaga tcttcccagc caaagtgaca aaaaatgcag    1320
ttaaaaacca aactttagta ttattggtgc caacatgtct atcctaatga ggacctttc    1380
tgctgttgga cactcagtca gcttttggaa catgattata tcaaaatagt ggctgtagat    1440
gctccagtgg gactgaactg tgatgagcgg gtatatttcg ttgtttactg ggttttttaat    1500
ggagatgtta gagatcaagg agcctgggct gagggtgtat aatggttgtc aggtaaagtt    1560
taaagagtgc cagggagcag atttttctacc tggaaatatg aaaactgaac ccataacttt    1620
gataaggtct tgagatgtgt ggacatgttg ggttacagaa gaatagtttc ttccataacc    1680
ttgacttgga aaccctaggg ctaagcatat tgcaaatatg cttatttgtc tcctaaatat    1740
gggagattat ttaggcctgt tagcaaggaa agaatgggag ttcaggagcc tatcttgtca    1800
aatagggaga tcaggatcca gcgagatcct ggtgagctac ataacacagt ccatttggtg    1860
aaccctatta cagtttggtc caactgtact tctggtgaag gaaactaata atgtaagaaa    1920
atggaaagag aggcccagct tctcttttcag atatcttaat ttgtgatact ggcttcttct    1980
ctgaactctt ccttctgcct ctcttttaaat aaagaacact gaatctcaaa tggtaggaga    2040
```

```
cttattagcc cagtcactaa gcttgctctg tcagcctgta tcttaagacc tcaaagatcc    2100
agtgccctgt gtctttcctc ccttgtaatt ttgaaaaggt cttagacttg tagggtgaat    2160
tttacccatg tgtaatgagg acttttctca taatctcctt ttttgtactg tctcccatct    2220
ctgttcaccc tttcctgtag ccctaggtg gaaaaaaaaa aaaaaaaaaa a              2271
```

<210> SEQ ID NO 7
<211> LENGTH: 302
<212> TYPE: PRT
<213> ORGANISM: Equus caballus

<400> SEQUENCE: 7

```
Met Ser Glu Asp Glu Glu Lys Val Lys Leu Arg Arg Leu Glu Pro Ala
1               5                   10                  15

Ile Gln Lys Phe Ile Lys Ile Val Ile Pro Thr Asp Leu Glu Arg Leu
            20                  25                  30

Arg Lys His Gln Ile Asn Ile Glu Lys Tyr Gln Arg Cys Arg Ile Trp
        35                  40                  45

Asp Lys Leu His Glu His Ile Asn Ala Gly Arg Thr Val Gln Gln
    50                  55                  60

Leu Arg Ser Asn Ile Arg Glu Met Glu Lys Leu Cys Leu Lys Val Arg
65                  70                  75                  80

Lys Asp Asp Val Gly Leu Leu Lys Arg Met Ile Asp Pro Val Lys Glu
                85                  90                  95

Glu Ala Ser Val Ala Thr Ala Glu Phe Leu Gln Leu His Leu Glu Ser
            100                 105                 110

Val Glu Glu Leu Lys Lys Gln Phe Asn Asp Glu Glu Thr Leu Leu Gln
        115                 120                 125

Pro Ser Leu Thr Arg Ser Met Thr Val Gly Gly Ala Phe His Thr Ala
    130                 135                 140

Glu Ala Glu Thr Asp Pro Gln Ser Val Thr Gln Ile Tyr Ala Leu Pro
145                 150                 155                 160

Glu Ile Pro Arg Asp Gln Asn Ala Ala Glu Ser Trp Glu Thr Leu Glu
                165                 170                 175

Ala Asp Leu Ile Glu Leu Ser Gln Leu Val Thr Asp Phe Ser Leu Leu
            180                 185                 190

Val Asn Ser Gln Gln Glu Lys Ile Asp Ser Ile Glu Asp His Val Asn
        195                 200                 205

Thr Ala Ala Val Asn Val Glu Val Gly Thr Lys Asn Leu Gly Lys Ala
    210                 215                 220

Ala Lys Tyr Lys Leu Ala Ala Leu Pro Val Ala Gly Ala Leu Ile Gly
225                 230                 235                 240

Gly Ala Val Gly Gly Pro Ile Gly Leu Leu Ala Gly Phe Lys Val Ala
                245                 250                 255

Gly Ile Ala Ala Ala Leu Gly Gly Gly Val Leu Gly Phe Thr Gly Gly
            260                 265                 270

Lys Leu Ile Gln Arg Lys Lys Gln Lys Met Met Glu Lys Leu Ala Ser
        275                 280                 285

Ser Cys Pro Asp Leu Pro Ser Gln Ser Asp Lys Lys Cys Ser
    290                 295                 300
```

<210> SEQ ID NO 8
<211> LENGTH: 2207
<212> TYPE: DNA
<213> ORGANISM: Equus caballus

<400> SEQUENCE: 8

```
atatgccctg cgtgcaagcc cagtatagcc cttcgcctcc aggttccagt tatgcagcgc    60
agacctacgg ctcagcggaa taccaccg agatcatgaa ccccgactac accaagctga    120
ccatggacct cggcagcacc gagatcacgg ccacggccac cacgtccctg cccagcttca    180
gtaccttcat ggagggctac tcgagcaact acgaactcaa gccctcctgc ctgtaccaaa    240
tgccgccatc ggggccgcgg cccttgatca agatggagga gggccgcgcg cacggctacc    300
accatcacca ccatcaccac caccaccacc accatcacca gcagcagcag cagcagccat    360
ccattccgcc ccctccggc ccggaggacg aggtgctgcc cagcacctcc atgtacttca    420
agcagtcccc gccgtccacc ccgaccacgc cgggcttccc ccgcaggcg ggggcgctgt    480 gggacgacgc gctgccctcc cgcagggct cctcgcgcc cggcccgctg ctcgacccgc    540
cgatgaaggc ggtgcccacg gtggccggcg cgcgcttccc gctcttccac ttcaagacct    600
cgccgccgca cccgcctgcg cccagcccgg cggcggcca ccactggcc tacgacccga    660 cggccgccgc cgcgctcagc ctgccgcttg agccgccgc cgccgcgggc agccaggccg    720
ccgcgctcga gggccactcg tacgggctgc cgctgcccaa gagggcggcc gcgctggcct    780
tctcgccgct cggcctcacc gcctcccca ccgcgtccag cctgctggcc gagagcccca    840
gcctgccgtc ccgcccaac aggagtttgt cgtcgggcga gggaacgtgc gccgtgtgcg    900
gggacaacgc cgcctgccag cactacggcg tgcgaacctg cgagggctgc aagggctttt    960
tcaagagaac ggtgcagaaa atgcaaaat atgtttgcct ggcaaataaa aactgccctg    1020
tagacaagag acgtcgaaac cgatgtcagt actgtcgatt tcagaagtgt ctcagtgtcg    1080
gaatggttaa agaagttgtc cgtacagata gtctgaaagg gaggagaggt cggctgcctt    1140
ccaaaccaaa gagcccgtta cagcaggaac cttctcagcc ctctccaccg tctcctccga    1200
tctgcatgat gaatgccctt gtccgagctt taacagactc aacgcccaga gatctcgatt    1260
attccagata ctgccccact gaccaggccg ctgccggcac agatgctgag catgtgcaac    1320
agttctacaa ccttctgaca gcctccattg atgtatccag aagctgggca gaaaagattc    1380
ccggatttac tgatctcccc aaagaagatc agacattact tatagaatca gcctttttgg    1440 agctgttttgt tctcagactt tccatcaggt cgaacactgc tgaagataag tttgtgttct    1500
gcaatggact tgtcctgcat cgacttcagt gccttcgtgg atttggggag tggctcgact    1560
ccattaaaga cttttcctta agtttgcaga gcctgaacct ggatatccaa gccttagcat    1620
gcctgtcagc actgagcatg atcacagaac gacatgggtt aaaagaacca aagagagtgg    1680
aggagctatg caacaagatc acaagcagct aaaagacca ccagagcaag gggcaggctt    1740
tggagcccac ggagcccaag gtcctgcgcg ccctggtaga actgcggaag atatgcaccc    1800
tgggcctcca gcgcatcttc tacctgaagc tggaagactt ggtgtctcca ccttccatca    1860
tcgacaagct cttcctggac accctgcctt tctgagcagg agcagcctca tctgctagca    1920
cctgcttgct aagcagcaga gggatgggtc tggacaccta ccattttctg tccttcctta    1980
agagaaaaag cagctcctgt agaaaagaaa gactttttt tttttctgg cacttttcct    2040 tacaagctaa agccagaaaa cttgcagagt attgtgttgg ggttgtgttt tatatttagg    2100
ctttggggtt ggggtgggag gtgggtatag ttcatgaggg ttttctaaga aattgctaac    2160
agagcacttt tggacgatgc tatcccagca ggaaaaaaaa aaaaaaa              2207
```

<210> SEQ ID NO 9
<211> LENGTH: 630
<212> TYPE: PRT
<213> ORGANISM: Equus caballus

```
<400> SEQUENCE: 9

Met Pro Cys Val Gln Ala Gln Tyr Ser Pro Ser Pro Gly Ser Ser
 1               5                  10                  15

Tyr Ala Ala Gln Thr Tyr Gly Ser Ala Glu Tyr Thr Thr Glu Ile Met
             20                  25                  30

Asn Pro Asp Tyr Thr Lys Leu Thr Met Asp Leu Gly Ser Thr Glu Ile
         35                  40                  45

Thr Ala Thr Ala Thr Thr Ser Leu Pro Ser Phe Ser Thr Phe Met Glu
     50                  55                  60

Gly Tyr Ser Ser Asn Tyr Glu Leu Lys Pro Ser Cys Leu Tyr Gln Met
65                  70                  75                  80

Pro Pro Ser Gly Pro Arg Pro Leu Ile Lys Met Glu Glu Gly Arg Ala
                 85                  90                  95

His Gly Tyr His His His His His His His His His His His His
             100                 105                 110

Gln Gln Gln Gln Gln Pro Ser Ile Pro Pro Ser Gly Pro Glu
             115                 120                 125

Asp Glu Val Leu Pro Ser Thr Ser Met Tyr Phe Lys Gln Ser Pro Pro
130                 135                 140

Ser Thr Pro Thr Thr Pro Gly Phe Pro Pro Gln Ala Gly Ala Leu Trp
145                 150                 155                 160

Asp Asp Ala Leu Pro Ser Ala Gln Gly Cys Leu Ala Pro Gly Pro Leu
             165                 170                 175

Leu Asp Pro Pro Met Lys Ala Val Pro Thr Val Ala Gly Ala Arg Phe
         180                 185                 190

Pro Leu Phe His Phe Lys Thr Ser Pro Pro His Pro Ala Pro Ser
     195                 200                 205

Pro Ala Gly Gly His His Leu Ala Tyr Asp Pro Thr Ala Ala Ala
210                 215                 220

Leu Ser Leu Pro Leu Gly Ala Ala Ala Ala Gly Ser Gln Ala Ala
225                 230                 235                 240

Ala Leu Glu Gly His Ser Tyr Gly Leu Pro Leu Pro Lys Arg Ala Ala
             245                 250                 255

Ala Leu Ala Phe Ser Pro Leu Gly Leu Thr Ala Ser Pro Thr Ala Ser
         260                 265                 270

Ser Leu Leu Ala Glu Ser Pro Ser Leu Pro Ser Pro Asn Arg Ser
     275                 280                 285

Leu Ser Ser Gly Glu Gly Thr Cys Ala Val Cys Gly Asp Asn Ala Ala
290                 295                 300

Cys Gln His Tyr Gly Val Arg Thr Cys Glu Gly Cys Lys Gly Phe Phe
305                 310                 315                 320

Lys Arg Thr Val Gln Lys Asn Ala Lys Tyr Val Cys Leu Ala Asn Lys
             325                 330                 335

Asn Cys Pro Val Asp Lys Arg Arg Asn Arg Cys Gln Tyr Cys Arg
         340                 345                 350

Phe Gln Lys Cys Leu Ser Val Gly Met Val Lys Glu Val Val Arg Thr
     355                 360                 365

Asp Ser Leu Lys Gly Arg Arg Gly Arg Leu Pro Ser Lys Pro Lys Ser
370                 375                 380

Pro Leu Gln Gln Glu Pro Ser Gln Pro Ser Pro Pro Ser Pro Pro Ile
385                 390                 395                 400

Cys Met Met Asn Ala Leu Val Arg Ala Leu Thr Asp Ser Thr Pro Arg
                 405                 410                 415
```

```
Asp Leu Asp Tyr Ser Arg Tyr Cys Pro Thr Asp Gln Ala Ala Gly
            420                 425                 430

Thr Asp Ala Glu His Val Gln Gln Phe Tyr Asn Leu Leu Thr Ala Ser
        435                 440                 445

Ile Asp Val Ser Arg Ser Trp Ala Glu Lys Ile Pro Gly Phe Thr Asp
450                 455                 460

Leu Pro Lys Glu Asp Gln Thr Leu Leu Ile Glu Ser Ala Phe Leu Glu
465                 470                 475                 480

Leu Phe Val Leu Arg Leu Ser Ile Arg Ser Asn Thr Ala Glu Asp Lys
                485                 490                 495

Phe Val Phe Cys Asn Gly Leu Val Leu His Arg Leu Gln Cys Leu Arg
                500                 505                 510

Gly Phe Gly Glu Trp Leu Asp Ser Ile Lys Asp Phe Ser Leu Ser Leu
            515                 520                 525

Gln Ser Leu Asn Leu Asp Ile Gln Ala Leu Ala Cys Leu Ser Ala Leu
        530                 535                 540

Ser Met Ile Thr Glu Arg His Gly Leu Lys Glu Pro Lys Arg Val Glu
545                 550                 555                 560

Glu Leu Cys Asn Lys Ile Thr Ser Ser Leu Lys Asp His Gln Ser Lys
                565                 570                 575

Gly Gln Ala Leu Glu Pro Thr Glu Pro Lys Val Leu Arg Ala Leu Val
                580                 585                 590

Glu Leu Arg Lys Ile Cys Thr Leu Gly Leu Gln Arg Ile Phe Tyr Leu
                595                 600                 605

Lys Leu Glu Asp Leu Val Ser Pro Pro Ser Ile Ile Asp Lys Leu Phe
    610                 615                 620

Leu Asp Thr Leu Pro Phe
625                 630

<210> SEQ ID NO 10
<211> LENGTH: 2678
<212> TYPE: DNA
<213> ORGANISM: Homo Sapiens

<400> SEQUENCE: 10
ggcctcgagc gccccggcgg gaggttttc  tatatgagtg gagaagacag ctgttaccag    60
ggaggtcata caacattttt ttaggatgtc tgaagatgaa gaaaaagtga aattacgccg   120
tcttgaacca gctatccaga aattcattaa gatagtaatc ccaacaaacc tggaaaggtt   180
aagaaagcac cagataaata ttgagaagta tcaaaggtgc agaatctggg acaagttgca   240
tgaagagcat atcaatgcag gacgtacagt tcagcaactc cgatccaata tccgagaaat   300
tgagaaactt tgtttgaaag tccgaaagga tgacctagta cttctgaaga gaatgataga   360
tcctgttaaa gaagaagcat cagcagcaac agcagaattt ctccaactcc atttggaatc   420
tgtagaagaa cttaagaagc aatttaatga tgaagaaact ttgctacagc ctcctttgac   480
cagatccatg actgttggtg gagcatttca tactactgaa gctgaagcta gttctcagag   540
tttgactcag atatatgcct tacctgaaat tcctcaagat caaaatgctg cagaatcgcg   600
ggaaacctta gaagcggact taattgaact tagccaactg gtcactgact tctctctcct   660
agtgaactct cagcaggaga agattgacag cattgcagac catgtcaaca gtgctgctgt   720
gaatgttgaa gagggaacca aaaacttagg gaaggctgca aaatacaagc tggcagctct   780
gcctgtggca ggtgcactca tcgggggaat ggtaggggt  cctattggcc tccttgcatg   840
cttcaaagtg gcaggaattg cagctgcact tggtggtggg gtgttgggct tcacaggtgg   900
```

```
aaaattgata caaagaaaga aacagaaaat gatggagaag ctcacttcca gctgtccaga    960
tcttcccagc caaactgaca agaaatgcag ttaaaaacca aatttcagta ttattggtgc   1020
caacatgtct atcctgagga cctttgctgc tgttggacac tccgtcacct tttggaacac   1080
aagtatatca agatagtggc tactgatgtt caagtgggat tgaagtgtga taaatggata   1140
tattttgttg tttgctgggg tgttcatgga gatgttaaga gattgaggcc ctgggctgag   1200
ggtatataat gtatgtcagg taaagtttga agactgccaa ggagcagatt ttctccctgg   1260
aaatgtgaaa actgaaccta taactctgat aaggacttga gatgtgtaga acgttgggt    1320 tatgaagac tagtttcttc cataaccctg aattggagac cttaatgcta agtgtagatt    1380
attgaggttt gttagtgagg aaaagaataa gagttcagaa gcctttgtta tcagatagcg   1440
aaatcagggc ctagtgagga gcacaggtcg actacataat ggagtccatt ggcgaaccct   1500
attgcaattt ggtccaacta tatcttctgg tgaaggaaat taatgatgta agaaaatgca   1560
agaggctcaa cttctcttcc aaaaatcttc tggcttctga actcttcctc tgcctctctt   1620
taaataaata acacagaatt tcaagtggta ggagacttat taagccagtc accaagcttg   1680
gtctgtcagc ctgtcttcta acacctcaaa gatcttgtgc cctgtgctgt ccctcccttg   1740
taattatgaa aagttctttg gtttctgggg tgaactctac ccatgtataa tgaggaattc   1800
tctcataacc ttttttgtct tgtctgtcat ctctgttcat cccctcctat aacctctagg   1860 taaaagaaa agaaaaaaag aaatttcgag atattttcaa cattgttaga gtttgggcta    1920
aaatgagcaa ggagaaaaaa accaccaaga acatttcctg gggcatgttc cagttttgag   1980
gggtgatata tctgccagat agggggtatc tgacccagtc ttcttttcag ctggtctctg   2040
gggggagctg agaactcgct tgctacctca catccttttc cccagacttt ttatctccta   2100
tgcatccctt tgctttctat agctggtgtt tcttccccaa aatggcgttc ccatgcttac   2160
ctttctcaca ttctagacaa tgatggacaa agacgcatgc aagactcaga cccgggaat    2220 ggtgtggtgc taatctcaac acctgacatt cacagcaagc atgcccagc caaccgcat     2280 gtctatctca aaccgcagaa aggctttaat actggaaaaa aagaattcaa gactacaggc   2340
agctcccctc tgtaccccaa ctcatttaaa ataggaggaa tcactttttg ccttacttaa   2400 cgctttttc tgagcacagg gatgggcacc tgcaccccag aaggtgtgag ctgtctctct    2460
gccaggagct aaggttcatt aggggattgg atggtttatc acttctttct ttctgagttt   2520
acttttagta acttttattg atggctacct ttcatgtccc tgtctaaaga gactttctct   2580
ttcatacgtc ttaaatctca tcaatgaaat ccagtgaaac agcaccattt cttagtatca   2640
ttaaataact agaaagtatc aaaaaaaaaa aaaaaaa                            2678
```

<210> SEQ ID NO 11
<211> LENGTH: 2940
<212> TYPE: DNA
<213> ORGANISM: Homo sapiens

<400> SEQUENCE: 11

```
tcatactata ccattaaaag cagtacttgt tatatgtaaa ttctatctaa ataaagttga     60
attaaaaatg ggaatgtgtt cctacagcaa gtaatgagtt cgtgtcactg gaggtatctg    120
agcagaggtt cagtaaccac ttgtcaggaa tgttacagta gggcttcgca catcagagag    180
gagattgacc tgatgacctc aacattcctt ctacccagag attccatgag tcacagttgc    240
tgttgtgcca gcacaggtgt tgccatttta tgtagaatgc tttattaata tatttgatct    300
gaaacatttt aaactgtcat gattttaaaa tgtattaaga tacacaggtg taaagcacag    360
```

```
aacagtgatt tcattcactg ttccctactg catattacaa atggaaagat ctcataatag    420
atcaaaccgt attgtagtct tgttcctgaa acataacaat ttgtatttat tggaccaagg    480
gcattttact cctaaggtaa atgtgcctga tttaaactga atcctcaaag aaggtaagtt    540
agggaggtat tttggggttt gattttgttg ggttttttt ttccatcaaa cccaacatga    600
catgtaaatg cttatttgga ttttttttt ctggaaagta gattcatttg gagaataata    660
tgtttgtatg tttgagtgaa ttttagcgtg agatgctttt tgctgtaaag ttgccaccct    720
tttattacct aataattaag accccccct tttttttatg aaagttaatt tgtccttttcg    780 acatggctta tcagatgcta ttaatgaacc actattaaga tggcaaggct gcagtaccca    840
gggccctgat tacaggaatt aaaatagtgt gtgttggctc cctgctgctc cccagcagga    900
ccgctcactc ataattcctt tgcatctagt ctcagcagga aagattgac agcattgcag      960 accatgtcaa cagtgctgct gtgaatgttg aagagggaac caaaaactta gggaaggctg    1020
caaaatacaa gctggcagct ctgcctgtgg caggtgcact catcggggga atggtagggg    1080
gtcctattgg cctccttgca ggcttcaaag tggcaggaat tgcagctgca cttggtggtg    1140
gggtgttggg cttcacaggt ggaaaattga tacaaagaaa gaaacagaaa atgatggaga    1200
agctcacttc cagctgtcca gatcttccca gccaaactga caagaaatgc agttaaaaac    1260
caaatttcag tattattggt gccaacatgt ctatcctgag gaccttgct gctgttggac    1320 actccgtcac ctttggaac acaagtatat caagatagtg gctactgatg ttcaagtggg    1380
attgaagtgt gataaatgga tatattttgt tgtttgctgg ggtgttcatg gagatgttaa    1440
gagattgagg ccctgggctg agggtatata atgtatgtca ggtaaagttt gaagactgcc    1500
aaggagcaga ttttctccct ggaaatgtga aaactgaacc tataactctg ataaggactt    1560
gagatgtgta gaaacgttgg gttatggaag actagtttct tccataaccc tgaattggag    1620
accttaatgc taagtgtaga ttattgaggt ttgttagtga ggaaaagaat aagagttcag    1680
aagcctttgt tatcagatag cgaaatcagg gcctagtgag gagcacaggt cgactacata    1740
atggagtcca ttggcgaacc ctattgcaat ttggtccaac tatatcttct ggtgaaggaa    1800
attaatgatg taagaaaatg caagaggctc aacttctctt ccaaaaatct tctggcttct    1860
gaactcttcc tctgcctctc tttaaataaa taacacagaa tttcaagtgg taggagactt    1920
attaagccag tcaccaagct tggtctgtca gcctgtcttc taacacctca aagatcttgt    1980
gccctgtgct gtccctccct tgtaattatg aaaagttctt tggtttctgg ggtgaactct    2040
acccatgtat aatgaggaat tctctcataa ccttttttgt cttgtctgtc atctctgttc    2100
atcccctcct ataacctcta ggtaaaaaga aagaaaaaa agaaatttcg agatattttc    2160
aacattgtta gagtttgggc taaaatgagc aaggagaaaa aaaccaccaa gaacatttcc    2220
tggggcatgt tccagttttg aggggtgata tatctgccag ataggggta tctgacccag    2280 tcttcttttc agctggtctc tgggggagc tgagaactcg cttgctacct cacatccttt    2340
tccccagact ttttatctcc tatgcatccc tttgctttct atagctggtg tttcttcccc    2400
aaaatggcgt tccatgctt acctttctca cattctagac aatgatggac aaagacgcat    2460
gcaagactca gacccgggga atggtgtggt gctaatctca acacctgaca ttcacagcaa    2520
gcatggccca gcccaaccgc atgtctatct caaaccgcag aaaggcttta atactggaaa    2580
aaaagaattc aagactacag gcagctcccc tctgtacccc aactcattta aaataggagg    2640
aatcactttt tgccttactt aacgcttttt tctgagcaca gggatgggca cctgcacccc    2700
agaaggtgtg agctgtctct ctgccaggag ctaaggttca ttagggggatt ggatggttta    2760
```

```
tcacttctttt ctttctgagt ttacttttag taactttat tgatggctac ctttcatgtc    2820
cctgtctaaa gagactttct ctttcatacg tcttaaatct catcaatgaa atccagtgaa    2880
acagcaccat ttcttagtat cattaaataa ctagaaagta tcaaaaaaaa aaaaaaaaa     2940
```

<210> SEQ ID NO 12
<211> LENGTH: 302
<212> TYPE: PRT
<213> ORGANISM: Homo sapiens

<400> SEQUENCE: 12

```
Met Ser Glu Asp Glu Glu Lys Val Lys Leu Arg Arg Leu Glu Pro Ala
  1               5                  10                  15

Ile Gln Lys Phe Ile Lys Ile Val Ile Pro Thr Asn Leu Glu Arg Leu
             20                  25                  30

Arg Lys His Gln Ile Asn Ile Glu Lys Tyr Gln Arg Cys Arg Ile Trp
         35                  40                  45

Asp Lys Leu His Glu Glu His Ile Asn Ala Gly Arg Thr Val Gln Gln
     50                  55                  60

Leu Arg Ser Asn Ile Arg Glu Ile Glu Lys Leu Cys Leu Lys Val Arg
 65                  70                  75                  80

Lys Asp Asp Leu Val Leu Leu Lys Arg Met Ile Asp Pro Val Lys Glu
                 85                  90                  95

Glu Ala Ser Ala Ala Thr Ala Glu Phe Leu Gln Leu His Leu Glu Ser
            100                 105                 110

Val Glu Glu Leu Lys Lys Gln Phe Asn Asp Glu Thr Leu Leu Gln
            115                 120                 125

Pro Pro Leu Thr Arg Ser Met Thr Val Gly Gly Ala Phe His Thr Thr
        130                 135                 140

Glu Ala Glu Ala Ser Ser Gln Ser Leu Thr Gln Ile Tyr Ala Leu Pro
145                 150                 155                 160

Glu Ile Pro Gln Asp Gln Asn Ala Ala Glu Ser Arg Glu Thr Leu Glu
                165                 170                 175

Ala Asp Leu Ile Glu Leu Ser Gln Leu Val Thr Asp Phe Ser Leu Leu
            180                 185                 190

Val Asn Ser Gln Gln Glu Lys Ile Asp Ser Ile Ala Asp His Val Asn
        195                 200                 205

Ser Ala Ala Val Asn Val Glu Glu Gly Thr Lys Asn Leu Gly Lys Ala
    210                 215                 220

Ala Lys Tyr Lys Leu Ala Leu Pro Val Ala Gly Ala Leu Ile Gly
225                 230                 235                 240

Gly Met Val Gly Gly Pro Ile Gly Leu Leu Ala Cys Phe Lys Val Ala
                245                 250                 255

Gly Ile Ala Ala Ala Leu Gly Gly Val Leu Gly Phe Thr Gly Gly
            260                 265                 270

Lys Leu Ile Gln Arg Lys Lys Gln Lys Met Met Glu Lys Leu Thr Ser
        275                 280                 285

Ser Cys Pro Asp Leu Pro Ser Gln Thr Asp Lys Lys Cys Ser
    290                 295                 300
```

<210> SEQ ID NO 13
<211> LENGTH: 6382
<212> TYPE: DNA
<213> ORGANISM: Homo sapiens

<400> SEQUENCE: 13

```
ataaatgacg tgccgagaga gcgagcgaac gcgcagccgg gagagcggag tctcctgcct    60
cccgccccca cccctccag ctcctgctcc tcctccgctc cccatacaca gacgcgctca    120
cacccgctcc ctcactcgca cacacagaca caagcgcgca cacaggctcc gcacacacac    180
ttcgctctcc cgcgcgctca cacccctctt gccctgagcc cttgccggtg cagcgcggcg    240
ccgcagctgg acgcccctcc cgggctcact ttgcaacgct gacggtgccg gcagtggccg    300
tggaggtggg aacagcggcg gcatcctccc ccctggtcac agcccaagcc aggacgcccg    360
cggaacctct cggctgtgct ctcccatgag tcgggatcgc agcatccccc accagccgct    420
caccgcctcc gggagccgct gggcttgtac accgcagccc ttccgggaca gcagctgtga    480
ctccccccca gtgcagattt cgggacagct ctctagaaac tcgctctaaa gacggaaccg    540
ccacagcact caaagcccac tgcggaagag ggcagcccgg caagcccggg ccctgagcct    600
ggacccttag cggtgccggg cagcactgcc ggcgcttcgc ctcgccggac gtccgctcct    660
cctacactct cagcctccgc tggagagacc cccagcccca ccattcagcg cgcaagatag    720
tgtgtatata tatatatatg ggtgggtgtt ttgttgcagc tgctgatctt tttctttgca    780
gatggtacaa actctcccga gtcaatttcc tgggcctatg tccccaccta gctgactgaa    840
gttatcaaca ggggtccagt tgtgcaggc tgctagccct attggaagag tggggatgag    900
gtgggagaaa gcaaccacaa cgtgtgtggg caacctcaat tggcactcat aaaatgttag    960
aatgtcaact ctctcccttg gccactaaat ctctcacagg gtagtttttc ttgcctaact   1020
caggtttaca aatcaatgtg tatgccttgg gggaccaatg gcctcttttcc tcccaaataa   1080 accactggct ttctctttgt cccctaggt tatagctgag gagcccactc caattagttt   1140
ataggattca aagcctcttt ttaaaaacat ctctgagctt atgaggaaag acttcaagtt   1200
tcccaaatct agtggaggac agggcaaggg aggaaagata ggtacaggag tccacaggag   1260
gccaggtttt ggcaccccctt tgtcaggaat tcagcttcct tactagggat gaagaaaata   1320
agtgtggggc tttgtgtcta tgctaccaga aggaggagag gatgacactt cctctctgtt   1380
tcccagatta gagaacagtg aacccaatgc tgcctgttgg ctagaaaaca agtgttaact   1440
tgcttctgag agacccttttt ctctgtccct gcagatatgc cctgcgtcca agcccaatat   1500
agcccttccc ctccaggttc cagttatgcg gcgcagacat acagctcgga atacaccacg   1560
gagatcatga cccccgacta caccaagctg accatggacc ttggcagcac tgagatcacg   1620
gctacagcca ccacgtccct gccccagcatc agtaccttcg tggagggcta ctcgagcaac   1680
tacgaactca agccttcctg cgtgtaccaa atgcagcggc ccttgatcaa agtggaggag   1740
gggcgggcgc ccagctacca tcaccataca caccaccacc accaccacca ccaccatcac   1800
cagcagcagc atcagcagcc atccattcct ccagcctcca gcccggagga cgaggtgctg   1860
cccagcacct ccatgtactt caagcagtcc ccaccgtcca cccccaccac gccggccttc   1920
cccccgcagg cggggggcgtt atgggacgag gcactgcccc cggcgcccgg ctgcatcgca   1980
cccggcccgc tgctggaccc gccgatgaag gcggtcccca cggtggccgg cgcgcgcttc   2040
ccgctcttcc acttcaagcc ctcgccgcgc catcccccccg cgcccagccc ggccggcggc   2100
caccacctcg gctacgaccc gacggccgct gccgcgctca gcctgccgct gggagccgca   2160
gccgccgcgg gcagccaggc cgccgcgctt gagagccacc cgtacgggct gccgctggcc   2220
aagagggcgg cccgctggc cttcccgcct ctcggcctca cgccctcccc taccgcgtcc   2280
agcctgctgg gcgagagtcc cagcctgccg tcgccgccca gcaggagctc gtcgtctggc   2340
gagggcacgt gtgccgtgtg cggggacaac gccgcctgcc agcactacgg cgtgcgaacc   2400
```

```
tgcgagggct gcaagggctt tttcaagaga acagtgcaga aaaatgcaaa atatgtttgc   2460
ctggcaaata aaaactgccc agtagacaag agacgtcgaa accgatgtca gtactgtcga   2520
tttcagaagt gtctcagtgt tggaatggta aagaagttg tccgtacaga tagtctgaaa   2580
gggaggagag gtcgtctgcc ttccaaacca agagcccat acaacagga accttctcag    2640 ccctctccac cttctcctcc aatctgcatg atgaatgccc ttgtccgagc tttaacagac   2700
tcaacaccca gagatcttga ttattccaga tactgtccca ctgaccaggc tgctgcaggc   2760
acagatgctg agcatgtgca acaattctac aacctcctga cagcctccat tgatgtatcc   2820
agaagctggg cagaaaagat tccgggattt actgatctcc ccaaagaaga tcagacatta   2880
cttattgaat cagcctttt ggagctgttt gtcctcagac tttccatcag gtcaaacact    2940
gctgaagata agtttgtgtt ctgcaatgga cttgtcctgc atcgacttca gtgccttcgt   3000
ggatttgggg agtggctcga ctctattaaa gacttttcct taaatttgca gagcctgaac   3060
cttgatatcc aagccttagc ctgcctgtca gcactgagca tgatcacaga agacatggg    3120 ttaaaagaac caagagagt cgaagagcta tgcaacaaga tcacaagcag tttaaaagac    3180
caccagagta agggacaggc tctggagccc accgagtcca aggtcctggg tgccctggta   3240
gaactgagga agatctgcac cctgggcctc cagcgcatct tctacctgaa gctggaagac   3300
ttggtgtctc caccttccat cattgacaag ctcttcctgg acaccctacc tttctaatca   3360
ggagcagtgg agcagtgagc tgcctcctct cctagcacct gcttgctacg cagcaaaggg   3420
ataggtttgg aaacctatca tttcctgtcc ttccttaaga ggaaaagcag ctcctgtaga   3480
aagcaaagac tttcttttt ttctggctct tttccttaca acctaaagcc agaaaacttg    3540
cagagtattg tgttgggtt gtgttttata tttaggcatt gggggatggg gtgggaggg    3600 gttatagttc atgagggttt tctaagaaat tgctaacaaa gcacttttgg acaatgctat   3660
cccagcagga aaaaaagga taatataact gttttaaaac tctttctggg gaatccaatt   3720
atagttgctt tgtatttaaa aacaagaaca gccaagggtt gttcgccagg gtaggatgtg   3780
tcttaaagat tggtcccttg aaaatatgct tcctgtatca aaggtacgta tgtggtgcaa   3840
acaaggcaga aacttccttt taatttcctt cttcctttat tttaacaaat ggtgaaagat   3900
ggaggattac ctacaaatca gacatggcaa acaataatg gctgtttgct tccataaaca    3960
agtgcaattt tttaaagtgc tgtcttacta agtcttgttt attaactctc ctttattcta   4020
tatggaaata aaaggagg agtcatgtta gcaaatgaca cgttaatatc cctagcagag    4080
gctgtgttca ccttccctgt cgatcccttc tgaggtatgg cccatccaag actttaggc    4140 cattcttgat ggaaccagat ccctgccctg actgtccagc tatcctgaaa gtggatcaga   4200
ttataaactg gattacatgt aactgttttg gttgtgttct atcaacccca ccagagttcc   4260
ctaaacttgc ttcagttata gtaactgact ggtatattca ttcagaagcg ccataagtca   4320
gttgagtatt tgatccctag ataagaacat gcaaatcagc aggaactggt catacagggt   4380
aagcaccagg gacaataagg atttttatag atataattta attttttgtta ttggttaagg   4440 agacaattt ggagagcaag caaatctttt taaaaaatag tatgaatgtg aatactagaa    4500
aagatttaaa aaatagtatg agtgtgagta ctaggaagga ttagtgggct gcgtttcaac   4560
attccgtgtt cgtactccct tttgtatgtt tctactgtta atgccatatt actatgagat   4620
aatttgttgc atagtgtcct tatttgtata aacatttgta tgcacgttat attgtaatag   4680 cttttgcctgt atttattgca agaccaccag ctcctggaag ctgagttaca gagtaattaa   4740
atggggtgtt cacagtgact tggatacacc aattagaaat taaataagca aatatatata   4800
```

```
tatatataaa tatagcaggt tacatatata tatttataat gtgtcttttt attaaccatt    4860
tgtacaataa atgtcacttc ccatgccgtt attttatggt tcatttgcag tgacttttaa    4920
ggcagtactg tttagcactt tgatattaaa attttgctta tgttttgcta aattcgaata    4980
atgtttgaag atttttaggt ctaaaagtct ttatattata tactctgtat caagtcaaaa    5040
tatctttggc cattttgcta agaaacaaac tttgaatgtc aaactgatgt cacagtagtt    5100
tttgttagct ttaaatcatt tttgctttag tcttttaaa ggaaaataac aaaactatgc    5160
tgtttatatt gtcattaaat tatacaatca aacaaatgcc aaatgaattg cctaattgct    5220
gcaaagtata acccagatag gaaatcatat gttttttcc aagagtcatt ctaatatttg    5280
attatgttat gtgtgcttttt atgaaagatt gttatttta tatatcaaga tgatagaacc    5340
tggaatgtta ggattttgaa atgttagact tggaaggggc ctggtctgtc aactagtcca    5400
accccttaaa attcatagag gagcaaactg gggcccattg aagggtgaag agttactcaa    5460
ggtcaaacag ctggtaacag aatcaagact aagacctaat ttacctttcc atactctttt    5520
tttttctcaa cttcatctat ataaaatcag gcttttaaac ataaccacta atatttacct    5580
gaagataacc atgagtaaag tatacttttg cattaatttt ttgagcttat atgcaaacat    5640
aataaatatt attaaatatc aggaaagcta acatttcata caagatagct tcagaccaaa    5700
ttcaaattga atttgaataa attagaaata ctgtgcatac ataaccttct tgtgcaccat    5760
gagtatttgg aaagttaatc cttgtttttg tcgtgtctat aaaggaagaa caaacaaaa    5820 taaaaacaga gccctagaga aatgctgtta cttttatttt ttacacccat cagatttaag    5880
gaaaagactt tttagccatt ataatctagt ggttggaagg aatgaagaag ctttttttagt    5940 aataggtcca gatatgagtg ctaaaaataa agatgatagc atgttcttct gtcttccata    6000
gttattacaa ctatgagagc ctcccaagtc atcttatcaa ctcaactccc tttttttgt    6060 cttaatgttg cacataagtt tatacagagt ggatgaccac actagcacag aagagaacaa    6120
catgtattaa agcaggtgat tcctccccctt ggcgggagag ctctctcagt gtgaacatgc    6180
cttctgtggg cggaaatcag gaagccacca gctgttaatg gagagtgcct tgcttttatt    6240
tcagacagca gagttttcca aagtttctct gctcctctaa cagcattgct ctttagtgtg    6300
tgttaacctg tggtttgaaa gaaatgctct tgtacattaa caatgtaaat ttaaatgatt    6360
aaattacatt ttatcaatgg ca                                            6382
```

<210> SEQ ID NO 14
<211> LENGTH: 626
<212> TYPE: PRT
<213> ORGANISM: Homo sapiens

<400> SEQUENCE: 14

```
Met Pro Cys Val Gln Ala Gln Tyr Ser Pro Ser Pro Gly Ser Ser
  1               5                  10                  15

Tyr Ala Ala Gln Thr Tyr Ser Ser Glu Tyr Thr Thr Glu Ile Met Asn
                 20                  25                  30

Pro Asp Tyr Thr Lys Leu Thr Met Asp Leu Gly Ser Thr Glu Ile Thr
             35                  40                  45

Ala Thr Ala Thr Thr Ser Leu Pro Ser Ile Ser Thr Phe Val Glu Gly
         50                  55                  60

Tyr Ser Ser Asn Tyr Glu Leu Lys Pro Ser Cys Val Tyr Gln Met Gln
 65                  70                  75                  80

Arg Pro Leu Ile Lys Val Glu Glu Gly Arg Ala Pro Ser Tyr His His
                 85                  90                  95
```

-continued

```
His His His His His His His His His Gln Gln Gln His
            100                 105             110

Gln Gln Pro Ser Ile Pro Pro Ala Ser Ser Pro Glu Asp Glu Val Leu
            115                 120             125

Pro Ser Thr Ser Met Tyr Phe Lys Gln Ser Pro Pro Ser Thr Pro Thr
130                 135                 140

Thr Pro Ala Phe Pro Pro Gln Ala Gly Ala Leu Trp Asp Glu Ala Leu
145                 150                 155                 160

Pro Ser Ala Pro Gly Cys Ile Ala Pro Gly Pro Leu Leu Asp Pro Pro
                165                 170                 175

Met Lys Ala Val Pro Thr Val Ala Gly Ala Arg Phe Pro Leu Phe His
                180                 185                 190

Phe Lys Pro Ser Pro Pro His Pro Pro Ala Pro Ser Pro Ala Gly Gly
            195                 200             205

His His Leu Gly Tyr Asp Pro Thr Ala Ala Ala Leu Ser Leu Pro
            210                 215             220

Leu Gly Ala Ala Ala Ala Gly Ser Gln Ala Ala Leu Glu Ser
225                 230                 235                 240

His Pro Tyr Gly Leu Pro Leu Ala Lys Arg Ala Ala Pro Leu Ala Phe
                245                 250                 255

Pro Pro Leu Gly Leu Thr Pro Ser Pro Thr Ala Ser Ser Leu Leu Gly
                260                 265                 270

Glu Ser Pro Ser Leu Pro Ser Pro Pro Ser Arg Ser Ser Ser Ser Gly
            275                 280             285

Glu Gly Thr Cys Ala Val Cys Gly Asp Asn Ala Ala Cys Gln His Tyr
            290                 295             300

Gly Val Arg Thr Cys Glu Gly Cys Lys Gly Phe Phe Lys Arg Thr Val
305                 310                 315                 320

Gln Lys Asn Ala Lys Tyr Val Cys Leu Ala Asn Lys Asn Cys Pro Val
                325                 330                 335

Asp Lys Arg Arg Arg Asn Arg Cys Gln Tyr Cys Arg Phe Gln Lys Cys
                340                 345                 350

Leu Ser Val Gly Met Val Lys Glu Val Val Arg Thr Asp Ser Leu Lys
            355                 360             365

Gly Arg Arg Gly Arg Leu Pro Ser Lys Pro Lys Ser Pro Leu Gln Gln
370                 375                 380

Glu Pro Ser Gln Pro Ser Pro Pro Ser Pro Ile Cys Met Met Asn
385                 390                 395             400

Ala Leu Val Arg Ala Leu Thr Asp Ser Thr Pro Arg Asp Leu Asp Tyr
                405                 410                 415

Ser Arg Tyr Cys Pro Thr Asp Gln Ala Ala Ala Gly Thr Asp Ala Glu
            420                 425             430

His Val Gln Gln Phe Tyr Asn Leu Leu Thr Ala Ser Ile Asp Val Ser
            435                 440             445

Arg Ser Trp Ala Glu Lys Ile Pro Gly Phe Thr Asp Leu Pro Lys Glu
            450                 455             460

Asp Gln Thr Leu Leu Ile Glu Ser Ala Phe Leu Glu Leu Phe Val Leu
465                 470                 475                 480

Arg Leu Ser Ile Arg Ser Asn Thr Ala Glu Asp Lys Phe Val Phe Cys
                485                 490                 495

Asn Gly Leu Val Leu His Arg Leu Gln Cys Leu Arg Gly Phe Gly Glu
                500                 505                 510

Trp Leu Asp Ser Ile Lys Asp Phe Ser Leu Asn Leu Gln Ser Leu Asn
            515                 520             525
```

```
Leu Asp Ile Gln Ala Leu Ala Cys Leu Ser Ala Leu Ser Met Ile Thr
    530                 535                 540

Glu Arg His Gly Leu Lys Glu Pro Lys Arg Val Glu Glu Leu Cys Asn
545                 550                 555                 560

Lys Ile Thr Ser Ser Leu Lys Asp His Gln Ser Lys Gly Gln Ala Leu
                565                 570                 575

Glu Pro Thr Glu Ser Lys Val Leu Gly Ala Leu Val Glu Leu Arg Lys
            580                 585                 590

Ile Cys Thr Leu Gly Leu Gln Arg Ile Phe Tyr Leu Lys Leu Glu Asp
        595                 600                 605

Leu Val Ser Pro Pro Ser Ile Ile Asp Lys Leu Phe Leu Asp Thr Leu
    610                 615                 620

Pro Phe
625

<210> SEQ ID NO 15
<211> LENGTH: 598
<212> TYPE: PRT
<213> ORGANISM: Homo sapiens

<400> SEQUENCE: 15

Met Pro Cys Ile Gln Ala Gln Tyr Gly Thr Pro Ala Pro Ser Pro Gly
1               5                   10                  15

Pro Arg Asp His Leu Ala Ser Asp Pro Leu Thr Pro Glu Phe Ile Lys
                20                  25                  30

Pro Thr Met Asp Leu Ala Ser Pro Glu Ala Ala Pro Ala Ala Pro Thr
            35                  40                  45

Ala Leu Pro Ser Phe Ser Thr Phe Met Asp Gly Tyr Thr Gly Glu Phe
        50                  55                  60

Asp Thr Phe Leu Tyr Gln Leu Pro Gly Thr Val Gln Pro Cys Ser Ser
65                  70                  75                  80

Ala Ser Ser Ser Ala Ser Ser Thr Ser Ser Ser Ala Thr Ser Pro
                85                  90                  95

Ala Ser Ala Ser Phe Lys Phe Glu Asp Phe Gln Val Tyr Gly Cys Tyr
                100                 105                 110

Pro Gly Pro Leu Ser Gly Pro Val Asp Glu Ala Leu Ser Ser Ser Gly
            115                 120                 125

Ser Asp Tyr Tyr Gly Ser Pro Cys Ser Ala Pro Ser Pro Ser Thr Pro
130                 135                 140

Ser Phe Gln Pro Pro Gln Leu Ser Pro Trp Asp Gly Ser Phe Gly His
145                 150                 155                 160

Phe Ser Pro Ser Gln Thr Tyr Glu Gly Leu Arg Ala Trp Thr Glu Gln
                165                 170                 175

Leu Pro Lys Ala Ser Gly Pro Pro Gln Pro Pro Ala Phe Phe Ser Phe
            180                 185                 190

Ser Pro Pro Thr Gly Pro Ser Pro Ser Leu Ala Gln Ser Pro Leu Lys
        195                 200                 205

Leu Phe Pro Ser Gln Ala Thr His Gln Leu Gly Glu Gly Glu Ser Tyr
    210                 215                 220

Ser Met Pro Thr Ala Phe Pro Gly Leu Ala Pro Thr Ser Pro His Leu
225                 230                 235                 240

Glu Gly Ser Gly Ile Leu Asp Thr Pro Val Thr Ser Thr Lys Ala Arg
                245                 250                 255

Ser Gly Ala Pro Gly Gly Ser Glu Gly Arg Cys Ala Val Cys Gly Asp
            260                 265                 270
```

```
Asn Ala Ser Cys Gln His Tyr Gly Val Arg Thr Cys Glu Gly Cys Lys
            275                 280                 285

Gly Phe Phe Lys Arg Thr Val Gln Lys Asn Ala Lys Tyr Ile Cys Leu
        290                 295                 300

Ala Asn Lys Asp Cys Pro Val Asp Lys Arg Arg Arg Asn Arg Cys Gln
305                 310                 315                 320

Phe Cys Arg Phe Gln Lys Cys Leu Ala Val Gly Met Val Lys Glu Val
                325                 330                 335

Val Arg Thr Asp Ser Leu Lys Gly Arg Arg Gly Arg Leu Pro Ser Lys
            340                 345                 350

Pro Lys Gln Pro Pro Asp Ala Ser Pro Ala Asn Leu Leu Thr Ser Leu
        355                 360                 365

Val Arg Ala His Leu Asp Ser Gly Pro Ser Thr Ala Lys Leu Asp Tyr
            370                 375                 380

Ser Lys Phe Gln Glu Leu Val Leu Pro His Phe Gly Lys Glu Asp Ala
385                 390                 395                 400

Gly Asp Val Gln Gln Phe Tyr Asp Leu Leu Ser Gly Ser Leu Glu Val
                405                 410                 415

Ile Arg Lys Trp Ala Glu Lys Ile Pro Gly Phe Ala Glu Leu Ser Pro
            420                 425                 430

Ala Asp Gln Asp Leu Leu Leu Glu Ser Ala Phe Leu Glu Leu Phe Ile
        435                 440                 445

Leu Arg Leu Ala Tyr Arg Ser Lys Pro Gly Glu Gly Lys Leu Ile Phe
        450                 455                 460

Cys Ser Gly Leu Val Leu His Arg Leu Gln Cys Ala Arg Gly Phe Gly
465                 470                 475                 480

Asp Trp Ile Asp Ser Ile Leu Ala Phe Ser Arg Ser Leu His Ser Leu
                485                 490                 495

Leu Val Asp Val Pro Ala Phe Ala Cys Leu Ser Ala Leu Val Leu Ile
            500                 505                 510

Thr Asp Arg His Gly Leu Gln Glu Pro Arg Arg Val Glu Glu Leu Gln
        515                 520                 525

Asn Arg Ile Ala Ser Cys Leu Lys Glu His Val Ala Ala Val Ala Gly
        530                 535                 540

Glu Pro Gln Pro Ala Ser Cys Leu Ser Arg Leu Leu Gly Lys Leu Pro
545                 550                 555                 560

Glu Leu Arg Thr Leu Cys Thr Gln Gly Leu Gln Arg Ile Phe Tyr Leu
                565                 570                 575

Lys Leu Glu Asp Leu Val Pro Pro Pro Ile Ile Asp Lys Ile Phe
            580                 585                 590

Met Asp Thr Leu Pro Phe
        595

<210> SEQ ID NO 16
<211> LENGTH: 598
<212> TYPE: PRT
<213> ORGANISM: Homo sapiens

<400> SEQUENCE: 16

Met Pro Cys Val Gln Ala Gln Tyr Gly Ser Ser Pro Gln Gly Ala Ser
1               5                   10                  15

Pro Ala Ser Gln Ser Tyr Ser Tyr His Ser Ser Gly Glu Tyr Ser Ser
            20                  25                  30

Asp Phe Leu Thr Pro Glu Phe Val Lys Phe Ser Met Asp Leu Thr Asn
        35                  40                  45
```

```
Thr Glu Ile Thr Ala Thr Thr Ser Leu Pro Ser Phe Ser Thr Phe Met
 50                  55                  60

Asp Asn Tyr Ser Thr Gly Tyr Asp Val Lys Pro Pro Cys Leu Tyr Gln
 65                  70                  75                  80

Met Pro Leu Ser Gly Gln Gln Ser Ser Ile Lys Val Glu Asp Ile Gln
                 85                  90                  95

Met His Asn Tyr Gln Gln His Ser His Leu Pro Pro Gln Ser Glu Glu
                100                 105                 110

Met Met Pro His Ser Gly Ser Val Tyr Tyr Lys Pro Ser Ser Pro Pro
                115                 120                 125

Thr Pro Thr Thr Pro Gly Phe Gln Val Gln His Ser Pro Met Trp Asp
            130                 135                 140

Asp Pro Gly Ser Leu His Asn Phe His Gln Asn Tyr Val Ala Thr Thr
145                 150                 155                 160

His Met Ile Glu Gln Arg Lys Thr Pro Val Ser Arg Leu Ser Leu Phe
                165                 170                 175

Ser Phe Lys Gln Ser Pro Pro Gly Thr Pro Val Ser Ser Cys Gln Met
                180                 185                 190

Arg Phe Asp Gly Pro Leu His Val Pro Met Asn Pro Glu Pro Ala Gly
                195                 200                 205

Ser His His Val Val Asp Gly Gln Thr Phe Ala Val Pro Asn Pro Ile
                210                 215                 220

Arg Lys Pro Ala Ser Met Gly Phe Pro Gly Leu Gln Ile Gly His Ala
225                 230                 235                 240

Ser Gln Leu Leu Asp Thr Gln Val Pro Ser Pro Pro Ser Arg Gly Ser
                245                 250                 255

Pro Ser Asn Glu Gly Leu Cys Ala Val Cys Gly Asp Asn Ala Ala Cys
                260                 265                 270

Gln His Tyr Gly Val Arg Thr Cys Glu Gly Cys Lys Gly Phe Phe Lys
                275                 280                 285

Arg Thr Val Gln Lys Asn Ala Lys Tyr Val Cys Leu Ala Asn Lys Asn
290                 295                 300

Cys Pro Val Asp Lys Arg Arg Arg Asn Arg Cys Gln Tyr Cys Arg Phe
305                 310                 315                 320

Gln Lys Cys Leu Ala Val Gly Met Val Lys Glu Val Val Arg Thr Asp
                325                 330                 335

Ser Leu Lys Gly Arg Arg Gly Arg Leu Pro Ser Lys Pro Lys Ser Pro
                340                 345                 350

Gln Glu Pro Ser Pro Pro Ser Pro Pro Val Ser Leu Ile Ser Ala Leu
                355                 360                 365

Val Arg Ala His Val Asp Ser Asn Pro Ala Met Thr Ser Leu Asp Tyr
            370                 375                 380

Ser Arg Phe Gln Ala Asn Pro Asp Tyr Gln Met Ser Gly Asp Asp Thr
385                 390                 395                 400

Gln His Ile Gln Gln Phe Tyr Asp Leu Leu Thr Gly Ser Met Glu Ile
                405                 410                 415

Ile Arg Gly Trp Ala Glu Lys Ile Pro Gly Phe Ala Asp Leu Pro Lys
            420                 425                 430

Ala Asp Gln Asp Leu Leu Phe Glu Ser Ala Phe Leu Glu Leu Phe Val
                435                 440                 445

Leu Arg Leu Ala Tyr Arg Ser Asn Pro Val Glu Gly Lys Leu Ile Phe
450                 455                 460

Cys Asn Gly Val Val Leu His Arg Leu Gln Cys Val Arg Gly Phe Gly
```

```
                465                 470                 475                 480
Glu Trp Ile Asp Ser Ile Val Glu Phe Ser Ser Asn Leu Gln Asn Met
                    485                 490                 495

Asn Ile Asp Ile Ser Ala Phe Ser Cys Ile Ala Ala Leu Ala Met Val
                500                 505                 510

Thr Glu Arg His Gly Leu Lys Glu Pro Lys Arg Val Glu Glu Leu Gln
                515                 520                 525

Asn Lys Ile Val Asn Cys Leu Lys Asp His Val Thr Phe Asn Asn Gly
                530                 535                 540

Gly Leu Asn Arg Pro Asn Tyr Leu Ser Lys Leu Leu Gly Lys Leu Pro
545                 550                 555                 560

Glu Leu Arg Thr Leu Cys Thr Gln Gly Leu Gln Arg Ile Phe Tyr Leu
                565                 570                 575

Lys Leu Glu Asp Leu Val Pro Pro Ala Ile Ile Asp Lys Leu Phe
                580                 585                 590

Leu Asp Thr Leu Pro Phe
            595

<210> SEQ ID NO 17
<211> LENGTH: 295
<212> TYPE: PRT
<213> ORGANISM: Homo sapiens

<400> SEQUENCE: 17

Met Glu His Gln Leu Leu Cys Cys Glu Val Glu Thr Ile Arg Arg Ala
  1                 5                  10                  15

Tyr Pro Asp Ala Asn Leu Leu Asn Asp Arg Val Leu Arg Ala Met Leu
                 20                  25                  30

Lys Ala Glu Glu Thr Cys Ala Pro Ser Val Ser Tyr Phe Lys Cys Val
             35                  40                  45

Gln Lys Glu Val Leu Pro Ser Met Arg Lys Ile Val Ala Thr Trp Met
         50                  55                  60

Leu Glu Val Cys Glu Glu Gln Lys Cys Glu Glu Val Phe Pro Leu
 65                  70                  75                  80

Ala Met Asn Tyr Leu Asp Arg Phe Leu Ser Leu Glu Pro Val Lys Lys
                 85                  90                  95

Ser Arg Leu Gln Leu Leu Gly Ala Thr Cys Met Phe Val Ala Ser Lys
            100                 105                 110

Met Lys Glu Thr Ile Pro Leu Thr Ala Glu Lys Leu Cys Ile Tyr Thr
        115                 120                 125

Asp Asn Ser Ile Arg Pro Glu Glu Leu Leu Gln Met Glu Leu Leu Leu
    130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Glu Asn Lys Gln
                165                 170                 175

Ile Ile Arg Lys His Ala Gln Thr Phe Val Ala Leu Cys Ala Thr Asp
            180                 185                 190

Val Lys Phe Ile Ser Asn Pro Pro Ser Met Val Ala Ala Gly Ser Val
        195                 200                 205

Val Ala Ala Val Gln Gly Leu Asn Leu Arg Ser Pro Asn Asn Phe Leu
    210                 215                 220

Ser Tyr Tyr Arg Leu Thr Arg Phe Leu Ser Arg Val Ile Lys Cys Asp
225                 230                 235                 240

Pro Asp Cys Leu Arg Ala Cys Gln Glu Gln Ile Glu Ala Leu Leu Glu
```

-continued

```
                245                 250                 255
Ser Ser Leu Arg Gln Ala Gln Gln Asn Met Asp Pro Lys Ala Ala Glu
            260                 265                 270

Glu Glu Glu Glu Glu Glu Glu Val Asp Leu Ala Cys Thr Pro Thr
            275                 280                 285

Asp Val Arg Asp Val Asp Ile
            290                 295

<210> SEQ ID NO 18
<211> LENGTH: 289
<212> TYPE: PRT
<213> ORGANISM: Homo sapiens

<400> SEQUENCE: 18

Met Glu Leu Leu Cys His Glu Val Asp Pro Val Arg Arg Ala Val Arg
  1               5                  10                  15

Asp Arg Asn Leu Leu Arg Asp Asp Arg Val Leu Gln Asn Leu Leu Thr
                 20                  25                  30

Ile Glu Glu Arg Tyr Leu Pro Gln Cys Ser Tyr Phe Lys Cys Val Gln
             35                  40                  45

Lys Asp Ile Gln Pro Tyr Met Arg Arg Met Val Ala Thr Trp Met Leu
     50                  55                  60

Glu Val Cys Glu Glu Gln Lys Cys Glu Glu Val Phe Pro Leu Ala
 65                  70                  75                  80

Met Asn Tyr Leu Asp Arg Phe Leu Ala Gly Val Pro Thr Pro Lys Ser
                 85                  90                  95

His Leu Gln Leu Leu Gly Ala Val Cys Met Phe Leu Ala Ser Lys Leu
            100                 105                 110

Lys Glu Thr Ser Pro Leu Thr Ala Glu Lys Leu Cys Ile Tyr Thr Asp
        115                 120                 125

Asn Ser Ile Lys Pro Gln Glu Leu Leu Glu Trp Glu Leu Val Val Leu
    130                 135                 140

Gly Lys Leu Lys Trp Asn Leu Ala Ala Val Thr Pro His Asp Phe Ile
145                 150                 155                 160

Glu His Ile Leu Arg Lys Leu Pro Gln Gln Arg Glu Lys Leu Ser Leu
                165                 170                 175

Ile Arg Lys His Ala Gln Thr Phe Ile Ala Leu Cys Ala Thr Asp Phe
            180                 185                 190

Lys Phe Ala Met Tyr Pro Pro Ser Met Ile Ala Thr Gly Ser Val Gly
        195                 200                 205

Ala Ala Ile Cys Gly Leu Gln Gln Asp Glu Glu Val Ser Ser Leu Thr
    210                 215                 220

Cys Asp Ala Leu Thr Glu Leu Leu Ala Lys Ile Thr Asn Thr Asp Val
225                 230                 235                 240

Asp Cys Leu Lys Ala Cys Gln Glu Gln Ile Glu Ala Val Leu Leu Asn
                245                 250                 255

Ser Leu Gln Gln Tyr Arg Gln Asp Gln Arg Asp Gly Ser Lys Ser Glu
            260                 265                 270

Asp Glu Leu Asp Gln Ala Ser Thr Pro Thr Asp Val Arg Asp Ile Asp
        275                 280                 285

Leu

<210> SEQ ID NO 19
<211> LENGTH: 317
<212> TYPE: PRT
<213> ORGANISM: Equus caballus
```

<400> SEQUENCE: 19

```
Met Pro Leu Gln Gly Pro Gln Arg Arg Leu Leu Gly Ser Leu Asn Ser
1               5                   10                  15

Thr Leu Pro Ala Thr Pro Tyr Leu Gly Leu Thr Thr Asn Gln Thr Glu
            20                  25                  30

Pro Pro Cys Leu Glu Val Ser Ile Pro Asp Gly Leu Phe Leu Ser Leu
        35                  40                  45

Gly Leu Val Ser Leu Val Glu Asn Val Leu Val Val Thr Ala Ile Ala
    50                  55                  60

Lys Asn Arg Asn Leu His Ser Pro Met Tyr Tyr Phe Ile Cys Cys Leu
65                  70                  75                  80

Ala Val Ser Asp Leu Leu Val Ser Met Ser Asn Val Leu Glu Met Ala
                85                  90                  95

Ile Leu Leu Leu Leu Glu Ala Gly Val Leu Ala Thr Gln Ala Ser Val
                100                 105                 110

Leu Gln Gln Leu Asp Asn Ile Ile Asp Val Leu Ile Cys Gly Ser Met
            115                 120                 125

Val Ser Ser Leu Cys Phe Leu Gly Ser Ile Ala Val Asp Arg Tyr Ile
130                 135                 140

Ser Ile Phe Tyr Ala Leu Arg Tyr His Ser Ile Met Met Leu Pro Arg
145                 150                 155                 160

Val Trp Arg Ala Ile Val Ala Ile Trp Val Val Ser Val Leu Ser Ser
                165                 170                 175

Thr Leu Phe Ile Ala Tyr Tyr Asn His Thr Ala Val Leu Leu Cys Leu
            180                 185                 190

Val Thr Phe Phe Val Ala Met Leu Val Leu Met Ala Val Leu Tyr Val
        195                 200                 205

His Met Leu Ala Arg Ala Cys Gln His Ala Arg Gly Ile Ala Arg Leu
    210                 215                 220

His Lys Arg Gln His Pro Ile His Gln Gly Phe Gly Leu Lys Gly Ala
225                 230                 235                 240

Ala Thr Leu Thr Ile Leu Leu Gly Val Phe Phe Leu Cys Trp Gly Pro
                245                 250                 255

Phe Phe Leu His Leu Ser Leu Leu Ile Leu Cys Pro Gln His Pro Thr
            260                 265                 270

Cys Gly Cys Val Phe Lys Asn Phe Lys Leu Phe Leu Thr Leu Ile Leu
        275                 280                 285

Cys Ser Ala Ile Val Asp Pro Leu Ile Tyr Ala Phe Arg Ser Gln Glu
    290                 295                 300

Leu Arg Lys Thr Leu Gln Glu Val Leu Leu Cys Ser Trp
305                 310                 315
```

<210> SEQ ID NO 20
<211> LENGTH: 1721
<212> TYPE: DNA
<213> ORGANISM: Equus caballus

<400> SEQUENCE: 20

```
tctgggcagg tccagaggag gccacacctg gagcagaggc ccagctggga gtgctggttg      60
gctgagtaca gggaggctgg gagtgcaaag gggagatgtc ctgctgtgtc taggagtctg     120
ggggcccggg gagcccagac ggtcgtgggt gccatttgcg ccacttggcg gcggcggcag     180
gagggtgtgt gggcgctctg atggtgcctt cccgggcacc cacccatcat gtgactgccc     240
tcaggaggag gggctccatg gaagccttta aagatgctga gaaaggctcc attcttccca     300
```

```
gtttccccaa cccacccctg ctctggggag gcaggaggcc tggcaggcca ggaggcagca    360
agagctagag atgtgcggac ctgagcaaca gcacctccag ggagaggccg ggaggtgggc    420
tgagaaccca atgagactcc agagcccaga gggttggtgc cacagagctt gggtcttggc    480
tgggaagtga ccagactctg gtggagaggc caggttctct ggctgggcca cggttgggcc    540 aacattttc cagccaggga gagcgtgagt gtgagggcag ccctgcgggt ggcaccatga    600
gctgagtggg acgcctggag agtgaggacc ccttcctgct tcctagaggg actatgcctc    660
tgcaggggcc ccagaggagg ctgctgggct ccctcaactc cacctctcca gccacccct    720 acctcgggct gaccaccaac cagacggagc ccccgtgcct ggaagtgtcc attcctgatg    780
ggctcttcct cagcctgggg ctggtgagcc tagtggaaaa tgtactggtg gtgactgcca    840
tcgccaagaa ccgcaacctg cactcaccca tgtactactt catctgctgc ctggccgtgt    900
ccgacctgct ggtgagcatg agcaacgtgc tggagatggc aatcttgctg ctgctggagg    960
ccggagtcct ggccacccag gcctcggtgt tgcagcagct ggacaacatc attgatgtgc    1020
tcatctgcgg ctccatggtg tccagcctct gcttcctggg cagcattgcc gtagaccgct    1080
acatctccat cttctatgcg ctgcggtacc acagcatcat gatgctgccc cgtgtgtggc    1140
gtgccatcgt ggccatctgg gtggttagtg tcctctctag caccctcttc atcgcttact    1200
acaaccacac ggctgtcctg ctctgtctcg tcaccttctt tgtggccatg ctggtgctca    1260
tggcagtgct gtacgtgcac atgctcgcca gggcgtgcca gcacgcccgg ggcatcgccc    1320
ggctccacaa gaggcagcac cccatccacc agggctttgg cctcaagggt ccgccaccc    1380 tcaccatcct gctgggcgtt ttcttcctct gctggggccc ctttttcctg cacctctcac    1440
tccttatcct ctgccctcaa caccccacct gcggctgtgt cttcaagaac ttcaagctct    1500
tcctcaccct catcctgtgc agcgccatcg tcgacccct catctatgcc ttccgcagcc    1560
aggaacttcg aaagacgctc caggaggtgc tgctgtgctc ctggtgaggg aggggagcc    1620 tgcgggccaa ggcagagggc tgtgcacagg gaggtggtga catcagggg ctcggttcct    1680 gtgtgaccgg ggcagtcact tgccaaagag ggtggcctat a    1721
```

<210> SEQ ID NO 21
<211> LENGTH: 28
<212> TYPE: DNA
<213> ORGANISM: Artificial Sequence
<220> FEATURE:
<223> OTHER INFORMATION: Primer

<400> SEQUENCE: 21
ttgtagtatc agcaccacct gggaactc                                        28

<210> SEQ ID NO 22
<211> LENGTH: 26
<212> TYPE: DNA
<213> ORGANISM: Artificial Sequence
<220> FEATURE:
<223> OTHER INFORMATION: Primer

<400> SEQUENCE: 22
tcatgtgtct atcccactag gaggga                                          26

<210> SEQ ID NO 23
<211> LENGTH: 20
<212> TYPE: DNA
<213> ORGANISM: Artificial Sequence
<220> FEATURE:
<223> OTHER INFORMATION: Primer

```
<400> SEQUENCE: 23
gtaggtctgc acccaggaac                                              20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
agaagttggg caagagcaga                                              20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
cacagtatgg ctgccaaaga                                              20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
caaagtgcca gagggaagtt                                              20

<210> SEQ ID NO 27
<211> LENGTH: 50
<212> TYPE: DNA
<213> ORGANISM: Artificial Sequence
<220> FEATURE:
<223> OTHER INFORMATION: Probe sequence

<400> SEQUENCE: 27
acctgggaac tcattagaaa tgcaaaatct cagaattgga attgaactta             50

<210> SEQ ID NO 28
<211> LENGTH: 40
<212> TYPE: DNA
<213> ORGANISM: Artificial Sequence
<220> FEATURE:
<223> OTHER INFORMATION: Probe sequence

<400> SEQUENCE: 28
ggaactcatt agaaatgcaa aatctcagaa ttggaattga                        40

<210> SEQ ID NO 29
<211> LENGTH: 36
<212> TYPE: DNA
<213> ORGANISM: Artificial Sequence
<220> FEATURE:
<223> OTHER INFORMATION: Probe sequence

<400> SEQUENCE: 29
aactcattag aaatgcaaaa tctcagaatt ggaatt                            36

<210> SEQ ID NO 30
<211> LENGTH: 30
```

-continued

```
<212> TYPE: DNA
<213> ORGANISM: Artificial Sequence
<220> FEATURE:
<223> OTHER INFORMATION: Probe sequence

<400> SEQUENCE: 30
tcattagaaa tgcaaaatct cagaattgga                                      30

<210> SEQ ID NO 31
<211> LENGTH: 28
<212> TYPE: DNA
<213> ORGANISM: Artificial Sequence
<220> FEATURE:
<223> OTHER INFORMATION: Probe sequence

<400> SEQUENCE: 31
cattagaaat gcaaaatctc agaattgg                                        28

<210> SEQ ID NO 32
<211> LENGTH: 20
<212> TYPE: DNA
<213> ORGANISM: Artificial Sequence
<220> FEATURE:
<223> OTHER INFORMATION: Probe sequence

<400> SEQUENCE: 32
agaaatgcaa aatctcagaa                                                 20

<210> SEQ ID NO 33
<211> LENGTH: 16
<212> TYPE: DNA
<213> ORGANISM: Artificial Sequence
<220> FEATURE:
<223> OTHER INFORMATION: Probe sequence

<400> SEQUENCE: 33
aaatgcaaaa tctcag                                                     16

<210> SEQ ID NO 34
<211> LENGTH: 10
<212> TYPE: DNA
<213> ORGANISM: Artificial Sequence
<220> FEATURE:
<223> OTHER INFORMATION: Probe sequence

<400> SEQUENCE: 34
tgcaaaatct                                                            10

<210> SEQ ID NO 35
<211> LENGTH: 17
<212> TYPE: DNA
<213> ORGANISM: Artificial Sequence
<220> FEATURE:
<223> OTHER INFORMATION: Probe sequence

<400> SEQUENCE: 35
gaaatgcaaa atctcag                                                    17

<210> SEQ ID NO 36
<211> LENGTH: 10
<212> TYPE: PRT
<213> ORGANISM: Artificial Sequence
<220> FEATURE:
<223> OTHER INFORMATION: synthetically generated peptide

<400> SEQUENCE: 36

Ser Pro Arg Arg Ser Glu Arg Leu Gly Trp
```

```
<210> SEQ ID NO 37
<211> LENGTH: 28
<212> TYPE: DNA
<213> ORGANISM: Artificial Sequence
<220> FEATURE:
<223> OTHER INFORMATION: Primer

<400> SEQUENCE: 37
ggaacataaa gtagatttgg tgggaaag                                      28

<210> SEQ ID NO 38
<211> LENGTH: 28
<212> TYPE: DNA
<213> ORGANISM: Artificial Sequence
<220> FEATURE:
<223> OTHER INFORMATION: Primer

<400> SEQUENCE: 38
ttctgataaa tgcataaacc cacgtaac                                      28

<210> SEQ ID NO 39
<211> LENGTH: 28
<212> TYPE: DNA
<213> ORGANISM: Artificial Sequence
<220> FEATURE:
<223> OTHER INFORMATION: Primer

<400> SEQUENCE: 39
ttccaattct gagattttgc atttctaa                                      28

<210> SEQ ID NO 40
<211> LENGTH: 18
<212> TYPE: DNA
<213> ORGANISM: Artificial Sequence
<220> FEATURE:
<223> OTHER INFORMATION: Primer

<400> SEQUENCE: 40
cctgccacag gcagagct                                                 18

<210> SEQ ID NO 41
<211> LENGTH: 28
<212> TYPE: DNA
<213> ORGANISM: Artificial Sequence
<220> FEATURE:
<223> OTHER INFORMATION: Primer

<400> SEQUENCE: 41
tggtcactga tttctctctc ctagtaaa                                      28

<210> SEQ ID NO 42
<211> LENGTH: 25
<212> TYPE: DNA
<213> ORGANISM: Artificial Sequence
<220> FEATURE:
<223> OTHER INFORMATION: Primer

<400> SEQUENCE: 42
gctcactcat aattcctttg catct                                         25

<210> SEQ ID NO 43
<211> LENGTH: 30
<212> TYPE: DNA
<213> ORGANISM: Artificial Sequence
<220> FEATURE:
```

```
<223> OTHER INFORMATION: Probe sequence

<400> SEQUENCE: 43
cttgtatttt gcagccttcc ccaagttttt                                    30

<210> SEQ ID NO 44
<211> LENGTH: 22
<212> TYPE: DNA
<213> ORGANISM: Artificial Sequence
<220> FEATURE:
<223> OTHER INFORMATION: Primer

<400> SEQUENCE: 44
gaatcagcct ttttggagct gt                                            22

<210> SEQ ID NO 45
<211> LENGTH: 25
<212> TYPE: DNA
<213> ORGANISM: Artificial Sequence
<220> FEATURE:
<223> OTHER INFORMATION: Primer

<400> SEQUENCE: 45
cattgcagaa cacaaactta tcttc                                         25

<210> SEQ ID NO 46
<211> LENGTH: 31
<212> TYPE: DNA
<213> ORGANISM: Artificial Sequence
<220> FEATURE:
<223> OTHER INFORMATION: Probe Sequence

<400> SEQUENCE: 46
tgttctcaga ctttccatca ggtcgaacac t                                  31

<210> SEQ ID NO 47
<211> LENGTH: 21
<212> TYPE: DNA
<213> ORGANISM: Artificial Sequence
<220> FEATURE:
<223> OTHER INFORMATION: Primer

<400> SEQUENCE: 47
agtccctgcc ctttgtacac a                                             21

<210> SEQ ID NO 48
<211> LENGTH: 21
<212> TYPE: DNA
<213> ORGANISM: Artificial Sequence
<220> FEATURE:
<223> OTHER INFORMATION: Primer

<400> SEQUENCE: 48
gatccgaggg cctcactaaa c                                             21

<210> SEQ ID NO 49
<211> LENGTH: 23
<212> TYPE: DNA
<213> ORGANISM: Artificial Sequence
<220> FEATURE:
<223> OTHER INFORMATION: Probe Sequence

<400> SEQUENCE: 49
cgcccgtcgc tactaccgat tgg                                           23

<210> SEQ ID NO 50
```

```
<211> LENGTH: 1669
<212> TYPE: DNA
<213> ORGANISM: Equus caballus

<400> SEQUENCE: 50
gagacttcag tcagatgacc atgcttagga aatatcctta tcccttcctc atatgaatgt      60
gcagtctaaa cttttccgtc tgaacatgtt taaagtgtat atatgtataa gttttataca     120
tctttatggt tttcttcttt cagcgacctt tttcaataaa ttggtcaacc taacacgyta     180
taaaagaggg ctcctgctgt atttaaaaac acagatagtg cattccagat aggggygagt     240
ggaaggggaa tacaccatgg ataggtca agttgacgtg gagaaggacc tccaatgtca       300
cagtgaggaa tttggacatt gcaataagca ataagggaac agtaagaggt tgtcgttttg     360
tcatttgata gtacagattt ttgagcatat caaaggacta gcccttatg aaattagttt      420
ggcagctagt aggcttgctg ctccggtccc cgtagtccac gtcattcctc cccatagcaa     480
aggctgctgg agtcttgctc cttaggctcc agacctgcgc tgtccaatag gtagcggtag     540
ccacatgtgg ctattgagca cttaaacgtg gctagccgga actgagatgt gctgtaagtg     600
taaaataaac ccagatttca gagacttagt atgagaaaag gaatgtaaaa tatcttatta     660
acgatgtttt attgcttaca tgttgaaacg atgatagcat atactgggtt aaataaaata     720
tactattaaa attcatttcc acttatttct ttttactttt ttaaaatgtg actacttgaa     780
aatttagaac tttaacatgt agctcggcat ctggaggctc acattatatt tatctttctg     840
gacagaaatg gctctagttc tagatcaatc ctgacacgag ataggagagt tgagccatcc     900
tgcccctag cccaatgctt tgggactcat ttctcctact gggtgtctga tttcaaataa      960
agaatctttg tcacactcct ctttctccac tttgggatgt ggtctggttt ccttgatttc    1020
tgctttgtaa tgtttaaggc tcaggttgct ggctccttag agatttgtct tctctctcat    1080
tttccgtcat gcacaaatcc atgtttcctc cttatgatga ctccttcctc tggagaagca    1140
gacacttcca gaaagatgga gatcaacaat agggcattgg atttggtgat cagggaatca    1200
ctacctttaa gagaacgacc atatcaacta tttgagcgga cggctgagca gttgtcagga    1260
ttgccacacc aacgatctca taggcttaaa gaccagaaga aaaaccaaat cacaccttag    1320
ccaatggtag aacaatgaca agcacactgg cacatccctc acccagtctt tgtctaccgg    1380
tggaactgag acttccagaa tgaagggcct cctccctgtc atttattatt ttgaagtagt    1440
gttaccaagt gctcactttg aagaagcatt cagctagaca gttagggatc acaatcaagt    1500
taaaagaaa aggaaataag tttgcagcac tggggctgca ttcagaaatg ggagagacat    1560
ccccacaagt cacgtcaccc tcatgcaagc aaagctgaat acacctgatt tatttgccta    1620
tccagggacc tggccagatt ttttctaaac tctggaggca gtcttggtt                1669

<210> SEQ ID NO 51
<211> LENGTH: 1429
<212> TYPE: DNA
<213> ORGANISM: Equus caballus

<400> SEQUENCE: 51
tgacttgtta gaggcggttc taattctctt gggctgctgg ggaatctcaa cagaaaatgg      60
tttagtacgt atgagcacgt gcatatctga gtgtacgtac atatgcctcc atcttatgtg     120
tgtacgtgtg tttatgcatc agggcacagt agctgataca atgcaataga tacctaaaaa     180
cacggcacca acaaaatcaa aatggactat tcactagaaa ataacaccaa cgaggttggc     240
taggtatatg tgttttattt tgtcttcatt tttttaagtc cccacattga actgcataac     300
```

```
ctcttacatt tcatcttaaa gaatttcata acatcttgta aaaagctrct tccttctgtt    360
cttcagtctt gcaaagtgct cactgacgtt gctgttgcag tctggaagaa ttgaaagctt    420
tagcattcgg ttctcaagga gctctccctc ctgaccacat tgaaggcagc atggcgtggt    480
acaaagggtc ctaaacagtg agccacagga catgggttta agccagaatc ctacccattg    540
tgaagttagg ctagaccctc acagccctga gtctatttcc tcatttgtaa aaaagggcta    600
ataacccttg acctgtcctt aaaaagagtc tctgggaatg ggcttcgtaa actctgcagc    660
actgaggcaa gccatggaaa gggattagta ccgccacaat tgtggaagta agtctcacgc    720
ctaagaagca gtcccagcga ggaggttttc ggtacaggga gacaggaagg aaagcrcagg    780
attccaacac acacctgtga cttcattcat gaaattcagg ggagaaattt aaaatatttc    840
cctagacttc cctcagaact acattggctt caaggaggc aaaagtcaag atgtaacagg    900
aatttttatt ctgatttgtt ctgaaatatg ggttttcaat catcatgatt ccttaaatta    960
gaatggatct gcaaaaatag atacatgcaa acatttttc ctaaatttt ttcatgtaag    1020 agtatgcagc ctgctgtgta atgtcacaca ctaaaataac attggcatag aatgggagta    1080
aaatcctttc tctggaaata agcatatgtt attaaaatta tatatcattt gtakccaact    1140
actagaaaag aatccacact gcagtgttta agtttaggat tgacttggcg tactgtgaca    1200
ttgtgcaatc aaggatagga ccaggaggca agggcttgag ttctacttcc agctattccg    1260
ctaaytaacc tggtgacttg aataaagcat tggcctccat gagctttatt tcttccatgg    1320
ggaaaatgaa ttaccacatg tgcctactca cctgcttcat agggttctta tggggatcaa    1380
atgaaagtgt ctatgaaaat ggctctctat aactatgaaa tggttgggt                1429
```

<210> SEQ ID NO 52
<211> LENGTH: 1048
<212> TYPE: DNA
<213> ORGANISM: Equus caballus
<220> FEATURE:
<223> OTHER INFORMATION: Synthetically generated oligonucleotide

<400> SEQUENCE: 52

```
agaagttgtg ggagctctaa tgtggcagtg gaggtgaagg tggggcccac ttgctacgaa     60
cagtctgctc tcacaaaaaa tttaaagcaa ggcaatattt tgcacacttt ttctgtaatt    120
gaatatcatt aaggtactaa atagataatg caccttgcct ttcttttttt tcaaaaacta    180
tttattgaat gcctactata taccaggmat tgtgcaagag ataaagggat aaaatggtga    240
tcaaagaaaa agagcaaaga aagctaaaag acagtcgagt ggaaagagta ggaatggaaa    300
agaaaaagcg gattgctggt gggctccttt attgccaaag tctttgtatg ttttggggtc    360
cttgagtcag gaaaaaaagt agttatgctg gatccctctg acaygtatgg caaggagtgt    420
gtgtgtgtgt gcatgcatgc acgtgtgtgt ggtgtgtttt ggagaagatg agagagcata    480
aggagaatac ctcaatttct gyccaataga agtgggagga tggaatcact gatgttccag    540
aagctaagaa aggaaaaatg taaattattt tctttacgca tgtggtttgc acaacatcct    600
ccaacataag actcccactt gggtcctaaa gttgaaaaaa tctagggagt acggagaaag    660
agaacagagc aacaagacga cacagtatac caggtgtcag cgctagcaca tcaactccga    720
aagggagacc tttgcaagac attctccagg ttcactagcc atgtgcatta cgaatctgga    780
attaatgcta tttacctaaa ttataaagac gtatttctca cataagtccc ttatgtgcaa    840
gcagggtagc aaaggaagag ttctttatat gggggtaact tgaagagccc ctaagaattt    900 cctacccca atagttcact gaaattcttc attttgtttc gctctttgga acctgtcttt    960
```

```
aattatctcc ctatgaccac agaagcagtt ataacacagt acagtaatta aagattctga    1020
aatcagattg ctttgttcac cctgggct                                      1048
```

<210> SEQ ID NO 53
<211> LENGTH: 862
<212> TYPE: DNA
<213> ORGANISM: Equus caballus

<400> SEQUENCE: 53

```
gaatcatcgc actgtggtgg attcatgttc cagaagctaa gaaggaaaaa tgtaaattat      60
tttctttacg catgtggttt gcacaacatc ctccaacata agactcccac ttgggtccta     120
aagttggaaa atctaggga gtacggagaa agagaacaga gcaacaagac gacacagtat     180
accaggtgtc agcgctagca catcaactcc gaaagggaga cctttgcaag acattctcca     240
ggttcactag ccatgtgcat tacgaatctg gaattaatgc tatttaccta aattataaag     300
acgtatttct cacataagtc cctaatgtgc aagcagggta gcaaaggaag agttctttat     360
atgggggtaa cttgaagagc ccctaagaat ttcctacccc aaatagttca ctgaaattct     420
tcattttgtt tcgctctttg gaacctgtct ttaattatct ccctatgacc acagaagcag     480
ttataacaca gtacagtaat taagattct gaaatcagat tgctttgttc accctgggct     540
tcaccactag tcactcctgt gattattggg tatgcttctt actaacagct aagaattaca     600
tttattgagc atgtaatcac ttagcaacta taggcacaag cattttacat gtattggcag     660
gtatcattaa tcctcacaat acccccatga ggtatgacgt aggtrtcatg atcatgatgt     720
catcttacgg atgaggaaac tgaggcacat atggaacttt caggtccaaa agtaataaga     780
gtgagctgaa attcaaacct aaacagactt aactatatac tacaggcccc tcacttaaac     840
gctctaagcc accataccta ct                                              862
```

<210> SEQ ID NO 54
<211> LENGTH: 793
<212> TYPE: DNA
<213> ORGANISM: Equus caballus

<400> SEQUENCE: 54

```
cgcgtttttt agcctcgatt cgggtgccac aaaacggcgg tgaacgcact gggtgctggg      60
caacccatac tcggctcccc caaggcggtg taatgcttct tgcccaggga ctccgttcac     120
cttaagcact gctttcttac ccttataatt ctttgtaatt aacgtagcat tcctcgaggc     180
ccccaccaac accccaacgc gcccggccca ggcgcggtg accccgcctg gtcccgctgt     240
gacctctgtc ctctctcccg gtgcccgcag agcccactgc ggaagagcgc agcccggcaa     300
gccccaggcc tgagactgga ccctcggcag agccgggcag caccgcagcc gcttcgcctc     360
gccrgacgtc ccccgcttct acactctcag cctccgctgg agagaccccc agccccacca     420
ttcagcgcgc aagatatcct ccaggtaggt ctgaaggcac gaccccttat tcctcgcagg     480
ctggaagaag tgggggaggg gatgggccct gggtccctgg caggggcggg ctggtcgact     540
tgcctagcgc caggacagtg actgctggcc gagcatttca cagcacaggt ggcttctttg     600
cacgaagctc ctctggatac cacaccctgt tgctaccgag tggaggagcc agattaaatt     660
aagcgttgca ttttcaaaa atattttttcc taagaaaaat gcaaatacac cgatagatta     720
ggatctttta atacactgta atgtcatgtt tgctgtcctt ttatatccgg tttacgcatt     780
taagagtatt ggg                                                        793
```

<210> SEQ ID NO 55

<211> LENGTH: 1231
<212> TYPE: DNA
<213> ORGANISM: Equus caballus

<400> SEQUENCE: 55

```
ttaaaataca ggaaaggcaa agttaaggta tggaccacat agagttcaga ttagtcacgc      60
ctgatactca tcaagctcct cttgtgtacc aggcactggg crtgggcttt caaatctttt     120
astttacagt catgcatcac ttaacaacag aggtatgctc tgagaaacgc atcattaggt     180
gattttatca ttatgcgaac atcgtagagt ggactaacac aaatctggac ggcatagcct     240
rctacacacc taggctctrt ggtactaatc ttatgggagc acggtcgcat atgtggtccg     300
tcgttgactg aatgttgtta tgcagcacat gactctattt aattcccaca acgatcgtag     360
gaggtagcaa ttagaagtcc tgttttatac ataaggaaaa ggaagcccag agagattaga     420
agtgcccagg gccccttagc taggtggtga tgtttcacca gaagtttcag ggtgtctttc     480
atgagagaga gaagagtggg atgattatgg acataatata aactatcacg gcagatttag     540
aaacagccct ccgcagcccc cctgttaaaa gcagagaggg taatacaaaa taagctctct     600
tttcacttta aggcgcttgt cagtttctga ttgacttctg gcggtcgcag tgactcggtg     660
gttttagagt ctgcacaatg gaattgtagt gtctagcgtc aggccttatc agtttctgac     720
attcaaggaa atgagggga agtcctggtg agggagcgct aaagagaaca gtctcaggtt     780
catggcagag gccacgcact gggcttcact tccacagtct gtgagcgcct gctcctctgt     840
gtcccgtccc aggggagcc agtaattgac tctagtaata agaaatcagg tgccccaccg     900
ccagcttccc cggggctga tgctcagcaa gaaagttagc acagacgcct ggtggtggct     960
gtgcatccct ggagtaccct cttcttcctc gagggcaccc gggcagattt cacaacacca    1020
cactacttct gaacgctgcc ccatggctgt gcgggtatct ctgtggtgtg atggtgtcct    1080
gtccgacaga ccgaacagac ctgtctaacg tatctccatc ctccgccccc cacgactttg    1140
tcttgtaggt cgaacactgc tgaagataag tttgtgttct gcaatggact tgtcctgcat    1200
cgacttcagt gccttcgtgg atttggggag t                                   1231
```

<210> SEQ ID NO 56
<211> LENGTH: 722
<212> TYPE: DNA
<213> ORGANISM: Equus caballus

<400> SEQUENCE: 56

```
tatagtttta accgtaattt gaatacacgt ctagtataat ctatagtttt atacatgtta      60
gtgttcacag tcatagaatt ttagtatcga agggaacctc aaagcatcat cttgtgctaa     120
tgcaaacctt tcaaagtaac gatggggact yagaggcctg aaggcgcaga ggcgtttagt     180
gacagagctg ggactagaga gccctggtcc ccgggcctta tcggctgtt ttgtgttcag      240
cctgggaccc aaattcaaaa aactgctccc atgatctgtg atcataactc atacctgaat     300
cagaatagcc atctcccagg ccttctgggg tataaattaa cctgctactt gccagataat     360
aaggagtgct agggtttttt tttgctttta ggaagattag ccctgagcta actgctgcca     420
gtcctctttt tgctgggaa gactggcagt gagctaacat ccatgcccat cctcctctac       480
tttatatgtg ggacgcctac cacagcatgg cttgccaagc ggtgccatgt ccacacccgg     540
gatctgaact ggcgaaccct gggccgccaa gaagcggacc gagcgaactt aactgctgca     600
ccactgggcc ggcctctggg agtgctaggt ttttaaccct tagctgagaa gttaagtatg     660
tctgaaccta gaaggagctc cttaggccca agacaatggt ggccacaact aagaggcaaa     720
```

-continued aa                                                                      722

<210> SEQ ID NO 57
<211> LENGTH: 154
<212> TYPE: DNA
<213> ORGANISM: Equus caballus

<400> SEQUENCE: 57
ttactgaact ggcaagacta cgagggacga acacctcttc attttgcagt cgccgatggg      60
aatgtgacgg tggttgatgt cttgacctcg tacgagagct gcaacataac rtcttatgat     120
aacttatttc gaaccccact tcactgggca gctc                                  154

<210> SEQ ID NO 58
<211> LENGTH: 1460
<212> TYPE: DNA
<213> ORGANISM: Equus caballus

<400> SEQUENCE: 58
cggagatatg gacagatgga accaagagtg catggtattg ctcctccagg tctggaggaa      60
ggaactgcaa gtaaaacccc caaagattat cccagtaagc aggaccacca agagtccatc     120
caagggcatc tcgggcacaa agtccaccag gcactcagtg ctcaagcaaa tctatggtaa     180
ctatccttct gggcactttg tagtttacar ttagcacccc cagagagtgt cacgtcataa     240
tctggaatgg gatttaatta cattgggcaa acatccattc aggtaggaac tttattatac     300
ctccaggcac caagagaatc ctcagcacca catttagtgc ctccctccca gccattctgg     360
gtcagaattg gtttcataag acattctggc atcacaacaa agagcttctc tgctgggctc     420
catgactgaa agcctcaccr tctctccagg ccattgcttg ggtcttcccc ttacattgtc     480
ctcttggagg aacccaggca cagaccaacc ttgcctgcct cacttggacs tttcctatgc     540
tacgayagtg cagggttgtc catctgtggg actgccccag accgagcacc gcagtaaaca     600
cgcgtttagc agatgaactg ctccacctct ggaagagccc acccagagaa aggcagcagg     660
caacaagtct ggctggctcc crrcagaaga aagttgagct gaggcaccgt tagaaacaat     720
ctgtgaacag gcaggaaact ctcaggagtt gacctgggtc tacatggtat ttccatacca     780
tgcctaattt atcttggcag acacctgaag cctcaagcct tcacctcaac aaagaattca     840
gaacctggtc aggccacagc tctcakggtc agagatacat gattattgtt ggttgattgc     900
aggttgttct caagaaggga aagtacatca tcccacaaga tcttcaaaag ctcattctgt     960
gctgcgtctc aactcaggta aggcaaacca ctgcactggc aaaaaaaacg ttagaacaga    1020
gatggccagg ggttcccaaa ggtcattttg atttccacta ggcatgggtt tcatccccgt    1080
ttcatggagt tgttactgca gtcaacatct gtctctataa ggggcaagtt attttccaaa    1140
taaaagctaa cattacctcc agtagaaact tgttcacata aaggaagggg gaaatgaaaa    1200
tgctatcgtt cttcaaagta ataccttggg aattcttgtt tcattttggt ttcacattag    1260
katcctccag ttccttccca agatgacaa aaagtccttt accacaaatt ctggcttttg     1320
ccttttagga cctactccat aaagatgtgt aatatttaat agcatgttca gctcaggctc    1380
agctgtgcac attttcactc atccaagagc agctcaggga actttctttt cagccacaag    1440
acaggagtgy ttactcagag                                                1460

<210> SEQ ID NO 59
<211> LENGTH: 809
<212> TYPE: DNA
<213> ORGANISM: Equus caballus

<400> SEQUENCE: 59

```
cttacaacct gcaatcagct attcaatcaa aaaacaaaac aaaagcttcg accgcctgyg      60
gaggaagact gtgtccaggg gcgctggaat agctagtgca gagtgctaat tctccgctca     120
ttatctccga catcttggga aaacgttaat acccatgcct gcagccttac tggcctgaaa     180
acgtgttaac aactgaaaga gaatgtcaga atrttttctt tctgctctca cacagcactg     240
ttttgtaaat tctcttagcc tgagctcaag gaccagggga aactatgcct gtgcaaaact     300
gcccagctgt ctgccttcac ctcagtcacg acggctggaa agaagaattt ataattaacg     360
gtaaagtcta agtaacacta agaacatagg tgctaaagag gctgctgggt tgggatttcg     420
gccagccagc tgctgctggc ctggtgtttt ggttccagtg aagaactgga atcagatgag     480
gaggagcctg tcctacagta gctgccttgt ttcactactt ttctggaatc taatgcaaca     540
aacttcctta gagataccgc atcctgttat tccaacatta ttagttttaa attttagacc     600
agaatcataa tccagccttt gcttttagaa actgcaagac cataagaggt atactgttga     660
ttccttacat ttacagttcc catgttggcc tctgaaggcc acaggttgct gcctcgtcct     720
ctcagaatgg tgttctcgtc gctgagcacc agcagcagta ttgggcacta aggaatcagt     780
cgggcaggtt tacagaccag accattcat                                       809
```

<210> SEQ ID NO 60
<211> LENGTH: 781
<212> TYPE: DNA
<213> ORGANISM: Equus caballus

<400> SEQUENCE: 60

```
cgtctgcaga gaaaacaaca gcaatgtgac actgcacccg aacygctgtc tcctcaccgt      60
attcttcaca cccaaacgaa cagtatcctc atctgtaagt caccacagga atcttactg      120
gaaaagggga cctattaact gggcattacc acaggcagcg aaaattccta gttacgacct     180
caagtacaag tactacyggt ttctcgtttg gtctgtgccc tcccatacat gctagagact     240
aatgaaattt caccatcaac aatcctacac tccagactcc cccmccttg gcattctagt     300
ctctcgctct ctgcactcaa atcaactgag aacacttcca cagagccgcc tgccaagtcc     360
tgtcattctc ttccttatgg aggtgagctg attctctaac ctcagaataa tccaaattct     420
tgacttttct tcccttctac tatttctgaa ttattattat atataccaat taataaaccc     480
ccccaatcma atacctatac aaaaaacccct ctaactctcc caaaccaaaa acaccaaaag    540
gaatcctaga ttacagagct gcctccacaa cacagagaac caagctccag acaaagctga     600
agctgtgact tccttcttcc aacttcttct tactctccgg tgaactaagt gactagagat     660
tggcctaaaa tttattactg ccaaataatt tccctaatga cagctagcat ttggtgagca     720
cttaataaat gttagctata ctaaaaacat tatttggatt atctcattta acggtcacca     780
a                                                                     781
```

<210> SEQ ID NO 61
<211> LENGTH: 768
<212> TYPE: DNA
<213> ORGANISM: Equus caballus

<400> SEQUENCE: 61

```
ttttctgtta cacaaaaaaa gagattcatt ggtaaagatt gggtttgcca tagccaggag      60
tgagtgagtc tycagaagtc taagcttaat acattccatg gcctttcaca gcatgatgct     120
gtggcaagaa ctgagaaatc ttggtgtttt tcctggctgc taactaatta attctgtgcc     180
```

-continued

| | |
|---|---|
| cttgggaaaa tctctttcc caggaccta ctttctacat ctgtgcaatg aaggaccttg | 240 |
| aaattctacc tcagatcctt ctgtcttgta atgctttaat taacatgtgt ctggtgtcag | 300 |
| tgtattgtga atccagcatc cagactgggg tctaattttc acctagagct ttggggtcta | 360 |
| aagctgggat gtcacctggc aggctcaagg cctartcact ggaagcaggg agctcagcca | 420 |
| tgagcctgac ttgtcttctg gccagtctct tgttccctcg gtattaaatt cacactaggt | 480 |
| atgcctgggt ttttgctttt aacttcttcc agtgtttcca ctttgacctc tggcttttat | 540 |
| tataataatt tattaagtgc aaggaaggga tcacaaactt tatcttccag aggactttca | 600 |
| cctgtttgga tatttttcag gcgtatctat tccctctttt ctttaaatat tattttcctt | 660 |
| aagttggaag agtactgctt tgaattcccc gtgctctttt ctccctgctc tcaaacttcc | 720 |
| aatccttagc ccgtgtgtct ccaaagatcc ccactttttt ttaacctg | 768 |

<210> SEQ ID NO 62
<211> LENGTH: 564
<212> TYPE: DNA
<213> ORGANISM: Equus caballus

<400> SEQUENCE: 62

| | |
|---|---|
| gagcaactta agaagatgg gacacttcca acaaacaata gaaagcttaa cataaaggta | 60 |
| agtcwtaagt gttgttttga taaaataaga ttttctttca aatcatctrg aatgttgtgt | 120 |
| ttttgtgaaa agttgtttta actcttaggg tttattaatg gctgaagttt ggagttcatc | 180 |
| tgttattcat atgtgatgtt gccatggcag ctttcccacc tcgtccagaa agacttgctc | 240 |
| agctaaaccc acagtggttt ctccctgtct acttatttga tgatttaata tatcatctca | 300 |
| aagkarttct tgtgtttaac ttttttgatgt gtcaaggtgt ttttttttgtt tgtttgtttt | 360 |
| ggtgaggaag attggcccta cactaacatc tgttgccagt cctcctcttt ttagttgaag | 420 |
| aagattgtta ctgagctaat actgtgctag tcttcctcta ttttgtgtgt gccacacact | 480 |
| gccacastgt ggcttaacga gtggtgctag gtctgcgcca tggatccgaa cctgcaaacc | 540 |
| tygggctccc aaagcagagg acat | 564 |

<210> SEQ ID NO 63
<211> LENGTH: 24
<212> TYPE: DNA
<213> ORGANISM: Artificial Sequence
<220> FEATURE:
<223> OTHER INFORMATION: Primer

<400> SEQUENCE: 63
agcatggttt agctgttttt taaa                                        24

<210> SEQ ID NO 64
<211> LENGTH: 21
<212> TYPE: DNA
<213> ORGANISM: Artificial Sequence
<220> FEATURE:
<223> OTHER INFORMATION: Primer

<400> SEQUENCE: 64
ctgtgtggta gtaatggaat g                                           21

<210> SEQ ID NO 65
<211> LENGTH: 20
<212> TYPE: DNA
<213> ORGANISM: Artificial Sequence
<220> FEATURE:
<223> OTHER INFORMATION: Primer

```
<400> SEQUENCE: 65
cccaaaggac ataaaggaca                                              20

<210> SEQ ID NO 66
<211> LENGTH: 17
<212> TYPE: DNA
<213> ORGANISM: Artificial Sequence
<220> FEATURE:
<223> OTHER INFORMATION: Primer

<400> SEQUENCE: 66
aagwgaaaca tcattcc                                                 17

<210> SEQ ID NO 67
<211> LENGTH: 24
<212> TYPE: DNA
<213> ORGANISM: Artificial Sequence
<220> FEATURE:
<223> OTHER INFORMATION: Primer

<400> SEQUENCE: 67
caataaattg gtcaacctaa cacg                                         24

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
catggtgtat tcccttcca                                               20

<210> SEQ ID NO 69
<211> LENGTH: 16
<212> TYPE: DNA
<213> ORGANISM: Artificial Sequence
<220> FEATURE:
<223> OTHER INFORMATION: Primer

<400> SEQUENCE: 69
ytataaaaag agggct                                                  16

<210> SEQ ID NO 70
<211> LENGTH: 24
<212> TYPE: DNA
<213> ORGANISM: Artificial Sequence
<220> FEATURE:
<223> OTHER INFORMATION: Primer

<400> SEQUENCE: 70
caataaattg gtcaacctaa cacg                                         24

<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71
catggtgtat tcccttcca                                               20

<210> SEQ ID NO 72
<211> LENGTH: 24
<212> TYPE: DNA
```

```
<213> ORGANISM: Artificial Sequence
<220> FEATURE:
<223> OTHER INFORMATION: Primer

<400> SEQUENCE: 72
cacagatagt gcattccaga tagg                                              24

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73
ggtcgagatg gagggaata                                                    20

<210> SEQ ID NO 74
<211> LENGTH: 25
<212> TYPE: DNA
<213> ORGANISM: Artificial Sequence
<220> FEATURE:
<223> OTHER INFORMATION: Primer

<400> SEQUENCE: 74
ctgcagtgtt taagtttagg attga                                             25

<210> SEQ ID NO 75
<211> LENGTH: 20
<212> TYPE: DNA
<213> ORGANISM: Artificial Sequence
<220> FEATURE:
<223> OTHER INFORMATION: Primer

<400> SEQUENCE: 75
taaagctcat ggaggccaat                                                   20

<210> SEQ ID NO 76
<211> LENGTH: 22
<212> TYPE: DNA
<213> ORGANISM: Artificial Sequence
<220> FEATURE:
<223> OTHER INFORMATION: Primer

<400> SEQUENCE: 76
ttctacttcc agctattccg ct                                                22

<210> SEQ ID NO 77
<211> LENGTH: 15
<212> TYPE: DNA
<213> ORGANISM: Artificial Sequence
<220> FEATURE:
<223> OTHER INFORMATION: Primer

<400> SEQUENCE: 77
aaytaacctg gtgac                                                        15

<210> SEQ ID NO 78
<211> LENGTH: 20
<212> TYPE: DNA
<213> ORGANISM: Artificial Sequence
<220> FEATURE:
<223> OTHER INFORMATION: Primer

<400> SEQUENCE: 78
tgcaccttgc ctttctttt                                                    20
```

<210> SEQ ID NO 79
<211> LENGTH: 20
<212> TYPE: DNA
<213> ORGANISM: Artificial Sequence
<220> FEATURE:
<223> OTHER INFORMATION: Primer

<400> SEQUENCE: 79
cagcaatccg cttttctttt                                          20

<210> SEQ ID NO 80
<211> LENGTH: 21
<212> TYPE: DNA
<213> ORGANISM: Artificial Sequence
<220> FEATURE:
<223> OTHER INFORMATION: Primer

<400> SEQUENCE: 80
tccctttatc tcttgcacaa t                                        21

<210> SEQ ID NO 81
<211> LENGTH: 14
<212> TYPE: DNA
<213> ORGANISM: Artificial Sequence
<220> FEATURE:
<223> OTHER INFORMATION: Primer

<400> SEQUENCE: 81
kcctggtata tagt                                                14

<210> SEQ ID NO 82
<211> LENGTH: 23
<212> TYPE: DNA
<213> ORGANISM: Artificial Sequence
<220> FEATURE:
<223> OTHER INFORMATION: Primer

<400> SEQUENCE: 82
gcattttaca tgtattggca ggt                                      23

<210> SEQ ID NO 83
<211> LENGTH: 21
<212> TYPE: DNA
<213> ORGANISM: Artificial Sequence
<220> FEATURE:
<223> OTHER INFORMATION: Primer

<400> SEQUENCE: 83
cctcagtttc ctcatccgta a                                        21

<210> SEQ ID NO 84
<211> LENGTH: 20
<212> TYPE: DNA
<213> ORGANISM: Artificial Sequence
<220> FEATURE:
<223> OTHER INFORMATION: Primer

<400> SEQUENCE: 84
cccatgaggt atgacgtagg                                          20

<210> SEQ ID NO 85
<211> LENGTH: 18
<212> TYPE: DNA
<213> ORGANISM: Artificial Sequence
<220> FEATURE:
<223> OTHER INFORMATION: Primer

```
<400> SEQUENCE: 85
trtcatgatc atgatgtc                                                  18

<210> SEQ ID NO 86
<211> LENGTH: 21
<212> TYPE: DNA
<213> ORGANISM: Artificial Sequence
<220> FEATURE:
<223> OTHER INFORMATION: Primer

<400> SEQUENCE: 86
tgtgacctct gtcctctctc c                                              21

<210> SEQ ID NO 87
<211> LENGTH: 19
<212> TYPE: DNA
<213> ORGANISM: Artificial Sequence
<220> FEATURE:
<223> OTHER INFORMATION: Primer

<400> SEQUENCE: 87
atatcttgcg cgctgaatg                                                 19

<210> SEQ ID NO 88
<211> LENGTH: 20
<212> TYPE: DNA
<213> ORGANISM: Artificial Sequence
<220> FEATURE:
<223> OTHER INFORMATION: Primer

<400> SEQUENCE: 88
gtgtagaagc gggggacgtc                                                20

<210> SEQ ID NO 89
<211> LENGTH: 19
<212> TYPE: DNA
<213> ORGANISM: Artificial Sequence
<220> FEATURE:
<223> OTHER INFORMATION: Primer

<400> SEQUENCE: 89
yggcgaggcg aagcggctg                                                 19

<210> SEQ ID NO 90
<211> LENGTH: 23
<212> TYPE: DNA
<213> ORGANISM: Artificial Sequence
<220> FEATURE:
<223> OTHER INFORMATION: Primer

<400> SEQUENCE: 90
catgcatcac ttaacaacag agg                                            23

<210> SEQ ID NO 91
<211> LENGTH: 19
<212> TYPE: DNA
<213> ORGANISM: Artificial Sequence
<220> FEATURE:
<223> OTHER INFORMATION: Primer

<400> SEQUENCE: 91
gtcaacgacg gaccacata                                                 19

<210> SEQ ID NO 92
<211> LENGTH: 17
<212> TYPE: DNA
```

```
<213> ORGANISM: Artificial Sequence
<220> FEATURE:
<223> OTHER INFORMATION: Primer

<400> SEQUENCE: 92
ctacacacct aggctct                                                      17

<210> SEQ ID NO 93
<211> LENGTH: 14
<212> TYPE: DNA
<213> ORGANISM: Artificial Sequence
<220> FEATURE:
<223> OTHER INFORMATION: Primer

<400> SEQUENCE: 93
rtggtactaa tctt                                                         14

<210> SEQ ID NO 94
<211> LENGTH: 22
<212> TYPE: DNA
<213> ORGANISM: Artificial Sequence
<220> FEATURE:
<223> OTHER INFORMATION: Primer

<400> SEQUENCE: 94
aacctcaaag catcatcttg tg                                                22

<210> SEQ ID NO 95
<211> LENGTH: 18
<212> TYPE: DNA
<213> ORGANISM: Artificial Sequence
<220> FEATURE:
<223> OTHER INFORMATION: Primer

<400> SEQUENCE: 95
tctctagtcc cagctctg                                                     18

<210> SEQ ID NO 96
<211> LENGTH: 20
<212> TYPE: DNA
<213> ORGANISM: Artificial Sequence
<220> FEATURE:
<223> OTHER INFORMATION: Primer

<400> SEQUENCE: 96
tcaaagtaac gatggggact                                                   20

<210> SEQ ID NO 97
<211> LENGTH: 17
<212> TYPE: DNA
<213> ORGANISM: Artificial Sequence
<220> FEATURE:
<223> OTHER INFORMATION: Primer

<400> SEQUENCE: 97
yagaggcctg aaggcgc                                                      17

<210> SEQ ID NO 98
<211> LENGTH: 21
<212> TYPE: DNA
<213> ORGANISM: Artificial Sequence
<220> FEATURE:
<223> OTHER INFORMATION: Primer

<400> SEQUENCE: 98
gtacgagagc tgcaacataa c                                                 21
```

<210> SEQ ID NO 99
<211> LENGTH: 18
<212> TYPE: DNA
<213> ORGANISM: Artificial Sequence
<220> FEATURE:
<223> OTHER INFORMATION: Primer

<400> SEQUENCE: 99
gagctgccca gtgaagtg                                             18

<210> SEQ ID NO 100
<211> LENGTH: 24
<212> TYPE: DNA
<213> ORGANISM: Artificial Sequence
<220> FEATURE:
<223> OTHER INFORMATION: Primer

<400> SEQUENCE: 100
ggttcgaaat aagttatcat aaga                                      24

<210> SEQ ID NO 101
<211> LENGTH: 12
<212> TYPE: DNA
<213> ORGANISM: Artificial Sequence
<220> FEATURE:
<223> OTHER INFORMATION: Primer

<400> SEQUENCE: 101
ygttatgttg ca                                                   12

<210> SEQ ID NO 102
<211> LENGTH: 22
<212> TYPE: DNA
<213> ORGANISM: Artificial Sequence
<220> FEATURE:
<223> OTHER INFORMATION: Primer

<400> SEQUENCE: 102
tcagtgctca agcaaatcta tg                                        22

<210> SEQ ID NO 103
<211> LENGTH: 22
<212> TYPE: DNA
<213> ORGANISM: Artificial Sequence
<220> FEATURE:
<223> OTHER INFORMATION: Primer

<400> SEQUENCE: 103
aatcccattc cagattatga cg                                        22

<210> SEQ ID NO 104
<211> LENGTH: 21
<212> TYPE: DNA
<213> ORGANISM: Artificial Sequence
<220> FEATURE:
<223> OTHER INFORMATION: Primer

<400> SEQUENCE: 104
ctgggcactt tgtagtttac a                                         21

<210> SEQ ID NO 105
<211> LENGTH: 15
<212> TYPE: DNA
<213> ORGANISM: Artificial Sequence
<220> FEATURE:
<223> OTHER INFORMATION: Primer

```
<400> SEQUENCE: 105
rttagcaccc ccaga                                                    15

<210> SEQ ID NO 106
<211> LENGTH: 19
<212> TYPE: DNA
<213> ORGANISM: Artificial Sequence
<220> FEATURE:
<223> OTHER INFORMATION: Primer

<400> SEQUENCE: 106
agaacctggt caggccaca                                                19

<210> SEQ ID NO 107
<211> LENGTH: 23
<212> TYPE: DNA
<213> ORGANISM: Artificial Sequence
<220> FEATURE:
<223> OTHER INFORMATION: Primer

<400> SEQUENCE: 107
tcttgtggga tgatgtactt tcc                                           23

<210> SEQ ID NO 108
<211> LENGTH: 20
<212> TYPE: DNA
<213> ORGANISM: Artificial Sequence
<220> FEATURE:
<223> OTHER INFORMATION: Primer

<400> SEQUENCE: 108
ataatcatgt atctctgacc                                               20

<210> SEQ ID NO 109
<211> LENGTH: 11
<212> TYPE: DNA
<213> ORGANISM: Artificial Sequence
<220> FEATURE:
<223> OTHER INFORMATION: Primer

<400> SEQUENCE: 109
mtgagagctg t                                                        11

<210> SEQ ID NO 110
<211> LENGTH: 20
<212> TYPE: DNA
<213> ORGANISM: Artificial Sequence
<220> FEATURE:
<223> OTHER INFORMATION: Primer

<400> SEQUENCE: 110
caagagcagc tcagggaact                                               20

<210> SEQ ID NO 111
<211> LENGTH: 20
<212> TYPE: DNA
<213> ORGANISM: Artificial Sequence
<220> FEATURE:
<223> OTHER INFORMATION: Primer

<400> SEQUENCE: 111
ctggcattag ctgctgacag                                               20

<210> SEQ ID NO 112
<211> LENGTH: 20
<212> TYPE: DNA
```

<213> ORGANISM: Artificial Sequence
<220> FEATURE:
<223> OTHER INFORMATION: Primer

<400> SEQUENCE: 112
tcagccacaa gacaggagtg                                              20

<210> SEQ ID NO 113
<211> LENGTH: 11
<212> TYPE: DNA
<213> ORGANISM: Artificial Sequence
<220> FEATURE:
<223> OTHER INFORMATION: Primer

<400> SEQUENCE: 113
yttactcaga g                                                        11

<210> SEQ ID NO 114
<211> LENGTH: 19
<212> TYPE: DNA
<213> ORGANISM: Artificial Sequence
<220> FEATURE:
<223> OTHER INFORMATION: Primer

<400> SEQUENCE: 114
catgcctgca gccttactg                                                19

<210> SEQ ID NO 115
<211> LENGTH: 20
<212> TYPE: DNA
<213> ORGANISM: Artificial Sequence
<220> FEATURE:
<223> OTHER INFORMATION: Primer

<400> SEQUENCE: 115
ggtccttgag ctcaggctaa                                               20

<210> SEQ ID NO 116
<211> LENGTH: 22
<212> TYPE: DNA
<213> ORGANISM: Artificial Sequence
<220> FEATURE:
<223> OTHER INFORMATION: Primer

<400> SEQUENCE: 116
ctgtgtgaga gcagaaagaa aa                                            22

<210> SEQ ID NO 117
<211> LENGTH: 15
<212> TYPE: DNA
<213> ORGANISM: Artificial Sequence
<220> FEATURE:
<223> OTHER INFORMATION: Primer

<400> SEQUENCE: 117
yattctgaca ttcac                                                    15

<210> SEQ ID NO 118
<211> LENGTH: 18
<212> TYPE: DNA
<213> ORGANISM: Artificial Sequence
<220> FEATURE:
<223> OTHER INFORMATION: Primer

<400> SEQUENCE: 118
cgtctgcaga gaaaacaa                                                 18

```
<210> SEQ ID NO 119
<211> LENGTH: 18
<212> TYPE: DNA
<213> ORGANISM: Artificial Sequence
<220> FEATURE:
<223> OTHER INFORMATION: Primer

<400> SEQUENCE: 119
gaggatactg ttcgtttg                                                 18

<210> SEQ ID NO 120
<211> LENGTH: 19
<212> TYPE: DNA
<213> ORGANISM: Artificial Sequence
<220> FEATURE:
<223> OTHER INFORMATION: Primer

<400> SEQUENCE: 120
tgtgacactg cacccgaac                                                19

<210> SEQ ID NO 121
<211> LENGTH: 15
<212> TYPE: DNA
<213> ORGANISM: Artificial Sequence
<220> FEATURE:
<223> OTHER INFORMATION: Primer

<400> SEQUENCE: 121
ygctgtctcc tcacc                                                    15

<210> SEQ ID NO 122
<211> LENGTH: 20
<212> TYPE: DNA
<213> ORGANISM: Artificial Sequence
<220> FEATURE:
<223> OTHER INFORMATION: Primer

<400> SEQUENCE: 122
ggggtctaaa gctgggatgt                                               20

<210> SEQ ID NO 123
<211> LENGTH: 19
<212> TYPE: DNA
<213> ORGANISM: Artificial Sequence
<220> FEATURE:
<223> OTHER INFORMATION: Primer

<400> SEQUENCE: 123
cagtctcttg ttccctcgg                                                19

<210> SEQ ID NO 124
<211> LENGTH: 18
<212> TYPE: DNA
<213> ORGANISM: Artificial Sequence
<220> FEATURE:
<223> OTHER INFORMATION: Primer

<400> SEQUENCE: 124
```
tggcaggctc aaggccta                                                          18

<210> SEQ ID NO 125
<211> LENGTH: 16
<212> TYPE: DNA
<213> ORGANISM: Artificial Sequence
<220> FEATURE:
<223> OTHER INFORMATION: Primer

<400> SEQUENCE: 125
rtcactggaa gcaggg                                                            16

<210> SEQ ID NO 126
<211> LENGTH: 20
<212> TYPE: DNA
<213> ORGANISM: Artificial Sequence
<220> FEATURE:
<223> OTHER INFORMATION: Primer

<400> SEQUENCE: 126
tgggacactt ccaacaaaca                                                        20

<210> SEQ ID NO 127
<211> LENGTH: 24
<212> TYPE: DNA
<213> ORGANISM: Artificial Sequence
<220> FEATURE:
<223> OTHER INFORMATION: Primer

<400> SEQUENCE: 127
ccaaacttca gccattaata aacc                                                   24

<210> SEQ ID NO 128
<211> LENGTH: 18
<212> TYPE: DNA
<213> ORGANISM: Artificial Sequence
<220> FEATURE:
<223> OTHER INFORMATION: Primer

<400> SEQUENCE: 128
ttatcaaaac aacactta                                                          18

<210> SEQ ID NO 129
<211> LENGTH: 19
<212> TYPE: DNA
<213> ORGANISM: Artificial Sequence
<220> FEATURE:
<223> OTHER INFORMATION: Primer

<400> SEQUENCE: 129
wgacttacct ttatgttaa                                                         19

<210> SEQ ID NO 130
<211> LENGTH: 22
<212> TYPE: DNA
<213> ORGANISM: Artificial Sequence
<220> FEATURE:
<223> OTHER INFORMATION: Primer

<400> SEQUENCE: 130
cctatgtcga caatctttgt ac                                                     22

<210> SEQ ID NO 131
<211> LENGTH: 24
<212> TYPE: DNA
<213> ORGANISM: Artificial Sequence
<220> FEATURE:

```
<223> OTHER INFORMATION: Primer

<400> SEQUENCE: 131
attagtagca gaacgaagaa attc                                              24

<210> SEQ ID NO 132
<211> LENGTH: 20
<212> TYPE: DNA
<213> ORGANISM: Artificial Sequence
<220> FEATURE:
<223> OTHER INFORMATION: Primer

<400> SEQUENCE: 132
tgagaaatat ttgatgcttt                                                   20

<210> SEQ ID NO 133
<211> LENGTH: 13
<212> TYPE: DNA
<213> ORGANISM: Artificial Sequence
<220> FEATURE:
<223> OTHER INFORMATION: Primer

<400> SEQUENCE: 133
rttggctttt tta                                                          13

<210> SEQ ID NO 134
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 134
cugcugcugu gaauguugat t                                                 21

<210> SEQ ID NO 135
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 135
ucaacauuca cagcagcagt g                                                 21

<210> SEQ ID NO 136
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 136 guuuaaacu gaaucuucat t                                                  21

<210> SEQ ID NO 137
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 137
ugaagauuca guuuaaaaca g                                                 21

<210> SEQ ID NO 138
```

```
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 138
gaucaaacca uauuguauut t                                              21

<210> SEQ ID NO 139
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 139
aaucaaauau gguugauct g                                               21

<210> SEQ ID NO 140
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 140
cacugagcau gaucacagat t                                              21

<210> SEQ ID NO 141
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 141
ucugugauca ugcucagugc t                                              21

<210> SEQ ID NO 142
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 142
cauuaaagac uuuccuuat t                                               21

<210> SEQ ID NO 143
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 143
uaaggaaaag ucuuuaaugg a                                              21

<210> SEQ ID NO 144
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 144
```

```
ccacgagaaa uaugacaaut t                                                21

<210> SEQ ID NO 145
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 145 auugcauau uucucguggt t                                                 21
```